US007774143B2

(12) United States Patent
Khan et al.

(10) Patent No.: US 7,774,143 B2
(45) **Date of Patent: *Aug. 10, 2010**

(54) METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

(75) Inventors: Javed Khan, Derwood, MD (US); Markus Ringnér, Lund (SE); Carsten Peterson, Lund (SE); Paul Meltzer, Rockville, MD (US)

(73) Assignee: The United States of America as represented by the Secretary, Department of Health and Human Services, Washington, DC (US)

( * ) Notice: Subject to any disclaimer, the term of this patent is extended or adjusted under 35 U.S.C. 154(b) by 472 days.

This patent is subject to a terminal disclaimer.

(21) Appl. No.: 10/133,937

(22) Filed: Apr. 25, 2002

(65) Prior Publication Data

US 2003/0207278 A1 Nov. 6, 2003

(51) Int. Cl.

*G06F 19/00* (2006.01)
*G06F 17/10* (2006.01)
*G06N 3/00* (2006.01)
*G06G 7/00* (2006.01)
*G06G 7/58* (2006.01)

(52) U.S. Cl. ............................ 702/19; 706/13; 706/15; 703/2; 703/11

(58) Field of Classification Search .................. 702/19; 706/15; 703/2

See application file for complete search history.

(56) References Cited

U.S. PATENT DOCUMENTS 6,794,137 B2 9/2004 Blumenberg
7,062,384 B2 6/2006 Rocke et al.
7,229,774 B2 6/2007 Chinnaiyan et al.
7,341,552 B2 3/2008 Zhang et al.
7,370,021 B2 5/2008 Reeve et al.
7,384,736 B2 6/2008 Hakonarson
7,402,388 B2 7/2008 Gillis et al.
7,402,399 B2 7/2008 Mukherjeei et al.
2004/0009154 A1 1/2004 Khan et al.
2008/0181896 A1 7/2008 Khan et al.
2009/0035766 A1 2/2009 Khan et al.

OTHER PUBLICATIONS

Golub et al. (Science (1999) vol. 286, pp. 531-537).*
Gruvberger et al. (Cancer Research (2001) vol. 61, pp. 5979-5984).*
Kwon et al (Genome Informatics (2001) vol. 12, p. 252-254).*
Herrero et al. (Bioinformatics (2001) vol. 17, No. 2, pp. 126-136).*
Furey et al. (Bioinformatics (2000) vol. 16, No. 10, pp. 906-914).*
Muller (IEEE Transactions on Neural Networks (2001) vol. 12, No. 2, pp. 181-201).*
Raychaudhuri et al. (Trends in Biotechnology (2001) vol. 19, No. 5, pp. 189-193).*
OfSperduti et al. (IEEE Transactions on Neural Networks (1997) vol. 8, pp. 714-735).*
Raychaudhuri et al. (Pacific Symposium on Biocomputing (2000) pp. 455-466).*
Khan, J. et al., "Classification and diagnostic prediction of cancers using gene expression profiling and artificial neural networks", *Nature Medicine*, vol. 7, No. 6., pp. 673-679 (Jun. 2001).
Peterson, C. et al., "JETNET 3.0—A versatile artificial neural network package", *Computer Physics Communications*, vol. 81, pp. 185-220 (1994).
Tusher, V. et al., "Significance analysis of microarrays applied to the ionizing radiation response", *PNAS*, vol. 98, No. 9, pp. 5116-5121 (Apr. 24, 2001).
Van Gelder, R. et al., "Amplified RNA synthesized from limited quantities of heterogeneous cDNA", *Proc. Natl. Acad. Sci. USA*, vol. 87, No. 5, pp. 1663-1667 (Mar. 1990).
NHGRI Protocol, http://www.nhgri.hih.gov/DIR/LGG/SK/HTML/protocol.html, 27 pages (Apr. 25, 2002).
GenBank Accession No. NM_000612, dated Oct. 31, 2000.
Blast Alignment between GenBank Accession No. NM_000612 and SEQ ID No. 72, dated Aug. 16, 2007.
Agilent Technology Webpage, dated Aug. 16, 2007.
Image Consortium Record printed Aug. 15, 2007.
GenBank Accession No. N54901, dated Jan. 28, 1997.
GenBank Sequence Revision History page printed Aug. 15, 2007.
GenCard Database Record IGF2 printed Aug. 15, 2007.
Ancoca et al., "On the statistical assessment of classifiers using DNA microarray data", *BMC Bioinformatics*, 7:387 (2006).
Chen et al., "Diagnosis of the Small Round Blue Cell Tumors Using Multiplex Polymerase Chain Reaction", *Journal of Molecular Diagnostics*, 9(1):80-88 (2007).
Mateos et al., "Supervised Neural Networks for Clustering Conditions in DNA Array Data after Reducing Noise by Clustering Gene Expression Profiles", *Microarrav data analysis II*, Kluwer Academic Publ., pp. 91-103 (2002).
U.S. Appl. No. 10/159,563 Office Action dated Jun. 10, 2008.
Li et al., Human Pathology, 2008, 39:1792-1801.
U.S. Appl. No. 10/159,653 Form PTO-892 from Office Action dated Jun. 10, 2008.
U.S. Appl. No. 10/159,563 Office Action dated Feb. 12, 2009.
U.S. Appl. No. 11/928,901 Office Action dated Dec. 11, 2008.
Wang et al., Human Genetics, 2006, 120:297-300.

* cited by examiner

*Primary Examiner*—Lori A Clow
(74) *Attorney, Agent, or Firm*—Merchant & Gould P.C.

(57) ABSTRACT

A method of diagnosing, predicting, or prognosticating about a disease that includes obtaining experimental data, wherein the experimental data is high dimensional data, filtering the data, reducing the dimensionality of the data through use of one or more methods, training a supervised pattern recognition method, ranking individual data points from the data, wherein the ranking is dependent on the outcome of the supervised pattern recognition method, choosing multiple data points from the data, wherein the choice is based on the relative ranking of the individual data points, and using the multiple data points to determine if an unknown set of experimental data indicates a diseased condition, a predilection for a diseased condition, or a prognosis about a diseased condition.

35 Claims, 9 Drawing Sheets

Obtain Experimental Data
101
Filter Data
102
Reduce Dimensionality PSA
103
Randomly Partition Data into 3 Groups
104
115
105
1/3
1/3
1/3
107
106
Select Validation Group
108
109
2/3 Training
1/3 Validation
110
111
Supervised Pattern Recognition Method
Validating Training
112
Rank Data
113
Minimize Amount of Data
114

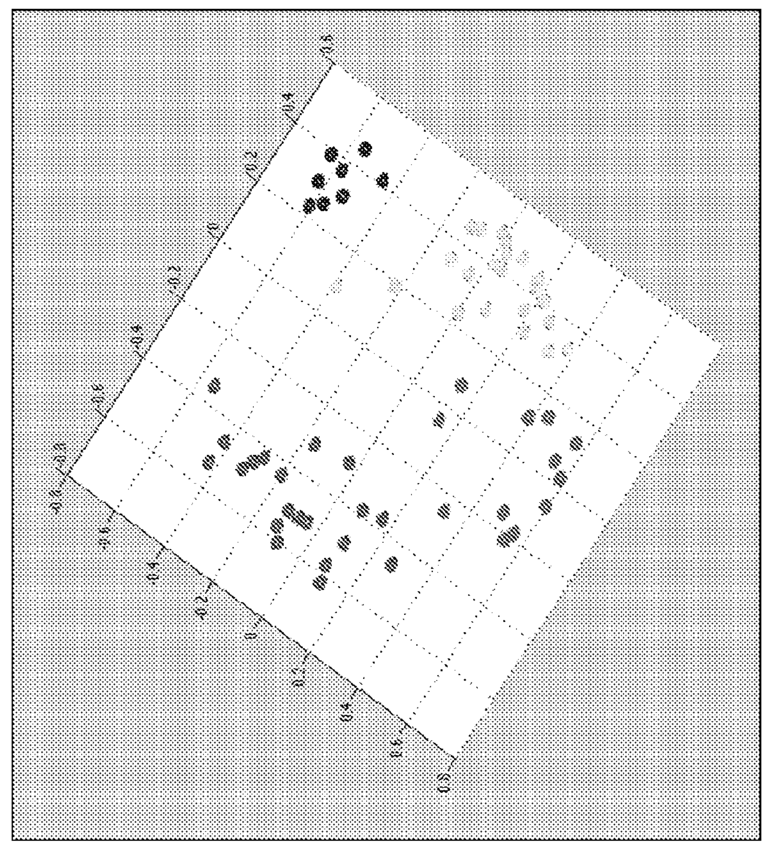
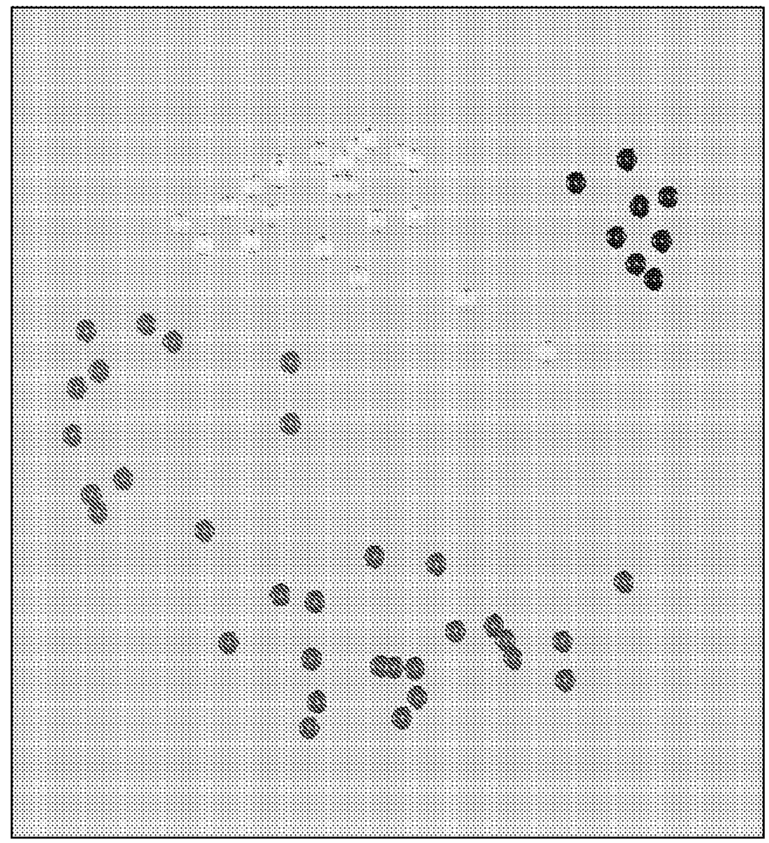
FIG. 7

FIG. 8

| Image Id. | Gene | Class | Rank |
|---|---|---|---|
| 291756 | TUBB5 | EWS* | 86 |
| 208718 | ANXA1 | EWS* | 52 |
| 1416782 | CKB | NOT BL | 36 |
| 289645 | APLP1 | EWS/NB | 32 |
| 841641 | CCND1 | EWS/NB | 3 |
| 811000 | LGALS3BP | EWS/NB | 20 |
| 782503 | EST | EWS/NB | 17 |
| 841620 | DPYSL2 | EWS/NB | 60 |
| 897788 | PTPRF | NOT BL | 66 |
| 563673 | ATQ1 | NOT BL | 34 |
| 504791 | GSTA4 | NOT BL | 59 |
| 364934 | DAPK1 | EWS* | 82 |
| 52076 | NOE1 | EWS* | 19 |
| 80338 | SELENBP1 | EWS* | 63 |
| 1473131 | TLE2 | EWS* | 35 |
| 866702 | PTPN13 | EWS* | 15 |
| 814260 | FVT1 | EWS* | 75 |
| 357031 | TNFAIP6 | EWS* | 16 |
| 377461 | CAV1 | EWS* | 18 |
| 770394 | FCGRT | EWS* | 6 |
| 43733 | GYG2 | EWS | 9 |
| 1435862 | MIC2 | EWS | 73 |
| 377731 | GSTM5 | EWS* | 67 |
| 308497 | EST | EWS* | 93 |
| 755599 | IFI17 | EWS* | 84 |
| 295985 | EST | NOT EWS | 10 |
| 323371 | APP | NOT BL | 65 |
| 233721 | IGFBP2 | NOT BL | 8 |
| 416959 | NFIB | RMS/NB | 81 |
| 395708 | DPYSL4 | NB* | 80 |
| 325182 | CDH2 | NB | 72 |
| 812105 | AF1Q | NB* | 22 |
| 875280 | CRMP1 | NB* | 38 |
| 784257 | KIF3C | NB* | 76 |
| 44563 | GAP43 | NB | 31 |
| 292522 | EST | NB* | 92 |
| 629896 | MAP1B | NB | 11 |
| 383188 | RCV1 | NB* | 29 |
| 308231 | EST | NB* | 53 |
| 377048 | EST | NB* | 74 |
| 784593 | EST | RMS/NB | 50 |
| 82225 | SFRP1 | NB* | 30 |
| 486787 | CNN3 | RMS/NB | 5 |
| 135688 | GATA2 | NB* | 47 |
| 486110 | PFN2 | NB* | 54 |
| 768370 | TIMP3 | NOT BL | 96 |
| 813266 | FHL1 | NB* | 94 |
| 854899 | DUSP6 | NOT BL | 90 |
| 755750 | NME2 | RMS* | 91 |
| 859359 | PIG3 | RMS/NB | 61 |
| 246377 | EST | RMS* | 85 |
| 788107 | AMPHL | RMS* | 49 |
| 212542 | EST | NOT BL | 27 |
| 45291 | DRPLA | NOT BL | 64 |
| 809910 | 1-8U | RMS/EWS | 44 |
| 21652 | CTNNA1 | NOT BL | 55 |
| 308163 | EST | RMS/EWS | 21 |
| 204545 | EST | NOT BL | 28 |
| 365826 | GAS1 | EWS/RMS | 4 |
| 41591 | MN1 | EWS/RMS | 14 |
| 839736 | CRYAB | EWS/RMS | 79 |
| 324494 | HSPB2 | RMS* | 33 |
| 39093 | MNPEP | EWS/RMS | 26 |
| 45542 | IGFBP5 | RMS | 62 |
| 756556 | C1NH | RMS/EWS | 51 |
| 122159 | COL3A1 | RMS* | 40 |
| 809901 | COL15A1 | RMS* | 87 |
| 377671 | ITGA7 | RMS* | 56 |
| 769959 | COL4A2 | RMS* | 88 |
| 1409509 | TNNT1 | RMS | 48 |
| 784224 | FGFR4 | RMS* | 68 |
| 296448 | IGF2 | RMS | 1 |
| 207274 | IGF2 | RMS | 2 |
| 298062 | TNNT2 | RMS* | 25 |
| 461425 | MYL4 | RMS | 42 |
| 796258 | SGCA | RMS | 89 |
| 244618 | EST | RMS* | 7 |
| 245330 | IGF2 | RMS | 46 |
| 42558 | GATM | RMS* | 77 |
| 293500 | EST | RMS* | 69 |
| 417226 | MYC | EWS/BL | 37 |
| 812965 | MYC | EWS/BL | 39 |
| 714453 | IL4R | RMS/BL | 24 |
| 824602 | IFI16 | EWS/BL | 45 |
| 745343 | REG1A | EWS/BL | 57 |
| 868304 | ACTA2 | BL* | 83 |
| 840942 | HLA-DPB1 | BL | 12 |
| 80109 | HLA-DQA1 | BL | 13 |
| 183337 | HLA-DMA | BL | 23 |
| 241412 | ELF1 | BL | 58 |
| 767183 | HCLS1 | BL | 70 |
| 1469292 | PIM2 | BL | 43 |
| 297392 | MT1L | BL | 71 |
| 200814 | MME | BL | 95 |
| 609663 | PRKAR2B | BL* | 41 |
| 814526 | HSRNASEB | RMS/BL | 78 |

<0.1 0.2 1 5 >10

SEQUENCE LISTING

<160> NUMBER OF SEQ ID NOS: 99

<210> SEQ ID NO 1
<211> LENGTH: 2318
<212> TYPE: DNA
<213> ORGANISM: Homo sapiens

<400> SEQUENCE: 1
cgcagggacc gtgctccgcc gtctccgccg catcttccac cctcgccgcc gccgcagctc 60
cccgcgctcg tgccaccgcc gccgcgtcca ccctcagcgc caccgccatg cgggagatcg 120
tgcacctgca ggccggccag tgcggcaacc agatcggggc caagttttgg gaggttatca 180
gtgacgaaca tggcatcgac cccacaggca cataccatgg ggacagtgac ctgcaactgg 240
agaggatcaa cgtgtactac aacgaggcca caggaggaaa ttatgtcccc agagcggtgc 300
tggtggacct ggaacccggc accatggact ctgtccgttc tggccccttc ggtcagatct 360
ttcggccgga caacttcgtg tttggccaat ccggagccgg caacaactgg gcaaaggggc 420
actacacgga gggcgcagag ctggtggacg ctgtcctgga cgtagtccgg aaggaggccg 480
agagctgcga ctgccttcag ggcttccagc tgacccactc gctgggggt ggcacggggt 540 ccggaatggg cacgctgctc atcagtaaga tccgcgagga gttcccagac cgcatcatga 600
acaccttcag cgtggtgccc tcgcccaaag tgtcagacac ggtggtggag ccctacaacg 660
ccacgctgtc tgtgcaccag ctggtggaga atacggatga gacctactgc atcgacaacg 720
aggcactcta cgacatctgt ttccgcaccc tcaagctgac cacccccacc tacggggacc 780
tcaaccacct ggtgtcggcc accatgagcg gggtcaccac ctgcctgcgc ttcccgggcc 840
agctgaacgc cgacctgcgc aagctggccg tcaacatggt tccctttcct cgcctgcact 900
tcttcatgcc cggcttcgca cccctgacca gccggggcag ccagcagtac cgggccctga 960
cggtgcccga gctcacccag cagatgttcg atgccaagaa catgatggcg gcgtgcgacc 1020
cgcgccacgg ccgctacctg accgtggccg ccgtgttccg gggccgcatg tccatgaagg 1080

-continued

```
aggtggacga gcagatgctg agcgtgcaga gcaagaacag cagctacttc gtggagtgga   1140
tccccaacaa cgtgaagacg gccgtgtgcg acatcccgcc ccgcggcctg aagatggccg   1200
cgaccttcat cggcaacagc acggccatcc aggagctgtt caagcgcatc tccgagcagt   1260
tcacggccat gttccggcgc aaggccttct tgcactggta cacgggcgag ggcatggacg   1320
agatggagtt caccgaggcc gagagcaaca tgaatgacct ggtatctgag taccagcagt   1380
accaggacgc cacggccgag gagggcgagt tcgaggagga ggcggaggag gaggtggcct   1440
aggctgctcc catcgcttcc cacctgtccc ctcgaggctt ctgacctttg atccgctagg   1500
ccccccatct ctgaacccta gagccccgct ttccctccaa ggctgactcc ccgctgaccc   1560
taacaatacc tttggagctc gctttacctc tggctacttc atctccgacc ctggctcccc   1620
tttgagccct aatttatctt taaccccctt gagctcttcc aaccttgaca ttcccaggag   1680
gagccccgct tcaccccttc tgactctgga aaccgcacct ttaactttgc agaccttcct   1740
tcacccctga cttctgcttc acctttgacc tctgcccccc atgaatccca ttttacctct   1800
agacctataa gttctggttt atgtttgacc cctccctctg agctgcactt caccgctgac   1860
cttgcctcac ctttaacccc ccacctgagc cccagctcct acctctgacc ccaacttctc   1920
tttgatctct gaatcccctc tgactccaac ttctctttca ccctctatga gtcccatttt   1980
acttctacac ctgcaagtcc tggtttatat tggacccctc cctccgagct gcagttcacc   2040
tttgaccttg cctcaccttt cacccccac cccccacagc gtcagctcct acctctgacc   2100
ccagcttctc tctgattccc acaggcccca tgcatcctcc ctgcctcact cccctcagcc   2160
cctgccgacc ttagcttatc tgggagagaa acaaggcctg gtgcctgtga ggaagagagg   2220
tcacccctac cctccctccc cgcttccctg cctcaccctc aataaataaa ttaattgttg   2280
tcatggaaaa aaaaaaaaaa aaaaaaaaaa aaaaaaaa                            2318
```

<210> SEQ ID NO 2
<211> LENGTH: 1399
<212> TYPE: DNA
<213> ORGANISM: Homo sapiens

<400> SEQUENCE: 2

```
agtgtgaaat cttcagagaa gaatttctct ttagttcttt gcaagaaggt agagataaag     60
acactttttc aaaaatggca atggtatcag aattcctcaa gcaggcctgg tttattgaaa    120
atgaagagca ggaatatgtt caaactgtga agtcatccaa aggtggtccc ggatcagcgg    180
tgagccccta tcctaccttc aatccatcct cggatgtcgc tgccttgcat aaggccataa    240
tggttaaagg tgtggatgaa gcaaccatca ttgacattct aactaagcga aacaatgcac    300
agcgtcaaca gatcaaagca gcatatctcc aggaaacagg aaagcccctg gatgaaacac    360
ttaagaaagc ccttacaggt caccttgagg aggttgtttt agctctgcta aaaactccag    420
cgcaatttga tgctgatgaa cttcgtgctg ccatgaaggg ccttggaact gatgaagata    480
ctctaattga gattttggca tcaagaacta acaaagaaat cagagacatt aacagggtct    540
acagagagga actgaagaga gatctggcca aagacataac ctcagacaca tctggagatt    600
ttcggaacgc tttgctttct cttgctaagg gtgaccgatc tgaggacttt ggtgtgaatg    660
aagacttggc tgattcagat gccagggcct tgtatgaagc aggagaaagg agaaagggga    720
cagacgtaaa cgtgttcaat accatcctta ccaccagaag ctatccacaa cttcgcagag    780
tgtttcagaa atacaccaag tacagtaagc atgacatgaa caaagttctg gacctggagt    840
```

-continued

```
tgaaaggtga cattgagaaa tgcctcacag ctatcgtgaa gtgcgccaca agcaaaccag    900

ctttctttgc agagaagctt catcaagcca tgaaaggtgt tggaactcgc cataaggcat    960

tgatcaggat tatggtttcc cgttctgaaa ttgacatgaa tgatatcaaa gcattctatc   1020

agaagatgta tggtatctcc ctttgccaag ccatcctgga tgaaaccaaa ggagattatg   1080

agaaaatcct ggtggctctt tgtggaggaa actaaacatt cccttgatgg tctcaagcta   1140

tgatcagaag actttaatta tatattttca tcctataagc ttaaatagga aagtttcttc   1200

aacaggatta cagtgtagct acctacatgc tgaaaaatat agcctttaaa tcatttttat   1260

attataactc tgtataatag agataagtcc atttttaaa aatgttttcc ccaaaccata   1320

aaaccctata caagttgttc tagtaacaat acatgagaaa gatgtctatg tagctgaaaa   1380

taaaatgacg tcacaagac                                                1399
```

<210> SEQ ID NO 3
<211> LENGTH: 1432
<212> TYPE: DNA
<213> ORGANISM: Homo sapiens

<400> SEQUENCE: 3

```
gctgttcggc ctgcgtcgct ccgggagctg ccgacggacg gagcgccccc gcccccgccc     60

ggccgcccgc ccgccgccgc catgcccttc tccaacagcc acaacgcact gaagctgcgc    120

ttcccggccg aggacgagtt ccccgacctg agcgcccaca acaaccacat ggccaaggtg    180

ctgacccccg agctgtacgc ggagctgcgc gccaagagca cgccgagcgg cttcacgctg    240

gacgacgtca tccagacagg cgtggacaac ccgggccacc cgtacatcat gaccgtgggc    300

tgcgtggcgg gcgacgagga gtcctacgaa gtgttcaagg atctcttcga ccccatcatc    360

gaggaccggc acggcggcta caagcccagc gatgagcaca agaccgacct caaccccgac    420

aacctgcagg gcggcgacga cctggacccc aactacgtgc tgagctcgcg ggtgcgcacg    480

ggccgcagca tccgtggctt ctgcctcccc ccgcactgca gccgcgggga gcgccgcgcc    540

atcgagaagc tcgcggtgga agccctgtcc agcctggacg gcgacctggc gggccgatac    600

tacgcgctca agagcatgac ggaggcggag cagcagcagc tcatcgacga ccacttcctc    660

ttcgacaagc ccgtgtcgcc cctgctgctg gcctcgggca tggcccgcga ctggcccgac    720

gcccgcggta tctggcacaa tgacaataag accttcctgg tgtgggtcaa cgaggaggac    780

cacctgcggg tcatctccat gcagaagggg ggcaacatga aggaggtgtt cacccgcttc    840

tgcaccggcc tcacccagat tgaaactctc ttcaagtcta aggactatga gttcatgtgg    900

aaccctcacc tgggctacat cctcacctgc ccatccaacc tgggcaccgg gctgcgggca    960

ggtgtgcata tcaagctgcc caacctgggc aagcatgaga agttctcgga ggtgcttaag   1020

cggctgcgac ttcagaagcg aggcacaggc ggtgtggaca cggctgcggt gggcggggtc   1080

ttcgacgtct ccaacgctga ccgcctgggc ttctcagagg tggagctggt gcagatggtg   1140

gtggacggag tgaagctgct catcgagatg gagcagcggc tggagcaggg ccaggccatc   1200

gacgacctca tgcctgccca gaaatgaagc ccggcccaca cccgacacca gccctgctgc   1260

ttcctaactt attgcctggg cagtgcccac catgcacccc tgatgttcgc cgtctggcga   1320

gcccttagcc ttgctgtaga gacttccgtc acccttggta gagtttattt ttttgatggc   1380

taagatactg ctgatgctga aataaactag ggttttggcc tgcctgcgtc tg           1432
```

<210> SEQ ID NO 4
<211> LENGTH: 2384

-continued

<212> TYPE: DNA
<213> ORGANISM: Homo sapiens

<400> SEQUENCE: 4

```
gagctcctgt caccgctggg gccgggccgg gcgggagtgc aggggacgtg agggcgcaag     60
ggccgggaca tggggcccgc cagccccgct gctcgcggtc taagtcgccg cccgggccag    120
ccgccgctgc cgctgctgct gccactattg ctgctgcttc tgcgcgcgca gcccgccatc    180
gggagcctgg ccggtgggag ccccggcgcg gccgaggccc cggggtcggc ccaggtggct    240
ggactatgcg ggcgcctaac ccttcaccgg gacctgcgca ccggccgctg ggaaccagac    300
ccacagcgct ctcgacgctg tctccgggac ccgcagcgcg tgctggagta ctgcagacag    360
atgtacccgg agctgcagat tgcacgtgtg gagcaggcta cgcaggccat ccccatggag    420
cgctggtgcg gggttcccg gagcggcagc tgcgcccacc cccaccacca ggttgtgccc    480
ttccgctgcc tgcctggtga atttgtgagt gaggccctgc tggtgcctga aggctgccgg    540
ttcttgcacc aggagcgcat ggaccaatgt gagagttcaa cccggaggca tcaggaggca    600
caggaggcct gcagctccca gggcctcatc ctgcacggct cgggcatgct cttaccctgt    660
ggctcggatc ggttccgtgg tgtggagtat gtgtgctgtc cccctccagg gaccccccgac    720
ccatctggga cagcagttgg tgacccctcc acccggtcct ggcccccggg gagcagagta    780
gagggggctg aggacgagga agaggaggaa tccttcccac agccagtaga tgattacttc    840
gtggagcctc cgcaggctga agaggaagag gaaacggtcc cacccccaag ctcccataca    900
cttgcagtgg tcggcaaagt cactcccacc ccgaggccca cagacggtgt ggatatttac    960
tttggcatgc ctggggaaat cagtgagcac gaggggttcc tgagggccaa gatggacctg   1020
gaggagcgta ggatgcgcca gattaatgag gtgatgcgtg aatgggccat ggcagacaac   1080
cagtccaaga acctgcctaa agccgacaga caggccctga atgagcactt ccagtccatt   1140
ctgcagactc tggaggagca ggtgtctggt gagcgacagc gcctggtgga aacccacgcc   1200
acccgcgtca tcgcccttat caacgaccag cgccgggctg ccttggaggg cttcctggca   1260
gccctgcagg cagatccgcc tcaggcggag cgtgtcctgt tggccctgcg gcgctacctg   1320
cgtgcggagc agaaggaaca gaggcacacg ctgcgccact accagcatgt ggccgccgtg   1380
gatcccgaga aggcacagca gatgcgcttc caggtgcata cccaccttca agtgattgag   1440
gagagggtga atcagagcct gggcctgctt gaccagaacc cccacctggc tcaggagctg   1500
cggccccaaa tccaggaact cctccactct gaacacctgg gtcccagtga attggaagcc   1560
cctgcccctg gggcagcag cgaggacaag ggtgggctgc agcctccaga ttccaaggat   1620
gacaccccca tgaccttcc aaaagggtcc acagaacaag atgctgcatc ccctgagaaa   1680
gagaagatga acccgctgga acagtatgag cgaaaggtga atgcgtctgt tccaaggggt   1740
ttccctttcc actcatcgga gattcagagg gatgagctgg caccagctgg gacaggggtg   1800
tcccgtgagg ctgtgtcggg tctgctgatc atgggagcgg gcggaggctc cctcatcgtc   1860
ctctccatgc tgctcctgcg caggaagaag ccctacgggg ctatcagcca tggcgtggtg   1920
gaggtggacc ccatgctgac cctggaggag cagcagctcc gcgaactgca gcggcacggc   1980
tatgagaacc ccacttaccg cttcctggag gaacgaccct gacccggccc ccttcacccc   2040
ttcagccgag cccagacctc ccctcttcct ggagccccag aaccccaact cccagcctag   2100
ggcagcaggg agtcttgaag tgatcatttc acacccttt gtgagacggc tggaaattct   2160
tatttcccct ttccaattcc aaaattccat ccctaagaat tcccagatag tcccagcagc   2220
```

-continued

```
ctccccacgt ggcacctcct caccttaatt tattttttaa gtttatttat ggctctttaa   2280

ggtgaccgcc accttggtcc tagtgtctat tccctggaat tcaccctctc atgtttccct   2340

actaacatcc caataaagtc ctcttcccta aaaaaaaaaa aaaa                   2384
```

<210> SEQ ID NO 5
<211> LENGTH: 1325
<212> TYPE: DNA
<213> ORGANISM: Homo sapiens

<400> SEQUENCE: 5

```
gcagtagcag cgagcagcag agtccgcacg ctccggcgag gggcagaaga gcgcgaggga     60

gcgcggggca gcagaagcga gagccgagcg cggacccagc caggacccac agccctcccc    120

agctgcccag gaagagcccc agccatggaa caccagctcc tgtgctgcga agtggaaacc    180

atccgccgcg cgtaccccga tgccaacctc ctcaacgacc gggtgctgcg ggccatgctg    240

aaggcggagg agacctgcgc gccctcggtg tcctacttca aatgtgtgca gaaggaggtc    300

ctgccgtcca tgcggaagat cgtcgccacc tggatgctgg aggtctgcga ggaacagaag    360

tgcgaggagg aggtcttccc gctggccatg aactacctgg accgcttcct gtcgctggag    420

cccgtgaaaa agagccgcct gcagctgctg gggggccactt gcatgttcgt ggcctctaag    480

atgaaggaga ccatccccct gacggccgag aagctgtgca tctacaccga cggctccatc    540

cggcccgagg agctgctgca aatggagctg ctcctggtga acaagctcaa gtggaacctg    600

gccgcaatga ccccgcacga tttcattgaa cacttcctct ccaaaatgcc agaggcggag    660

gagaacaaac agatcatccg caaacacgcg cagaccttcg ttgcctcttg tgccacagat    720

gtgaagttca tttccaatcc gccctccatg gtggcagcgg ggagcgtggt ggccgcagtg    780

caaggcctga acctgaggag ccccaacaac ttcctgtcct actaccgcct cacacgcttc    840

ctctccagag tgatcaagtg tgacccagac tgcctccggg cctgccagga gcagatcgaa    900

gccctgctgg agtcaagcct gcgccaggcc cagcagaaca tggaccccaa ggccgccgag    960

gaggaggaag aggaggagga ggaggtggac ctggcttgca cacccaccga cgtgcgggac   1020

gtggacatct gaggggccca ggcaggcggg cgccaccgcc acccgcagcg agggcggagc   1080

cggccccagg tgctccacat gacagtccct cctctccgga gcattttgat accagaaggg   1140

aaagcttcat tctccttgtt gttggttgtt ttttcctttg ctctttcccc cttccatctc   1200

tgacttaagc aaaagaaaaa gattacccaa aaactgtctt taaaagagag agagagaaaa   1260

aaaaaaaaaa aaaaaaaaaa aaaaaaaaaa aaaaaaaaaa aaaaaaaaaa aaaaaaaaaa   1320

aaaaa                                                               1325
```

<210> SEQ ID NO 6
<211> LENGTH: 2254
<212> TYPE: DNA
<213> ORGANISM: Homo sapiens

<400> SEQUENCE: 6

```
aatcgaaagt agactctttt ctgaagcatt tcctgggatc agcctgacca cgctccatac     60

tgggagaggc ttctgggtca aaggaccagt ctgcagaggg atcctgtggc tggaagcgag    120

gaggctccac acggccgttg cagctaccgc agccaggatc tgggcatcca ggcacggcca    180

tgacccctcc gaggctcttc tgggtgtggc tgctggttgc aggaacccaa ggcgtgaacg    240

atggtgacat gcggctggcc gatgggggcg ccaccaacca gggccgcgtg gagatcttct    300

acagaggcca gtggggcact gtgtgtgaca acctgtggga cctgactgat gccagcgtcg    360
```

-continued

```
tctgccgggc cctgggcttc gagaacgcca cccaggctct gggcagagct gccttcgggc    420
aaggatcagg ccccatcatg ctggacgagg tccagtgcac gggaaccgag gcctcactgg    480
ccgactgcaa gtccctgggc tggctgaaga gcaactgcag gcacgagaga gacgctggtg    540
tggtctgcac caatgaaacc aggagcaccc acaccctgga cctctccagg gagctctcgg    600
aggcccttgg ccagatcttt gacagccagc ggggctgcga cctgtccatc agcgtgaatg    660
tgcagggcga ggacgccctg ggcttctgtg gccacacggt catcctgact gccaacctgg    720
aggcccaggc cctgtggaag gagccgggca gcaatgtcac catgagtgtg gatgctgagt    780
gtgtgcccat ggtcagggac cttctcaggt acttctactc ccgaaggatt gacatcaccc    840
tgtcgtcagt caagtgcttc cacaagctgg cctctgccta tggggccagg cagctgcagg    900
gctactgcgc aagcctcttt gccatcctcc tcccccagga cccctcgttc cagatgcccc    960
tggacctgta tgcctatgca gtggccacag gggacgccct gctggagaag ctctgcctac   1020
agttcctggc ctggaacttc gaggccttga cgcaggccga ggcctggccc agtgtcccca   1080
cagacctgct ccaactgctg ctgcccagga gcgacctggc ggtgcccagc gagctggccc   1140
tactgaaggc cgtggacacc tggagctggg gggagcgtgc ctcccatgag gaggtggagg   1200
gcttggtgga gaagatccgc ttccccatga tgctccctga ggagctcttt gagctgcagt   1260
tcaacctgtc cctgtactgg agccacgagg ccctgttcca gaagaagact ctgcaggccc   1320
tggaattcca cactgtgccc ttccagttgc tggcccggta caaaggcctg aacctcaccg   1380
aggataccta caagccccgg atttacacct cgcccacctg gagtgccttt gtgacagaca   1440
gttcctggag tgcacggaag tcacaactgg tctatcagtc cagacggggg cctttggtca   1500
aatattcttc tgattacttc caagcccccct ctgactacag atactacccc taccagtcct   1560
tccagactcc acaacacccc agcttcctct tccaggacaa gagggtgtcc tggtccctgg   1620
tctacctccc caccatccag agctgctgga actacggctt ctcctgctcc tcggacgagc   1680
tccctgtcct gggcctcacc aagtctggcg gctcagatcg caccattgcc tacgaaaaca   1740
aagccctgat gctctgcgaa gggctcttcg tggcagacgt caccgatttc gagggctgga   1800
aggctgcgat tcccagtgcc ctggacacca acagctcgaa gagcacctcc tccttcccct   1860
gcccggcagg gcacttcaac ggcttccgca cggtcatccg cccccttctac ctgaccaact   1920
cctcaggtgt ggactagacg cgtggccaag ggtggtgaga accggagaac cccaggacgc   1980
cctcactgca ggctcccctc ctcggcttcc ttcctctctg caatgacctt caacaaccgg   2040
ccaccagatg tcgccctact cacctgaggc tcagcttcaa gaaattactg gaaggcttcc   2100
actagggtcc accaggagtt ctcccaccac ctcaccagtt tccaggtggt aagcaccagg   2160
aggccctcga ggttgctctg gatccccccca cagcccctgg tcagtctgcc cttgtcactg   2220
gtctgaggtc attaaaatta cattgaggtt ccta                               2254
```

<210> SEQ ID NO 7
<211> LENGTH: 4213
<212> TYPE: DNA
<213> ORGANISM: Homo sapiens

<400> SEQUENCE: 7

```
tccactcctg gagcccgcgg accccgagca cgcgcctgac agcccctgct ggcccggcgc     60
gcggcgtcgc caggccagct atggcccccg acccggtggc cgccgagacc gcggctcagg    120
gacctacccc gcgctacttc acctgggacg aggtggccca gcgctcaggg tgcgaggagc    180
```

-continued

```
ggtggctagt gatcgaccgt aaggtgtaca acatcagcga gttcacccgc cggcatccag    240
ggggctcccg ggtcatcagc cactacgccg ggcaggatgc cacggatccc tttgtggcct    300
tccacatcaa caagggcctt gtgaagaagt atatgaactc tctcctgatt ggagaactgt    360
ctccagagca gcccagcttt gagcccacca agaataaaga gctgacagat gagttccggg    420
agctgcgggc cacagtggag cggatggggc tcatgaaggc caaccatgtc ttcttcctgc    480
tgtacctgct gcacatcttg ctgctggatg gtgcagcctg gctcaccctt tgggtctttg    540
ggacgtcctt tttgcccttc ctcctctgtg cggtgctgct cagtgcagtt caggcccagg    600
ctggctggct gcagcatgac tttgggcacc tgtcggtctt cagcacctca aagtggaacc    660
atctgctaca tcattttgtg attggccacc tgaagggggc ccccgccagt tggtggaacc    720
acatgcactt ccagcaccat gccaagccca actgcttccg caaagaccca gacatcaaca    780
tgcatccctt cttctttgcc ttggggaaga tcctctctgt ggagcttggg aaacagaaga    840
aaaaatatat gccgtacaac caccagcaca aatacttctt cctaattggg cccccagcct    900
tgctgcctct ctacttccag tggtatattt tctattttgt tatccagcga aagaagtggg    960
tggacttggc ctggatgatt accttctacg tccgcttctt cctcacttat gtgccactat   1020
tggggctgaa agccttcctg ggccttttct tcatagtcag gttcctggaa agcaactggt   1080
ttgtgtgggt gacacagatg aaccatattc ccatgcacat tgatcatgac cggaacatgg   1140
actgggtttc cacccagctc caggccacat gcaatgtcca caagtctgcc ttcaatgact   1200
ggttcagtgg acacctcaac ttccagattg agcaccatct tttcccacg atgcctcgac    1260
acaattacca caaagtggct cccctggtgc agtccttgtg tgccaagcat ggcatagagt   1320
accagtccaa gcccctgctg tcagccttcg ccgacatcat ccactcacta aaggagtcag   1380
ggcagctctg gctagatgcc tatcttcacc aataacaaca gccaccctgc ccagtctgga   1440
agaagaggag gaagactctg gagccaaggc agaggggagc ttgagggaca atgccactat   1500
agtttaatac tcagaggggg ttgggtttgg ggacataaag cctctgactc aaactcctcc   1560
cttttatctt ctagccacag ttctaagacc caaagtgggg ggtggacaca gaagtcccta   1620
ggagggaagg agctgttggg gcaggggtgt aaattatttc ctttttctag tttggcacat   1680
gcaggtagtt ggtgaacaga gagaaccagg agggtaacag aagaggaggg acctactgaa   1740
cccagagtca ggaagagatt taacactaaa attccactca tgccgggcgt ggtggcacgc   1800
gcctgtaatc ccagctaccc aggaggctga ggcaggagaa tcgcttgaac cggggaggtg   1860
gaggttgcag tgagctgaga tcacgccatt gtactccagc ctgggcgaca gagcaagact   1920
ccatttcaaa aaaaaaaaaa aaatccactc atataaaagg tgagctcagc tcactggtcc   1980
atttctcagt ggcttctcca tcctcatttg caaacctcag agggataagg cagttgaacc   2040
tgatgagcaa gaattataac agcaaggaaa cattaatgct tagaattctg agatccagca   2100
caactcagtc tgtgggagct cagctcgctg cccagggata ggtatgacct atgtctgcct   2160
taggctgctg ggagatgcca ttctccagtt tcagaagcag gcagggcaaa ggtcaagact   2220
gtggtattgg ggtcttttgg ctctgaagga tcctggaacc actgattttg gtttattccc   2280
tccagggtct aaagagaaca agaggtgcta gctcttacca aaacagatgg tagagagagt   2340
tgctggctat ttaaaaagct ctttcatctt ttaattcacc tcttcttttc acctctttaa   2400
ccactcctca ggaacagaac acttctagga ctgggggtct tttagctcca taagcaagtg   2460
agcagatggg acaagttagt cttttctccc tagaaacaaa ggggatgccc agtggtttcc   2520
ctttgcttcc caacctaaaa tttcaagttt aataaaatag caattagcag aagtgaccaa   2580
```

-continued

```
attgggagat aattatcagt catgaggaaa gacacagatt tcggtcataa agaatgtaag   2640

ggctataagt agaaactttc tataacctaa atgatgttat agaattattt ttgagcagga   2700

gcagaaagat taaatatgat cacttcatac ttctaaatca gaaataggaa gattaaaacc   2760

acagaacagt ttgtgatttc tattgctgta gctaggtatc ttactctgtc cactcttgtt   2820

caagtatcta actcttctgg aaaccaaata ggctttagaa gagattatcc tatattccta   2880

tcagtataat actaaaatgt aactttttaa tcatctggtt tttaaaagat aaacagttta   2940

gcccatctct ccagagagca aacataggaa tatgactcag gagcctccta gggcttatca   3000

tcagccctca cacccgcttc cccctccaac ccacagcctt tgcttccagg tggcaggatt   3060

actactttgc ctcttcagca gcatctactc taggcatatt gatcatttta gacactggga   3120

gaagagaacc tcaaactagg aggaaaagac agagcctcca cttagttttg ggaggggatg   3180

gcagacagtc aaggagatga gcgtcctaag gcatgttggg atagggtcag atgcaccacc   3240

catggagagg tttgtcaaca caaagacatg gaaggttaga ggtttgtcaa caaaaagaca   3300

tggaaggtta ggtttgtcaa cacaaagaca tggaagatta gaggtttgtc aacacaaaga   3360

cacaggaaga atgggctgca gaagatttag atgttttcca tttgggcaca ttttacttag   3420

ctggagaact aggtttaaaa cagcctgggt aggaaaatta gaagcaagct ggatgcagtg   3480

gctcatgcct gtaatcccaa cacttttggg aggtccaggc aggaggatca cttgggccca   3540

ggaggtcaag cctgcagcga gctgagatca caccactgca ctccagcctg ggtgataga   3600

acaagaccct gtctcaaaaa aaaaaaaaaa caacaaaaac ttagaattga ggagttgtac   3660

ctccattggc ttcctcactc caaaataggt gctgatcctt cctattccta ttctttgcca   3720

ccttttgggt gtggtgtcac cagcctgttt agccaagtag ctttgggcat aggctgccca   3780

atctgagcaa acaccagtga ggctctattg agccaagacc aagtcctcaa agcacctgaa   3840

ccactgtggc cttctcagcc tacagcagtg tggtctctta catggccaca aagggacaca   3900

cagtgacaaa aggctcggaa tgttacaatg gtaaaatgag tgatctcaaa tccactgaca   3960

gatataaaat aggcttagag aggaaaagct gcctctggtc aagtagatca tggcagcatg   4020

aattccaact cactttttta caactccaac ttctatgttt atctttgtta ctttcacttt   4080

tttacaacct ggccagaggc attttttaaa tcaggcccaa tatcagtatt ctttttgtgt   4140

gtgccaattt tgttatcaca tccctatgaa gttgaaaaat aaagttaatt ttgaccaaaa   4200

aaaaaaaaaa aag                                                       4213


<210> SEQ ID NO 8
<211> LENGTH: 4459
<212> TYPE: DNA
<213> ORGANISM: Homo sapiens

<400> SEQUENCE: 8

gtttctctct ctccttctct ctctctctct ctctctcttt tttttccgcc ctagctgggg     60

ctgtgttgga ggagaggaag aaagagagac agaggattgc attcatccgt tacgttcttg    120

aaatttccta atagcaagac cagcgaagcg gttgcaccct tttcaatctt gcaaaggaaa    180

aaaacaaaac aaaacaaaaa aaacccaagt ccccttcccg gcagtttttg ccttaaagct    240

gccctcttga aattaatttt ttcccaggag agagatgtct tatcagggga agaaaaatat    300

tccacgcatc acgagcgatc gtcttctgat caaaggaggt aaaattgtta atgatgacca    360

gtcgttctat gcagacatat acatggaaga tgggttgatc aagcaaatag gagaaaatct    420
```

-continued

```
gattgtgcca ggaggagtga agaccatcga ggcccactcc cggatggtga tccccggagg    480

aattgacgtc cacactcgtt tccagatgcc tgatcaggga atgacgtctg ctgatgattt    540

cttccaagga accaaggcgg ccctggctgg gggaaccact atgatcattg accacgttgt    600

tcctgagcct gggacaagcc tgctcgctgc ctttgaccag tggagggaat gggccgacag    660

caagtcctgc tgtgactact ctctgcatgt ggacatcagc gagtggcata agggcatcca    720

ggaggagatg gaagcgcttg tgaaggatca cggggtaaat tccttcctcg tgtacatggc    780

tttcaaagat cgcttccagc taacggattg ccagatttat gaagtactga gtgtgatccg    840

ggatattggc gccatagccc aagtccacgc agaaaatggc gacatcattg cagaggagca    900

gcagaggatc ctggatctgg gcatcacggg ccccgaggga catgtgctga gccgacctga    960

ggaggtcgag gccgaagccg tgaatcgtgc catcaccatc gccaaccaga ccaactgccc   1020

gctgtatatc accaaggtga tgagcaaaag ctctgctgag gtcatcgccc aggcacggaa   1080

gaagggaact gtggtgtatg gcgagcccat cactgccagc ttgggaacgg acggctccca   1140

ttactggagc aagaactggg ccaaggctgc tgcctttgtc acctccccac ccttgagccc   1200

tgatccaacc actccagact ttctcaactc cttgctgtcc tgtggagacc tccaggtcac   1260

gggcagtgcc cattgcacgt ttaacactgc ccagaaggct gtaggaaagg acaacttcac   1320

cctgattccg gagggcacca atggcactga ggagcggatg tccgtcatct gggacaaggc   1380

tgtggtcact gggaagatgg atgagaacca gtttgtggct gtgaccagca ccaatgcagc   1440

caaagtcttc aacctttacc cccggaaagg ccgcattgct gtgggatccg atgccgacct   1500

ggtcatctgg gaccccgaca gcgttaaaac catctctgcc aagacacaca acagctctct   1560

cgagtacaac atctttgaag gcatggagtg ccgcggctcc ccactggtgg tcatcagcca   1620

ggggaagatt gtcctggagg acggcaccct gcatgtcacc gaaggctctg gacgctacat   1680

tccccggaag cccttccctg attttgttta caagcgtatc aaggcaagga gcaggctggc   1740

tgagctgaga ggggttcctc gtggcctgta tgacggacct gtgtgtgaag tgtctgtgac   1800

gcccaagaca gtcactccag cctcctcggc caagacgtct cctgccaagc agcaggcccc   1860

acctgtccgg aacctgcacc agtctggatt cagtttgtct ggtgctcaga ttgatgacaa   1920

cattccccgc cgcaccaccc agcgtatcgt ggcgcccccc ggtggccgtg ccaacatcac   1980

cagcctgggc tagagctcct gggctgtgcg tccactgggg actggggatg ggacacctga   2040

ggacattctg agacttcttt cttccttcct tttttttttt ttgttttttt ttttaagagc   2100

ctgtgatagt tactgtggag cagccagttc atggggtccc ccttggggcc ccacaccccg   2160

tctctcacca agagttactg attttgctca tccacttccc tacacatcta tgggtatcac   2220

acccaagact acccaccaag ctcatacagg gaaccacacc caacacttag acatgcgaac   2280

aagcagcccc cagcgagggt ctccttcgcc ttcaacctcc tagtgtctgt tagcatcttc   2340

cttttcatgg ggggagggaa gataaagtga attgcccaga gctgcctttt tcttttcttt   2400

ttaaaaattt taagaagttt tccttgtggg gctggggagg ggccggggtc agggagagtc   2460

tttttttttt ttttttaaa tactaaattg gaacatttaa ttccatatta atacaagggg   2520

tttgaactgg acatcctaat gatgcaatta cgtcatcacc cagctgattc cgggtggttg   2580

gcaaactcat cgtgtctgtc ctgagaggct ccacaatgcc cacccgcatc gccattctgt   2640

agtcttcagg gtcagctgtt gataaagggg caggcttgcg ttattggcct agattttgct   2700

gcagattaaa tcctttgagg attctcttct cttttaccat ttttctgcgt gctctcactc   2760

tctctttctc tctctagctt tttaattcat gaatattttc gtgtctgtct ctctctctct   2820
```

-continued

```
ctgtgtttcc tccagccctt gtctcggaga cggtgttttc ctcccttgcc ccattatctt   2880
ttcacctccc aggtctacca tttcatggtg gtcgttgggt ccgcctaaag gatttgagcg   2940
tttgccattg caagcatagt gctgtgtcat cctggtccat gtaggactgg tgctaaccac   3000
ctgccatcat gaggatgtgt gctagagtgt gggaccctgg ccaagtgcag gaatgggcca   3060
tgccgtctca cccacagtat cacacgtgga accgcagaca gggcccagaa gctttagagg   3120
tatgaggctg cagaaccgga gagattttcc tctgtgcagt gctctctggc taaagtcacg   3180
gtcaaaccta aacaccgagc ctcattaacc caagtgaacc aaccaaagtc accagttcag   3240
aagtgctaag ctaataggag tctgacccga gggcctgctg cttcctggtt aagtatcttt   3300
tgagattcta gaacacatgg gagcttttta ttttcgggga aaaaccgtat tttttttcttg   3360
tccaattatt tctaaagaca cactacatag aaagaggccc tataaactca aaaagtcatt   3420
gggaaactta aagtctattc tactttgcaa gaggagaaat gtgttttatg aacgatagat   3480
cacatcagaa ctcctgtggg gaggaaacct tataaattaa acacatggcc cccttagaga   3540
ccacaggtga tgtctgtctc catccttccc tctcctttc tgtcaccttt cccccctagct   3600
ggctcctttg gacctacccc tgtccttgct gacttgtgtt gcattgtatt ccaaacgtgt   3660
ttacaggttc tcttaagcaa tgttgtattt gcaggctttt ctgaatacca aatctgcttt   3720
ttgtaaagcg taaaaacatc acaaagtagg tcattccatc accacccttg tctctctaca   3780
cattttgcct ttggggatct ggttggggtt ttgggttttt tgttgttgtt gtttatttgt   3840
tattttaaag gtaaattgca cttttaaaaa aataattggt tgacttaata tatttgcttt   3900
ttttctcacc tgcacttaga ggaaatttga acaagttgga aaaaaacaat ttttgtttca   3960
attctaagaa acacttgcag ctctagtatt cacttgagtc ttcctgtttt tcctgtaccg   4020
ggtcatggta atttttggtt gttttggttg ttttcttaaa aaacaagtta aaacctgacg   4080
atttctgcag gctgtgtaag catgtttacc tgttggcttg ctttgtgtgt ctgttaaatg   4140
aatgtcatat gtaaatgcta aaataaatcg acagtgtctc agaactgaat aactgcagtg   4200
acttgatgct ctaaaacagt gtaggattta agaatagatg gtttttaatc ctggaaattg   4260
tgattgtgac ccatgagtgg aggaactttc agttctaaag ctgataaagt gtgtagccag   4320
aagagtactt tttttttgt aaccactgtc ttgatggcaa aataattatg gtaaaaaaca   4380
agtctcgtgt ttattattcc ttaagaactc tgtgttatat taccatggaa cgcctaataa   4440
agcaaaatgt ggttgtttc                                               4459
```

```
<210> SEQ ID NO 9
<211> LENGTH: 7718
<212> TYPE: DNA
<213> ORGANISM: Homo sapiens

<400> SEQUENCE: 9

cgggagcggc gggagcggtg gcggcggcag aggcggcggc tccagcttcg gctccggctc     60
gggctcgggc tccggctccg gctccggctc cggctccagc tcgggtggcg gtggcgggag    120
cgggaccagg tggaggcggc ggcggcagag gagtgggagc agcggcccta gcggcttgcg    180
gggggacatg cggaccgacg gcccctggat aggcggaagg agtggaggcc ctggtgcccg    240
gcccttggtg ctgagtatcc agcaagagtg accggggtga agaagcaaag actcggttga    300
ttgtcctggg ctgtggctgg ctgtggagct agagccctgg atggcccctg agccagcccc    360
agggaggacg atggtgcccc ttgtgcctgc actggtgatg cttggtttgg tggcaggcgc    420
```

-continued

```
ccatggtgac agcaaacctg tcttcattaa agtccctgag gaccagactg ggctgtcagg    480
aggggtagcc tccttcgtgt gccaagctac aggagaaccc aagccgcgca tcacatggat    540
gaagaagggg aagaaagtca gctcccagcg cttcgaggtc attgagtttg atgatggggc    600
agggtcagtg cttcggatcc agccattgcg ggtgcagcga gatgaagcca tctatgagtg    660
tacagctact aacagcctgg gtgagatcaa cactagtgcc aagctctcag tgctcgaaga    720
ggaacagctg ccccctgggt tcccttccat cgacatgggg cctcagctga aggtggtgga    780
gaaggcacgc acagccacca tgctatgtgc cgcaggcgga aatccagacc ctgagatttc    840
ttggttcaag gacttccttc ctgtagaccc tgccacgagc aacggccgca tcaagcagct    900
gcgttcaggt gccttgcaga tagagagcag tgaggaatcc gaccaaggca agtacgagtg    960
tgtggcgacc aactcggcag gcacacgtta ctcagcccct gcgaacctgt atgtgcgagt   1020
gcgccgcgtg gctcctcgtt tctccatccc tcccagcagc caggaggtga tgccaggcgg   1080
cagcgtgaac ctgacatgcg tggcagtggg tgcacccatg ccctacgtga agtggatgat   1140
gggggccgag gagctcacca aggaggatga gatgccagtt ggccgcaacg tcctggagct   1200
cagcaatgtc gtacgctctg ccaactacac ctgtgtggcc atctcctcgc tgggcatgat   1260
cgaggccaca gcccaggtca cagtgaaagc tcttccaaag cctccgattg atcttgtggt   1320
gacagagaca actgccacca gtgtcaccct cacctgggac tctgggaact cggagcctgt   1380
aacctactat ggcatccagt accgcgcagc gggcacggag ggcccctttc aggaggtgga   1440
tggtgtggcc accacccgct acagcattgg cggcctcagc cctttctcgg aatatgcctt   1500
ccgcgtgctg gcggtgaaca gcatcgggcg agggccgccc agcgaggcag tgcgggcacg   1560
cacgggagaa caggcgccct ccagcccacc gcgccgcgtg caggcacgca tgctgagcgc   1620
cagcaccatg ctggtgcagt gggagcctcc cgaggagccc aacggcctgg tgcggggata   1680
ccgcgtctac tatactccgg actcccgccg ccccccgaac gcctggcaca agcacaacac   1740
cgacgcgggg ctcctcacga ccgtgggcag cctgctgcct ggcatcacct acagcctgcg   1800
cgtgcttgcc ttcaccgccg tgggcgatgg ccctcccagc cccaccatcc aggtcaagac   1860
gcagcaggga gtgcctgccc agcccgcgga cttccaggcc gaggtggagt cggacaccag   1920
gatccagctc tcgtggctgc tgccccctca ggagcggatc atcatgtatg aactggtgta   1980
ctgggcggca gaggacgaag accaacagca caaggtcacc ttcgacccaa cctcctccta   2040
cacactagag gacctgaagc ctgacacact ctaccgcttc cagctggctg cacgctcgga   2100
tatgggggtg ggcgtcttca cccccaccat tgaggcccgc acagcccagt ccaccccctc   2160
cgcccctccc cagaaggtga tgtgtgtgag catgggctcc accacggtcc gggtaagttg   2220
ggtcccgccg cctgccgaca gccgcaacgg cgttatcacc cagtactccg tggcccacga   2280
ggcggtggac ggcgaggacc gcgggcggca tgtggtggat ggcatcagcc gtgagcactc   2340
cagctgggac ctggtgggcc tggagaagtg gacggagtac cgggtgtggg tgcgggcaca   2400
cacagacgtg ggccccggcc ccgagagcag cccggtgctg gtgcgcaccg atgaggacgt   2460
gcccagcggg cctccgcgga aggtggaggt ggagccactg aactccactg ctgtgcatgt   2520
ctactggaag ctgcctgtcc ccagcaagca gcatggccag atccgcggct accaggtcac   2580
ctacgtgcgg ctggagaatg gcgagccccg tggactcccc atcatccaag acgtcatgct   2640
agccgaggcc cagtggcggc cagaggagtc cgaggactat gaaaccacta tcagcggcct   2700
gaccccggag accacctact ccgttactgt tgctgcctat accaccaagg gggatggtgc   2760
ccgcagcaag cccaaaattg tcactacaac aggtgcagtc ccaggccggc ccaccatgat   2820
```

-continued

```
gatcagcacc acggccatga acactgcgct gctccagtgg cacccaccca aggaactgcc   2880
tggcgagctg ctgggctacc ggctgcagta ctgccgggcc gacgaggcgc ggcccaacac   2940
catagatttc ggcaaggatg accagcactt cacagtcacc ggcctgcaca aggggaccac   3000
ctacatcttc cggcttgctg ccaagaaccg ggctggcttg ggtgaggagt tcgagaagga   3060
gatcaggacc cccgaggacc tgcccagcgg cttcccccaa aacctgcatg tgacaggact   3120
gaccacgtct accacagaac tggcctggga cccgccagtg ctggcggaga ggaacgggcg   3180
catcatcagc tacaccgtgg tgttccgaga catcaacagc caacaggagc tgcagaacat   3240
cacgacagac acccgcttta cccttactgg cctcaagcca gacaccactt acgacatcaa   3300
ggtccgcgca tggaccagca aaggctctgg cccactcagc cccagcatcc agtcccggac   3360
catgccggtg gagcaagtgt ttgccaagaa cttccgggtg gcggctgcaa tgaagacgtc   3420
tgtgctgctc agctgggagg ttcccgactc ctataagtca gctgtgccct ttaagattct   3480
gtacaatggg cagagtgtgg aggtggacgg gcactcgatg cggaagctga tcgcagacct   3540
gcagcccaac acagagtact cgtttgtgct gatgaaccgt ggcagcagcg caggggggcct  3600
gcagcacctg gtgtccatcc gcacagcccc cgacctcctg cctcacaagc cgctgcctgc   3660
ctctgcctac atagaggacg gccgcttcga tctctccatg ccccatgtgc aagacccctc   3720
gcttgtcagg tggttctaca ttgttgtggt acccattgac cgtgtgggcg ggagcatgct   3780
gacgccaagg tggagcacac ccgaggaact ggagctggac gagcttctag aagccatcga   3840
gcaaggcgga gaggagcagc ggcggcggcg gcggcaggca gaacgtctga agccatatgt   3900
ggctgctcaa ctggatgtgc tcccggagac ctttaccttg gggggacaaga agaactaccg   3960
gggcttctac aaccggcccc tgtctccgga cttgagctac cagtgctttg tgcttgcctc   4020
cttgaaggaa cccatggacc agaagcgcta tgcctccagc ccctactcgg atgagatcgt   4080
ggtccaggtg acaccagccc agcagcagga ggagccggag atgctgtggg tgacgggtcc   4140
cgtgctggca gtcatcctca tcatcctcat tgtcatcgcc atcctcttgt tcaaaaggaa   4200
aaggacccac tctccgtcct ctaaggatga gcagtcgatc ggactgaagg actccttgct   4260
ggcccactcc tctgaccctg tggagatgcg gaggctcaac taccagaccc caggtatgcg   4320
agaccaccca cccatcccca tcaccgacct ggcggacaac atcgagcgcc tcaaagccaa   4380
cgatggcctc aagttctccc aggagtatga gtccatcgac cctggacagc agttcacgtg   4440
ggagaattca aacctggagg tgaacaagcc caagaaccgc tatgcgaatg tcatcgccta   4500
cgaccactct cgagtcatcc ttacctctat cgatggcgtc cccgggagtg actacatcaa   4560
tgccaactac atcgatggct accgcaagca gaatgcctac atcgccacgc agggcccccct  4620
gcccgagacc atgggcgatt tctggagaat ggtgtgggaa cagcgcacgg ccactgtggt   4680
catgatgaca cggctggagg agaagtcccg ggtaaaatgt gatcagtact ggccagcccg   4740
tggcaccgag acctgtggcc ttattcaggt gaccctgttg gacacagtgg agctggccac   4800
atacactgtg cgcaccttcg cactccacaa gagtggctcc agtgagaagc gtgagctgcg   4860
tcagtttcag ttcatggcct ggccagacca tggagttcct gagtacccaa ctcccatcct   4920
ggccttccta cgacgggtca aggcctgcaa ccccctagac gcagggccca tggtggtgca   4980
ctgcagcgcg ggcgtgggcc gcaccggctg cttcatcgtg attgatgcca tgttggagcg   5040
gatgaagcac gagaagacgg tggacatcta tggccacgtg acctgcatgc gatcacagag   5100
gaactacatg gtgcagacgg aggaccagta cgtgttcatc catgaggcgc tgctggaggc   5160
```

-continued

```
tgccacgtgc ggccacacag aggtgcctgc ccgcaacctg tatgcccaca tccagaagct   5220
gggccaagtg cctccagggg agagtgtgac cgccatggag ctcgagttca agttgctggc   5280
cagctccaag gcccacacgt cccgcttcat cagcgccaac ctgccctgca acaagttcaa   5340
gaaccggctg gtgaacatca tgccctacga attgacccgt gtgtgtctgc agcccatccg   5400
tggtgtggag ggctctgact acatcaatgc cagcttcctg gatggttata gacagcagaa   5460
ggcctacata gctacacagg ggcctctggc agagagcacc gaggacttct ggcgcatgct   5520
atgggagcac aattccacca tcatcgtcat gctgaccaag cttcgggaga tgggcaggga   5580
gaaatgccac cagtactggc cagcagagcg ctctgctcgc taccagtact ttgttgttga   5640
cccgatggct gagtacaaca tgccccagta tatcctgcgt gagttcaagg tcacggatgc   5700
ccgggatggg cagtcaagga caatccggca gttccagttc acagactggc cagagcaggg   5760
cgtgcccaag acaggcgagg gattcattga cttcatcggg caggtgcata agaccaagga   5820
gcagtttgga caggatgggc ctatcacggt gcactgcagt gctggcgtgg gccgcaccgg   5880
ggtgttcatc actctgagca tcgtcctgga gcgcatgcgc tatgagggcg tggtcgacat   5940
gtttcagacc gtgaagaccc tgcgtacaca gcgtcctgcc atggtgcaga cagaggacca   6000
gtatcagctg tgctaccgtg cggccctgga gtacctcggc agctttgacc actatgcaac   6060
gtaactaccg ctcccctctc ctccgccacc cccgccgtgg ggctccggag gggacccagc   6120
tcctctgagc cataccgacc atcgtccagc cctcctacgc agatgctgtc actggcagag   6180
cacagcccac ggggatcaca gcgtttcagg aacgttgcca caccaatcag agagcctaga   6240
acatccctgg gcaagtggat ggcccagcag gcaggcactg tggcccttct gtccaccaga   6300
cccacctgga gcccgcttca agctctctgt tgcgctcccg catttctcat gcttcttctc   6360
atggggtggg gttggggcaa agcctccttt ttaatacatt aagtggggta gactgaggga   6420
ttttagcctc ttccctctga tttttccttt cgcgaatccg tatctgcaga atgggccact   6480
gtaggggttg gggtttattt tgttttgttt tttttttttt tttgtatgac ttctgctgaa   6540
ggacagaaca ttgccttcct cgtgcagagc tggggctgcc agcctgagcg gaggctcggc   6600
cgtgggccgg gaggcagtgc tgatccggct gctcctccag cccttcagac gagatcctgt   6660
ttcagctaaa tgcagggaaa ctcaatgttt ttttaagttt tgttttccct ttaaagcctt   6720
tttttaggcc acattgacag tggtgggcgg ggagaagata gggaacactc atccctggtc   6780
gtctatccca gtgtgtgttt aacattcaca gcccagaacc acagatgtgt ctgggagagc   6840
ctggcaaggc attcctcatc accatcgtgt ttgcaaaggt taaaacaaaa acaaaaaacc   6900
acaaaaataa aaaacaaaaa aaacaaaaaa cccaaaaaaa aaaaaaaaaa gagtcagccc   6960
ttggcttctg cttcaaaccc tcaagagggg aagcaactcc gtgtgcctgg ggttcccgag   7020
ggagctgctg gctgacctgg gcccacagag cctggctttg gtccccagca ttgcagtatg   7080
gtgtggtgtt tgtaggctgt ggggtctggc tgtgtggcca aggtgaatag cacaggttag   7140
ggtgtgtgcc acaccccatg cacctcaggg ccaagcgggg gcgtggctgg cctttcaggt   7200
ccaggccagt gggcctggta gcacatgtct gtcctcagag caggggccag atgattttcc   7260
tccctggttt gcagctgttt tcaaagcccc cgataatcgc tcttttccac tccaagatgc   7320
cctcataaac caatgtggca agactactgg acttctatca atggtactct aatcagtcct   7380
tattatccca gcttgctgag ggcagggag agcgcctctt cctctgggca gcgctatcta   7440
gataggtaag tgggggcggg gaagggtgca tagctgtttt agctgaggga cgtggtgccg   7500
acgtccccaa acctagctag gctaagtcaa gatcaacatt ccagggttgg taatgttgga   7560
```

```
tgatgaaaca ttcattttta ccttgtggat gctagtgctg tagagttcac tgttgtacac   7620

agtctgtttt ctatttgtta agaaaaacta cagcatcatt gcataattct tgatggtaat   7680

aaatttgaat aatcagattt cttacaaaaa aaaaaaaa                           7718
```

<210> SEQ ID NO 10
<211> LENGTH: 1809
<212> TYPE: DNA
<213> ORGANISM: Homo sapiens

<400> SEQUENCE: 10

```
cctgctccaa ggtccagaga gctttctggt ctttgcagca ggcctgccgc cttcatgtcc     60

actctcctca tcaatcagcc ccagtatgcg tggctgaaag agctggggct ccgcgaggaa    120

aacgagggcg tgtataatgg aagctgggga ggccggggag aggttattac gacctattgc    180

cccgctaaca acgagccaat agcaagagtc cgacaggcca gtgtggcaga ctatgaagaa    240

actgtaaaga aagcaagaga agcatggaaa atctgggcag atattcctgc tccaaaacga    300

ggagaaatag taagacagat tggcgatgcc ttgcgggaga agatccaagt actaggaagc    360

ttggtgtctt tggagatggg gaaaatctta gtggaaggtg tgggtgaagt tcaggagtat    420

gtggatatct gtgactatgc tgttggttta tcaaggatga ttggaggacc tatcttgcct    480

tctgaaagat ctggccatgc actgattgag cagtggaatc ccgtaggcct ggttggaatc    540

atcacggcat tcaatttccc tgtggcagtg tatggttgga acaacgccat cgccatgatc    600

tgtggaaatg tctgcctctg gaaaggagct ccaaccactt ccctcattag tgtggctgtc    660

acaaagataa tagccaaggt tctggaggac aacaagctgc ctggtgcaat ttgttccttg    720

acttgtggtg gagcagatat tggcacagca atggccaaag atgaacgagt gaacctgctg    780

tccttcactg ggagcactca ggtgggaaaa caggtgggcc tgatggtgca ggagaggttt    840

gggagaagtc tgttggaact tggaggaaac aatgccatta ttgcctttga agatgcagac    900

ctcagcttag ttgttccatc agctctcttc gctgctgtgg gaacagctgg ccagaggtgt    960

accactgcga ggcgactgtt tatacatgaa agcatccatg atgaggttgt aaacagactt   1020

aaaaaggcct atgcacagat ccgagttggg aacccatggg accctaatgt tctctatggg   1080

ccactccaca ccaagcaggc agtgagcatg tttcttggag cagtggaaga agcaaagaaa   1140

gaaggtggca cagtggtcta tgggggcaag gttatggatc gccctggaaa ttatgtagaa   1200

ccgacaattg tgacaggtct tggccacgat gcgtccattg cacacacaga gactttcgct   1260

ccgattctct atgtctttaa attcaagaat gaagaagagg tctttgcatg gaataatgaa   1320

gtaaaacagg gactttcaag tagcatcttt accaaagatc tgggcagaat ctttcgctgg   1380

cttggaccta aaggatcaga ctgtggcatt gtaaatgtca acattccaac aagtggggct   1440

gagattggag gtgcctttgg aggagaaaag cacactggtg gtggcaggga gtctggcagt   1500

gatgcctgga aacagtacat gagaaggtct acttgtacta tcaactacag taaagacctt   1560

cctctggccc aaggaatcaa gtttcagtaa aggtgtttta gatgaacatc ccttaatttg   1620

aggtgttcca gcagctgttt ttggagaaga caaagaagat taaagttttc cctgaataaa   1680

tgcattatta tgactgtgac agtgactaat ccccctatga ccccaaagcc ctgattaaat   1740

caagagattc ctttttttaaa aatcaaaata aaattgttac aacatagcca tagttactaa   1800

aaaaaaaaa                                                           1809
```

<210> SEQ ID NO 11

-continued

<211> LENGTH: 1317
<212> TYPE: DNA
<213> ORGANISM: Homo sapiens

<400> SEQUENCE: 11

```
agctcccgcg cgctagagcc gcctgctggt ctcacccagc cgggaccgct gacctggcgc     60
tttgtgcggc tccaggcctc cgagtggact ccagaaagcc tgaaaagcta tcatggcagc    120
aaggcccaag ctccactatc ccaacggaag aggccggatg gagtccgtga gatgggtttt    180
agctgccgcc ggagtcgagt ttgatgaaga atttctggaa acaaaagaac agttgtacaa    240
gttgcaggat ggtaaccacc tgctgttcca acaagtgccc atggttgaaa ttgacgggat    300
gaagttggta cagacccgaa gcattctcca ctacatagca gacaagcaca atctctttgg    360
caagaacctc aaggagagaa ccctgattga catgtacgtg gaggggacac tggatctgct    420
ggaactgctt atcatgcatc ctttcttaaa accagatgat cagcaaaagg aagtggttaa    480
catggcccag aaggctataa ttagatactt tcctgtgttt gaaaagattt taaggggtca    540
cggacaaagc tttcttgttg gtaatcagct gagccttgca gatgtgattt tactccaaac    600
cattttagct ctagaagaga aaattcctaa tatcctgtct gcatttcctt tcctccagga    660
atacacagtg aaactaagta atatccctac aattaagaga ttccttgaac ctggcagcaa    720
gaagaagcct ccccctgatg aaatttatgt gagaaccgtc tacaacatct ttaggccata    780
aaacaacaca tccatgtgtg agtgacagtg tgttcctaga gatggtattg tctacagtca    840
tgtcttaatg gatcccagct ctgtcatggt gctatctatg tattaagttg ggtcctaagt    900
tgggtctttt gtgtcaacga gatcatctct tctagaaata tcaacctttt ttgtccagta    960
aataattgtt aggggatctt tattggaaaa ctttttttgga gaggctggta tttaagttag   1020
atctgattgg gctactcatg tcctgtagcc agttcatcct cataataaga atgggcagga   1080
tctcttgttc tctcctgagt gtctttctac tctcctgagc gtctttctgc tctccttatc   1140
ctgttctctt atccttatcc cctccagtct ctgcctaatt tttagtgttt aataacaacc   1200
gaatgtctag taaatgactc tcctctgagc tgtaataaat aaaatggtag taatgaatgc   1260
aatcagtatt agccaaaata aagaatttat gagtcattaa aaaaaaaaaa aaaaaaa       1317
```

<210> SEQ ID NO 12
<211> LENGTH: 5910
<212> TYPE: DNA
<213> ORGANISM: Homo sapiens

<400> SEQUENCE: 12

```
cggaggacag ccggaccgag ccaacgccgg ggactttgtt ccctccacgg aggggactcg     60
gcaactcgca gcggcagggt ctggggccgg cgcctgggag ggatctgcgc cccccactca    120
ctccctagct gtgttcccgc cgccgccccg gctagtctcc ggcgctggcg cctatggtcg    180
gcctccgaca gcgctccgga gggaccgggg gagctcccag gcgcccggga ctggagactg    240
atgcatgagg ggcctacgga ggcgcaggag cggtggtgat ggtctgggaa gcggagctga    300
agtcccctgg gctttggtga ggcgtgacag tttatcatga ccgtgttcag gcaggaaaac    360
gtggatgatt actacgacac cggcgaggaa cttggcagtg gacagtttgc ggttgtgaag    420
aaatgccgtg agaaaagtac cggcctccag tatgccgcca aattcatcaa gaaaaggagg    480
actaagtcca gccggcgggg tgtgagccgc gaggacatcg agcgggaggt cagcatcctg    540
aaggagatcc agcaccccaa tgtcatcacc ctgcacgagg tctatgagaa caagacggac    600
gtcatcctga tcttggaact cgttgcaggt ggcgagctgt ttgacttctt agctgaaaag    660
```

-continued

```
gaatctttaa ctgaagagga agcaactgaa tttctcaaac aaattcttaa tggtgtttac    720
tacctgcact cccttcaaat cgcccacttt gatcttaagc ctgagaacat aatgcttttg    780
gatagaaatg tccccaaacc tcggatcaag atcattgact ttgggttggc ccataaaatt    840
gactttggaa atgaatttaa aaacatattt gggactccag agtttgtcgc tcctgagata    900
gtcaactatg aacctcttgg tcttgaggca gatatgtgga gtatcggggt aataacctat    960
atcctcctaa gtggggcctc cccatttctt ggagacacta agcaagaaac gttagcaaat   1020
gtatccgctg tcaactacga atttgaggat gaatacttca gtaataccag tgccctagcc   1080
aaagatttca taagaagact tctggtcaag gatccaaaga agagaatgac aattcaagat   1140
agtttgcagc atccctggat caagcctaaa gatacacaac aggcacttag tagaaaagca   1200
tcagcagtaa acatggagaa attcaagaag tttgcagccc ggaaaaaatg gaaacaatcc   1260
gttcgcttga tatcactgtg ccaaagatta tccaggtcat tcctgtccag aagtaacatg   1320
agtgttgcca gaagcgatga tactctggat gaggaagact cctttgtgat gaaagccatc   1380
atccatgcca tcaacgatga caatgtccca ggcctgcagc accttctggg ctcattatcc   1440
aactatgatg ttaaccaacc caacaagcac gggacacctc cattactcat tgctgctggc   1500
tgtgggaata ttcaaatact acagttgctc attaaaagag gctcgagaat cgatgtccag   1560
gataagggcg ggtccaatgc cgtctactgg gctgctcggc atggccacgt cgataccttg   1620
aaatttctca gtgagaacaa atgccctttg gatgtgaaag acaagtctgg agagatggcc   1680
ctccacgtgg cagctcgcta tggccatgct gacgtggctc aagttacttg tgcagcttcg   1740
gctcaaatcc caatatccag gacaaaggaa gaagaaaccc ccctgcactg tgctgcttgg   1800
cacggctatt actctgtggc caaagccctt tgtgaagccg gctgtaacgt gaacatcaag   1860
aaccgagaag gagagacgcc cctcctgaca gcctctgcca ggggctacca cgacatcgtg   1920
gagtgtctgg ccgaacatgg agccgacctt aatgcttgcg acaaggacgg acacattgcc   1980
cttcatctgg ctgtaagacg gtgtcagatg gaggtaatca agactctcct cagccaaggg   2040
tgtttcgtcg attatcaaga caggcacggc aatactcccc tccatgtggc atgtaaagat   2100
ggcaacatgc ctatcgtggt ggccctctgt gaagcaaact gcaatttgga catctccaac   2160
aagtatgggc gaacgcctct gcaccttgcg gccaacaacg gaatcctaga cgtggtccgg   2220
tatctctgtc tgatgggagc cagcgttgag gcgctgacca cggacggaaa gacggcagaa   2280
gatcttgcta gatcggaaca gcacgagcac gtagcaggtc tccttgcaag acttcgaaag   2340
gatacgcacc gaggactctt catccagcag ctccgaccca cacagaacct gcagccaaga   2400
attaagctca agctgtttgg ccactcggga tccgggaaaa ccacccttgt agaatctctc   2460
aagtgtgggc tgctgaggag ctttttcaga aggcgtcggc ccagactgtc ttccaccaac   2520
tccagcaggt tcccaccttc acccctggct tctaagccca cagtctcagt gagcatcaac   2580
aacctgtacc caggctgcga gaacgtgagt gtgaggagcc gcagcatgat gttcgagccg   2640
ggtcttacca aagggatgct ggaggtgttt gtggccccga cccaccaccc gcactgctcg   2700
gccgatgacc agtccaccaa ggccatcgac atccagaacg cttatttgaa tggagttggc   2760
gatttcagcg tgtgggagtt ctctggaaat cctgtgtatt tctgctgtta tgactatttt   2820
gctgcaaatg atcccacgtc aatccatgtt gttgtcttta gtctagaaga gccctatgag   2880
atccagctga acccagtgat ttctggctc agtttcctga agtcccttgt cccagttgaa    2940
gaacccatag ccttcggtgg caagctgaag aacccactcc aagttgtcct ggtggccacc   3000
```

-continued

```
cacgctgaca tcatgaatgt tcctcgaccg gctggaggcg agtttggata tgacaaagac   3060
acatcgttgc tgaaagagat taggaacagg tttggaaatg atcttcacat ttcaaataag   3120
ctgtttgttc tggatgctgg ggcttctggg tcaaaggaca tgaaggtact tcgaaatcat   3180
ctgcaagaaa tacgaagcca gattgtttcg gtctgtcctc ccatgactca cctgtgtgag   3240
aaaatcatct ccacgctgcc ttcctggagg aagctcaatg gacccaacca gctgatgtcg   3300
ctgcagcagt ttgtgtacga cgtgcaggac cagctgaacc ccctggccag cgaggaggac   3360
ctcaggcgca ttgctcagca gctccacagc acaggcgaga tcaacatcat gcaaagtgaa   3420
acagttcagg acgtgctgct cctggacccc cgctggctct gcacaaacgt cctggggaag   3480
ttgctgtccg tggagacccc acgggcgctg caccactacc ggggccgcta caccgtggag   3540
gacatccagc gcctggtgcc cgacagcgac gtggaggagc tgctgcagat cctcgatgcc   3600
atggacatct gcgcccggga cctgagcagc gggaccatgg tggacgtccc agccctgatc   3660
aagacagaca acctgcaccg ctcctgggct gatgaggagg acgaggtgat ggtgtatggt   3720
ggcgtgcgca tcgtgcccgt ggaacacctc acccccttcc catgtggcat ctttcacaag   3780
gtccaggtga acctgtgccg gtggatccac cagcaaagca cagagggcga cgcggacatc   3840
cgcctgtggg tgaatggctg caagctggcc aaccgtgggg ccgagctgct ggtgctgctg   3900
gtcaaccacg gccagggcat tgaggtccag gtccgtggcc tggagacgga gaagatcaag   3960
tgctgcctgc tgctggactc ggtgtgcagc accattgaga acgtcatggc caccacgctg   4020
ccagggctcc tgaccgtgaa gcattacctg agcccccagc agctgcggga gcaccatgag   4080
cccgtcatga tctaccagcc acgggacttc ttccgggcac agactctgaa ggaaacctca   4140
ctgaccaaca ccatgggggg gtacaaggaa agcttcagca gcatcatgtg cttcgggtgt   4200
cacgacgtct actcacaggc cagcctcggc atggacatcc atgcatcaga cctgaacctc   4260
ctcactcgga ggaaactgag tcgcctgctg gacccgcccg accccctggg gaaggactgg   4320
tgccttctcg ccatgaactt aggcctccct gacctcgtgg caaagtacaa caccaataac   4380
ggggctccca aggatttcct ccccagcccc ctccacgccc tgctgcggga atggaccacc   4440
taccctgaga gcacagtggg caccctcatg tccaaactga gggagctggg tcgccgggat   4500
gccgcagacc ttttgctgaa ggcatcctct gtgttcaaaa tcaacctgga tggcaatggc   4560
caggaggcct atgcctcgag ctgcaacagc ggcacctctt acaattccat tagctctgtt   4620
gtatcccggt gagggcagcc tctggcttgg acagggtctg tttggactgc agaaccaagg   4680
gggtgatgta gcccatcctt ccctttggag atgctgaggg tgtttcttcc tgcacccaca   4740
gccaggggga tgccactcct ccctccggct tgacctgttt ctctgccgct acctccctcc   4800
ccgtctcatt ccgttgtctg tggatggtca ttgcagttta agagcagaac agatctttta   4860
ctttggccgc ttgaaaagct agtgtacctc ctctcagtgt tttggactcc atctctcatc   4920
ctccagtacc ttgcttctta ctgataattt tgctggaatt cctaactttt caatgacatt   4980
tttttaact atcatattga ttgtccttta aaaaagaaaa gtgcatattt atccaaaatg   5040
tgtatttctt atacgctttt ctgtgttata ccatttcctc agcttatctc ttttatattt   5100
gtaggagaaa ctcccatgta tggaatccca ctgtatgatt tataaacaga caatatgtga   5160
gtgccttttg cagaagaggg tgtgtttgaa atcatcggag tcagccagga gctgtcacca   5220
aggaaacgct acctctctgt cccttgctgt atgctgatca tcgccagagg tgcttcaccc   5280
tgagttttgt tttgtattgt tttctgacag tttttctgtt ttgtttggca aggaaagggg   5340
agaagggaat cctcctccag ggtgatttta tgatcagtgt tgttgctcta ggaagacatt   5400
```

-continued

```
tttccgtttg cttttgttcc aatgtcaatg tgaacgtcca catgaaacct acacactgtc   5460

atgcttcatc attccctctc atctcaggta gaaggttgac acagttgtag ggttacagag   5520

acctatgtaa gaattcagaa gacccctgac tcatcatttg tggcagtccc ttataattgg   5580

tgcatagcag atggtttcca catttagatc ctggtttcat aacttcctgt acttgaagtc   5640

taaaagcaga aaataaagga agcaagtttt cttccatgat tttaaattgt gatcgagttt   5700

taaattgata ggagggaaca tgtcctaatt cttctgtcct gagaagcatg taatgttaat   5760

gttatatcat atgtatatat atatatgcac tatgtatata catatatatt aatactggta   5820

tttttactta atctataaaa tgtcgttaaa aagttgtttg tttttttctt tttttataaa   5880

taaactgttg ctcgttaaaa aaaaaaaaaa                                    5910
```

<210> SEQ ID NO 13
<211> LENGTH: 980
<212> TYPE: DNA
<213> ORGANISM: Homo sapiens

<400> SEQUENCE: 13

```
gcgcggggga gccattagga ggcgaggaga gaggagggcg cagctcccgc ccagcccagc     60

cctgcccagc cctgcccgga ggcagacgcg ccggaaccgg gacgcgataa atatgcagag    120

cggaggcttc gcgcagcaga gcccgcgcgc cgcccgctcc gggtgctgaa tccaggcgtg    180

gggacacgag ccaggcgccg ccgccggagc cagcggagcc ggggccagag ccggagcgcg    240

tccgcgtcca cgcagccgcc ggccggccag cacccagggc cctgcatgcc aggtcgttgg    300

aggtggcagc gagacatgca cccggcccgg aagctcctca gcctcctctt cctcatcctg    360

atgggcactg aactcactca aaataaaaga gaaaacaaag cagagaagat gggagggcca    420

gagagcgaga ggaagaccac aggagagaag acactgaacg agcttccctt gttttgcctg    480

gaagcccacg ctggctccct ggctctgccc aggatgtgca gtccaaatcc caatccagca    540

gtggggttat gtcgtcccgc ttaccctcag agcccttctc ctggtgctgc ccagacgatc    600

agccagtccc tcctggagag gttctgcatg gcctctagga gagaagtttt cttggcccca    660

ggaaggcctg gtggagggtg gtggttgtgc actgttgctg gacagatgca ttcattcatg    720

tgcacacaca cacacacaca tgcacacaca ggggagcaga tacctgcaga gaagagccaa    780

ccaggtcctg attagtggca agctgcccca caaagggcta tgcctgtgtc ttattgagac    840

accttggcaa agagatggct gattctgggt ggtcctggac atggccgcac ccaagggccc    900

tccaagcctt aatggcaccc tgaagcctcc atgcccaggc caaaagatgc ttttcctccc    960

taaaaaaaaa aaaaaaaaaa                                                980
```

<210> SEQ ID NO 14
<211> LENGTH: 1721
<212> TYPE: DNA
<213> ORGANISM: Homo sapiens

<400> SEQUENCE: 14

```
caccagcaca gcaaacccgc cgggatcaaa gtgtaccagt cggcagcatg gctacgaaat     60

gtgggaattg tggacccggc tactccaccc ctctggaggc catgaaagga cccagggaag    120

agatcgtcta cctgccctgc atttaccgaa acacaggcac tgaggcccca gattatctgg    180

ccactgtgga tgttgacccc aagtctcccc agtattgcca ggtcatccac cggctgccca    240

tgcccaacct gaaggacgag ctgcatcact caggatggaa cacctgcagc agctgcttcg    300
```

-continued

```
gtgatagcac caagtcgcgc accaagctgg tgctgcccag tctcatctcc tctcgcatct    360
atgtggtgga cgtgggctct gagccccggg ccccaaagct gcacaaggtc attgagccca    420
aggacatcca tgccaagtgc gaactggcct ttctccacac cagccactgc ctggccagcg    480
gggaagtgat gatcagctcc ctgggagacg tcaagggcaa tggcaaaggg ggttttgtgc    540
tgctggatgg ggagacgttc gaggtgaagg ggacatggga gagacctggg ggtgctgcac    600
cgttgggcta tgacttctgg taccagcctc gacacaatgt catgatcagc actgagtggg    660
cagctcccaa tgtcttacga gatggcttca accccgctga tgtggaggct ggactgtacg    720
ggagccactt atatgtatgg gactggcagc gccatgagat tgtgcagacc ctgtctctaa    780
aagatgggct tattcccttg gagatccgct tcctgcacaa cccagacgct gcccaaggct    840
ttgtgggctg cgcactcagc tccaccatcc agcgcttcta caagaacgag ggaggtacat    900
ggtcagtgga gaaggtgatc caggtgcccc ccaagaaagt gaagggctgg ctgctgcccg    960
aaatgccagg cctgatcacc gacatcctgc tctccctgga cgaccgcttc ctctacttca   1020
gcaactggct gcatggggac ctgaggcagt atgacatctc tgacccacag agaccccgcc   1080
tcacaggaca gctcttcctc ggaggcagca ttgttaaggg aggccctgtg caagtgctgg   1140
aggacgagga actaaagtcc cagccagagc ccctagtggt caagggaaaa cgggtggctg   1200
gaggccctca gatgatccag ctcagcctgg atgggaagcg cctctacatc accacgtcgc   1260
tgtacagtgc ctgggacaag cagttttacc ctgatctcat cagggaaggc tctgtgatgc   1320
tgcaggttga tgtagacaca gtaaaaggag ggctgaagtt gaaccccaac ttcctggtgg   1380
acttcgggaa ggagcccctt ggcccagccc ttgcccatga gctccgctac cctgggggcg   1440
attgtagctc tgacatctgg atttgaactc caccctcatc acccacactc cctattttgg   1500
gccctcactt ccttggggac ctggcttcat tctgctctct cttggcaccc gacccttggc   1560
agcatgtacc acacagccaa gctgagactg tggcaatgtg ttgagtcata tacatttact   1620
gaccactgtt gcttgttgct cactgtgctg cttttccatg agctcttgga ggcaccaaga   1680
aataaactcg taaccctgtc cttcaaaaaa aaaaaaaaaa a                       1721
```

<210> SEQ ID NO 15
<211> LENGTH: 2588
<212> TYPE: DNA
<213> ORGANISM: Homo sapiens

<400> SEQUENCE: 15

```
ggcacgaggc tctctcctcc ctctttcttc gggcagcctc cccaccaccc cacttcagcc     60
tcccccactc ttgccgcctc catatcatca agctctggtg gcgcctgggg ggcttttcgg    120
atcggcagga tgtacccccca gggaaggcac ccgaccccgc tccagtccgg ccagcccttc    180
aagttctcga tcttggagat ctgcgaccgc atcaaagaag aattccagtt tcttcaggct    240
caataccaca gcctcaagct agaatgtgag aagctggcca gcgagaagac ggaaatgcag    300
cgacattatg tcatgtatta tgagatgtcg tacgggctca acattgaaat gcataagcag    360
gcggagattg tgaagcgtct gagcggtatc tgcgctcaga ttatcccctt cctgacccag    420
gagcatcagc agcaggtgct ccaggccgta gaacgcgcca agcaggtcac cgtgggggag    480
ctgaacagcc tcatcgggca gcagctccag ccgctgtccc accacgcacc ccctgtgccc    540
ctcacccccc gcccagccgg gctggtgggc ggcagtgcta cggggctgct tgctctgtct    600
ggagccctgg ctgcccaggc tcagctggcg gcggctgtca aggaggaccg tgcgggcgtg    660
gaggccgagg ggtccagagt ggagagagcc ccgagcagga gtgcatctcc ctcgcccccct    720
```

-continued

```
gagagtctcg tggaggagga gcgaccgagt ggccctggtg gtggcgggaa gcagagagca    780

gatgagaagg agccatcagg accttatgaa agcgacgaag acaagagtga ttacaatctg    840

gtggtggacg aggaccaacc ctcagagccc cccagcccgg ctaccacccc ctgcggaaag    900

gtacccatct gcattcctgc ccgtcgggac ctggtggaca gtccagcctc cttggcctct    960

agccttggct caccgctgcc tagagccaag gagctcatcc tgaatgacct tcccgccagc   1020

actcctgcct ccaaatcctg tgactcctcc ccgccccagg acgcttccac ccccgggccc   1080

agctcggcca gtcacctctg ccagcttgct gccaagccag caccttccac ggacagcgtc   1140

gccctgagga gcccccctgac tctgtccagt cccttcacca cgtccttcag cctgggctcc   1200

cacagcactc tcaacggaga cctctccgtg cccagctcct acgtcagcct ccacctgtcc   1260

ccccaggtca gcagctctgt ggtgtacgga cgctcccccg tgatggcatt tgagtctcat   1320

ccccatctcc gagggtcatc cgtctcttcc tccctaccca gcatccctgg gggaaagccg   1380

gcctactcct tccacgtgtc tgcggacggg cagatgcagc cggttccctt cccctcggat   1440

gcactggtag gcgcgggcat cccgcggcac gcccggcagc tgcacacgct ggcccatggc   1500

gaggtggtct gcgcggtcac catcagcggc tccacacagc atgtgtacac gggcggcaag   1560

ggctgtgtga aggtgtggga cgtgggccag cctggggcca agacgcccgt ggcccagctc   1620

gactgcctga accgagacaa ctacattcgt tcctgcaagt tgctgccgga tggccggagt   1680

ctgatcgtgg gcggtgaggc cagcaccttg tccatttggg acctggcggc gcccaccccc   1740

cgtatcaagg ccgagctgac ttcctcagcc ccagcctgct acgccctggc cgtcagcccc   1800

gacgccaagg tttgcttctc ctgctgcagc gatggcaaca ttgtggtctg ggacctgcag   1860

aatcagacta tggtcaggca gttccagggc cacacggacg gcgccagctg cattgatatt   1920

tccgattacg gcactcggct ctggacaggg ggcctggaca acacggtgcg ctgctgggac   1980

ctgcgggagg gccgccagct gcagcagcat gacttcagct cccagatttt ctccctgggc   2040

cactgcccta accaggactg gctggcggtc ggaatggaga gtagcaacgt ggagatcctg   2100

cacgtccgca agccggagaa ataccagctg cacctccacg agagctgcgt gctgtccctg   2160

aagtttgcct cctgcggacg gtggtttgtg agcaccggga aggacaacct gctcaacgcc   2220

tggaggacgc cgtacggggc cagcattttc cagtccaagg agtcgtcctc agtcctgagt   2280

tgtgacatct ccagaaataa caaatacatc gtgacaggct cgggggacaa gaaggccacc   2340

gtgtatgagg tggtctactg agacatgacc ccccttcctg tacccgaagt ccagactccc   2400

aggggaatca gcagccagga cagacatcct agcagccgcc tcccagccct gcctaggaac   2460

cgtacatccc atctgctctc tggccaacgg cttcacacct tcccctgctg catgtggggg   2520

ccgatgggca ggggacctcg gtggaaataa aatgtatcta tcacatccgc aaaaaaaaaa   2580

aaaaaaaa                                                            2588
```

<210> SEQ ID NO 16
<211> LENGTH: 8133
<212> TYPE: DNA
<213> ORGANISM: Homo sapiens

<400> SEQUENCE: 16

```
cgtccctgca gccctcgccc ggcgctccag tagcaggacc cggtctcggg accagccggt     60

aatatgcacg tgtcactagc tgaggccctg gaggttcggg gtggaccact tcaggaggaa    120

gaaatatggg ctgtattaaa tcaaagtgct gaaagtctcc aagaattatt cagaaaagta    180
```

-continued

```
agcctagctg atcctgctgc ccttggcttc atcatttctc catggtctct gctgttgctg    240
ccatctggta gtgtgtcatt tacagatgaa aatatttcca atcaggatct tcgagcattc    300
actgcaccag aggttcttca aaatcagtca ctaacttctc tctcagatgt tgaaaagatc    360
cacatttatt ctcttggaat gacactgtat tggggggctg attatgaagt gcctcagagc    420
caacctatta agcttggaga tcatctcaac agcatactgc ttggaatgtg tgaggatgtt    480
atttacgctc gagtttctgt tcggactgtg ctggatgctt gcagtgccca cattaggaat    540
agcaattgtg caccctcatt ttcctacgtg aaacacttgg taaaactggt tctgggaaat    600
ctttctggga cagatcagct ttcctgtaac agtgaacaaa agcctgatcg aagccaggct    660
attcgagatc gattgcgagg aaaaggatta ccaacaggaa gaagctctac ttctgatgta    720
ctagacatac aaaagcctcc actctctcat cagacctttc ttaacaaagg gcttagtaaa    780
tctatgggat ttctgtccat caaagataca caagatgaga attatttcaa ggacatttta    840
tcagataatt ctggacgtga agattctgaa aatacattct ccccttacca gttcaaaact    900
agtggcccag aaaaaaaacc catccctggc attgatgtgc tttctaagaa gaagatctgg    960
gcttcatcca tggacttgct ttgtacagct gacagagact tctcttcagg agagactgcc   1020
acatatcgtc gttgtcaccc tgaggcagta acagtgcgga cttcaactac tcctagaaaa   1080
aaggaggcaa gatactcaga tggaagtata gccttggata tctttggccc tcagaaaatg   1140
gatccaatat atcacactcg agaattgccc acctcctcag caatatcaag tgctttggac   1200
cgaatccgag agagacaaaa gaaacttcag gttctgaggg aagccatgaa tgtagaagaa   1260
ccagttcgaa gatacaaaac ttatcatggt gatgtcttta gtacctccag tgaaagtcca   1320
tctattattt cctctgaatc agatttcaga caagtgagaa gaagtgaagc ctcaaagagg   1380
tttgaatcca gcagtggtct cccaggggta gatgaaacct taagtcaagg ccagtcacag   1440
agaccgagca gacaatatga aacacccttt gaaggcaact taattaatca agagatcatg   1500
ctaaaacggc aagaggaaga actgatgcag ctacaagcca aaatggccct tagacagtct   1560
cggttgagcc tatatccagg agacacaatc aaagcgtcca tgcttgacat caccagggat   1620
ccgttaagag aaattgccct agaaacagcc atgactcaaa gaaaactgag gaatttcttt   1680
ggccctgagt ttgtgaaaat gacaattgaa ccatttatat ctttggattt gccacggtct   1740
attcttacta agaaagggaa gaatgaggat aaccgaagga aagtaaacat aatgcttctg   1800
aacgggcaaa gactggaact gacctgtgat accaaaacta tatgtaaaga tgtgtttgat   1860
atggttgtgg cacatattgg cttagtagag catcatttgt ttgctttagc taccctcaaa   1920
gataatgaat atttctttgt tgatcctgac ttaaaattaa ccaaagtggc cccagaggga   1980
tggaaagaag aaccaaagaa aaagaccaaa gccactgtta attttacttt gtttttcaga   2040
attaaatttt ttatggatga tgttagtcta atacaacata ctctgacgtg tcatcagtat   2100
taccttcagc ttcgaaaaga tattttggag gaaaggatgc actgtgatga tgagacttcc   2160
ttattgctgg catccttggc tctccaggct gagtatggag attatcaacc agaggttcat   2220
ggtgtgtctt actttagaat ggagcactat ttgcccgcca gagtgatgga gaaacttgat   2280
ttatcctata tcaaagaaga gttacccaaa ttgcataata cctatgtggg agcttctgaa   2340
aaagagacag agttagaatt tttaaaggtc tgccaaagac tgacagaata tggagttcat   2400
tttcaccgag tgcaccctga gaagaagtca caaacaggaa tattgcttgg agtctgttct   2460
aaaggtgtcc ttgtgtttga agttcacaat ggagtgcgca cattggtcct tcgctttcca   2520
tggagggaaa ccaagaaaat atcttttcct aaaaagaaaa tcacattgca aaatacatca   2580
```

-continued

```
gatggaataa aacatggctt ccagacagac aacagtaaga tatgccagta cctgctgcac   2640
ctctgctctt accagcataa gttccagcta cagatgagag caagacagag caaccaagat   2700
gcccaagata ttgagagagc ttcgtttagg agcctgaatc tccaagcaga gtctgttaga   2760
ggatttaata tgggacgagc aatcagcact ggcagtctgg ccagcagcac cctcaacaaa   2820
cttgctgttc gacctttatc agttcaagct gagattctga agaggctatc ctgctcagag   2880
ctgtcgcttt accagccatt gcaaaacagt tcaaaagaga agaatgacaa agcttcatgg   2940
gaggaaaagc ctagagagat gagtaaatca taccatgatc tcagtcaggc ctctctctat   3000
ccacatcgga aaaatgtcat tgttaacatg gaacccccac cacaaaccgt tgcagagttg   3060
gtgggaaaac cttctcacca gatgtcaaga tctgatgcag aatctttggc aggagtgaca   3120
aaacttaata attcaaagtc tgttgcgagt ttaaatagaa gtcctgaaag gaggaaacat   3180
gaatcagact cctcatccat tgaagaccct gggcaagcat atgttctagg aatgactatg   3240
catagttctg gaaactcttc atcccaagta cccttaaaag aaaatgatgt gctacacaaa   3300
agatggagca tagtatcttc accagaaagg gagatcacct tagtgaacct gaaaaaagat   3360
gcaaagtatg gcttgggatt tcaaattatt ggtggggaga agatgggaag actggaccta   3420
ggcatattta tcagttcagt tgcccctgga ggaccagctg acttggatgg atgcttgaag   3480
ccaggagacc gtttgatatc tgtgaatagt gtgagtctgg agggagtcag ccaccatgct   3540
gcaattgaaa ttttgcaaaa tgcacctgaa gatgtgacac ttgttatctc tcagccaaaa   3600
gaaaagatat ccaaagtgcc ttctactcct gtgcatctca ccaatgagat gaaaaactac   3660
atgaagaaat cttcctacat gcaagacagt gctatagatt cttcttccaa ggatcaccac   3720
tggtcacgtg gtaccctgag gcacatctcg gagaactcct ttgggccgtc tgggggcctg   3780
cgggaaggaa gcctgagttc tcaagattcc aggactgaga gtgccagctt gtctcaaagc   3840
caggtcaatg gtttctttgc cagccattta ggtgaccaaa cctggcagga atcacagcat   3900
ggcagccctt ccccatctgt aatatccaaa gccaccgaga aagagacttt cactgatagt   3960
aaccaaagca aaactaaaaa gccaggcatt tctgatgtaa ctgattactc agaccgtgga   4020
gattcagaca tggatgaagc cacttactcc agcagtcagg atcatcaaac accaaaacag   4080
gaatcttcct cttcagtgaa tacatccaac aagatgaatt ttaaaacttt ttcttcatca   4140
cctcctaagc ctggagatat ctttgaggtt gaactggcta aaaatgataa cagcttgggg   4200
ataagtgtca cggtactgtt tgacaaggga ggtgtgaata cgagtgtcag acatggtggc   4260
atttatgtga aagctgttat tccccaggga gcagcagagt ctgatggtag aattcacaaa   4320
ggtgatcgcg tcctagctgt caatggagtt agtctagaag gagccaccca taagcaagct   4380
gtggaaacac tgagaaatac aggacaggtg gttcatctgt tattagaaaa gggacaatct   4440
ccaacatcta aagaacatgt cccggtaacc ccacagtgta ccctttcaga tcagaatgcc   4500
caaggtcaag gcccagaaaa agtgaagaaa acaactcagg tcaaagacta cagctttgtc   4560
actgaagaaa atacatttga ggtaaaatta tttaaaaata gctcaggtct aggattcagt   4620
ttttctcgag aagataatct tataccggag caaattaatg ccagcatagt aagggttaaa   4680
aagctctttc ctggacagcc agcagcagaa agtggaaaaa ttgatgtagg agatgttatc   4740
ttgaaagtga atggagcctc tttgaaagga ctatctcagc aggaagtcat atctgctctc   4800
aggggaactg ctccagaagt attcttgctt ctctgcagac ctccacctgg tgtgctaccg   4860
gaaattgata ctgcgctttt gaccccactt cagtctccag cacaagtact tccaaacagc   4920
```

-continued

```
agtaaagact cttctcagcc atcatgtgtg gagcaaagca ccagctcaga tgaaaatgaa   4980
atgtcagaca aaagcaaaaa acagtgcaag tccccatcca gaagagacag ttacagtgac   5040
agcagtggga gtggagaaga tgacttagtg acagctccag caaacatatc aaattcgacc   5100
tggagttcag ctttgcatca gactctaagc aacatggtat cacaggcaca gagtcatcat   5160
gaagcaccca agagtcaaga agataccatt tgtaccatgt tttactatcc tcagaaaatt   5220
cccaataaac cagagtttga ggacagtaat ccttcccctc taccaccgga tatggctcct   5280
gggcagagtt atcaacccca atcagaatct gcttcctcta gttcgatgga taagtatcat   5340
atacatcaca tttctgaacc aactagacaa gaaaactgga cacctttgaa aaatgacttg   5400
gaaaatcacc ttgaagactt tgaactggaa gtagaactcc tcattaccct aattaaatca   5460
gaaaaaggaa gcctgggttt tacagtaacc aaaggcaatc agagaattgg ttgttatgtt   5520
catgatgtca tacaggatcc agccaaaagt gatggaaggc taaaacctgg ggaccggctc   5580
ataaaggtta atgatacaga tgttactaat atgactcata cagatgcagt taatctgctc   5640
cgggctgcat ccaaaacagt cagattagtt attggacgag ttctagaatt acccagaata   5700
ccaatgttgc ctcatttgct accggacata acactaacgt gcaacaaaga ggagttgggt   5760
ttttccttat gtggaggtca tgacagcctt tatcaagtgg tatatattag tgatattaat   5820
ccaaggtccg tcgcagccat tgagggtaat ctccagctat tagatgtcat ccattatgtg   5880
aacggagtca gcacacaagg aatgaccttg gaggaagtta acagagcatt agacatgtca   5940
cttccttcat tggtattgaa agcaacaaga aatgatcttc cagtggtccc cagctcaaag   6000
aggtctgctg tttcagctcc aaagtcaacc aaaggcaatg gttcctacag tgtggggtct   6060
tgcagccagc ctgccctcac tcctaatgat tcattctcca cggttgctgg ggaagaaata   6120
aatgaaatat cgtaccccaa aggaaaatgt tctacttatc agataaaggg atcaccaaac   6180
ttgactctgc ccaaagaatc ttatatacaa gaagatgaca tttatgatga ttcccaagaa   6240
gctgaagtta tccagtctct gctggatgtt gtggatgagg aagcccagaa tcttttaaac   6300
gaaaataatg cagcaggata ctcctgtggt ccaggtacat taaagatgaa tgggaagtta   6360
tcagaagaga gaacagaaga tacagactgc gatggttcac ctttacctga gtattttact   6420
gaggccacca aaatgaatgg ctgtgaagaa tattgtgaag aaaaagtaaa aagtgaaagc   6480
ttaattcaga agccacaaga aaagaagact gatgatgatg aaataacatg gggaaatgat   6540
gagttgccaa tagagagaac aaaccatgaa gattctgata aagatcattc ctttctgaca   6600
aacgatgagc tcgctgtact ccctgtcgtc aaagtgcttc cctctggtaa atacacgggt   6660
gccaacttaa aatcagtcat tcgagtcctg cggggtttgc tagatcaagg aattccttct   6720
aaggagctgg agaatcttca agaattaaaa cctttggatc agtgtctaat tgggcaaact   6780
aaggaaaaca gaaggaagaa cagatataaa aatatacttc cctatgatgc tacaagagtg   6840
cctcttggag atgaaggtgg ctatatcaat gccagcttca ttaagatacc agttgggaaa   6900
gaagagttcg tttacattgc ctgccaagga ccactgccta caactgttgg agacttctgg   6960
cagatgattt gggagcaaaa atccacagtg atagccatga tgactcaaga agtagaagga   7020
gaaaaaatca aatgccagcg ctattggccc aacatcctag gcaaaacaac aatggtcagc   7080
aacagacttc gactggctct tgtgagaatg cagcagctga agggctttgt ggtgagggca   7140
atgacccttg aagatattca gaccagagag gtgcgccata tttctcatct gaatttcact   7200
gcctggccag accatgatac accttctcaa ccagatgatc tgcttacttt tatctcctac   7260
atgagacaca tccacagatc aggcccaatc attacgcact gcagtgctgg cattggacgt   7320
```

-continued tcagggaccc tgatttgcat agatgtggtt ctgggattaa tcagtcagga tcttgatttt 7380
gacatctctg atttggtgcg ctgcatgaga ctacaaagac acggaatggt tcagacagag 7440
gatcaatata ttttctgcta tcaagtcatc ctttatgtcc tgacacgtct tcaagcagaa 7500
gaagagcaaa aacagcagcc tcagcttctg aagtgacatg aaaagagcct ctggatgcat 7560
ttccatttct ctccttaacc tccagcagac tcctgctctc tatccaaaat aagatcacag 7620
agcagcaagt tcatacaaca tgcatgttct cctctatctt agaggggtat tcttcttgaa 7680
aataaaaaat attgaaatgc tgtattttta cagctacttt aacctatgat aattatttac 7740
aaaattttaa cactaaccaa acaatgcaga tcttagggat gattaaaggc agcatttgat 7800
gatagcagac attgttacaa ggacatggtg agtctatttt taatgcacca atcttgttta 7860
tagcaaaaat gttttccaat attttaataa agtagttatt ttatagggga tacttgaaac 7920
cagtatttaa gctttaaatg acagtaatat tggcatagaa aaaagtagca aatgtttact 7980
gtatcaattt ctaatgttta ctatatagaa tttcctgtaa tatatttata tactttttca 8040
tgaaaatgga gttatcagtt atctgtttgt tactgcatca tctgtttgta atcattatct 8100
cactttgtaa ataaaaacac accttaaaac atg 8133

<210> SEQ ID NO 17
<211> LENGTH: 2272
<212> TYPE: DNA
<213> ORGANISM: Homo sapiens

<400> SEQUENCE: 17
aggcgcccgc ccgccgcgcg tgattctcgc ctcgccgcag cccagccctg cgcgccttgc 60
ccggcggccc ccgcccggcc gctccgggcc cctggccccg cggagcgatg ctgctgctgg 120
ctgccgcctt cctcgtggcc ttcgtgctgc tgctgtacat ggtgtctccg ctcatcagcc 180
ccaagcccct cgccctgccc ggggcgcatg tggtggttac aggaggttcc agtggcatcg 240
ggaagtgcat tgctatcgag tgctataaac aaggagcttt tataactctg gttgcacgaa 300
atgaggataa gctgctgcag gcaaagaaag aaattgaaat gcactctatt aatgacaaac 360
aggtggtgct ttgcatatca gttgatgtat ctcaagacta taaccaagta gagaatgtca 420
taaaacaagc acaggagaaa ctgggtccag tggacatgct ggtaaattgt gcaggaatgg 480
cagtgtcagg aaaatttgaa gatcttgaag ttagtacctt tgaaaggtta atgagcatca 540
attacctggg cagcgtgtac cccagccggg ccgtgatcac caccatgaag gagcgccggg 600
tgggcaggat cgtgtttgtg tcctcccagg caggacagtt gggattattc ggtttcacag 660
cctactctgc atccaagttt gccataaggg gattggcaga agctttgcag atggaggtga 720
agccatataa tgtctacatc acagttgctt acccaccaga cacagacaca cctggctttg 780
ccgaagaaaa cagaacaaag cctttggaga ctcgacttat ttcagagacc acatctgtgt 840
gcaaaccaga acaggtggcc aaacaaattg ttaaagatgc catacaagga aatttcaaca 900
gttcccttgg ctcagatggg tacatgctct cggccctgac ctgtgggatg gctccagtaa 960
cttctattac tgaggggctc cagcaggtgg tcaccatggg ccttttccgc actattgctt 1020
tgttttacct tggaagtttt gacagcatag ttcgtcgctg catgatgcag agagaaaaat 1080
ctgaaaatgc agacaaaact gcctaatctt cttacccctt ggaagaagac tgtttccaaa 1140
taatttgaac agcttgctgc taaatgggac ccaatttttg gcctatagac acttatgtat 1200
tgttttcgaa tacgtcagat tggaccagtg ctcttcagga atgtggctgc aagcaagggg 1260

-continued

```
ctagaagttc acctcctgac agtattatta atactatgca aatatggaat aggagaccat   1320

ttgattttct aggctttgtg gtagagaggt gaaggtatga gaattaatag cgtgtgaaca   1380

aagtaaagaa caggattcca gaatgatcat taaatttgtt tctatttatt cttttttgcc   1440

cccctagaga ttaagtccag aaatgtactt tctggcacat aaagaaatct tgaggacttt   1500

gtttaaacct tccataaaaa aacaattttc ggtttctcgg gttctctctc tctgtctctc   1560

tgtctctctg tctctctgtc tctctgtctc tctctctctc tctctttctt tctttgtgta   1620

ttttattcaa gatgagttgg acccattgcc agtgagtctg aatgtcactg acagccctgt   1680

gttgtgctca ggactcactc tgctgctggt ggaaactcat ggcttctctc tctctttgat   1740

cccataaagc tacgaggggg acgggagagg gcagtgcaat gggaagtaaa gagatatttt   1800

ccagtaggaa aagcaatgct ttcttgtctt tagactcaaa tgcttaggga acgtttcatt   1860

tctcattcat ggggaaaggc agcctcctta aatgttttct gaagagcggt aaaatctaga   1920

agcttaagaa tttacagttc cttcaataac catgatgacc tgaagttcac ctatcccatt   1980

ttagcatcta cttgtttttc ccatctcttc ctttccaatt ttgcttatac tgctgtaata   2040

tttttgtaaa aaaaaaaaaa aaggaaaaaa aagaccagct aaaattttcg acttgacttt   2100

ttaacttaac tcatgaatta attaaagcaa atgaaaaaat taaaaagtgt gactttttct   2160

cggagcatat atgtagcttt taggaaaggc tgatgatggt ataaagtttg ctcattaaga   2220

aaaaaagaca aggctgattt tgaagagagt tgcttttgaa ataaaatgat ca           2272


<210> SEQ ID NO 18
<211> LENGTH: 1414
<212> TYPE: DNA
<213> ORGANISM: Homo sapiens

<400> SEQUENCE: 18

gaattcgcac tgctctgaga atttgtgagc agcccctaac aggctgttac ttcactacaa     60

ctgacgatat gatcatctta atttacttat ttctcttgct atgggaagac actcaaggat    120

ggggattcaa ggatggaatt tttcataact ccatatggct tgaacgagca gccggtgtgt    180

accacagaga agcacggtct ggcaaataca agctcaccta cgcagaagct aaggcggtgt    240

gtgaatttga aggcggccat ctcgcaactt acaagcagct agaggcagcc agaaaaattg    300

gatttcatgt ctgtgctgct ggatggatgg ctaagggcag agttggatac cccattgtga    360

agccagggcc caactgatga tttggaaaaa ctggcattat tgattatgga atccgtctca    420

ataggagtga aagatgggat gcctattgct acaacccaca cgcaaaggag tgtggtggcg    480

tctttacaga tccaaagcga atttttaaat ctccaggctt cccaaatgag tacgaagata    540

accaaatctg ctactggcac attagactca agtatggtca gcgtattcac ctgagttttt    600

tagattttga ccttgaagat gacccaggtt gcttggctga ttatgttgaa atatatgaca    660

gttacgatga tgtccatggc tttgtgggaa gatactgtgg agatgagctt ccagatgaca    720

tcatcagtac aggaaatgtc atgaccttga agtttctaag tgatgcttca gtgacagctg    780

gaggtttcca aatcaaatat gttgcaatgg atcctgtatc caaatccagt caaggaaaaa    840

atacaagtac tacttctact ggaaataaaa actttttagc tggaagattt agccacttat    900

aaaaaaaaaa aaggatgatc aaaacacaca gtgtttatgt tggaatcttt tggaactcct    960

ttgatctcac tgttattatt aacatttatt tattattttt ctaaatgtga aagaaataca   1020

taatttaggg aaaattggaa aatataggaa actttaaacg agaaaatgaa acctctcata   1080

atcccactgc atagaaataa caagcgttaa cattttcata ttttttctt tcagtcattt   1140
```

```
ttgtatttgt ggtatatgta tatatgtacc tatatgtatt tgcatttgaa attttggaat   1200

cctgctctat gtacagtttt gtattatact ttttaaatct tgaactttat gaacattttc   1260

tgaaatcatt gattattcta caaaaacatg attttaaaca gctgtaaaat attctatgat   1320

atgaatgttt tatgcattat ttaagcctgt ctctattgtt ggaatttcag gtcattttca   1380

taaatattgt tgcaataaat atccttcgga attc                              1414
```

```
<210> SEQ ID NO 19
<211> LENGTH: 2704
<212> TYPE: DNA
<213> ORGANISM: Homo sapiens

<400> SEQUENCE: 19

gggagaaacg ttctcactcg ctctctgctc gctgcgggcg ctccccgccc tctgctgcca     60

gaaccttggg gatgtgccta gacccggcgc agcacacgtc cgggccaacc gcgagcagaa    120

caaacctttg gcgggcggcc aggaggctcc ctcccagcca ccgccccct ccagcgcctt    180

tttttccccc catacaatac aagatcttcc ttcctcagtt cccttaaagc acagcccagg    240

gaaacctcct cacagttttc atccagccac gggccagcat gtctgggggc aaatacgtag    300

actcggaggg acatctctac accgttccca tccgggaaca gggcaacatc tacaagccca    360

acaacaaggc catggcagac gagctgagcg agaagcaagt gtacgacgcg cacaccaagg    420

agatcgacct ggtcaaccgc gaccctaaac acctcaacga tgacgtggtc aagattgact    480

ttgaagatgt gattgcagaa ccagaaggga cacacagttt tgacggcatt tggaaggcca    540

gcttcaccac cttcactgtg acgaaatact ggttttaccg cttgctgtct gccctctttg    600

gcatcccgat ggcactcatc tggggcattt acttcgccat tctctctttc ctgcacatct    660

gggcagttgt accatgcatt aagagcttcc tgattgagat tcagtgcatc agccgtgtct    720

attccatcta cgtccacacc gtctgtgacc cactctttga agctgttggg aaaatattca    780

gcaatgtccg catcaacttg cagaaagaaa tataaatgac atttcaagga tagaagtata    840

cctgattttt tttcctttta attttcctgg tgccaatttc aagttccaag ttgctaatac    900

agcaacaatt tatgaattga attatcttgg ttgaaaataa aaagatcact ttctcagttt    960

tcataagtat tatgtctctt ctgagctatt tcatctattt ttggcagtct gaatttttaa   1020

aacccattta aatttttttc cttacctttt tatttgcatg tggatcaacc atcgctttat   1080

tggctgagat atgaacatat tgttgaaagg taatttgaga gaaatatgaa gaactgagga   1140

ggaaaaaaaa aaaaaagaaa agaaccaaca acctcaactg cctactccaa aatgttggtc   1200

attttatgtt aagggaagaa ttccagggta tggccatgga gtgtacaagt atgtgggcag   1260

attttcagca aactcttttc ccactgttta aggagttagt ggattactgc cattcacttc   1320

ataatccagt aggatccagt gatccttaca agttagaaaa cataatcttc tgccttctca   1380

tgatccaact aatgccttac tcttcttgaa attttaacct atgatatttt ctgtgcctga   1440

atatttgtta tgtagataac aagacctcag tgccttcctg tttttcacat tttccttttc   1500

aaatagggtc taactcagca actcgcttta ggtcagcagc ctccctgaag accaaaatta   1560

gaatatccat gacctagttt tccatgcgtg tttctgactc tgagctacag agtctggtga   1620

agctcacttc tgggcttcat ctggcaacat ctttatccgt agtgggtatg gttgacacta   1680

gcccaatgaa atgaattaaa gtggaccaat agggctgagc tctctgtggg ctggcagtcc   1740

tggaagccag ctttccctgc ctctcatcaa ctgaatgagg tcagcatgtc tattcagctt   1800
```

-continued cgtttatttt caagaataat cacgctttcc tgaatccaaa ctaatccatc accggggtgg 1860
tttagtggct caacattgtg ttcccatttc agctgatcag tgggcctcca aggaggggct 1920
gtaaaatgga ggccattgtg tgagcctatc agagttgctg caaacctgac ccctgctcag 1980
taaagcactt gcaaccgtct gttatgctgt gacacatggc ccctccccct gccaggagct 2040
ttggacctaa tccaagcatc cctttgccca gaaagaagat gggggaggag gcagtaataa 2100
aaagattgaa gtattttgct ggaataagtt caaattcttc tgaactcaaa ctgaggaatt 2160
tcacctgtaa acctgagtcg tacagaaagc tgcctggtat atccaaaagc tttttattcc 2220
tcctgctcat attgtgattc tgcctttggg gacttttctt aaaccttcag ttatgatttt 2280
tttttcatac acttattgga actctgcttg atttttgcct cttccagtct tcctgacact 2340
ttaattacca acctgttacc tactttgact ttttgcattt aaaacagaca ctggcatgga 2400
tatagtttta cttttaaact gtgtacataa ctgaaaatgt gctatactgc atacttttta 2460
aatgtaaaga tatttttatc tttatatgaa gaaaatcact taggaaatgg ctttgtgatt 2520
caatctgtaa actgtgtatt ccaagacatg tctgttctac atagatgctt agtccctcat 2580
gcaaatcaat tactggtcca aaagattgct gaaattttat atgcttactg atatatttta 2640
caatttttta tcatgcatgt cctgtaaagg ttacaagcct gcacaataaa aatgtttaac 2700
ggtt 2704

<210> SEQ ID NO 20
<211> LENGTH: 1440
<212> TYPE: DNA
<213> ORGANISM: Homo sapiens

<400> SEQUENCE: 20
cgggcgcaga agcccctcct cggcgtcctg gtcccggccg tgcccgcggt gtcccgggag 60
gaaggggcgg gccgggggtc gggaggagtc acgtgccccc tcccgcccca ggtcgtcctc 120
tcagcatggg ggtcccgcgg cctcagccct gggcgctggg gctcctgctc tttctccttc 180
ctgggagcct gggcgcagaa agccacctct ccctcctgta ccaccttacc gcggtgtcct 240
cgcctgcccc ggggactcct gccttctggg tgtccggctg gctgggcccg cagcagtacc 300
tgagctacaa tagcctgcgg ggcgaggcgg agccctgtgg agcttgggtc tgggaaaacc 360
aggtgtcctg gtattgggag aaagagacca cagatctgag gatcaaggag aagctctttc 420
tggaagcttt caaagctttg gggggaaaag gtccctacac tctgcagggc ctgctgggct 480
gtgaactggg ccctgacaac acctcggtgc ccaccgccaa gttcgccctg aacggcgagg 540
agttcatgaa tttcgacctc aagcagggca cctggggtgg ggactggccc gaggccctgg 600
ctatcagtca gcggtggcag cagcaggaca aggcggccaa caaggagctc accttcctgc 660
tattctcctg cccgcaccgc ctgcgggagc acctggagag gggccgcgga aacctggagt 720
ggaaggagcc cccctccatg cgcctgaagg cccgacccag cagccctggc ttttccgtgc 780
ttacctgcag cgccttctcc ttctaccctc cggagctgca acttcggttc ctgcggaatg 840
ggctggccgc tggcaccggc cagggtgact tcggccccaa cagtgacgga tccttccacg 900
cctcgtcgtc actaacagtc aaaagtggcg atgagcacca ctactgctgc attgtgcagc 960
acgcggggct ggcgcagccc ctcagggtgg agctggaatc tccagccaag tcctccgtgc 1020
tcgtggtggg aatcgtcatc ggtgtcttgc tactcacggc agcggctgta ggaggagctc 1080
tgttgtggag aaggatgagg agtgggctgc cagccccttg gatctccctt cgtggagacg 1140
acaccggggt cctcctgccc accccagggg aggcccagga tgctgatttg aaggatgtaa 1200

-continued

```
atgtgattcc agccaccgcc tgaccatccg ccattccgac tgctaaaagc gaatgtagtc   1260

aggccccttt catgctgtga gacctcctgg aacactggca tctctgagcc tccagaaggg   1320

gttctgggcc tagttgtcct ccctctggag ccccgtcctg tggtctgcct cagtttcccc   1380

tcctaataca tatggctgtt ttccacctcg ataatataac acgagtttgg gcccgaaaaa   1440
```

<210> SEQ ID NO 21
<211> LENGTH: 1634
<212> TYPE: DNA
<213> ORGANISM: Homo sapiens

<400> SEQUENCE: 21

```
ccctaagtga gaggaccaac agttccgaca gcgagcgctc cccagatctg ggccacagca     60

cgcagattcc aagaaaggtg gtgtatgacc agctcaatca gatcctggtg tcagatgcag    120

ccctcccaga aaatgtcatt ctggtgaaca ccactgactg gcagggccag tatgtggctg    180

agctgctcca ggaccagcgg aagcctgtgg tgtgcacctg ctccaccgtg gaggtccagg    240

ccgtgctgtc cgccctgctc acccggatcc agcgctactg caactgcaac tcttccatgc    300

cgaggccagt gaaggtggct gctgtgggag gccagagcta cctgagctcc atcctcaggt    360

tctttgtcaa gtccctggcc aacatgacct ccgactggct tggctacatg cgcttcctca    420

tcatccccct cggttctcac cctgtggcca aatacttggg gtcagtcgac agtaaataca    480

gtagttcctt cctggattct ggttggagag atctgttcag tcgctcggag ccaccagtgt    540

cagagcaact ggacgtggca gggcgggtga tgcagtacgt caacggggca gccacgacac    600

accagcttcc cgtggccgaa gccatgctga cttgccggca taagttccct gatgaagact    660

cctatcagaa gtttattccc ttcattggcg tggtgaaggt gggtctggtt gaagactctc    720

cctccacagc aggcgatggg gacgattctc ctgtggtcag ccttactgtg ccctccacat    780

caccaccctc cagctcgggc ctgagccgag acgccacggc cacccctccc tcctccccat    840

ctatgagcag cgccctggcc atcgtgggga gccctaatag cccatatggg gacgtgattg    900

gcctccaggt ggactactgg ctgggccacc ccggggagcg gaggagggaa ggcgacaaga    960

gggacgccag ctcgaagaac accctcaaga gtgtcttccg ctcagtgcag gtgtcccgcc   1020

tgccccatag tggggaggcc cagctttctg gcaccatggc catgactgtg gtcaccaaag   1080

aaaagaacaa gaaagttccc accatcttcc tgagcaagaa accccgagaa aaggaggtgg   1140

attctaagag ccaggtcatt gaaggcatca gccgcctcat ctgttcttcc ccctccttag   1200

gccccagcct gggcccagac ccatcctccc agccaggttt ccctccagca ggctccttcc   1260

ctccctgtca cctccctctc accaacccgg ggtctgagcc cctcattcct gaccgtccgt   1320

gttctcagga gtggttgagg acacagggcc ccagcccagc cctctgcacc ccccagcccg   1380

gccatctgcg ccccacagcc cctttggagc ttttctcttg tcctctcact ccttcccaga   1440

agtttttgca cagaacttca ttttgaaagt gtttttctca ttctccatac ctcccccaag   1500

ctctcctcca gcccttccca gggctcagcc ctgctgtcct gagcgtctcc tgggccagag   1560

agaggagatg gggtgggag ggactgagtt gatgttgggt ttttcattca ataaattggt   1620

gatttcttac cgac                                                      1634
```

<210> SEQ ID NO 22
<211> LENGTH: 1264
<212> TYPE: DNA
<213> ORGANISM: Homo sapiens -continued

<400> SEQUENCE: 22

```
ggcacgaggg gaggccgggg cggggcgggc gcagccggcg ctgagcttgc agggccgctc     60
ccctcacccg cccccttcga gtccccgggc ttcgccccac ccggcccgtg ggggagtatc    120
tgtcctgccg ccttcgccca cgccctgcac tccgggaccg tccctgcgcg ctctgggcgc    180
accatggccc gcggggctgc gctggcgctg ctgctcttcg gcctgctggg tgttctggtc    240
gccgccccgg atggtggttt cgatttatcc gatgcccttc ctgacaatga aaacaagaaa    300
cccactgcaa tccccaagaa acccagtgct ggggatgact ttgacttagg agatgctgtt    360
gttgatggag aaaatgacga cccacgacca ccgaacccac ccaaaccgat gccaaatcca    420
aaccccaacc accctagttc ctccggtagc ttttcagatg ctgaccttgc ggatggcgtt    480
tcaggtggag aaggaaaagg aggcagtgat ggtggaggca gccacaggaa agaaggggaa    540
gaggccgacg ccccaggcgt gatccccggg attgtggggg ctgtcgtggt cgccgtggct    600
ggagccatct ctagcttcat tgcttaccag aaaaagaagc tatgcttcaa agaaaatgca    660
gaacaagggg aggtggacat ggagagccac cggaatgcca acgcagagcc agctgttcag    720
cgtactcttt tagagaaata gaagattgtc ggcagaaaca gcccaggcgt tggcagcagg    780
gttagaacag ctgcctgagg ctcctccctg aaggacacct gcctgagagc agagatggag    840
gccttctgtt cacggcggat tctttgtttt aatcttgcga tgtgctttgc ttgttgctgg    900
gcggatgatg tttactaacg atgaatttta catccaaagg gggataggca cttggacccc    960
cattctccaa ggcccggggg ggcggtttcc catgggatgt gaaaggctgg ccattattaa   1020
gtccctgtaa ctcaaatgtc aaccccaccg aggcaccccc ccgtccccca gaatcttggc   1080
tgtttacaaa tcacgtgtcc atcgagcacg tctgaaaccc ctggtagccc cgacttcttt   1140
ttaattaaaa taaggtaagc ccttcaattt gtttcttcaa tatttctttc atttgtaggg   1200
atatttgttt ttcatatcag actaataaaa agaaattaga aaccaaaaaa aaaaaaaaaa   1260
aaaa                                                                1264
```

<210> SEQ ID NO 23
<211> LENGTH: 1567
<212> TYPE: DNA
<213> ORGANISM: Homo sapiens

<400> SEQUENCE: 23

```
tcctgggcct ctcaaagtct gagccccgct ccgctgatgc ctgtctgcag aatccgcacc     60
aaccagcacc atgcccatga ctctggggta ctgggacatc cgtgggctgg cccacgccat    120
ccgcttgctc ctggaataca cagactcaag ctatgtggaa aagaagtaca cgctgggggga    180
cgctcctgac tatgacagaa gccagtggct gaatgaaaaa ttcaagctgg gcctggactt    240
tcccaatctg ccctacttga ttgatggggc tcacaagatc acccagagca atgccatcct    300
gcgctacatt gcccgcaagc acaacctgtg tggggagaca gaagaggaga agattcgtgt    360
ggacattttg gagaaccagg ttatggataa ccacatggag ctggtcagac tgtgctatga    420
cccagatttt gagaaactga agccaaaata cttggaggaa ctccctgaaa agctaaagct    480
ctactcagag tttctgggga agcggccatg gtttgcagga gacaagatca cctttgtgga    540
tttccttgcc tatgatgtcc ttgacatgaa gcgtatattt gagcccaagt gcttggacgc    600
cttcctaaac ttgaaggact tcatctcccg ctttgagggt ttgaagaaga tctctgccta    660
catgaagtcc agccaattcc tccgaggtct tttgtttgga aagtcagcta catggaacag    720
caaatagggc ccagtgatgc cagaagatgg gagggaggag ccaaccttgc tgcctgcgac    780
```

-continued

```
cctggaggac agcctgactc cctggacctg ccttcttcct ttttccttct ttctactctc    840

ttctcttccc caaggcctca ttggcttcct ttcttctaac atcatccctc cccgcatcga    900

ggctctttaa agcttcagct ccccactgtc ctccatcaaa gtccccctcc taacgtcttc    960

ctttccctgc actaacgcca acctgactgc ttttcctgtc agtgcttttc tcttctttga   1020

gaagccagac tgatctctga gctccctagc actgtcctca aagaccatct gtatgccctg   1080

ctccctttgc tgggtcccta ccccagctcc gtgtgatgcc cagtaaagcc tgaaccatgc   1140

ctgccatgtc ttgtcttatt ccctgaggct cccttgactc aggactgtgc tcgaattgtg   1200

ggtggttttt tgtcttctgt tgtccacagc cagagcttag tggatgggtg tgtgtgtgtg   1260

tgtgttgggg gtggtgatca ggcaggttca taaatttcct tggtcatttc tgccctctag   1320

ccacatccct ctgttcctca ctgtggggat tactacagaa aggtgctctg tgccaagttc   1380

ctcactcatt cgcgctcctg taggccgtct agaactggca tggttcaaag aggggctagg   1440

ctgatgggga agggggctga gcagctccca ggcagactgc cttctttcac cctgtcctga   1500

tagacttccc tgatctagat atccttcgtc atgacacttc tcaataaaac gtatcccacc   1560

gtattgt                                                             1567
```

```
<210> SEQ ID NO 24
<211> LENGTH: 900
<212> TYPE: DNA
<213> ORGANISM: Homo sapiens

<400> SEQUENCE: 24

ggcacgagcg tgcgtgctgg cgtgcgttca ctttcagcct ggtgtggggc ttgtaaacat     60

ataacataaa aatggcttcc aaaagagctc tggtcatcct ggctaaagga gcagaggaaa    120

tggagacggt catccctgta gatgtcatga ggcgagctgg gattaaggtc accgttgcag    180

gcctggctgg aaaagaccca gtacagtgta gccgtgatgt ggtcatttgt cctgatgcca    240

gccttgaaga tgcaaaaaaa gagggaccat atgatgtggt ggttctacca ggaggtaatc    300

tgggcgcaca gaatttatct gagtctgctg ctgtgaagga gatactgaag gagcaggaaa    360

accggaaggg cctgatagcc gccatctgtg caggtcctac tgctctgttg gctcatgaaa    420

taggttttgg aagtaaagtt acaacacacc ctcttgctaa agacaaaatg atgaatggag    480

gtcattacac ctactctgag aatcgtgtgg aaaaagacgg cctgattctt acaagccggg    540

ggcctgggac cagcttcgag tttgcgcttg caattgttga agccctgaat ggcaaggagg    600

tggcggctca agtgaaggct ccacttgttc ttaaagacta gagcagcgaa ctgcgacgat    660

cacttagaga aacaggccgt taggaatcca ttctcactgt gttcgctcta aacaaaacag    720

tggtaggtta atgtgttcag aagtcgctgt ccttactact tttgcggaag tatggaagtc    780

acaactacac agagatttct cagcctacaa attgtgtcta tacatttcta agccttgttt    840

gcagaataaa cagggcattt agcaaaaaaa aaaaaaaaaa aaaaaaaaaa aaaaaaaaaa    900
```

```
<210> SEQ ID NO 25
<211> LENGTH: 647
<212> TYPE: DNA
<213> ORGANISM: Homo sapiens

<400> SEQUENCE: 25

gctcactgag caccgtccca gcatccggac accacagcgg cccttcgctc cacgcagaaa     60

accacacttc tcataccttc actcaacact tccttcccca aagccagaag atgcacaagg    120
```

-continued

```
aggaacatga ggtggctgtg ctgggggcac cccccagcac catccttcca aggtccaccg    180

tgattaacat ccacagcgag acctccgtgc ccgaccatgt cgtctggtcc ctgttcaaca    240

ccctcttctt gaactggtgc tgtctgggct tcatagcatt cgcctactcc gtaaagtcta    300

gggacaggaa gatggttggc gacgtgaccg gggcccaggc ctatgcctcc accgccaagt    360

gcctgaacat ctgggccctg attctgggca tcctcatgac cattggattc atcctgttac    420

tggtattcgg ctctgtaaca gtctaccata ttatgttaca gataatacag gaaaaacggg    480

gttactagta gccgcccata gcctgcaacc tttgcactcc actgtgcaat gctggccctg    540

cacgctgggg ctgttgcccc tgccccccttg gtcctgcccc tagatacagc agtttatacc   600

cacacacctg tctacagtgt cattcaataa agtgcacgtg cttgtga                  647
```

<210> SEQ ID NO 26
<211> LENGTH: 2850
<212> TYPE: DNA
<213> ORGANISM: Homo sapiens

<400> SEQUENCE: 26

```
aaaagaccag gtaattttaa catttgtgga atcacaaatg taaattcata agaagctcta     60

attaaaaaaa aaaagtctga agtatatgag cataacaact taggagtgtg tctacatact    120

taacttttga agtttttttgg caactttata tactttttt aaatttacaa gtctacttaa    180

agacttctta taccccaaat gattaagtta attttagagg tcacctttct cacagcagtg    240

tcacttgaaa tttagtaggg aaggatattg cagtattttt cagtttcctt agcacagcac    300

cacagaaagc agcttattcc ttttgagtgg cagacactcg acggtgcctg cccaactttc    360

ctcctgagtg gcaagcagat gagtctcagt aattcatact gaaccaaaat gccacataca    420

ctaggggcag tcagaaactg gctgagaaat cccccgcctc attcgcccct ctgctcccag    480

gaactagagt ccagttaaag cccctatgcg aaaggccgaa ttccaccccca gggtttgtta   540

taacagtggc cagtctgaac cccatttgct cgtgctcaaa acttgattcc cacttgaaag    600

ccttccgggc gcgctgcctc gttgccccgc ccctttggca ggagagaggc agtgggcgag    660

gccgggctgg ggccccgcct cccactcacc tgccggtgcc tgaaattatg tgcggccccg    720

cgggctgctt tccgaggtca gagtgccctg ctgctgtctc agaggcatct gttctgcaaa    780

tcttaggaag aaaaatgtcc ctagtagcaa acgggtgtct tctgtgcata aataagtaca    840

acacaattct ccgaaagttc gggtaaaaag agatgcggta gcagctgccc tgtgtgaagc    900

tgtctacccc gcatctctca ggcgctaagc tcagttttttg tttttgtttt tgttttttta   960

aagaaaagat gtataattgc aggaattttt ttttattttt ttattttcca tcattctata   1020

tatgtgatgg tgaaagatat gcctggaaaa gttttgtttt gaaaagttta ttttctgctt   1080

cgtcttcagt tggcaaaagc tctcaattct ttagcttcca gtttcttttc tctctttttc   1140

tttgttaggt aattaaaggt atgtaaacaa attatctcat gtagcagggg attttcatgt   1200

tgagaggaat cttccgtgtg agttgtttgg tcacacaaat aaccctttct caattttagg   1260

agtttggatt gtcaaatgta ggtttttctc aaagggggca tataactaca tattgactgc   1320

caagaactat gactgtagca ctaatcagca cacatagagc cacacaatta tttaatttct   1380

aactctctgt ggtccctaga aaaattccgt tgatgtgctt aggttaaagt tctgaagata   1440

cccgttgtac ccttacttga aagtttctaa tcttaagttt tatgaaatgc aataatatgt   1500

atcagctagc aatatttctg tgatcaccaa caactctcag tttgatctta aagtctgaat   1560

aataaaacaa atcccagcag taatacattt cttaaacctc acagtgcatg atatatcttt   1620
```

-continued tcattctgat cctgtgtttg caaaaatata cacatgtata tcatagttcc tcacttttta 1680
ttcatttgtt ttcctattac ctgtagtaaa tatattagtt agtacatgga atttatagca 1740
tcagctaccc ccaggaacag cacctgacag gcgggggatt ttttttcaag ttgttctaca 1800
tttgcataaa ttatttctat tattattcat gtatgttatt tatttctgaa tcacactagt 1860
cctgtgaaag tacaactgaa ggcagaaagt gttaggattt tgcatctaat gttcattatc 1920
atggtattga tggacctaag aaaataaaaa ttagactaag cccccaaata agctgcatgc 1980
atttgtaaca tgattagtag atttgaatat atagatgtag tattttgggt atctaggtgt 2040
tttatcatta tgtaaaggaa ttaaagtaaa ggactttgta gttgttttta ttaaatatgc 2100
atatagtaga gtgcaaaaat atagcaaaaa taaaaactaa aggtagaaaa gcattttaga 2160
tatgccttaa tttagaaact gtgccaggtg gccctcggaa tagatgccag gcagagacca 2220
gtgcctgggt ggtgcctcct cttgtctgcc ctcatgaaga agcttccctc acgtgatgta 2280
gtgccctcgt aggtgtcatg tggagtagtg ggaacaggca gtactgttga gaggagagca 2340
gtgtgagagt tttctgtag aagcagaact gtcagcttgt gccttgaggc ttccagaacg 2400
tgtcagatgg agaagtccaa gtttccatgc ttcaggcaac ttagctgtgt acagaagcaa 2460
tccagtgtgg taataaaaag caaggattgc ctgtataatt tattataaaa taaaagggat 2520
tttaacaacc aacaattccc aacacctcaa aagcttgttg catttttgg tatttgaggt 2580 ttttatctga aggttaaagg gcaagtgttt ggtatagaag agcagtatgt gttaagaaaa 2640
gaaaaatatt ggttcgcgta gagtgcaaat tagaactaga aagttttata cgattatcat 2700
tttgagatgt gttaaagtag gttttcactg taaaatgtat tagtgtttct gcattgccat 2760
agggcctggt taaaactttc tcttaggttt caggaagact gtcacataca gtaagctttt 2820
ttccttctga cttataatag aaaatgtttt 2850

<210> SEQ ID NO 27
<211> LENGTH: 3579
<212> TYPE: DNA
<213> ORGANISM: Homo sapiens

<400> SEQUENCE: 27
agtttcctcg gcagcggtag gcgagagcac gcggaggagc gtgcgcgggg gccccgggag 60
acggcggcgg tggcggcgcg ggcagagcaa ggacgcggcg gatcccactc gcacagcagc 120
gcactcggtg ccccgcgcag ggtcgcgatg ctgcccggtt tggcactgct cctgctggcc 180
gcctggacgg ctcgggcgct ggaggtaccc actgatggta atgctggcct gctggctgaa 240
ccccagattg ccatgttctg tggcagactg aacatgcaca tgaatgtcca gaatgggaag 300
tgggattcag atccatcagg gaccaaaacc tgcattgata ccaaggaagg catcctgcag 360
tattgccaag aagtctaccc tgaactgcag atcaccaatg tggtagaagc caaccaacca 420
gtgaccatcc agaactggtg caagcggggc cgcaagcagt gcaagaccca tccccacttt 480
gtgattccct accgctgctt agttggtgag tttgtaagtg atgcccttct cgttcctgac 540
aagtgcaaat tcttacacca ggagaggatg gatgtttgcg aaactcatct tcactggcac 600
accgtcgcca aagagacatg cagtgagaag agtaccaact tgcatgacta cggcatgttg 660
ctgccctgcg gaattgacaa gttccgaggg gtagagtttg tgtgttgccc actggctgaa 720
gaaagtgaca atgtggattc tgctgatgcg gaggaggatg actcggatgt ctggtggggc 780
ggagcagaca cagactatgc agatgggagt gaagacaaag tagtagaagt agcagaggag 840

-continued

```
gaagaagtgg ctgaggtgga agaagaagaa gccgatgatg acgaggacga tgaggatggt    900

gatgaggtag aggaagaggc tgaggaaccc tacgaagaag ccacagagag aaccaccagc    960

attgccacca ccaccaccac caccacagag tctgtggaag aggtggttcg agaggtgtgc   1020

tctgaacaag ccgagacggg gccgtgccga gcaatgatct cccgctggta ctttgatgtg   1080

actgaaggga agtgtgcccc attcttttac ggcggatgtg gcggcaaccg gaacaacttt   1140

gacacagaag agtactgcat ggccgtgtgt ggcagcgcca tgtcccaaag tttactcaag   1200

actacccagg aacctcttgc ccgagatcct gttaaacttc ctacaacagc agccagtacc   1260

cctgatgccg ttgacaagta tctcgagaca cctggggatg agaatgaaca tgcccatttc   1320

cagaaagcca aagagaggct tgaggccaag caccgagaga gaatgtccca ggtcatgaga   1380

gaatgggaag aggcagaacg tcaagcaaag aacttgccta aagctgataa gaaggcagtt   1440

atccagcatt tccaggagaa agtggaatct ttggaacagg aagcagccaa cgagagacag   1500

cagctggtgg agacacacat ggccagagtg gaagccatgc tcaatgaccg ccgccgcctg   1560

gccctggaga actacatcac cgctctgcag gctgttcctc ctcggcctcg tcacgtgttc   1620

aatatgctaa agaagtatgt ccgcgcagaa cagaaggaca gacagcacac cctaaagcat   1680

ttcgagcatg tgcgcatggt ggatcccaag aaagccgctc agatccggtc ccaggttatg   1740

acacacctcc gtgtgattta tgagcgcatg aatcagtctc tctccctgct ctacaacgtg   1800

cctgcagtgg ccgaggagat tcaggatgaa gttgatgagc tgcttcagaa agagcaaaac   1860

tattcagatg acgtcttggc caacatgatt agtgaaccaa ggatcagtta cggaaacgat   1920

gctctcatgc catctttgac cgaaacgaaa accaccgtgg agctccttcc cgtgaatgga   1980

gagttcagcc tggacgatct ccagccgtgg cattcttttg gggctgactc tgtgccagcc   2040

aacacagaaa acgaagttga gcctgttgat gcccgccctg ctgccgaccg aggactgacc   2100

actcgaccag gttctgggtt gacaaatatc aagacggagg agatctctga agtgaagatg   2160

gatgcagaat tccgacatga ctcaggatat gaagttcatc atcaaaaatt ggtgttcttt   2220

gcagaagatg tgggttcaaa caaaggtgca atcattggac tcatggtggg cggtgttgtc   2280

atagcgacag tgatcgtcat caccttggtg atgctgaaga agaaacagta cacatccatt   2340

catcatggtg tggtggaggt tgacgccgct gtcaccccag aggagcgcca cctgtccaag   2400

atgcagcaga acggctacga aaatccaacc tacaagttct ttgagcagat gcagaactag   2460

acccccgcca cagcagcctc tgaagttgga cagcaaaacc attgcttcac tacccatcgg   2520

tgtccattta tagaataatg tgggaagaaa caaacccgtt ttatgattta ctcattatcg   2580

ccttttgaca gctgtgctgt aacacaagta gatgcctgaa cttgaattaa tccacacatc   2640

agtaatgtat tctatctctc tttacatttt ggtctctata ctacattatt aatgggtttt   2700

gtgtactgta aagaatttag ctgtatcaaa ctagtgcatg aatagattct ctcctgatta   2760

tttatcacat agccccttag ccagttgtat attattcttg tggtttgtga cccaattaag   2820

tcctacttta catatgcttt aagaatcgat gggggatgct tcatgtgaac gtgggagttc   2880

agctgcttct cttgcctaag tattcctttc ctgatcacta tgcattttaa agttaaacat   2940

ttttaagtat ttcagatgct ttagagagat tttttttcca tgactgcatt ttactgtaca   3000

gattgctgct tctgctatat ttgtgatata ggaattaaga ggatacacac gtttgtttct   3060

tcgtgcctgt tttatgtgca cacattaggc attgagactt caagcttttc ttttttttgtc   3120

cacgtatctt tgggtctttg ataaagaaaa gaatccctgt tcattgtaag cacttttacg   3180

gggcgggtgg ggaggggtgc tctgctggtc ttcaattacc aagaattctc caaaacaatt   3240
```

-continued

```
ttctgcagga tgattgtaca gaatcattgc ttatgacatg atcgctttct acactgtatt   3300

acataaataa attaaataaa ataaccccgg gcaagacttt tctttgaagg atgactacag   3360

acattaaata atcgaagtaa ttttgggtgg ggagaagagg cagattcaat tttctttaac   3420

cagtctgaag tttcatttat gatacaaaag aagatgaaaa tggaagtggc aatataaggg   3480

gatgaggaag gcatgcctgg acaaaccctt cttttaagat gtgtcttcaa tttgtataaa   3540

atggtgtttt catgtaaata aatacattct tggaggagc                          3579
```

<210> SEQ ID NO 28
<211> LENGTH: 1433
<212> TYPE: DNA
<213> ORGANISM: Homo sapiens

<400> SEQUENCE: 28

```
attcggggcg agggaggagg aagaagcgga ggaggcggct cccgctcgca gggccgtgca     60

cctgcccgcc cgcccgctcg ctcgctcgcc cgccgcgccg cgctgccgac cgccagcatg    120

ctgccgagag tgggctgccc cgcgctgccg ctgccgccgc cgccgctgct gccgctgctg    180

ccgctgctgc tgctgctact gggcgcgagt ggcggcggcg gcggggcgcg cgcggaggtg    240

ctgttccgct gcccgccctg cacacccgag cgcctggccg cctgcgggcc cccgccggtt    300

gcgccgcccg ccgcggtggc cgcagtggcc ggaggcgccc gcatgccatg cgcggagctc    360

gtccgggagc cgggctgcgg ctgctgctcg gtgtgcgccc ggctggaggg cgaggcgtgc    420

ggcgtctaca ccccgcgctg cggccagggg ctgcgctgct atccccaccc gggctccgag    480

ctgcccctgc aggcgctggt catgggcgag ggcacttgtg agaagcgccg ggacgccgag    540

tatggcgcca gcccggagca ggttgcagac aatggcgatg accactcaga aggaggcctg    600

gtggagaacc acgtggacag caccatgaac atgttgggcg ggggaggcag tgctggccgg    660

aagcccctca agtcgggtat gaaggagctg gccgtgttcc gggagaaggt cactgagcag    720

caccggcaga tgggcaaggg tggcaagcat caccttggcc tggaggagcc caagaagctg    780

cgaccacccc ctgccaggac tccctgccaa caggaactgg accaggtcct ggagcggatc    840

tccaccatgc gccttccgga tgagcggggc cctctggagc acctctactc cctgcacatc    900

cccaactgtg acaagcatgg cctgtacaac ctcaaacagt gcaagatgtc tctgaacggg    960

cagcgtgggg agtgctggtg tgtgaacccc aacaccggga agctgatcca gggagccccc   1020

accatccggg gggaccccga gtgtcatctc ttctacaatg agcagcagga ggcttgcggg   1080

gtgcacaccc agcggatgca gtagaccgca gccagccggt gcctggcgcc cctgcccccc   1140

gcccctctcc aaacaccggc agaaaacgga gagtgcttgg gtggtgggtg ctggaggatt   1200

ttccagttct gacacacgta tttatatttg gaaagagacc agcaccgagc tcggcacctc   1260

cccggcctct ctcttcccag ctgcagatgc cacacctgct ccttcttgct ttccccgggg   1320

gaggaagggg gttgtggtcg gggagctggg gtacaggttt ggggaggggg aagagaaatt   1380

tttatttttg aacccctgtg tcccttttgc ataagattaa aggaaggaaa agt          1433
```

<210> SEQ ID NO 29
<211> LENGTH: 2370
<212> TYPE: DNA
<213> ORGANISM: Homo sapiens

<400> SEQUENCE: 29

```
cctggaactc tagcacgccg agtgaacttg aatctttggc tatttaagga ggactgggtt     60
```

-continued

```
tgttgtgaag ttgcggtgat ccagcgcaga gccccgtcct gattgatcgc atcgcggggc    120
tcagatgact gtaaaatgaa tagatgaaat tcttgcttct cgaagatttt cttgggcatc    180
tcccggaaag tgcgttttaa ggcgaagtca tgatgtattc tcccatctgt ctcactcagg    240
atgaatttca cccattcatg gaagcacttc ttccacatgt ccgtgcaatt gcctatactt    300
ggttcaacct gcaggctcga aaacgcaagt actttaaaaa gcatgagaag cgaatgtcaa    360
aggatgaaga aagagcagtc aaagatgagc ttctcagtga aaagcctgaa atcaaacaga    420
agtgggcatc caggctcctt gccaaactgc gcaaagatat tcgccaggag tatcgagagg    480
actttgtgct caccgtgact ggcaagaagc acccgtgctg tgtcttatcc aatcccgacc    540
agaagggtaa gattaggaga atcgactgcc tgcgacaggc agacaaagtc tggcgtctgg    600
atctagtcat ggtgatcctg ttcaaaggca tccccttgga aagtaccgat ggagagcggc    660
tcatgaaatc cccacattgc acaaacccag cactttgtgt ccagccacat catatcacag    720
tatcagttaa ggagcttgat ttgtttttgg catactacgt gcaggagcaa gattctggac    780
aatcaggaag tccaagccac aatgatcctg ccaagaatcc tccaggttac cttgaggata    840
gttttgtaaa atctggagtc ttcaatgtat cagaacttgt aagagtatcc agaacgccca    900
taacccaggg aactggagtc aacttcccaa ttggagaaat cccaagccaa ccatactatc    960
atgacatgaa ctcgggggtc aatcttcaga ggtctctgtc ttctccacca agcagcaaaa   1020
gacccaaaac tatatccata gaygaaaata tggaaccaag tcctacagga gacttttacc   1080
cctctccaag ttcaccagct gctggaagtc gaacatggca cgaaagagat caagatatgt   1140
cttctccgac tactatgaag aagcctgaaa agccattgtt cagctctgca tctccacagg   1200
attcttcccc aagactgagc actttccccc agcaccacca tcccggaata cctggagttg   1260
cacacagtgt catctcaact cgaactccac ctccaccttc accgttgcca tttccaacac   1320
aagctatcct tcctccagcc ccatcgagct acttttctca tccaacaatc agatatcctc   1380
cccacctgaa tcctcaggat actctgaaga actatgtacc ttcttatgac ccatccagtc   1440
cacaaaccag ccagtcctgg tacctgggct agcttggttc ctttccaagt gtcaaatagg   1500
acacccatct taccggccaa tgtccaaaat tacggtttga acataattgg agaacctttc   1560
cttcaagcag aaacaagcaa ctgagggaaa aagaaacaca acaatagttt aagaaatttt   1620
ttttttaaat aaaaaaaagg aaaagaggaa gactggacaa aacaacacaa aggcagaaag   1680
gaaagaaact gaagaaagaa gataatagac cagcaattgc agcacttaca atcactaatt   1740
cccttaaggt taaactgtaa tgacataaaa agggtcgatg atatttcact gatggtagat   1800
cgcagcccct gcaacgtagc ctttgttaca tgaagtccgc tgggaaatag atgttctgtc   1860
tctatgacaa tatattttaa ctgactttct agatgcctta atatttgcat gataagctag   1920
ttttattggt ttagtattct tgttgtttac gcatggaatc actattcctg gttatctcac   1980
caacgaaggc taggaggcgg cgtcagagat gctgggtgac agagccatga gccagccatt   2040
ttataagcac tctgatttct aaaagttaaa aaaaatatat gaaatctctg tagcctttag   2100
ttatcagtac agatttatta aatttcggcc cttaacccag ccttttccag tgtgtaaccc   2160
agtttgaaat cttaaaaaaa gaaaaaatga aaaaaaaagg aaaaaaagaa aaaaggaaaa   2220
aaacagtttg aacacaaagg ctctatggaa gaaatgcctc tatgtaggtg aagtgttctc   2280
tctgcatgca acagtaaaaa ttaatataat attttcccca caaaagaaac acttaacaga   2340
gggcaagtgc aatttattaa atttatattc                                    2370
```

<210> SEQ ID NO 30
<211> LENGTH: 2699
<212> TYPE: DNA
<213> ORGANISM: Homo sapiens

<400> SEQUENCE: 30

```
gcccagcggg ggcgggactg gaacggagcc gtgcggcccc gcgcgctcgc agtctgtctc     60
ccgccgtccc cacgcacgcg tcccggctca cgcgtccgcc cgcccgcccc cgcttgtgcc    120
gcccctacca gagacccccca ggagcaggat gtccttccag ggcaagaaaa gcatccccccg    180
gatcacgagt gaccgccttc tgatcagagg tgggaggatc gtgaatgacg accagtcctt    240
ttacgctgat gtgcacgtgg aagatggctt gataaaacaa atcggagaaa acctcatcgt    300
ccctgggggc atcaagacca ttgacgccca cggcctgatg gtccttcctg gtggcgttga    360
cgtccacaca aggctgcaga tgcctgtcct gggcatgaca ccggctgacg acttctgtca    420
gggcaccaag gcagcgctag caggaggaac caccatgatc ttggaccacg tcttccccga    480
cacgggtgtg agcctgctgg cggcctacga gcggtggcgg gagcgggcgg acagcgcggc    540
ctgctgcgac tactccctgc acgtggacat cacccgatgg catgagagca tcaaggagga    600
gctggaggcc ctggtcaagg agaagggtgt gaactccttc ctggtcttca tggcatacaa    660
ggaccggtgc cagtgcagcg acagccagat gtacgagatc ttcagcatca tccgggacct    720
gggggccttg gcccaggtgc acgctgagaa cggggacatc gtggaggagg agcagaagcg    780
gttgctggag ctcggcatca ctggccccga gggccacgtg ctcagccacc ccgaggaggt    840
ggaggctgag gcggtgtacc gagctgtcac catcgccaag caggcaaact gcccgctgta    900
cgtcaccaag gtgatgagca agggggcggc cgacgccatc gctcaggcca agcgcagagg    960
ggtggtcgtg tttggggagc ccatcaccgc cagcctgggc accgacggtt cacactactg   1020
gagcaagaac tgggccaagg ccgcagcctt cgtcacatca cccccctgtca acccagaccc   1080
caccacggca gaccacctca cctgcttgct gtccagcggg gacctccagg tgacaggcag   1140
cgcccactgc accttcacca ctgcccagaa ggctgtgggc aaggacaact tcgcgctgat   1200
ccccgagggc accaacggca ttgaggagcg catgtcgatg gtctgggaga aatgtgtggc   1260
ctctgggaag atggacgaga atgagttcgt cgcggtgacc agtacaaatg ctgccaaaat   1320
cttcaatttt tacccaagga aggggcgagt ggctgtgggc tctgacgctg acctggtcat   1380
atggaacccc aaggccacca agatcatctc tgccaagacc cacaatctga acgtggagta   1440
caacatcttc gagggagtgg agtgccgggg agcgcctgcc gtggtcataa gtcagggccg   1500
agtggcgctg gaggacggga agatgtttgt caccccgggg gcgggccgct tcgtccctcg   1560
gaaaacattc ccggactttg tctacaagag gatcaaagct cgcaacaggc tggcggagat   1620
ccacggtgtg ccccgtgggc tgtatgacgg gcccgtccac gaggtgatgg tgcctgccaa   1680
gccagggagt ggcgctccgg cccgcgcgtc ctgcccaggc aagatctccg tgcctcctgt   1740
gcgcaaccta catcagtcgg ggttcagcct atctgggtct caggctgatg accacatcgc   1800
ccgacgcaca gcacagaaga tcatggcacc acctggcggc cgctccaaca tcacctctct   1860
ctcctagacg cccaggaccg gccctgtgag ccgtgctggc cccacccgag gccgcggggg   1920
ccccagggca ctcgcccccc tccttagcat ttcttttgt agaagtttct cgaaggtgct    1980
tggcggtctt gccttccccc tccccacagg ctctccttgt ggggtcccag gtcctgctgc   2040
caagagcccc tcaagagaag ggctgaacct ggggagatgt cactgccagg gtgaggtgga   2100
gccacatggc agggacaatg ccggcagcct gagcccaggc accccagtgc ccgctgggcc   2160
```

-continued

```
cagcctgggg acagggaacc tgccgggctc acagtgtggg agcagctgga caccaggctt   2220

cttggtgaac cggcgagggg ccgagtcccg cctggtgggc atttgctgcc gcctccccac   2280

caccagtcac tgcctcgcag agccctacac tcccgcagcc gctcctcaga ggcctgtgcc   2340

catcgcaggc ctgggaggaa agtgggcgca gagccctcct gctcacacag ctgctgagac   2400

ttcagggacc catcagaact tggtgcagca cagccccgcc cgtggagggt ccccttttacg  2460

caccccaagg cccacaccta agcttccatg tagccctcat ccagggaagt tttgcgatcc   2520

tttaggaaga cactgtcctc ttattacaga ttgtgtattt ccgtaggctt cttagtagca   2580

gctttgtaca ctgaggacac tgtagccagg aacctgtgca tgccacccac cgcctggaca   2640

ggcagtcatc ctgcctctga tgtgaatcag gcccattaaa gacgtctggg tttgaagcc    2699
```

```
<210> SEQ ID NO 31
<211> LENGTH: 4122
<212> TYPE: DNA
<213> ORGANISM: Homo sapiens

<400> SEQUENCE: 31

tttgtcatca gctcgctctc cattggcggg gagcggagag cagcgaagaa gggggtgggg     60

aggggagggg aagggaaggg ggtggaaact gcctggagcc gtttctccgc gccgctgttg    120

gtgctgccgc tgcctcctcc tcctccgccg ccgccgccgc cgccgccgcc tcctccggct    180

cttcgctcgg cccctctccg cctccatgtg ccggatagcg ggagcgctgc ggaccctgct    240

gccgctgctg gcggccctgc ttcaggcgtc tgtagaggct tctggtgaaa tcgcattatg    300

caagactgga tttcctgaag atgtttacag tgcagtctta tcgaaggatg tgcatgaagg    360

acagcctctt ctcaatgtga agtttagcaa ctgcaatgga aaaagaaaag tacaatatga    420

gagcagtgag cctgcagatt ttaaggtgga tgaagatggc atggtgtatg ccgtgagaag    480

ctttccactc tcttctgagc atgccaagtt cctgatatat gcccaagaca aagagaccca    540

ggaaaagtgg caagtggcag taaaattgag cctgaagcca accttaactg aggagtcagt    600

gaaggagtca gcagaagttg aagaaatagt gttcccaaga caattcagta agcacagtgg    660

ccacctacaa aggcagaaga gagactgggt catccctcca atcaacttgc cagaaaactc    720

caggggacct tttcctcaag agcttgtcag gatcaggtct gatagagata aaaacctttc    780

actgcggtac agtgtaactg ggccaggagc tgaccagcct ccaactggta tcttcattat    840

caaccccatc tcgggtcagc tgtcggtgac aaagcccctg gatcgcgagc agatagcccg    900

gtttcatttg agggcacatg cagtagatat taatggaaat caagtggaga accccattga    960

cattgtcatc aatgttattg acatgaatga caacagacct gagttcttac accaggtttg   1020

gaatgggaca gttcctgagg gatcaaagcc tggaacatat gtgatgaccg taacagcaat   1080

tgatgctgac gatcccaatg ccctcaatgg gatgttgagg tacagaatcg tgtctcaggc   1140

tccaagcacc ccttcaccca acatgtttac aatcaacaat gagactggtg acatcatcac   1200

agtggcagct ggacttgatc gagaaaaagt gcaacagtat acgttaataa ttcaagctac   1260

agacatggaa ggcaatccca catatggcct ttcaaacaca gccacggccg tcatcacagt   1320

gacagatgtc aatgacaatc ctccagagtt tactgccatg acgttttatg gtgaagttcc   1380

tgagaacagg gtagacatca tagtagctaa tctaactgtg accgataagg atcaacccca   1440

tacaccagcc tggaacgcag tgtacagaat cagtggcgga gatcctactg gacggttcgc   1500

catccagacc gacccaaaca gcaacgacgg gttagtcacc gtggtcaaac caatcgactt   1560

tgaaacaaat aggatgtttg tccttactgt tgctgcagaa aatcaagtgc cattagccaa   1620
```

-continued

```
gggaattcag cacccgcctc agtcaactgc aaccgtgtct gttacagtta ttgacgtaaa   1680
tgaaaaccct tattttgccc ccaatcctaa gatcattcgc caagaagaag ggcttcatgc   1740
cggtaccatg ttgacaacat tcactgctca ggacccagat cgatatatgc agcaaaatat   1800
tagatacact aaattatctg atcctgccaa ttggctaaaa atagatcctg tgaatggaca   1860
aataactaca attgctgttt tggaccgaga atcaccaaat gtgaaaaaca atatatataa   1920
tgctactttc cttgcttctg acaatggaat tcctcctatg agtggaacag gaacgctgca   1980
gatctattta cttgatatta atgacaatgc ccctcaagtg ttacctcaag aggcagagac   2040
ttgcgaaact ccagacccca attcaattaa tattacagca cttgattatg acattgatcc   2100
aaatgctgga ccatttgctt ttgatcttcc tttatctcca gtgactatta agagaaattg   2160
gaccatcact cggcttaatg gtgattttgc tcagcttaat ttaaagataa aatttcttga   2220
agctggtatc tatgaagttc ccatcataat cacagattcg ggtaatcctc ccaaatcaaa   2280
tatttccatc ctgcgcgtga aggtttgcca gtgtgactcc aacggggact gcacagatgt   2340
ggacaggatt gtgggtgcgg ggcttggcac cggtgccatc attgccatcc tgctctgcat   2400
catcatcctg cttatccttg tgctgatgtt tgtggtatgg atgaaacgcc gggataaaga   2460
acgccaggcc aaacaacttt taattgatcc agaagatgat gtaagagata atattttaaa   2520
atatgatgaa gaaggtggag gagaagaaga ccaggactat gacttgagcc agctgcagca   2580
gcctgacact gtggagcctg atgccatcaa gcctgtggga atccgacgaa tggatgaaag   2640
acccatccac gctgagcccc agtatccggt ccgatctgca gccccacacc ctggagacat   2700
tggggacttc attaatgagg gccttaaagc ggctgacaat gaccccacag ctccaccata   2760
tgactccctg ttagtgtttg actatgaagg cagtggctcc actgctgggt ccttgagctc   2820
ccttaattcc tcaagtagtg gtggtgagca ggactatgat tacctgaacg actgggggcc   2880
acggttcaag aaacttgctg acatgtatgg tggaggtgat gactgaactt cagggtgaac   2940
ttggtttttg gacaagtaca aacaatttca actgatattc ccaaaaagca ttcagaagct   3000
aggctttaac tttgtagtct actagcacag tgcttgctgg aggctttggc ataggctgca   3060
aaccaatttg ggctcagagg gaatatcagt gatccatact gtttggaaaa acactgagct   3120
cagttacact tgaattttac agtacagaag cactgggatt ttatgtgcct ttttgtacct   3180
ttttcagatt ggaattagtt ttctgtttaa ggctttaatg gtactgattt ctgaaacgat   3240
aagtaaaaga caaaatattt tgtggtggga gcagtaagtt aaaccatgat atgcttcaac   3300
acgcttttgt tacattgcat ttgcttttat taaaatacaa aattaaacaa acaaaaaaac   3360
tcatggagcg attttattat cttgggggat gagaccatga gattggaaaa tgtacattac   3420
ttctagtttt agactttagt ttgttttttt tttttcacta aaatcttaaa acttactcag   3480
ctggttgcaa ataaagggag ttttcatatc accaatttgt agcaaaattg aatttttttca   3540
taaactagaa tgttagacac attttggtct taatccatgt acactttttt atttctgtat   3600
ttttccactt cactgtaaaa atagtatgtg tacataatgt tttattggca tagtctatgg   3660
agaagtgcag aaacttcaga acatgtgtat gtattatttg gactatggat tcaggttttt   3720
tgcatgttta tatctttcgt tatggataaa gtatttacaa aacagtgaca tttgattcaa   3780
ttgttgagct gtagttagaa tactcaattt ttaatttttt taattttttt atttttttatt   3840
ttctttttgg tttggggagg gagaaaagtt cttagcacaa atgttttaca taatttgtac   3900
caaaaaaaaa aaaaaggaaa ggaaagaaag gggtggcctg acactggtgg cactactaag   3960
```

-continued

```
tgtgtgtttt ttaaaaaaaa aaatggaaaa aaaaaagctt ttaaactgga gagacttctg   4020

acaacagctt tgcctctgta ttgtgtacca gaatataaat gatacacctc tgaccccagc   4080

gttctgaata aaatgctaat tttggaaaaa aaaaaaaaaa aa                      4122
```

<210> SEQ ID NO 32
<211> LENGTH: 1653
<212> TYPE: DNA
<213> ORGANISM: Homo sapiens

<400> SEQUENCE: 32

```
agtcagcacg ggggtgctgg aagagatcgg gaataatagc gcagaccaat gagcctaggg     60

agatgctttc atcgtctctc cttccctcaa gtgttctgga acctatcatt tgaattagcc    120

gagtcaggca ggagggggcg gggaatcctt ccgcccttct taggaggggc tgcattgcag    180

ggggagagtg aactgacaga ctcagtcact gaagagggaa aaggagtgag aagacaaagc    240

cgtcaaagcc ccaacagctt tgtatttctc cagcccggcg cagaccccgg agctcccgag    300

gcactccctc catctttgga acacgccagt aattgattga taacaggaag ctatgaggga    360

ccctgtgagt agccagtaca gttcctttct tttctggagg atgcccatcc cagaactgga    420

tctgtcggag ctggaaggcc tgggtctgtc agatacagcc acctacaagg tcaaagacag    480

cagcgttggc aaaatgatcg ggcaagcaac tgcagcagac caggagaaaa accctgaagg    540

tgatggcctc cttgagtaca gcaccttcaa cttctggaga gctcccattg ccagcatcca    600

ctccttcgaa ctggacttgc tctaaggcca agacttctct ctcccatcac cttgccctca    660

ttgtcttccc tctcaagccc cttcctttcc actcctttcc cattttaatc ttgttctctc    720

cctactgtgt tggtggtgct gatgaatctg ccagagttga gttctatgta tttatttatc    780

tatctgtcta ctccatttct ctcaaaagcc ctcaagtcac aaagtaaatg gttcaagcaa    840

tggagtactg ggtcacaggg attcctcctt tccccccaa atattaactc cagaaactag     900

gcctgactgg ggacacctga gagtagtata gtagtgcaaa atggaagact gatttttgac    960

tctattataa tcagcttcag agattcctta aaccttccta atttcctgct ccagggcagt   1020

aaacacaaat atttcttcaa ggggtgatga aaacctcgga agttttaatt tgaggttatc   1080

tgctacgaaa cagtatttct aaaaggctaa agtgataagt ctcttgcttt tttttgatcc   1140

tgctcttata ttcttttttt tcctcagaga aatcaggagg gtagttagag gtataaaaca   1200

ggaggaaata ttatggaaaa tgaaaatagg gaaaataatt gaatcatttt agaagtagct   1260

aatttctttt ctcaaaagag tgtcccttct tcacacctac tcactttaca actttgctcc   1320

taactgtggg ttgaaaactc tagctaaaga aagttatcaa atcttaacat gcattcctac   1380

tattatgata gtttttaagg tttcaattca atcttctgaa cggcataagt cctattttag   1440

ccttacctcc tgcatttgca atacgtaata ctgatcagtg ggcacagttc ttcagctaca   1500

ttgagaccct gaaatgaaca attatattct gactcgacat cttgtcccca atccttccaa   1560

aaatattgat ggtgatttgt gctaccattt actcgtttat ttaataaaga cattcaatcc   1620

cagaaaaaaa aaaaaaaaaa aaaaaaaaaa aaa                                1653
```

<210> SEQ ID NO 33
<211> LENGTH: 2928
<212> TYPE: DNA
<213> ORGANISM: Homo sapiens

<400> SEQUENCE: 33

```
ccgatccggg cggtgctggc agccggagcg gcggcgggcg ggccgagcag ccggggcagc     60
```

```
cgcgcgtggg catccacggg cgccgagcct ccgtccgtgt ctctatccct cccgggcctt    120
tgtcagcgcg cccgctggga gcggggccga gagcgccggt tccagtcaga cagccccgca    180
ggtcagcggc cgggccgagg gcgccagagg gggccatgtc gtaccagggc aagaagagca    240
tcccgcacat cacgagtgac cgactcctca tcaaaggtgg acggatcatc aacgatgacc    300
aatcccttta tgctgacgtc tacctggagg atggacttat caaacaaata ggagagaact    360
taatcgttcc tggtggagtg aagaccattg aagccaacgg gcggatggtt attcccggag    420
gtattgatgt caacacgtac ctgcagaagc cctcccaggg gatgactgcg gctgatgact    480
tcttccaagg gaccagggcg gcactggtgg gcgggaccac gatgatcatt gaccatgttg    540
ttcctgaacc tgggtccagc ctactgacct ctttcgagaa gtggcacgaa gcagctgaca    600
ccaaatcctg ctgtgattac tccctccacg tggacatcac aagctggtac gatggcgttc    660
gggaggagct ggaggtgctg gtgcaggaca aaggcgtcaa ttccttccaa gtctacatgg    720
cctataagga tgtctaccaa atgtccgaca gccagctcta tgaagccttt accttcctta    780
agggcctggg agctgtgatc ttggtccatg cagaaaatgg agatttgata gctcaggaac    840
aaaagcggat cctggagatg ggcatcacgg gtcccgaggg ccatgccctg agcagacctg    900
aagagctgga ggccgaggcg gtgttccggg ccatcaccat tgcgggccgg atcaactgcc    960
ctgtgtacat caccaaggtc atgagcaaga gtgcagccga catcatcgct ctggccagga   1020
agaaagggcc cctagttttt ggagagccca ttgccgccag cctggggacc gatggcaccc   1080
attactggag caagaactgg gccaaggctg cggcgttcgt gacttcccct cccctgagcc   1140
cggaccctac cacgcccgac tacttgacct ccctactggc ctgtggggac ttgcaggtca   1200
caggcagcgg ccactgtccc tacagcactg cccagaaggc ggtgggcaag gacaacttta   1260
ccctgatccc cgagggtgtc aacgggatag aggagcggat gacggtcgtc tgggacaagg   1320
cggtggctac tggcaaaatg gatgagaacc agtttgtcgc tgtcaccagc accaatgcag   1380
ccaagatctt taacctgtac ccaaggaaag ggcggattgc cgtgggctcg gatgccgacg   1440
tggtcatctg ggaccccgac aagttgaaga ccataacagc caaaagtcac aagtcggcgg   1500
tggagtacaa catcttcgag ggtatggagt gccacggctc cccactagtg gtcatcagcc   1560
agggcaagat cgtctttgaa gacggaaaca tcaacgtcaa caagggcatg ggccgcttca   1620
ttccgcggaa ggcgttcccg gagcacctgt accagcgcgt caaaatcagg aataaggttt   1680
ttggattgca aggggtttcc aggggcatgt atgacggtcc tgtgtacgag gtaccagcta   1740
cacccaaata tgcaactccc gctccttcag ccaaatcttc gccttctaaa caccagcccc   1800
cacccatcag aaacctccac cagtccaact tcagcttatc aggtgcccag atagatgaca   1860
acaatcccag gcgcaccggc caccgcatcg tggcgccccc tggtggccgc tccaacatca   1920
ccagcctcgg ttgaacgtgg atgcgcggag gagctagcct gaaggattct gggaatcatg   1980
tccatccctt ttcctgtcag tgtttttgaa acccacagtt ttagttggtg ctgatggagg   2040
gagggggaag tcgaaggatg ctctttccct tttctgttta ggaagaagtg gtactagtgt   2100
ggtgtgtttg cttggaaatt ccttgcccca cagttgtgtt catgctgaat ccacctcgga   2160
gcatggtgtt ttcattcccc cttcctagtg aaccacaggt tttagcattg tcttgttctg   2220
tcccttccac ttctaactcc actggctcca tgattctctg agtggtggtt cctttgcacc   2280
ctgtagatgt tctaggatag ttgatgcatg ttactaaatt acgtatgcaa gtctgtgagt   2340
gcgtctgagg ggacatcgcc aaggactgac tgagacacga tgccgagacc tcaagccctg   2400
```

-continued

```
aggggcagtc ccaaaaccct tacagtgaag atgtttactc attgccccca cctctggtcc   2460

acactagaaa gaagctcgcc ccacctccac ctgtgagatc cgtgaattct cggaatggca   2520

ggggaagcct tgcactaggt tgcagagaag catcctccac atcctgtgtc agaaaccctg   2580

gtctccgtgg cacttgtaac tcaccgtgct gtcttctggt ctgtgtgtgt tcttcaagcc   2640

agctctaggc ttcaggccga gccaggttca cactcagaaa gaggtctccc catccccatt   2700

cggggctgac gatgggggc tgatggctgc ccctgcgtgg cctgagtcct ggtccctctg   2760

aggcagttga cggggcagtc agatttttaa agttttgtac aaagttttcc tttgtaatca   2820

ctcccatttt tacttaacaa ccaacttgtt gtggctctta tttctgaatt caaagcttgt   2880

gaaaaaataa agaaaatgaa ctgcccactg aaaaaaaaaa aaaaaaaa              2928
```

<210> SEQ ID NO 34
<211> LENGTH: 4913
<212> TYPE: DNA
<213> ORGANISM: Homo sapiens

<400> SEQUENCE: 34

```
cctcccagcg tccccaccct aggaggctgc atgcggattg aagacgtgcg cctgggggct     60

gggccggccc cgctgatccc gacctagcga gcaggatagc aggaccgccc aggctgcgga    120

ggggctcggg ggcaggaagg tcagagcagc aagatggcca gtaagaccaa ggccagcgag    180

gccctcaagg tggtggcccg gtgccgcccc ctcagcagga aggaggaggc tgctggtcac    240

gagcagatcc tgaccatgga cgtgaaactg ggccaggtga ccctgcggaa cccccgcgcc    300

gccccggggg agctgcccaa gaccttcacc tttgacgccg tgtatgatgc cagctccaag    360

caggccgacc tgtatgacga aaccgtgagg cccctgatag actccgtgct ccagggtttc    420

aatggcacgg tgtttgccta tggccagacg ggcactggca agacctatac catgcagggg    480

acctgggtgg agcccgagct gcgcggggtc atcccgaatg cctttgagca catcttcacc    540

cacatctccc gctcccagaa ccaacagtac ctggtccggg cctcctattt ggagatctac    600

caggaagaga ttcgagacct gctctccaag gagccgggca agaggctaga gctgaaagag    660

aaccccgaga ctggcgtcta catcaaggac ctctcctcct tcgtcaccaa gaatgtcaag    720

gagattgagc atgtgatgaa cctggggaac cagacccggg ctgtgggcag cacccacatg    780

aatgaggtca gctcccgctc ccatgccatc ttcatcatca ctgtggagtg cagcgaacgt    840

ggctctgatg gccaggacca catccgagtg ggcaagctca acctcgtgga cctggctggc    900

agcgagaggc agaacaaggc aggccccaac acagcgggag ggcagccac accatcctcg     960

ggtggcggtg gtggcggtgg aggcagtggt ggtggtgctg gtggagagag gcctaaggaa   1020

gcctccaaaa tcaacctctc attatctgcc ctgggcaacg tgattgctgc cctggcgggc   1080

aacaggagca cccacattcc ctaccgggac tccaagctga cccggctgct ccaggactcc   1140

ctggggggga atgcgaagac catcatggta gccacactgg ggccagcttc tcacagctac   1200

gatgagagcc tctccacctt gcgctttgcc aaccgagcca agaacatcaa gaacaagccc   1260

cgggtgaacg aggaccccaa ggacacactg ctgcgggaat tccaagagga gattgcccgc   1320

ctgaaggccc agctggagaa gagggggatg ctggggaagc ggcccccggag gaagagcagc   1380

cgcaggaaga aggccgtgtc cgccccgcct gggtaccctg agggcccagt gattgaggct   1440

tgggtggcag aagaggagga tgacaacaac aacaaccacc gcccgcccca gcccatcctg   1500

gagtcagcct tggagaagaa catggagaat tacctgcagg aacagaagga gcggctggag   1560

gaggagaagg cagccatcca ggatgaccgc agcctggtga gcgaggagaa gcagaagctg   1620
```

```
ctggaggaga aggagaagat gctggaggac ctgcggcggg aacagcaggc cacagagctg   1680
cttgcggcca agtacaaggc catggagagc aagctcctca tcgggggcag gaacatcatg   1740
gatcacacca acgaacagca gaagatgttg gaactgaaga ggcaggagat tgccgagcag   1800
aaacgtcgtg agcgggagat gcagcaggag atgatgctcc gggacgagga gactatggag   1860
ctccggggca cctacacatc cctgcagcag gaggtggagg tcaaaaccaa gaaactcaag   1920
aagctctacg ccaagctgca ggcggtgaag gcggagatcc aggaccagca tgatgagtat   1980
atccgcgtgc ggcaggacct ggaggaggcg cagaacgagc agacccgcga actcaagctc   2040
aagtacctaa tcatcgagaa cttcatcccg ccggaggaga agaacaagat catgaaccgg   2100
cttttcctgg actgtgagga ggagcagtgg aagttccagc cactggtgcc agccggcgtc   2160
agtagcagcc agatgaagaa gcggccaaca tctgcagtgg gctacaagag gcctatcagc   2220
cagtatgctc gggttgccat ggcaatgggg tcccacccca ggtacagggc tgaaaacata   2280
atgtttctgg agttggatgt gtcccctcca gctgtctttg agatggaatt ctctcacgac   2340
caagaacaag accctcgtgc gctacacatg gagaggctca tgcgattgga cagctttctg   2400
gaaagacctt ccacgtctaa agtccgaaag tccagatcct ggtgccagag tcctcagcgg   2460
cctccacctt ccaccacaca tgcctccctg gcctctgctt ctctgcgccc tgcaacagtg   2520
gcggaccatg agtgacaacc atcacgtcag gctgcccatc caatagactc ctgggatggg   2580
gcagccaacc ctggctcatc tcatctgccg cttggtgcgt gtgcgtgtgc gtgcatgtgc   2640
gtgtgcgtgt gtgcaggggt gagaatctgg cagatggtgc ctctgcctgc tcttcttcgc   2700
ctcctttatt taattcatgt tatttattcg cggacgtctg ttcgtgttgg ggagatgccc   2760
tcgcctgagc cgtctgggcc taccgtggtc actgcgtacg ctctttttct tctgacttga   2820
gagctccccc agtcagatct caggcttgtc cccctgtcag ctgcctccag aagggaaggt   2880
agccagtgcc tgagaagaca gtccctttc tacccaccgc actccataac ctccatcttc   2940
tcccacactg atggcgagca gcccctgagc actttctggg actgggagac tgcttggtgt   3000
tccctgagga caagagacat cctgacagtg ttgggcatct gctccccgtg gacacagccc   3060
cactctccac tttctgagcc tcagacaacc tcattcagcc tcttgggctc cttttcaagg   3120
acattaataa cctcaccaac atagctcatg cccttcagct ttgacaagaa ctcacggctt   3180
cccaaactct gctttctgcc caccttggat gggaactgtg gaccaagcaa ttaccatcgc   3240
cttggaacct gcaggaaatg gaacagcaat tgagacaact tgaacagtca tcaacggaag   3300
tccctccact ggattccttt gtttctgtcc cctccgagga gtcattttgg tcgacaggct   3360
ctcaaggcaa ctccccattt tcaagaggct gctcctgcct gcttcgatca tttctccctg   3420
cagctgccta gaccccgttc acagtgggag gagtcaatgt cattctaccc ctcgctaaac   3480
gaagatatta acatctattg ctttttccct tcatctgtca caggaaacag aagcccaggc   3540
acaatctttt ccagctttgc ctgttacccc tgtttctgaa ttgcatcttt aaggtattat   3600
tttgttgaca atagatcctt tattcactag ttacgcaaat tggttcctag ggggatactc   3660
cttaccttcc tttgtgatgg cccaaaatgt ctctaggtat ctcaagtgat aagtaaattt   3720
ctacaaaaaa aaaatggtta atgttcattg actggctttt taagtgtata ttttggagga   3780
cgggtgaaga ggtcataacg aaagcaagcg agtgaattag gatttcaaag tgccctaata   3840
gtgtgagtct ccagttccta gaatatgaag agtgctgtcg ttggggtgaa accatgagac   3900
tgacagatct gcctgaaatg gggggtgtgg gaggtggtgg cgggggttat tctctttcct   3960
```

-continued

```
tcaggaaatg aacccttctt acatcattca agttctgctc tgaggatcaa gcttgggtct   4020

gatttaactc agcgacactg tcatttctgc ttcattactg gactagaggg ttgagccacc   4080

cacttgccat ttgctcctgt ccttccagga aatcacaatt ttcatcagag cccaagagat   4140

tatttgagac tcaggattca gatcagaggt tcgactgtgg ctgggacagg agttgtgtgt   4200

agaaattcac caggtggcct gagcgcaggg ggacctccag gctgcgttga gcagcctctc   4260

ccactgacct ctttctcgtt tgtggacaaa gcagcacgta tcacctcatt catcacttgg   4320

acacatcgcc tttgcattgt cttgtcacac ctccctcaca gtcttatagc acaatatacc   4380

caaatcagcc cccccagtcc gaggctgggc ccaaggtatg gtcggaggag gagctcctgc   4440

ctgcggtttt gtgtatgtgt gtatgtgtgt gcgtgtttgt gtgcgtgttt acctccacag   4500

gggacactct acactcagtg taagatctgc tgggaacagg gccaccagga gtgcgtggat   4560

ctcagtctct ctgtctctct ttctctcctt ttaattttgg tgtatcaaat atttgattga   4620

caaagtaagg gccttgatta ggaccaaatt ctcgtgtgtt gctatggtct ttatttagga   4680

caacaattaa caatgcagtg gcccattctt gtcactctac acatatgact atacgggaca   4740

tatgtaatat ataaatatat atataaaaca ttcccctctg tccccttggc ttcggatgga   4800

ggaatttctg ttgagctgaa atgcacctgc agctgggtgc tgccagcagc ttgcaggccc   4860

cagccctgtt ccaatcaatg cagttgacaa taaaggaatg agtatcgtca cgg          4913
```

```
<210> SEQ ID NO 35
<211> LENGTH: 1231
<212> TYPE: DNA
<213> ORGANISM: Homo sapiens

<400> SEQUENCE: 35

gaattccaga aaagaggtgg agaggggggg aataagaaag agagagaagg aaaggagaga     60

aggcaggaag aaggcaaggg acgagacaac catgctgtgc tgtatgagaa gaaccaaaca    120

ggttgaaaaa aatgatgacg accaaaagat tgaacaagat ggtatcaaac cagaagataa    180

agctcataag gccgcaacca aaattcaggc tagcttccgt ggacacataa caaggaaaaa    240

gctcaaagga gagaagaagg atgatgtcca agctgctgag gctgaagcta ataagaagga    300

tgaagcccct gttgccgatg ggggtggagaa gaagggagaa ggcaccacta ctgccgaagc    360

agccccagcc actggctcca agcctgatga gcccggcaaa gcaggagaaa ctccttccga    420

ggagaagaag gggggagggtg atgctgccac agagcaggca gccccccagg ctcctgcatc    480

ctcagaggag aaggccggct cagctgagac agaaagtgcc actaaagctt ccactgataa    540

ctcgccgtcc tccaaggctg aagatgcccc agccaaggag gagcctaaac aagccgatgt    600

gcctgctgct gtcactgctg ctgctgccac cacccctgcc gcagaggatg ctgctgccaa    660

ggcaacagcc cagcctccaa cggagactgg ggagagcagc caagctgaag agaacataga    720

agctgtagat gaaaccaaac ctaaggaaag tgcccggcag gacgagggta aagaagagga    780

acctgaggct gaccaagaac atgcctgaac tctaagaaat ggctttccac atccccaccc    840

tcccctctcc tgagcctgtc tctccctacc ctcttctcag ctccactctg aagtcccttc    900

ctgtcctgct cacgtctgtg agtctgtcct ttcccaccca ctagccctct ttctctctgt    960

gtggcaaaca tttaaaaaaa aaaaaaaaaa gcaggaaaga tcccaagtca aacagtgtgg   1020

cttaaacatt ttttgtttct tggtgttgtt atggcaagtt tttggtaatg atgattcaat   1080

cattttggga aattcttgca ctgtatccaa gttatttgat ctggtgcgtg tggccctgtg   1140

ggagtccact ttcctctctc tctctctctc tgttccaagt gtgtgtgcaa tgttccgttc   1200
```

-continued atctgaggag tccaaaatat tgagtgaatt c 1231

<210> SEQ ID NO 36
<211> LENGTH: 1587
<212> TYPE: DNA
<213> ORGANISM: Homo sapiens

<400> SEQUENCE: 36
ccacgcgtcc gcgttcttgc tacaattgta ccatctggta attcctgaaa atgtcaattt 60
ttttgtgtta atatttttgg tttcaaacaa taacaaatgt ctctagaaag aaattttaag 120
aaagcttaat taatagtaaa aatgcctttc ctgaaataat cttggaaaat tttttaaatg 180
tcaaaatgat gagtcatgct aatacattga gggtttgttt ttttgtttgt ttgtttgttt 240
ttgagacaga gtttcgctct tgttgcccag gctggagtgc aatggcccga tctcagctca 300
ccgcaacctc cacctcccgg attccagcga ttctcctgcc tcagcctaca ttaagggttt 360
tgtcagacaa ttgtcacacg aagaatagtg tcacttatct gctcttgaca cacagaactg 420
gcctggcata tagctttcca gattttactc aaacttggta ctccagtttg aaaatttaaa 480
ttttgactgc tgattagctg gaaagcctag ttttaatgga aagaaagttt gcttttaaaa 540
ctgaaagtag tttctttttg ctaacaaatc taacttcata cataattggc catattagta 600
aaacacctca tgatagcagt gtatatatag tcttgtttgt agttggaagt catcttttag 660
gagttattct caaatatata taatagctac ccatgcatca ttattaaaat ccccaaattc 720
aaaaaacctc tgatatatat atataatttt tttttttttt ttttttggc caactgagat 780 tgaaatccaa gtgctggttt ctagttctga acatcaacta aagagttttg gaaatgacag 840
caatttataa caagttcata ttgacttcct ctctatggca ggaagacatt ctgtgctgtt 900
ttgaacagat taaagatttg tgtagtttgt gggaaattga cgtttttgtt taaattccac 960
ccgcgtttgt cttttcctac cacctgtggc caggtgctcg ctggccatca cagttgcgat 1020
tccatgagta gctgctttat gactgctttt tgtactatct ggatgtgccc agagttactt 1080
ctgtacaagc tctgtatctg tgtccgttga gaacattatt ttaacaagaa gaacaccaac 1140
agtagcatga aatataatac tgttttataa ttctaaagct gctgttaatt tatgaagtac 1200
ataataatct aatgtaaact gcagaagtca gagcaagtgc ctacattttg ttatttttgg 1260
cattactaca gagccatgta caatagaaag caatgcaaga cttgtaaact ctcaccactt 1320
cttgtaatat caaatgttcc ccctcaggtt attttgctta tggtacccat gagttgcctc 1380
tctctgtaca tagataaatt gttccaatat tttcctttga tgtttggaac tacagatagt 1440
caagggctgg aaattttagt tttcaatata agcttccagc ttagcaatta cctctagtcc 1500
aagacaatat ttgattccta gttctgtttg gggcaaattt tcatttatct aaataaaatg 1560
caatctaatt aaaaaaaaaa aaaaaaa 1587

<210> SEQ ID NO 37
<211> LENGTH: 9161
<212> TYPE: DNA
<213> ORGANISM: Homo sapiens

<400> SEQUENCE: 37
ctgaaaactg gagagtgtga gagcgggagg agcccccgac cacacaaacc cagcctgggg 60
aggaacctac tagtggctgc accctctttt ttaatagcac caattgtgtt tcccaagatg 120
atgtagagaa tttcagtgct gtgtaccacg tcggaggcag aaattcctct gctgtcccag 180

-continued

```
gagcaggcag ggcagttttt atctggaaaa gctaaaggtc tcctcttttg tttgtgtttt    240
tgtgcctgca caggacaaaa gatccttcat caccgaagtg acgttttaga aacagtggtc    300
ctgatcaacc cttctgatga agcagtcagc accgaggtgc gcttaatgat cactgatgct    360
gcccgacaca agctgctcgt gctgaccggg cagtgctttg aaaataccgg agagctcatt    420
ctccagtccg gctctttctc cttccagaac ttcatagaga ttttcaccga tcaagagatc    480
ggggagttac taagcaccac ccatcctgcc aacaaagcca gcttaaccct gttctgtcct    540
gaagaagggg actggaagaa ctccaatctt gacagacaca atctccaaga cttcatcaat    600
attaaactca attcagcttc tatcttgcca gaaatggaag gactttctga gtttaccgag    660
tatctctcag aatcagtgga agtcccatct ccctttgaca tcttggaacc tcccacatcg    720
ggtggatttc tgaagctctc caagccctgc tgttatattt ttccaggagg gaggggcgat    780
tctgccttgt ttgcagtgaa tggtttcaat atgctcatca atggcggatc agagagaaaa    840
tcctgcttct ggaagctcat ccgacactta gaccgagtgg actccatcct gctcacccac    900
attggggatg acaatttgcc tggaataaac agcatgttac agcggaaaat tgcagagctc    960
gaggaagaac agtcccaggg ctccaccaca aatagtgact ggatgaaaaa cctcatctcc   1020
cctgacttag gagttgtatt tctcaatgta cctgaaaatc tcaaaaatcc agagccaaac   1080
atcaagatga agagaagcat agaagaagcc tgcttcactc tccagtacct aaacaaattg   1140
tccatgaaac cagaacctct gtttagaagt gtaggcaata ctattgatcc tgtcattctt   1200
ttccaaaaaa tgggagtagg taaacttgag atgtatgtgc ttaatccagt caagagcagc   1260
aaggaaatgc agtattttat gcagcagtgg actggtacca acaaagacaa ggctgaattc   1320
attctgccta atggtcaaga agtagatctc ccgatttcct acttaacttc agtctcatct   1380
ttgattgtgt ggcatccagc aaaccctgcg gagaaaatca tccgagtcct gtttcctggg   1440
aacagcaccc agtacaacat cctggaaggg ttggaaaagc tcaaacatct agactttctg   1500
aagcagccac tggccaccca aaaggatctc actggccagg tgcccactcc tgtggtgaaa   1560
caaacaaaac tgaaacagag ggctgatagc cgagaaagtc tgaagccagc cgcaaaacca   1620
cttcctagca aatccgtgcg caaggagtca aaagaagaaa cccctgaggt cacaaaagtg   1680
aatcacgtgg aaaagccacc caaagttgaa agcaaagaaa aggtaatggt gaaaaaagac   1740
aagccagtaa aaacagagac caaaccttca gtgactgaaa aggaggttcc cagcaaagaa   1800
gagccatctc cagtgaaagc cgaggtggct gagaagcaag ccacagatgt caaacccaaa   1860
gctgccaagg agaagacggt gaaaaaggaa acaaaggtaa agcctgaaga caagaaagag   1920
gagaaagaaa agccaaagaa agaagtggct aaaaaggagg acaaaacacc tatcaagaag   1980
gaggaaaaac caaaaaagga agaggtgaaa aaagaagtca aaaaagagat caagaaagaa   2040
gagaaaaaag aacccaagaa agaggttaag aaagaaacac cgccaaagga agtcaagaag   2100
gaagttaaga aggaagagaa gaaggaagtg aaaaaggaag aaaaggaacc caaaaaagaa   2160
attaagaagc tccctaaaga cgcaaagaaa tcatctactc ctctgtctga agcaaaaaaa   2220
ccagctgctt taaaaccaaa agtacccaag aaggaagagt ctgtcaagaa agattctgtt   2280
gctgccggaa agccaaagga gaaggggaaa ataaaagtca ttaagaagga aggcaaggcc   2340
gcagaggctg tcgctgcagc tgtcggcact ggagccacca cagcagctgt catggcggca   2400
gctggaatag cagccattgg ccctgccaaa gaactcgaag ctgagaggtc ccttatgtca   2460
tctcctgagg atctaaccaa ggactttgaa gagttaaagg ctgaagaggt cgatgtaaca   2520
aaggacatca agcctcagct ggagctaatc gaagacgaag agaaactgaa ggaaactgag   2580
```

-continued

```
ccagtcgaag cctacgtcat ccagaaggag agagaagtca ccaaaggtcc tgccgagtcc   2640
cctgatgagg gaatcactac cactgaaggg gagggcgaat gtgaacagac acctgaggag   2700
ctggagcccg tcgagaagca gggagtagac gacattgaaa aatttgaaga tgaaggagcc   2760
ggttttgaag aatcttcaga gactggagac tatgaagaga aggcagaaac tgaggaggct   2820
gaggagccag aagaggatgg ggaggaacac gtatgtgtga gcgcctccaa gcacagcccc   2880
actgaggatg aggaaagtgc caaggcggag gctgatgcat acatcaggga gaagagggag   2940
tctgtggcca gtggggatga ccgagccgaa gaagacatgg atgaggccat tgagaaagga   3000
gaggctgaac aatctgaaga ggaggctgat gaggaggaca aagctgaaga tgccagagag   3060
gaggaatatg agccggaaaa aatggaagct gaagactatg tgatggctgt ggtcgacaag   3120
gctgcagagg ctggtggtgc cgaggagcag tatggattcc tcaccacacc aaccaagcaa   3180
ctaggagccc agtctcctgg ccgagaacct gcatcttcaa ttcatgatga gactttacct   3240
ggaggctcag agagcgaggc caccgcttct gatgaggaga atcgagaaga ccagcctgag   3300
gaattcactg ccacctctgg ctacactcag tctactattg agatatccag tgagcccacc   3360
cccatggatg agatgtctac ccctcgagac gtgatgagtg atgagaccaa caatgaagag   3420
acggagtccc cttctcagga attcgtaaat atcaccaaat atgaatcttc attgtattct   3480
caggaatact ctaaacctgc tgatgttaca ccgctcaacg gattttctga aggatcaaaa   3540
acagatgcca ctgatggcaa ggattacaat gcttcagcct ctaccatatc accaccctct   3600
tccatggagg aagacaaatt cagcagatct gctttacgtg atgcttactg ctctgaagtg   3660
aaagccagca ccactttgga catcaaagat agcatctcag ctgtttcaag tgaaaaggtc   3720
agcccatcga agagcccgtc cctgagtcca tctccaccat cacccttaga aaagaccccc   3780
ctgggtgaac gtagtgtgaa cttctctctg acgcccaatg agattaaagt ctctgcagag   3840
gcagaagtag ccccggtgtc tcctgaggtg acccaagaag tagttgaaga acattgtgct   3900
agtcctgagg acaagactct ggaagtggtg tcaccatctc agtccgtgac tggcagtgct   3960
ggtcacacac cttactatca atctcctact gacgagaaat ccagtcatct ccctacagaa   4020
gtcattgaaa aaccaccagc agttccagtg agttttgaat tcagtgatgc caaagatgag   4080
aatgaaaggg cttcagtaag ccccatggat gagcccgtgc ctgactcaga gtctcctatt   4140
gaaaaagttt tgtctccttt acgcagcccg cccctcattg gatccgagtc tgcttatgaa   4200
agttttctaa gtgctgatga caaggcttct ggcagaggtg ccgaaagtcc ttttgaagaa   4260
aagagtggaa aacaaggctc tccagaccaa gtaagtccag tttctgaaat gacttctact   4320
agtctttacc aagacaaaca ggaagggaaa agcacagact ttgcaccaat aaaagaagac   4380
tttggccaag aaaagaaaac tgatgatgtt gaagccatga gttctcaacc agcactggct   4440
ctggatgaaa ggaaattagg agatgtttct cccacacaaa tagatgtcag tcagtttgga   4500
tcttttaaag aagacactaa gatgtccatt tctgaaggta ctgtctcaga caagtcagct   4560
actcctgttg atgagggcgt agcagaagac acgtactctc atatggaggg tgtggcctca   4620
gtgtccacag cctcagtggc tacgagctca tttccagagc caacaacaga tgatgtgtct   4680
ccatctctgc atgctgaggt tggctcccca cattccacag aagtagatga ctccctttca   4740
gtgtctgttg tgcaaacacc taccacattc caggaaacag aaatgtctcc atctaaagaa   4800
gaatgcccaa gaccgatgtc aatttctcca ccagatttct cccctaaaac tgcaaagtcc   4860
aggacacccg ttcaagatca cagatctgaa cagtcctcaa tgtctattga atttggccaa   4920
```

-continued

```
gaatctcctg agcaatccct tgctatggac ttcagtcgac agtctccaga tcaccctaca   4980
gtgggtgcag gcgtgcttca catcactgaa aatgggccaa ctgaagtgga ctacagtcct   5040
tctgacatgc aggactccag tttatcacat aagataccac ctatggagga gccgtcctac   5100
acccaagata atgatctttc tgagctcatc tcagtatctc aggtagaggc ctccccgtcc   5160
acctcttctg ctcataccc ttctcagatc gcttctcctc tccaagaaga tactctatcc    5220
gatgttgctc ctcccagaga tatgtcctta tatgcctcac tcacctctga aaaagtgcaa   5280
agtctggaag gagagaagct ctctccaaaa tctgatatct ctccactcac cccacgagag   5340
tcctctcctt tatattcacc tactttttca gattctacct ctgcagtcaa agagaaaaca   5400
gcaacttgcc acagttcctc ttctccacca atagatgcag catccgcaga gccctatggc   5460
ttccgtgcct cagtgttatt cgatacaatg caacaccatc tagccttgaa tagagatttg   5520
tccacacctg gcctggagaa ggacagtgga gggaagacac ctggtgactt tagctatgcc   5580
tatcaaaagc ctgaggaaac aaccaggtcc ccagatgaag aagattatga ctatgagtct   5640
tatgagaaga ccacccggac ctcagatgtg ggtggctatt actatgagaa gatagagaga   5700
accacaaaat ctccaagtga cagtggctac tcctatgaga ccattgggaa aactaccaag   5760
acccctgaag atggtgacta ttcctatgaa attattgaga agaccacacg gacccctgaa   5820
gagggtgggt actcatatga cataagtgaa aagaccacca gcccccccga agtgagtggt   5880
tacagctatg aaaagactga gaggtctaga aggcttctgg atgacatcag caatggctat   5940
gatgactctg aggatggtgg ccacacactt ggggacccca gctactctta tgaaaccact   6000
gagaaaatta ccagtttccc tgagtctgaa ggttattcct atgagacatc tacaaagaca   6060
acacgaaccc ctgatacttc cacatactgt tacgagactg cagagaaaat cactagaacc   6120
cctcaggcat ccacatattc ctacgagact tcagacctat gctacactgc agaaaagaag   6180
tccccctcag aagcccgtca ggatgtcgat ttatgcctcg tgtcctcttg tgaatacaag   6240
caccccaaga cagagctttc accctctttc attaatccca atcctcttga gtggtttgcc   6300
agtgaagaac ccactgaaga atctgaaaag cccctcactc aatcaggggg agccccaccg   6360
cctccaggag gaaagcaaca gggccgacag tgtgatgaaa cccctcccac ctcagtcagc   6420
gagtcagccc catcccagac cgactctgat gttcccccgg agactgaaga gtgcccctcc   6480
atcacggccg atgccaatat cgactctgaa gacgagtcgg aaaccatccc cacagacaaa   6540
actgtcacgt acaaacacat ggacccacct ccagctcccg tgcaagaccg cagcccttcg   6600
ccacgccacc ctgatgtgtc catggtggac ccagaggcct tggccattga gcagaacctg   6660
ggcaaagctc taaagaaaga tctgaaagag aagaccaaaa ccaaaaagcc aggtacaaag   6720
accaagtcat cttcacctgt caaaaagagt gatgggaagt ctaagccctt ggcagcttca   6780
ccaaaaccag cgggcttgaa agaatcctcg gataaagtgt ccagggtggc ttctcctaag   6840
aagaaagaat ctgtggaaaa ggcagcaaaa cccaccacca ctcctgaggt caaagctgca   6900
cgtggggaag agaaagacaa ggagaccaag aatgctgcca atgcctctgc atccaagtcg   6960
gccaagaccg ccactgcagg accaggaact accaagacga ccaagtcatc tgctgtgccc   7020
ccaggcctcc ctgtgtattt ggacctgtgc tacattccta accacagcaa tagtaagaat   7080
gttgatgtgg aatttttcaa gagagtgcgg tcttcctact acgtggtgag tgggaatgac   7140
cctgctgctg aggagcccag ccgggctgtc ctggacgctt tgttggaagg aaaggctcag   7200
tggggcagca acatgcaggt gacactgatc ccaactcatg actcagaagt gatgagggaa   7260
tggtaccagg agacccatga gaaacagcaa gatctcaaca tcatggtttt agcaagcagc   7320
```

```
agcacagtgg ttatgcaaga tgaatccttc cctgcatgca agattgaact gtaaaaacca   7380

aggccagcca caccacagga tctgaacttt gtttccagaa attcttcaat ttgaaatcac   7440

cttttctaaa aagtcaattc atctagttaa gtcgctgaac aattacctgc caaatgctat   7500

actgtgtcat ggtgatgcaa gtcactaaat ttctcagttt ttgctgattg ctaagggaaa   7560

taacagtatt tccacaatag ggttcaaatt cctgcaaaat tacctacccc agttcatctc   7620

tgctgaacat ttggaaacca tgcactagcc aacccaactg acttctgcta ggtagaggca   7680

tttgtcttag agagagagag agcgcgggag agagtgagag agagtgagag cacaaagata   7740

acgcaggaga gagagagaga aagaatgaga aagaaaagga atgcaagaga aggagatgta   7800

atgacagaga gttctggtga gatacccaga gagaaaaaga gagagcaggg tggggtaagg   7860

aggagaaaat aaaccaacaa ttaggtctgc attttctcag gcagtaggca ttctttagtc   7920

tacataggca aagttttcca tttttgtcag tctgagtcat caaaaagagt cttaattttc   7980

taaaacaagt tggctagaag aaagtaaaaa gaacaacact tgttatgagg gcatgtgata   8040

ttttcacatc ttaattaagc tccttcagtt tgaaggctgc acactgacat aatgtagtga   8100

gtgtagactg gccatgcaag tggtttgggc cccattcaga actctcagac tctaaacaca   8160

caagtagatt gatctaaggc atgctcccag catttgtcca cccacttagt ccactctgag   8220

tcgattaacc tgcatgcagc aacacccaag tccaccccaa ttaactgaag caaataccaa   8280

agcagttggg agtacatatg gtagacaatt tgccttagga agtgacttga atgtacaaag   8340

atacttgatg cacttatttt ttaatgtgag acagcaagtt tataaaacat ccatatagga   8400

ttatagatac ttaaaggaac acgtgggtga gcgtgtgtgg gggtactaga agctgatctg   8460

attggtccaa cagtttgatg ctgagtcatg cgtgttgaat cccacttcag tgcacctgtg   8520

gcctctcagt caaacaagtt gtgcctttca cagcttcttt actactgcaa gttcaagact   8580

gaaatggctt ctatgatcag aactgggaaa acagtgaatc ttatggtgga agaggttctc   8640

agcaagtgta cagtatttac cttcctttgt cttacattgg ctttttaaat tttccattaa   8700

tttcaacata attatgggaa caagtgtaca gaagaatttt ttttttaaga tatgtgagaa   8760

cttttcatag atgaactttt taacaaatgt tttcatttac aggaaattgc aaagaaaatt   8820

ctcaagtgat agtctttttt tttaagtgtt tcgtaagaca aaaattgaat aatgtttttt   8880

gaagttctgg caagattgaa gtctgatatt gcagtaatga tatttattaa aaacccataa   8940

ctaccaggaa taatgatacc tcccacccct tgattcccat aacataaaag tgctacttga   9000

gagtggggga gaatggcatg gtaggctact tttcagggcc ttgacaagta catcacccag   9060

tggtatccta catacttctt tcaagatctt caaccatgag gtaaaagagc caagttcaaa   9120

gaaccctagc acaaatttgc tttgggattt tcttttctgg a                        9161
```

<210> SEQ ID NO 38
<211> LENGTH: 1190
<212> TYPE: DNA
<213> ORGANISM: Homo sapiens

<400> SEQUENCE: 38

```
gccctccaca aagctcctgg gcccctcctc ccttcaagga ttgcgaagaa ctggtcgcaa     60

atcctcctaa gccaccagca tctcggtctt cagctcacac cagccttgag cccagcctgc    120

ggccagggga ccacgcacgt cccacccacc cagcgactcc ccagccgctg cccactcttc    180

ctcactcatg ggaacagca aaagtggggc cctgtccaag gagatcctgg aggagctgca     240
```

-continued

```
gctgaacacc aagttctcgg aggaggagct gtgctcctgg taccagtcct tcctgaagga    300

ctgtcccacc ggccgcatca cccagcagca gttccagagc atctacgcca agttcttccc    360

cgacaccgac cccaaggcct acgcccagca tgtgttccgc agcttcgatt ccaacctcga    420

cggcaccctg gacttcaagg agtacgtcat cgccctgcac atgaccaccg cgggcaagac    480

caaccagaag ctggagtggg ccttctccct ctacgacgtg gacggtaacg ggaccatcag    540

caagaatgaa gtgctggaga tcgtcatggc tattttcaaa atgatcactc ccgaggacgt    600

gaagctcctt ccagacgatg aaaacacgcc ggaaaagcga gccgagaaga tctggaagta    660

ctttggaaag aatgatgatg ataaacttac agagaaagaa ttcattgagg ggacactggc    720

caataaggaa attctgcgac tgatccagtt tgagcctcaa aaagtgaagg aaaagatgaa    780

gaacgcctga tgccaactgt tcagctgtcc tccctccacc taccactcac atgacacccg    840

tgagcgcctg tgcacacaca cacacatgca cacacacgcg cgcgcacaca cacacacaca    900

catccacccc agggccaaga gaaaggcctg cacacaagcc cacagcacag ctccctgcca    960

aactgaagca tctgtagtga cccactggtt ccttcttcct gggtcttcag cattccctcc   1020

catcatgccc ggtcccaccc ctccctctgt ccaccagccc atgtccctgt gctaatccca   1080

ggattaggcc ataggagtcc taagtgtcac cccgctgtaa gctcctttgt ggagtgctgg   1140

gtaagcagtt tccaataaac gcaagctgag ctggaaaaaa aaaaaaaaaa              1190
```

<210> SEQ ID NO 39
<211> LENGTH: 1880
<212> TYPE: DNA
<213> ORGANISM: Homo sapiens

<400> SEQUENCE: 39

```
aggatgcaag agtcagagtg agggatctgt ccctggatgg ggacaataag gggtcagttc     60

agggggactt ccttgagctc tgaagtttca cctgagaatg ggagattcag aacttggtga    120

cagagtttgt ggagctcact gtgtctttgc tgatccttca gcaaaggaag tgagattgtt    180

tctagctttt ctgtttgggg tgcttctctg tcaactaaaa gtcttcatcc tttaaatatt    240

gcatcatttg tgtatacttc attcattcac ttactcatga cccactcctc gagtgcctgc    300

aatgggcaag cgtctgtcct aggagccgtg tgctgggcca cagttaaatc tgagagatca    360

tgtgtggcat ttctcatgga ttgagatgtc tgagtgtcat tgttttgaga gagctagtgg    420

catggtttat aaagctgttt ttcattttct ccatacagga caacagcttt gagcagttca    480

ttattaatta ttgtaacgaa aagctgcaac aaatcttcat tgaacttact cttaaagaag    540

agcaggagga gtatatacgg gaggatatag aatggactca cattgactac ttcaataatg    600

ctatcatttg tgacctaata gaaaataaca caaatggaat cctggccatg ctggatgaag    660

agtgcctcag acctggcaca gtcactgatg agaccttctt agaaaagctg aaccaagtat    720

gtgccaccca ccagcatttt gaaagcagga tgagcaagtg ctctcggttc ctcaatgaca    780

cgtctctgcc tcacagctgc ttcaggatcc agcattatgc tggaaaggtg ctgtaccagg    840

tggaaggatt cgttgacaaa aacaatgacc ttctctatcg agacctgccc caagccatgt    900

ggaaggccag ccatgccctc atcaagtctt tgttccccga agggaatccc gccaagatca    960

acctgaaaag gcctcctaca gcaggctcac agttcaaggc atccgtggcc actctgatga   1020

aaaacctaca gaccaagaac ccaaactata ttaggtattt ttggcacatg aaactttcac   1080

agttcaaatg tgagagcacc ccgaaggaat atcatttttc cctttgcttc aatctgagtg   1140

tagcccaagc agagggtaac taaaatactt acagattaaa taatacctta tctgggattg   1200
```

-continued

```
gcttaaaaaa tgctccacta tcctttcccc taaaataaga aagtaaaaaa gtaaagtgtg   1260

gtggagaaga tagtagatat ttaatgaagc tcagtggttg agacctaggg gttttcaact   1320

ttctgtatgt ttattattat ttttttaacg gcaagttaaa aaacaaaatg caagtgtttt   1380

ttctggtcag tgttttgcag aaaactcttg ttggcttcat ttgggattct tgttctatta   1440

gcttagagca cagcattgaa gcaagtgctt tagttaactg ctctggcact tcttaggaga   1500

catgcacttt tttcttccct gtgagaggtg taggcctgga gaaagtaatg attcctaaag   1560

caatctgaat tttttccaag gcagtagaaa gaccttctta aaaagggctg ggcgtggtgg   1620

ctcacaccta taatcccaac acttagggag gcggaggcag gtggatcacc tcaggtcagg   1680

aattcgagac tagcctggcc aacatggcaa aaccctgtct ctactaaaaa tataaaaatt   1740

agctgggcgt ggtggcaggg acctataatc ccaactactt gggaggctga ggcaggagaa   1800

tcgcttggag gcagaggttg cagtgagccg aggtcacgcc actgcactcc agcccgggtg   1860

acaatacaag actccatctc                                               1880
```

```
<210> SEQ ID NO 40
<211> LENGTH: 1880
<212> TYPE: DNA
<213> ORGANISM: Homo sapiens

<400> SEQUENCE: 40

aggatgcaag agtcagagtg agggatctgt ccctggatgg ggacaataag gggtcagttc     60

agggggactt ccttgagctc tgaagtttca cctgagaatg ggagattcag aacttggtga    120

cagagtttgt ggagctcact gtgtctttgc tgatccttca gcaaaggaag tgagattgtt    180

tctagctttt ctgtttgggg tgcttctctg tcaactaaaa gtcttcatcc tttaaatatt    240

gcatcatttg tgtatacttc attcattcac ttactcatga cccactcctc gagtgcctgc    300

aatgggcaag cgtctgtcct aggagccgtg tgctgggcca cagttaaatc tgagagatca    360

tgtgtggcat ttctcatgga ttgagatgtc tgagtgtcat tgttttgaga gagctagtgg    420

catggtttat aaagctgttt ttcattttct ccatacagga caacagcttt gagcagttca    480

ttattaatta ttgtaacgaa aagctgcaac aaatcttcat tgaacttact cttaaagaag    540

agcaggagga gtatatacgg gaggatatag aatggactca cattgactac ttcaataatg    600

ctatcatttg tgacctaata gaaaataaca caaatggaat cctggccatg ctggatgaag    660

agtgcctcag acctggcaca gtcactgatg agaccttctt agaaaagctg aaccaagtat    720

gtgccaccca ccagcatttt gaaagcagga tgagcaagtg ctctcggttc ctcaatgaca    780

cgtctctgcc tcacagctgc ttcaggatcc agcattatgc tggaaaggtg ctgtaccagg    840

tggaaggatt cgttgacaaa aacaatgacc ttctctatcg agacctgccc caagccatgt    900

ggaaggccag ccatgccctc atcaagtctt tgttccccga agggaatccc gccaagatca    960

acctgaaaag gcctcctaca gcaggctcac agttcaaggc atccgtggcc actctgatga   1020

aaaacctaca gaccaagaac ccaaactata ttaggtattt ttggcacatg aaactttcac   1080

agttcaaatg tgagagcacc ccgaaggaat atcatttttc cctttgcttc aatctgagtg   1140

tagcccaagc agagggtaac taaaatactt acagattaaa taatacctta tctgggattg   1200

gcttaaaaaa tgctccacta tcctttcccc taaaataaga aagtaaaaaa gtaaagtgtg   1260

gtggagaaga tagtagatat ttaatgaagc tcagtggttg agacctaggg gttttcaact   1320

ttctgtatgt ttattattat ttttttaacg gcaagttaaa aaacaaaatg caagtgtttt   1380
```

-continued

```
ttctggtcag tgttttgcag aaaactcttg ttggcttcat ttgggattct tgttctatta   1440

gcttagagca cagcattgaa gcaagtgctt tagttaactg ctctggcact tcttaggaga   1500

catgcacttt tttcttccct gtgagaggtg taggcctgga gaaagtaatg attcctaaag   1560

caatctgaat tttttccaag gcagtagaaa gaccttctta aaaagggctg ggcgtggtgg   1620

ctcacaccta taatcccaac acttagggag gcggaggcag gtggatcacc tcaggtcagg   1680

aattcgagac tagcctggcc aacatggcaa aaccctgtct ctactaaaaa tataaaaatt   1740

agctgggcgt ggtggcaggg acctataatc ccaactactt gggaggctga ggcaggagaa   1800

tcgcttggag gcagaggttg cagtgagccg aggtcacgcc actgcactcc agcccgggtg   1860

acaatacaag actccatctc                                                1880
```

<210> SEQ ID NO 41
<211> LENGTH: 2685
<212> TYPE: DNA
<213> ORGANISM: Homo sapiens

<400> SEQUENCE: 41

```
ggacttggga ggcgcggtga ggagtcaggc ttaaaacttg ttggagggga gtaaccagcc     60

tgctcctctc gctctcctcc tcgtctgcgc cgcgtttcag agagaaaatt cctgttccaa    120

gagaaaataa ggcaacatca atgaaggaga gaagagccag ccagaaatta tccagcaaat    180

ctatcatgga tcctaatcag aacgtgaaat gcaagatagt tgtggtggga gacagtcagt    240

gtggaaaaac tgcgctgctc catgtcttcg ccaaggactg cttccccgag aattacgttc    300

ctacagtgtt tgagaattac acggccagtt ttgaaatcga cacacaaaga atagagttga    360

gcctgtggga cacttcgggt tctccttact atgacaatgt ccgcccccctc tcttaccctg    420

attcggatgc tgtgctgatt tgctttgaca tcagtagacc agagaccctg gacagtgtcc    480

tcaaaaagtg gaaaggtgaa atccaggaat tttgtccaaa taccaaaatg ctcttggtcg    540

gctgcaagtc tgatctgcgg acagatgtta gtacattagt agagctctcc aatcacaggc    600

agacgccagt gtcctatgac caggggggcaa atatggccaa acagattgga gcagctactt    660

atatcgaatg ctcagcttta cagtcggaaa atagcgtcag agacattttt cacgttgcca    720

ccttggcatg tgtaaataag acaaataaaa acgttaagcg gaacaaatca cagagagcca    780

caaagcggat ttcacacatg cctagcagac cagaactctc ggcagttgct acggacttac    840

gaaaggacaa agcgaagagc tgcactgtga tgtgaatctt tcattatctt taatgaagac    900

aaaggaatct agtgtaaaaa acaacagcaa acaaaaaggt gaagtctaaa tgaagtgcac    960

agccaaagtc atgtatacca gaggcttagg aggcgtttga gaggatactc atctttttgg   1020

aatcctgacc ttaggttcgg catgtagacc aagtgatgag aagtgaatac atggaagagt   1080

ttttaagtgt gacttgaaaa atatgccaaa aaatgagaga tacaaatgag ctagaggaag   1140

atgagggggg atgcgagtac ctccaagaag aaaaatcaca ctctgaatgg tgcttgcatt   1200

tttgggtttt ttttttttt gttataatct attcatggat ctccactttg atttaatttt   1260

taaatgtttt aatctccttt acaaaaagta tacgttaata taccgtcctc aagggggaac   1320

tggcactgtg accttagcat ttagttttct agaggatgtg atctaatttc tttctagctc   1380

atcattaaaa aggaaattgt atcaggaccc atgggatata tccagaggca aactttatga   1440

ggctttgaaa tcttgccttc ctgaagatag ctgagtagga tggttctaag gaaagccttt   1500

gcaatcttgc aagatttgta gaccagcact acaaagatcg catagatcaa ataggaaaaa   1560

aaatgtcgat tttattcag tctgatggtt ctgttcttca ttgtgattgt cattaaaaag   1620
```

-continued

```
tggtaaattg ctcaatgtaa tatttttgtg cgctgtttag aagttgtgtg attttttgcc   1680

atcgttgata aaaatgcaaa gtcaaataaa aggtgtcttg gtttgatgtc atagaatgat   1740

ccaaggagag aaaaaaggta gttactgttt tcaccagaaa aggtaatgag tgaaggaaag   1800

aatagtagca gaaagcacag tttgtgagta aagctgtctg gaattaagtt accaaaaata   1860

caaagcaaaa ggactattat tttgggttga agctccaaaa ctgacagcat ctgataatct   1920

gttggtttat ttcacttttc attaaatgaa cattgatgag agaagatgcc acttacccaa   1980

gctttagaga atccctagtg gaagattata tgataaactt tcagtcctga cataacacta   2040

gggcatttct agagtgtcat tgctaaaacc tcactgaaca gacgcagcca aggtctgtgt   2100

tcagcacttg gtctctgttg ttacgtaaaa taataagcat ttaaaatagt ttacagatat   2160

ttttgaccag ttccttttag agattctttc agagaagaaa ccagatctga cctgtttatt   2220

gttggcgctt gttgaaaacg agctttcttt cccatgatag tgcttcgttt ttgaagtgtt   2280

gaagctgtgc tccccttaaa tcgtggcagg agagattaag gtaattacaa cactcagttc   2340

tatgtcttac aagcactttg tcttgtctct gcaagaaaat tcgattccag tcatttccca   2400

taaaatacag acattttacc aacataatat gctttgattg atgcagcatt atgctttggg   2460

cagtattaca aaatagctgg cgagtgcttt ctgtatttaa atattgtaaa aagaaaataa   2520

gttataactg ttataaagca gaacttttgt tgcatttttt aaactgttga agtcactgtg   2580

tatgtttgtt tggtcaatgt ttccgcagta tttattaaaa catacttttt tttttcttca   2640

aataaaaaag taaccatgtc tttgtctaaa aaaaaaaaaa aaaaa                   2685
```

<210> SEQ ID NO 42
<211> LENGTH: 4469
<212> TYPE: DNA
<213> ORGANISM: Homo sapiens

<400> SEQUENCE: 42

```
cctgcagcct ccggagtcag tgccgcgcgc ccgccgcccc gcgccttcct gctcgccgca     60

cctccgggag ccggggcgca cccagcccgc agcgccgcct ccccgcccgc gccgcctccg    120

accgcaggcc gagggccgcc actggccggg gggaccgggc agcagcttgc ggccgcggag    180

ccgggcaacg ctggggactg cgccttttgt ccccggaggt ccctggaagt ttgcggcagg    240

acgcgcgcgg ggaggcggcg gaggcagccc cgacgtcgcg gagaacaggg cgcagagccg    300

gcatgggcat cgggcgcagc gagggggggcc gccgcggggc cctgggcgtg ctgctggcgc    360

tgggcgcggc gcttctggcc gtgggctcgg ccagcgagta cgactacgtg agcttccagt    420

cggacatcgg cccgtaccag agcgggcgct tctacaccaa gccacctcag tgcgtggaca    480

tccccgcgga cctgcggctg tgccacaacg tgggctacaa gaagatggtg ctgcccaacc    540

tgctggagca cgagaccatg gcggaggtga agcagcaggc cagcagctgg gtgcccctgc    600

tcaacaagaa ctgccacgcc gggacccagg tcttcctctg ctcgctcttc gcgcccgtct    660

gcctggaccg gcccatctac ccgtgtcgct ggctctgcga ggccgtgcgc gactcgtgcg    720

agccggtcat gcagttcttc ggcttctact ggcccgagat gcttaagtgt gacaagttcc    780

cggaggggga cgtctgcatc gccatgacgc cgcccaatgc caccgaagcc tccaagcccc    840

aaggcacaac ggtgtgtcct ccctgtgaca acgagttgaa atctgaggcc atcattgaac    900

atctctgtgc cagcgagttt gcactgagga tgaaaataaa agaagtgaaa aaagaaaatg    960

gcgacaagaa gattgtcccc aagaagaaga agcccctgaa gttggggccc atcaagaaga   1020
```

-continued

```
aggacctgaa gaagcttgtg ctgtacctga agaatggggc tgactgtccc tgccaccagc   1080
tggacaacct cagccaccac ttcctcatca tgggccgcaa ggtgaagagc cagtacttgc   1140
tgacggccat ccacaagtgg gacaagaaaa acaaggagtt caaaaacttc atgaagaaaa   1200
tgaaaaacca tgagtgcccc acctttcagt ccgtgtttaa gtgattctcc cgggggcagg   1260
gtggggaggg agcctcgggt ggggtgggag cggggggggac agtgcccggg aacccgtggt   1320
cacacacacg cactgccctg tcagtagtgg acattgtaat ccagtcggct tgttcttgca   1380
gcattcccgc tccctttccc tccatagcca cgctccaaac cccagggtag ccatggccgg   1440
gtaaagcaag ggccatttag attaggaagg tttttaagat ccgcaatgtg gagcagcagc   1500
cactgcacag gaggaggtga caaaccattt ccaacagcaa cacagccact aaaacacaaa   1560
aagggggatt gggcggaaag tgagagccag cagcaaaaac tacattttgc aacttgttgg   1620
tgtggatcta ttggctgatc tatgcctttc aactagaaaa ttctaatgat tggcaagtca   1680
cgttgttttc aggtccagag tagtttcttt ctgtctgctt taaatggaaa cagactcata   1740
ccacacttac aattaaggtc aagcccagaa agtgataagt gcagggagga aaagtgcaag   1800
tccattatct aatagtgaca gcaaagggac caggggagag gcattgcctt ctctgcccac   1860
agtctttccg tgtgattgtc tttgaatctg aatcagccag tctcagatgc cccaaagttt   1920
cggttcctat gagcccgggg catgatctga tccccaagac atgtggaggg gcagcctgtg   1980
cctgcctttg tgtcagaaaa aggaaaccac agtgagcctg agagagacgg cgattttcgg   2040
gctgagaagg cagtagtttt caaaacacat agttaaaaaa gaaacaaatg aaaaaaattt   2100
tagaacagtc cagcaaattg ctagtcaggg tgaattgtga aattgggtga agagcttagg   2160
attctaatct catgtttttt ccttttcaca tttttaaaag aacaatgaca aacacccact   2220
tatttttcaa ggttttaaaa cagtctacat tgagcatttg aaaggtgtgc tagaacaagg   2280
tctcctgatc cgtccgaggc tgcttcccag aggagcagct ctccccaggc atttgccaag   2340
ggaggcggat ttccctggta gtgtagctgt gtggctttcc ttcctgaaga gtccgtggtt   2400
gccctagaac ctaacacccc ctagcaaaac tcacagagct ttccgttttt ttctttcctg   2460
taaagaaaca tttcctttga acttgattgc ctatggatca aagaaattca gaacagcctg   2520
cctgttcccc cgcacttttt acatatattt gtttcatttc tgcagatgga aagttgacat   2580
gggtggggtg tccccatcca gcgagagagt ttcaaaagca aaacatctct gcagtttttc   2640
ccaagtaccc tgagatactt cccaaagccc ttatgtttaa tcagcgatgt atataagcca   2700
gttcacttag acaactttac ccttcttgtc caatgtacag gaagtagttc taaaaaaaat   2760
gcatattaat ttcttccccc aaagccggat tcttaattct ctgcaacact ttgaggacat   2820
ttatgattgt ccctctgggc caatgcttat acccagtgag gatgctgcag tgaggctgta   2880
aagtggcccc ctgcggccct agcctgaccc ggagaaagga tggtagattc tgttaactct   2940
tgaagactcc agtatgaaaa tcagcatgcc cgcctagtta cctaccggag agttatcctg   3000
ataaattaac ctctcacagt tagtgatcct gtccttttaa caccttttt gtggggttct    3060
ctctgacctt tcatcgtaaa gtgctgggga ccttaagtga tttgcctgta attttggatg   3120
attaaaaaat gtgtatatat attagctaat tagaaatatt ctacttctct gttgtcaaac   3180
tgaaattcag agcaagttcc tgagtgcgtg gatctgggtc ttagttctgg ttgattcact   3240
caagagttca gtgctcatac gtatctgctc attttgacaa agtgcctcat gcaaccgggc   3300
cctctctctg cggcagagtc cttagtggag ggtttacct ggaacataag tagttaccac    3360
agaatacgga agagcaggtg actgtgctgt gcagctctct aaatgggaat tctcaggtag   3420
```

```
gaagcaacag cttcagaaag agctcaaaat aaattggaaa tgtgaatcgc agctgtgggt   3480
tttaccaccg tctgtctcag agtcccagga ccttgagtgt cattagttac tttattgaag   3540
gttttagacc catagcagct ttgtctctgt cacatcagca atttcagaac caaaagggag   3600
gctctctgta ggcacagagc tgcactatca cgagcctttg tttttctcca caaagtatct   3660
aacaaaacca atgtgcagac tgattggcct ggtcattggt ctccgagaga ggaggtttgc   3720
ctgtgatttg cctgtgattt cctaattatc gctagggcca aggtgggatt tgtaaagctt   3780
tacaataatc attctggata gagtcctggg aggtccttgg cagaactcag ttaaatcttt   3840
gaagaatatt tgtagttatc ttagaagata gcatgggagg tgaggattcc aaaaacattt   3900
tatttttaaa atatcctgtg taacacttgg ctcttggtac ctgtgggtta gcatcaagtt   3960
ctccccaggg tagaattcaa tcagagctcc agtttgcatt tggatgtgta aattacagta   4020
atcccatttc ccaaacctaa aatctgtttt tctcatcaga ctctgagtaa ctggttgctg   4080
tgtcataact tcatagatgc aggaggctca ggtgatctgt ttgaggagag caccctaggc   4140
agcctgcagg gaataacata ctggccgttc tgacctgttg ccagcagata cacaggacat   4200
ggatgaaatt cccgtttcct ctagtttctt cctgtagtac tcctctttta gatcctaagt   4260
ctcttacaaa agctttgaat actgtgaaaa tgttttacat tccatttcat ttgtgttgtt   4320
tttttaactg cattttacca gatgttttga tgttatcgct tatgttaata gtaattcccg   4380
tacgtgttca ttttattttc atgctttttc agccatgtat caatattcac ttgactaaaa   4440
tcactcaatt aatcaatgaa aaaaaaaaa                                     4469
```

<210> SEQ ID NO 43
<211> LENGTH: 1607
<212> TYPE: DNA
<213> ORGANISM: Homo sapiens

<400> SEQUENCE: 43

```
gctctgtagc acccaggagc ggggaagcga agtgcgagag accccggacc ccagcgctgt     60
ctcttcccgc cgcccgaacc accatgaccc acttcaacaa gggcccttcc tatgggctct    120
cggccgaagt caagaacaag attgcttcca agtatgatca tcaggcagaa gaagatcttc    180
gcaattggat agaagaggtg acaggcatga gcattggccc caacttccag ctgggcttaa    240
aggatggcat catcctctgc gaacttataa acaagctaca gccaggctca gtgaagaagg    300
tcaacgagtc ctcactgaac tggcctcagt tggagaatat tggcaacttt attaaagcta    360
ttcaggctta tggtatgaag ccacatgaca tattcgaagc aaatgatctt tttgagaatg    420
gaaacatgac ccaggttcag actactctgg tggctctagc aggtctggct aaaacaaaag    480
gattccatac aaccattgac attggagtta agtatgcaga aaaacaaaca agacgttttg    540
atgaaggaaa attaaaagct ggccaaagtg taattggtct gcagatggga accaacaaat    600
gtgccagcca ggcaggtatg acagcttacg ggactaggag gcatctttat gatcccaaaa    660
tgcaaactga caaacctttt gaccagacca caattagtct gcagatgggc actaataaag    720
gagccagcca ggcagggatg ttagcaccag gtaccagaag agacatctat gatcagaagc    780
taacattaca gccggtggac aactcgacaa tttccctaca gatgggtacc aacaaagttg    840
cttcccagaa aggaatgagt gtgtatgggc ttgggcggca agtatatgat cccaaatact    900
gtgctgctcc tacagaacct gtcattcaca acggaagcca aggaacagga acaaatggtt    960
cggaaatcag tgatagtgat tatcaggcag aataccctga tgagtatcat ggcgagtacc   1020
```

-continued

```
aggatgacta ccccagagat taccaatata gcgaccaagg cattgattat tagatccaca   1080

cagaaggagc tcagtattta gtcctttgtt tttattcagt gagaaccaag ctagccttga   1140

gtaattttta tcttgtcttc ctaaaacact attaagctta ttgtactttt aagaaaaatt   1200

gccttacgta cattcctttt tcctttttct gcctcttccc tcaatagttg ccttttagtg   1260

ctgtaatagg ttaaatccta cagcataatc aataactcgc atatgaagta aaaaggaata   1320

ctgtgaaagg ggagtactct tgtacagcca gttcttttat gcaaaaatct atgcattttt   1380

acaatcttat attaaactgg tattttcaaa caataggaaa cttttttttt ttttttttac   1440

agtttagtgt atctggtttc tacatggaag actaaactca tgcttattgc taaatgtggt   1500

ctttgccaac taaatttaag atgcagcatt ttagaaattt acatatcaat gtttctacag   1560

tattgtttgc taatttttaa ataaagtcat gatcagtgtg aaaaaaa                 1607
```

<210> SEQ ID NO 44
<211> LENGTH: 3144
<212> TYPE: DNA
<213> ORGANISM: Homo sapiens

<400> SEQUENCE: 44

```
ggcacgaggg tccgcccggg ggcgccgccc accgcgcctc gctcgggccg ttgccgtctg     60

cacccagacc ctgagccgcc gccgccggcc atggaggtgg cgccggagca gccgcgctgg    120

atggcgcacc cggccgtgct gaatgcgcag caccccgact cacaccaccc gggcctggcg    180

cacaactaca tggaacccgc gcagctgctg cctccagacg aggtggacgt cttcttcaat    240

cacctcgact cgcagggcaa cccctactat gccaaccccg ctcacgcgcg ggcgcgcgtc    300

tcctacagcc ccgcgcacgc ccgcctgacc ggaggccaga tgtgccgccc acacttgttg    360

cacagcccgg gtttgccctg gctggacggg ggcaaagcag ccctctctgc cgctgcggcc    420

caccaccaca accccctggac cgtgagcccc ttctccaaga cgccactgca cccctcagct    480

gctggaggcc ctggaggccc actctctgtg tacccagggg ctgggggtgg gagcggggga    540

ggcagcggga gctcagtggc ctccctcacc cctacagcag cccactctgg ctcccacctt    600

ttcggcttcc cacccacgcc acccaaagaa gtgtctcctg accctagcac cacgggggct    660

gcgtctccag cctcatcttc cgcgggggggt agtgcagccc gaggagagga caaggacggc    720

gtcaagtacc aggtgtcact gacggagagc atgaagatgg aaagtggcag tcccctgcgc    780

ccaggcctag ctactatggg cacccagcct gctacacacc accccatccc cacctacccc    840

tcctatgtgc cggcggctgc ccacgactac agcagcggac tcttccaccc cggaggcttc    900

ctgggggggac cggcctccag cttcacccct aagcagcgca gcaaggctcg ttcctgttca    960

gaaggccggg agtgtgtcaa ctgtggggcc acagccaccc ctctctggcg gcgggacggc   1020

accggccact acctgtgcaa tgcctgtggc ctctaccaca agatgaatgg gcagaaccga   1080

ccactcatca agcccaagcg aagactgtcg gccgccagaa gagccggcac ctgttgtgca   1140

aattgtcaga cgacaaccac caccttatgg cgccgaaacg ccaacgggga ccctgtctgc   1200

aacgcctgtg gcctctacta caagctgcac aatgttaaca ggccactgac catgaagaag   1260

gaagggatcc agactcggaa ccggaagatg tccaacaagt ccaagaagag caagaaaggg   1320

gcggagtgct tcgaggagct gtcaaagtgc atgcaggaga agtcatcccc cttcagtgca   1380

gctgccctgg ctggacacat ggcacctgtg ggccacctcc cgcccttcag ccactccgga   1440

cacatcctgc ccactccgac gcccatccac ccctcctcca gcctctcctt cggccacccc   1500

cacccgtcca gcatggtgac cgccatgggc tagggaacag atggacgtcg aggaccgggc   1560
```

-continued

```
actcccggga tgggtggacc aaacccttag cagcccagca tttcccgaag gccgacacca   1620

ctcctgccag cccggctcgg cccagcaccc cctctcctgg agggcgccca gcagcctgcc   1680

agcagttact gtgaatgttc cccaccgctg agaggctgcc tccgcacctg actgctgccc   1740

aggtggggtt tcctgcatgg acagttgttt ggagaacaac aaggacaact ttatgtagag   1800

aaaaggaggg gacgggacag acgaaggcaa ccatttttag aaggaaaaag gattaggcaa   1860

aaataattta ttttgctctt gtttctaaca aggacttgga gacttggtgg tctgagctgt   1920

cccaagtcct ccggttcttc ctcgggattg gcgggtccac ttgccagggc tctgggggca   1980

gatttgtggg gacctcagcc tgcaccctct tctcttctgg cttccctctc tgaaatagcc   2040

gaactccagg ctgggctgag ccaaagccag agtggccacg gcccagggag ggtgagctgg   2100

tgcctgcttt gacgggccag gccctggagg gcagagacaa tcacgggcgg tcctgcacag   2160

attcccaggc cagggctggg tcacaggaag gaaacaacat tttcttgaaa ggggaaacgt   2220

ctcccagatc gctcccttgg ctttgaggcc gaagctgctg tgactgtgtc cccttactga   2280

gcgcaagcca cagcctgtct tgtcaggtgg accctgtaaa tacatccttt ttctgctaac   2340

ccttcaaccc cctcgcctcc tactctgaga caaaagaaaa aatattaaaa aaatgcatag   2400

gcttaactcg ctgatgagtt aattgtttta tttttaaact ctttttgggt ccagttgatt   2460

gtacgtagcc acaggagccc tgctatgaaa ggaataaaac ctacacacaa ggttggagct   2520

ttgcaattct ttttggaaaa gagctgggat cccacagccc tagtatgaaa gctgggggtg   2580

gggaggggcc tttgctgccc ttggtttctg gggctggtt ggcatttgct ggcctggcag   2640

ggggtgaagg caggagttgg gggcaggtca ggaccaggac ccagggagag gctgtgtccc   2700

tgctggggtc tcaggtccag ctttactgtg gctgtctgga tccttcccaa ggtacagctg   2760

tatataaacg tgtcccgagc ttagattctg tatgcggtga cggcggggtg tggtggcctg   2820

tgaggggccc ctggcccagg aggaggattg tgctgatgta gtgaccaagt gcaatatggg   2880

cgggcagtcg ctgcagggag caccacggcc agaagtaact tattttgtac tagtgtccgc   2940

ataagaaaaa gaatcggcag tattttctgt ttttatgttt tatttggctt gttttatttt   3000

ggattagtga actaagttat tgttaattat gtacaacatt tatatattgt ctgtaaaaaa   3060

tgtatgctat cctcttattc ctttaaagtg agtactgtta agaataataa aatacttttt   3120

gtgaaaaaaa aaaaaaaaaa aaaa                                          3144
```

<210> SEQ ID NO 45
<211> LENGTH: 2038
<212> TYPE: DNA
<213> ORGANISM: Homo sapiens

<400> SEQUENCE: 45

```
cgaagggctc gaagatggcc ggttggcaga gctacgtgga taacctgatg tgcgatggct     60

gctgccagga ggccgccatt gtcggctact gcgacgccaa atacgtctgg gcagccacgg    120

ccgggggcgt ctttcagagc attacgccaa tagaaataga tatgattgta ggaaaagacc    180

gggaaggttt ctttaccaac ggtttgactc ttggcgcgaa gaaatgctca gtgatcagag    240

atagtctata cgtcgatggt gactgcacaa tggacatccg gacaaagagt caaggtgggg    300

agccaacata caatgtggct gtcggcagag ctggtagagt cttggtcttt gtaatgggaa    360

aagaaggggt ccatggaggc ggattgaata agaaggcata ctcaatggca aaatacttga    420

gagactctgg gttctagctg ctaggcagac tgttaagtat taggggaaaa ttgctcttaa    480
```

-continued

```
actttcctag ctataagctt aagtcttaat tctggaaatt ttattagcaa tgcagggtga    540
tggggtatga acctgtgtct cctttgtatc cctctgttgg tggggaaagg tgtctttctt    600
tctgccctcc ccccccaaaa taattctgtt cacttttgtt ttgtttcctt gtgtactcca    660
gcattggtta tagtcatggg aaaggaaggt gtccacggag gcacacttaa caagaaagca    720
tatgaactcg ctttatacct gaggaggtct gatgtgtaag cagcctctcc ccatctacct    780
agcaactgtc ttcatcaaca accctaatta tggtcacaat gctaccaaac tgtagatggt    840
agctaatttt tctttaccta ttttctaatg tcatgattcc tgtttgccca atggatcatt    900
tgtatgttaa ccactgtatg taaccaaccc ttatctggca acataattgc agcacaataa    960
tgatttgcat gataccttga aattgggggg agggggcatg ccaagttggg catcactttg   1020
tcttagcaat taatgggata ttgattacta aaataagtta atattaagca aggtgccggt   1080
tgtacaatct ctgatcagtg tcttttcagc actttgagca tttacttggc tcatttagtc   1140
ttccttttgt agcgcatggt tgggaggaaa aagtgcatgc atcattcctt cactcttctc   1200
tttttcccgc cccccctcc cttcgcacat aggcatttgg tttgcttcca tcttttttta   1260
tgcagtgcct gttttttttt aaccaattaa aatccctttt gttgatgagc tattgagagc   1320
tgcagtagtt tgcttttagt attgttgttg cacttgagca gagacaaacc tttattcata   1380
gtgtctacag gacatatgaa gagtgcaatg gcaaaacaag agcaaaaagc acttcctccc   1440
atgaccttac agtaaccata ctgattgaat ccccagggac attccatcat tgcaatagct   1500
cagattttc ttccttttc tttgcacacc agctctactc tttagtaaaa ttgtaaaagg   1560
ctgccattat ggacattagg tatcccaaca taaccatctg gagtgtgtcc agtttgttct   1620
tcataggacc aatttttatt tgcagcttga gtttttatat gaagttgcat tattgtggac   1680
ttggctgtct tgtgatgaat ttttttcata tgtattctgt gccatactat tgttaaaatg   1740
aactgttgct attgtgagat ggattttaac tgacctatta agggtttctt tcgaatggca   1800
ctactttagg gacattctag tatttgcttc tattgtttgg gccttgtgga taatgtacag   1860
atttaaaaac aaatcttgtt gctgatttgt ccatttcttt ccctgcactt tgttacatct   1920
gggatacagt ctaactcatc tgatttaata tgcatttaaa aaaatgccat aactattaaa   1980
caccttgttt acagacagat gaaataaatt tattccaacc aaaaaaaaaa aaaaaaaa     2038
```

<210> SEQ ID NO 46
<211> LENGTH: 5487
<212> TYPE: DNA
<213> ORGANISM: Homo sapiens

<400> SEQUENCE: 46

```
tctgtcgact tgccccagag ctgatccttg tctttgtcca cttctcagcg aggatggcac     60
ttcagggagc ccttccctta ctatcgcaga gagagcaggc cctccccagt catgtccaac    120
ccagaactct gttttgtttt cttcatagcc ctagcatcac agaaaatcac cctgtgcatt    180
catggatgtc cacgggggca agggctttgt gttgcttaac ccagcatcct gaaccgtgtt    240
tgttgaatga atacagaacc ccgtttgctc tgggagagca cagaaaacag tcttctatca    300
tatatcatag ccagctgcaa acagcagatg gcttcccata tcccagagag taagaaccag    360
agagagagag aaagagagag agtttgggtc tttctcctct gtgcctgctc tctccagaga    420
aactggaggg gtagcagtta gcattccccc gctggttcca ccaagcacag tcaaggtctc    480
taggacatgg ccacccctca cctgtggaag cggtcctgct ggggtgggtg ggtgttagtt    540
ggttctggtt tgggtcagag acacccagtg gcccaggtgg gcgtggggcc agggcgcaga    600
```

```
cgagaagggg cacgagggct ccgctccgag gacccagcgg caagcaccgg tcccgggcgc    660
gccccagccc acccactcgc gtgcccacgg cggcattatt ccctataagg atctgaacga    720
tccgggggcg gccccgcccc gttacccctt gcccccggcc ccgcccccctt tttggagggc   780
cgatgaggta atgcggctct gccattggtc tgagggggcg ggccccaaca gcccgaggcg    840
gggtccccgg gggcccagcg ctatatcact cggccgccca ggcagcggcg cagagcgggc    900
agcaggcagg cggcgggcgc tcagacggct tctcctcctc ctcttgctcc tccagctcct    960
gctccttcgc cgggaggccg cccgccgagt cctgcgccag cgccgaggca gcctcgctgc   1020
gccccatccc gtcccgccgg gcactcggag ggcagcgcgc cggaggccaa ggttgccccg   1080
cacggcccgg cgggcgagcg agctcgggct gcagcagccc cgccggcggc gcgcacggca   1140
actttggaga ggcgagcagc agccccggca gcggcggcag cagcggcaat gaccccttgg   1200
ctcgggctca tcgtgctcct gggcagctgg agcctggggg actggggcgc cgaggcgtgc   1260
acatgctcgc ccagccaccc ccaggacgcc ttctgcaact ccgacatcgt gatccgggcc   1320
aaggtggtgg ggaagaagct ggtaaaggag gggcccttcg gcacgctggt ctacaccatc   1380
aagcagatga agatgtaccg aggcttcacc aagatgcccc atgtgcagta catccacacg   1440
gaagcttccg agagtctctg tggccttaag ctggaggtca acaagtacca gtacctgctg   1500
acaggtcgcg tctatgatgg caagatgtac acggggctgt gcaacttcgt ggagaggtgg   1560
gaccagctca ccctctccca gcgcaagggg ctgaactatc ggtatcacct gggttgtaac   1620
tgcaagatca agtcctgcta ctacctgcct tgctttgtga cttccaagaa cgagtgtctc   1680
tggaccgaca tgctctccaa tttcggttac cctggctacc agtccaaaca ctacgcctgc   1740
atccggcaga agggcggcta ctgcagctgg taccgaggat gggccccccc ggataaaagc   1800
atcatcaatg ccacagaccc ctgagcgcca gaccctgccc cacctcactt ccctcccttc   1860
ccgctgagct tcccttggac actaactctt cccagatgat gacaatgaaa ttagtgcctg   1920
ttttcttgca aatttagcac ttggaacatt taaagaaagg tctatgctgt catatggggt   1980
ttattgggaa ctatcctcct ggccccaccc tgccccttct tttggtttt gacatcattc   2040
atttccacct gggaatttct ggtgccatgc cagaaagaat gaggaacctg tattcctctt   2100
cttcgtgata atataatctc tattttttta ggaaaacaaa aatgaaaaac tactccattt   2160
gaggattgta attcccaccc ctcttgcttc ttccccacct caccatctcc cagaccctct   2220
tccctttgcc cttctcctcc aatacataaa ggacacagac aaggaacttg ctgaaaggcc   2280
aaccatttca ggatcagtca aaggcagcaa gcagatagac tcaaggtgtg tgaaagatgt   2340
tatacaccag gagctgccac tgcatgtccc aaccagactg tgtctgtctg tgtctgcatg   2400
taagagtgag ggagggaagg aaggaactac aagagagtcg gagatgatgc agcacacaca   2460
caattcccca gcccagtgat gcttgtgttg accagatgtt cctgagtctg gagcaagcac   2520
ccaggccaga ataacagagc tttcttagtt ggtgaagact taaacatctg cctgaggtca   2580
ggaggcaatt tgcctgcctt gtacaaaagc tcaggtgaaa gactgagatg aatgtctttc   2640
ctctccctgc ctcccaccag acttcctcct ggaaaacgct ttggtagatt tggccaggag   2700
ctttctttta tgtaaattgg ataaatacac acaccataca ctatccacag atatagccaa   2760
gtagatttgg gtagaggata ctatttccag aatagtgttt agctcaccta gggggatatg   2820
tttgtataca catttgcata tacccacatg ggacataag ctaatttttt tacaggacac    2880
agaattctgt tcaatgctgt taaatatgcc aatagtttaa tctcttctat tttgttgtcg   2940
```

-continued

```
ttgcttgttt gaagaaaatc atgacattcc aagttgacat tttttttca ttttaattaa   3000
aatttgaaat tctgaacacc gtcagcaccc tctcttccct atcatgggtc atctgacccc   3060
tgtccgtctc cttgtccctg cttcatgttt gggggccttt ctttaactgc cttcctggct   3120
tagctcagat ggcagatgag agtgtagtca agggcctggg cacaggaggg agagctgcag   3180
agtgtcctgc ctgccttggc tggagggaca cctctcctgg gtgtggagac agcttggttc   3240
cctttcccta gctccctggt gggtgaatgc cacctcctga gatcctcacc tcttggaatt   3300
aaaattgttg gtcactgggg aaagcctgag tttgcaacca gttgtagggt ttctgttgtg   3360
ttttttttt tttttgaa ataaaactat aatataaatt ctcctattaa ataaaattat   3420
tttaagtttt agtgtcaaaa gtgagatgct gagagtaggt gataatgtat attttacaga   3480
gtgggggttg gcaggatggt gacattgaac atgattgctc tctgtctctt ttttcagctt   3540
atgggtattt atcttctatt agtatttgta tcttcagttc attccacttt aggaaacaga   3600
gctgccaatt gaaacagaag aagaaaaaaa aaaaaagcag cagacaacac actgtagagt   3660
cttgcacaca cacaagtgcc caggcaaggt gcttggcaga accgcagagt gggaagagag   3720
taccggcatc gggtttcctt gggatcaatt tcattaccgt gtacctttcc cattgtggtc   3780
atgccatttg gcagggggag aatgggaggc ttggccttct ttgtgaggca gtgtgagcag   3840
aagctgatgc cagcatgtca ctggttttga agggatgagc ccagacttga tgttttggga   3900
ttgtccttat tttaacctca aggtctcgca tggtggggcc cctgaccaac ctacacaagt   3960
tccctcccac aagtggacat cagtgtcttc tctgtgaggc atctggccat tcgcactccc   4020
tggtgtggtc agcctctctc acacaaggag gaacttgggt gaaggctgag tgtgaggcac   4080
ctgaagtttc cctgcggagt cgataaatta gcagaaccac atccccatct gttaggcctt   4140
ggtgaggagg ccctgggcaa agaagggtct ttcgcaaagc gatgtcagag ggcggttttg   4200
agctttctat aagctatagc tttgtttatt tcacccgttc acttactgta taatttaaaa   4260
tcatttatgt agctgagaca cttctgtatt tcaatcatat catgaacatt ttattttgct   4320
aaatcttgtg tcatgtgtag gctgtaatat gtgtacattg tgtttaagag aaaaatgaaa   4380
cccacatgcc gccattttcc tgaatcaaat tctgcagtgg aatggagagg aaaatacttc   4440
taggcaagca gctagactgg tgaattgggg gaaatagaag gaactagtaa ctgagactcc   4500
tccagcctcc tccctattgg aatcccaatg gctcctggag taggaaaaaa gtttaaacta   4560
cattcatgtt cttgttctgt gtcactcggc cctgggtagt ctaccattta cttcacccca   4620
agtcctgctg cccatccagt tgggaagcca tgattttcct aagaatccag ggccatggga   4680
gatacaattc caagttctcg cttcctcctt tgggcatctc ttctgcctcc caatcaagga   4740
agctccatgc tcaggctctc agctctcggg ccagtgctct gctctgtcca gggtaggtaa   4800
tactgggaga ctcctgtctt ttaccctccc ctcgttccag acctgcctca tggtggcaac   4860
atggttcttg aacaattaaa gaaacaaatg actttttgga atagccctgt ctagggcaaa   4920
ctgtggcccc caggagacac tacccttcca tgccccagac ctctgtcttg catgtgacaa   4980
ttgacaatct ggactacccc aagatggcac ccaagtgttt ggcttctggc tacctaaggt   5040
taacatgtca ctagagtatt tttatgagag acaaacatta taaaaatctg atggcaaaag   5100
caaaacaaaa tggaaagtag gggaggtgga tgtgacaaca acttccaaat tggctctttg   5160
gaggcgagag gaaggggaga acttggagaa tagtttttgc tttgggggta gaggcttctt   5220
agattctccc agcatccgcc tttcccttta gccagtctgc tgtcctgaaa cccagaagtg   5280
atggagagaa accaacaaga gatctcgaac cctgtctaga aggaatgtat ttgttgctaa   5340
```

```
atttcgtagc actgtttaca gttttcctcc atgttattta tgaattttat attccgtgaa   5400

tgtatattgt cttgtaatgt tgcataatgt tcacttttta tagtgtgtcc tttattctaa   5460

acagtaaagt ggttttattt ctatcac                                       5487


<210> SEQ ID NO 47
<211> LENGTH: 2407
<212> TYPE: DNA
<213> ORGANISM: Homo sapiens

<400> SEQUENCE: 47

ggcacgaggc ggaggggggct cagtccgcag ccgccgccgc caccgccgcg cctcggcctc    60

ggtgcaggca gcggccgccg ccgccgagac agctgcgcgg gcgagcatcc ccacgcagca   120

ccttggaagt tgttttcaac catatccagc ctttgccgaa tacatcctat ctgccacaca   180

tccagcgtga ggtccctcca gctacaaggt gggcaccatg gcggagaagt ttgactgcca   240

ctactgcagg gatcccttgc aggggaagaa gtatgtgcaa aaggatggcc accactgctg   300

cctgaaatgc tttgacaagt tctgtgccaa cacctgtgtg gaatgccgca agcccatcgg   360

tgcggactcc aaggaggtgc actataagaa ccgcttctgg catgacacct gcttccgctg   420

tgccaagtgc cttcacccct tggccaatga gacctttgtg gccaaggaca acaagatcct   480

gtgcaacaag tgcaccactc gggaggactc cccccaagtgc aaggggtgct tcaaggccat   540

tgtggcagga gatcaaaacg tggagtacaa ggggaccgtc tggcacaaag actgcttcac   600

ctgtagtaac tgcaagcaag tcatcgggac tggaagcttc ttccctaaag gggaggactt   660

ctactgcgtg acttgccatg agaccaagtt tgccaagcat tgcgtgaagt gcaacaaggc   720

catcacatct ggaggaatca cttaccagga tcagccctgg catgccgatt gctttgtgtg   780

tgttacctgc tctaagaagc tggctgggca gcgtttcacc gctgtggagg accagtatta   840

ctgcgtggat tgctacaaga actttgtggc caagaagtgt gctggatgca agaaccccat   900

cactgggttt ggtaaaggct ccagtgtggt ggcctatgaa ggacaatcct ggcacgacta   960

ctgcttccac tgcaaaaaat gctccgtgaa tctggccaac aagcgctttg ttttccacca  1020

ggagcaagtg tattgtcccg actgtgccaa aaagctgtaa actgacaggg gctcctgtcc  1080

tgtaaaatgg catttgaatc tcgttctttg tgtccttact ttctgcccta taccatcaat  1140

aggggaagag tggtccttcc cttctttaaa gttctccttc cgtcttttct cccattttac  1200

agtattactc aaataagggc acacagtgat catattagca tttagcaaaa agcaaccctg  1260

cagcaaagtg aatttctgtc cggctgcaat ttaaaaatga aaacttaggt agattgactc  1320

ttctgcatgt ttctcataga gcagaaaagt gctaatcatt tagccactta gtgatgtaag  1380

caagaagcat aggagataaa acccccactg agatgcctct catgcctcag ctgggaccca  1440

ccgtgtagac acacgacatg caagagttgc agcggctgct ccaactcact gctcaccctc  1500

ttctgtgagc aggaaaagaa ccctactgac atgcatggtt taacttcctc atcagaactc  1560

tgcccttcct tctgttcttt tgtgctttca aataactaac acgaacttcc agaaaattaa  1620

catttgaact tagctgtaat tctaaactga cctttccccg tactaacgtt tggtttcccc  1680

gtgtggcatg ttttctgagc gttcctactt taaagcatgg aacatgcagg tgatttggga  1740

agtgtagaaa gacctgagaa aacgagcctg tttcagagga acatcgtcac aacgaatact  1800

tctggaagct taacaaaact aaccctgctg tcctttttat tgtttttaat taatattttt  1860

gttttaattg atagcaaaat agtttatggg tttggaaact tgcatgaaaa tattttagcc  1920
```

```
ccctcagatg ttcctgcagt gctgaaattc atcctacgga agtaaccgca aaactctaga   1980

gggggagttg agcaggcgcc agggctgtca tcaacatgga tatgacattt cacaacagtg   2040

actagttgaa tcccttgtaa cgtagtagtt gtctgctctt tgtccatgtg ttaatgagga   2100

ctgcaaagtc ccttctgttg tgattcctag gacttttcct caagaggaaa tctggatttc   2160

cacctaccgc ttacctgaaa tgcaggatca cctacttact gtattctaca ttattatatg   2220

acatagtata atgagacaat atcaaaagta aacatgtaat gacaatacat actaacattc   2280

ttgtaggagt ggttagagaa gctgatgcct catttctaca ttctgtcatt agctattatc   2340

atctaacgtt tcagtgtatc cttacagaaa taaagcagca tatgaaaaaa aaaaaaaaaa   2400

aaaaaaa                                                             2407
```

<210> SEQ ID NO 48
<211> LENGTH: 2649
<212> TYPE: DNA
<213> ORGANISM: Homo sapiens

<400> SEQUENCE: 48

```
tccgaattaa ttggatttca ttcactgggg aggaacaaaa actatctggg cagcttcatt     60

gagagagatt cattgacact aagagccagc ggctgcagct gggtgcagag agaacctccg    120

gctttacttc tgtctcgtct gccccaaccg ctagcctcgg cttgggtaag gcgaggcgga    180

attaaacccc gctccgagag cggcagcttc gcgcgcggtg cgctcggcct atgcctgccc    240

cgaggggcgt ctggtaggca ccccgccctc tcccgcagct cgacccccat gatagatacg    300

ctcagacccg tgcccttcgc gtcggaaatg gcgatcagca agacggtggc gtggctcaac    360

gagcagctgg agctgggcaa cgagcggctg ctgctgatgg actgccggcc gcaggagcta    420

tacgagtcgt cgcacatcga gtcggccatc aacgtggcca tcccgggcat catgctgcgg    480

cgcctgcaga agggtaacct gccggtgcgc gcgctcttca cgcgcggcga ggaccgggac    540

cgcttcaccc ggcgctgtgg caccgacaca gtggtgctct acgacgagag cagcagcgac    600

tggaacgaga atacgggcgg cgagtcgttg ctcgggctgc tgctcaagaa gctcaaggac    660

gagggctgcc gggcgttcta cctggaaggt ggcttcagta agttccaagc cgagttctcc    720

ctgcattgcg agaccaatct agacggctcg tgtagcagca gctcgccgcc gttgccagtg    780

ctggggctcg gggcctgcg gatcagctct gactcttcct cggacatcga gtctgacctt     840

gaccgagacc ccaatagtgc aacagactcg gatggtagtc cgctgtccaa cagccagcct    900

tccttcccag tggagatctt gcccttcctc tacttgggct gtgccaaaga ctccaccaac    960

ttggacgtgt tggaggaatt cggcatcaag tacatcttga acgtcacccc caatttgccg   1020

aatctctttg agaacgcagg agagtttaaa tacaagcaaa tccccatctc ggatcactgg   1080

agccaaaacc tgtcccagtt tttccctgag gccatttctt tcatagatga agcccggggc   1140

aagaactgtg gtgtcttggt acattgcttg gctggcatta gccgctcagt cactgtgact   1200

gtggcttacc ttatgcagaa gctcaatctg tcgatgaacg atgcctatga cattgtcaaa   1260

atgaaaaaat ccaacatatc ccctaacttc aacttcatgg gtcagctgct ggacttcgag   1320

aggacgctgg gactcagcag cccatgtgac aacagggttc cagcacagca gctgtatttt   1380

accacccctt ccaaccagaa tgtataccag gtggactctc tgcaatctac gtgaaagacc   1440

ccacatccct ccttgctgga atgtgtctgg cccttcagca gtttctcttg gcagcatcag   1500

ctgggctgct ttctttgtgt gtggccccag gtgtcaaaat gacaccagct gtctgtacta   1560

gacaaggtta ccaagtgcgg aattggttaa tactaacaga gagatttgct ccattctctt   1620
```

```
tggaataaca ggacatgctg tatagataca ggcagtaggt ttgctctgta cccatgtgta   1680

cagcctaccc atgcagggac tgggattcga ggacttccag gcgcataggg tagaaccaaa   1740

tgatagggta ggagcatgtg ttctttaggg ccttgtaagg ctgtttcctt ttgcatctgg   1800

aactgactat ataattgtct tcaatgaaga ctaattcaat tttgcatata gaggagccaa   1860

agagagattt cagctctgta tttgtggtat cagtttggaa aaaaaaatct gatactccat   1920

ttgattattg taaatatttg atcttgaatc acttgacagt gtttgtttga attgtgtttg   1980

ttttttcctt tgatgggctt aaaagaaatt atccaaaggg agaaagagca gtatgccact   2040

tcttaaaaca gaacaaaaca aaaaaagaaa attgtgctct tttctaatcc aaagggtata   2100

tttgcagcat gcttgacttt accaattctg atgacatctt tacggacact attatcacta   2160

agaccttgtt atggcgaagt ctttagtctt tttcatgtat tttcctcatg atttttttctc  2220

tttatgtagt ttgactatgc cttacctttg taaatatttt tgcttgtgtt gtcgcaaagg   2280

ggataatctg ggaaagacac caaatcatgg gctcacttta aaaaaagaaa gaataaaaaa   2340

accttcagct gtgctaaaca gtatattacc tctgtataaa attcttcagg gagtgtcacc   2400

tcaaatgcaa tactttgggt tggtttcttt cctttaaaaa aatttgtata aaactggaag   2460

tgtgtgtgtg tgagcatggg tacccatttg ataagagaaa tgcatttgat tgtgaagaag   2520

ggagagttaa attctccatt atgttcgtgg tgtaaagttt agagctggaa tttattataa   2580

gaatgtaaaa ccttaaatta ttaataaata actattttgg ctattgaaaa aaaaaaaaaa   2640

aaaaaaaaa                                                           2649
```

```
<210> SEQ ID NO 49
<211> LENGTH: 670
<212> TYPE: DNA
<213> ORGANISM: Homo sapiens

<400> SEQUENCE: 49

cggccacgag gcggaatccc ttctgctctc ccagcgcagc gccgccgccc ggcccctcca     60

gcttcccgga ccatggccaa cctggagcgc accttcatcg ccatcaagcc ggacggcgtg    120

cagcgcggcc tggtgggcga gatcatcaag cgcttcgagc agaagggatt ccgcctcgtg    180

gccatgaagt tcctccgggc ctctgaagaa cacctgaagc agcactacat tgacctgaaa    240

gaccgaccat tcttccctgg gctggtgaag tacatgaact cagggccggt tgtggccatg    300

gtctgggagg ggctgaacgt ggtgaagaca ggccgagtga tgcttgggga gaccaatcca    360

gcagattcaa agccaggcac cattcgtggg gacttctgca ttcaggttgg caggaacatc    420

attcatggca gtgattcagt aaaaagtgct gaaaaagaaa tcagcctatg gtttaagcct    480

gaagaactgg ttgactacaa gtcttgtgct catgactggg tctatgaata agaggtggac    540

acaacagcag tctccttcag cacggcgtgg tgtgtccctg gacacagctc ttcattccat    600

tgacttagag gcaacaggat tgatcattct tttatagagc atatttgcca ataaagcttt    660

tggaagccgg                                                           670
```

```
<210> SEQ ID NO 50
<211> LENGTH: 1675
<212> TYPE: DNA
<213> ORGANISM: Homo sapiens

<400> SEQUENCE: 50

ccagccgtcc attccggtgg aggcagaggc agtcctgggg ctctggggct cgggctttgt     60
```

-continued

```
caccgggacc cgcaggagcc agaaccactc ggcgccgcct ggtgcatggg aggggagccg    120

ggccaggagt aagtaactca tacgggcgcc ggggacccgg gtcgggctgg gggcttccaa    180

ctcagaggga gtgtgatttg cctgatcctc ttcggcgttg tcctgctctg ccgcatccag    240

ccctgtaccg ccatcccact tcccgccgtt cccatctgtg ttccgggtgg gatcggtctg    300

gaggcggccg aggacttccc aggcaggagc tcggggcgga ggccgggtcc gcggcagacc    360

agggcagcga ggcgctggcc ggcagggggc gctgcggtgc cagcctgagg ctgggctgct    420

ccgcgaggat acagcggccc ctgccctgtc ctgtcctgcc ctgccctgtc ctgtcctgcc    480

ctgccctgcc ctgtcctgtc ctgccctgcc ctgccctgtg tcctcagaca atatgttagc    540

cgtgcacttt gacaagccgg gaggaccgga aaacctctac gtgaaggagg tggccaagcc    600

gagcccgggg gagggtgaag tcctcctgaa ggtggcggcc agcgccctga accgggcgga    660

cttaatgcag agacaaggcc agtatgaccc acctccagga gccagcaaca ttttgggact    720

tgaggcatct ggacatgtgg cagagctggg gcctggctgc cagggacact ggaagatcgg    780

ggacacagcc atggctctgc tccccggtgg gggccaggct cagtacgtca ctgtccccga    840

agggctcctc atgcctatcc cagagggatt gaccctgacc caggctgcag ccatcccaga    900

ggcctggctc accgccttcc agctgttaca tcttgtggga aatgttcagg ctggagacta    960

tgtgctaatc catgcaggac tgagtggtgt gggcacagct gctatccaac tcacccggat   1020

ggctggagct attcctctgg tcacagctgg ctcccagaag aagcttcaaa tggcagaaaa   1080

gcttggagca gctgctggat tcaattacaa aaaagaggat ttctctgaag caacgctgaa   1140

attcaccaaa ggtgctggag ttaatcttat tctagactgc ataggcggat cctactggga   1200

gaagaacgtc aactgcctgg ctcttgatgg tcgatgggtt ctctatggtc tgatgggagg   1260

aggtgacatc aatgggcccc tgttttcaaa gctacttttt aagcgaggaa gtctgatcac   1320

cagtttgctg aggtctaggg acaataagta caagcaaatg ctggtgaatg ctttcacgga   1380

gcaaattctg cctcacttct ccacggaggg cccccaacgt ctgctgccgg ttctggacag   1440

aatctaccca gtgaccgaaa tccaggaggc ccataagtac atggaggcca acaagaacat   1500

aggcaagatc gtcctggaac tgccccagtg aaggaggatg gggcaggaca ggacgcggcc   1560

accccaggcc tttccagagc aaacctggag aagattcaca atagacaggc caagaaaccc   1620

ggtgcttcct ccagagccgt ttaaagctga tatgaggaaa taaagagtga actgg        1675
```

<210> SEQ ID NO 51
<211> LENGTH: 4099
<212> TYPE: DNA
<213> ORGANISM: Homo sapiens

<400> SEQUENCE: 51

```
cagctgccag ccgaggaggc gcggcggaga ggggactgcg gtcagctgcg tccacttggg     60

gctgtgcggc ggtcccgcgc ccggcgatgt tcccgggcac tccctgagta gcggcagctt    120

atcccccgcc cgctagcccg ccctggtccc cggctcgctc gctggctggc gcggccccgg    180

ccccgctctg cgtcggcccc gccgcggtgg aggcgcgcga gggggacgcg gccggggatg    240

agcggattgc gggtgaactc gccgcccggg ggcccccgcga agccgtgagc cgctgctttt    300

ctccgagtcg ccgccctgcc cttggatttg agatcatgtc catccacatc gtggcgctgg    360

ggaacgaggg ggacacattc caccaggaca accggccgtc ggggcttatc cgcacttacc    420

tggggagaag ccctctggtc tccggggacg agagcagctt gttgctgaac gcggccagca    480

cggtcgcgcg tccggtgttc accgagtatc aggccagtgc gtttgggaat gtcaagctgg    540
```

-continued

```
tggtccacga ctgtcccgtc tgggacatat ttgacagtga ttggtacact tctcgaaatc    600

taattggggg cgctgacatc attgtgatca aatacaacgt taatgacaag ttttcattcc    660

atgaagtaaa ggataattat attccagtga taaaaagagc attaaattca gttccagtaa    720

ttattgctgc tgttggtacc agacaaaatg aagagttacc ttgtacatgc ccactatgta    780

cctcagacag agggagctgt gttagtacaa ctgaagggat ccaacttgca aaagaactag    840

gagcaaccta tcttgaactc cacagccttg atgacttcta cataggaaag tattttggag    900

gagtgttgga gtattttatg attcaagcct taaatcagaa gacaagtgaa aaaatgaaga    960

aaagaaaaat gagcaactcc tttcatggaa ttagaccacc tcaacttgaa caaccagaaa   1020

aaatgcctgt cttaaaggct gaagcgtcac attataactc tgacttaaat aacttgctgt   1080

tctgctgcca gtgtgtggac gtggtatttt ataaccccga tttaaagaaa gttgtagagg   1140

cccacaagat cgttctctgc gctgtaagcc atgttttcat gctgcttttc aatgtgaaga   1200

gtcccactga cattcaggat tccagtatca tccgaactac ccaggatctt tttgctataa   1260

acagagatac tgcatttcca ggtgctagcc atgaatcttc aggcaaccca ccattacgag   1320

tcattgttaa agacgccctc ttctgttctt gtttatcaga catccttcgc ttcatttatt   1380

caggtgcttt tcagtgggaa gaattggaag aagatatcag gaagaagttg aaagattctg   1440

gggatgtttc aaatgtaatc gagaaagtta aatgcatttt aaaaacacca ggaaagatta   1500

attgcctaag gaattgcaaa acctatcaag ccagaaaacc tttgtggttt tataacactt   1560

ccctcaagtt tttccttaat aagccgatgc ttgccgatgt tgtcttcgaa attcaaggta   1620

cgacagtgcc agcccacagg gccatcctgg tggcccgttg tgaagtgatg gcagccatgt   1680

ttaatggtaa ttacatggaa gcaaagagtg tcctgattcc cgtttatggt gtttccaaag   1740

agactttctt gtcattttta gaatacctgt acacagactc ctgctgccca gctggcatat   1800

tccaggccat gtgtctcctg atctgtgccg agatgtacca agtgtccaga ctgcagcaca   1860

tctgtgagct gttcatcatt acccagctgc agagcatgcc aagcagggaa ctggcatcca   1920

tgaaccttga tatagttgac ctgcttaaaa aggccaagtt tcaccactct gattgccttt   1980

caacctggct acttcatttc attgctacta actacctcat cttcagtcaa aagcctgaat   2040

ttcaggatct ttcagtggaa gaacgcagtt ttgttgaaaa gcacagatgg ccgtcgaata   2100

tgtacttgaa gcagcttgcg gaatacagga agtatattca ctcccggaaa tgtcgttgct   2160

tagtaatgta acctggagct tttatacact acatttcttt tttattatta tgaagaatgg   2220

gatacctcca ggttccagta aaattcttct gaccgaaacc aatgtgggtg ttagaaaaat   2280

taccatatag cttaatatgt ttattagttc tctttggaaa aaaactacca ctgtggtctt   2340

aaaagggaac aaaatatacc ataggctaaa actaaggctt tcactctaga atgcaaagct   2400

gttttgcagc tgttttccct taaagatgtc ctgttgcttt agtgatattt agacccctct   2460

cagttaagaa atgcttagat taaaaaaaaa aaattacgta ggattaatac agaaatttaa   2520

tcatgtctga ttaattgctc tattaaaata aggggcattt aaagacccag cataaccatt   2580

tgtataatga gaaatctagg ggaaaaccaa tcagtccaac atgagatttt aggaatagaa   2640

atttgccggc catttggaaa gtgaaatgcc acttagttct caattgatga cagtgtttga   2700

atcatcataa aaaaaatacc tgcttttcat ctggacaacc caattgagcc actttatctc   2760

cttttggcaa tctgagtagg cggggaacct aggcagggct ggctttctta gcgtgtaact   2820

tgtgtagcag cacagggccc acacttagaa ggaccccaca cttggttcaa ggctctgcta   2880
```

-continued

```
tagcggaaat tcttaataat gtttgaagaa gggccccatg atttcatttt gtgctgagcc   2940

ctcaaaatta tgtctgtttc gtggtgggaa atatcctatg ttttcttgct caaacacctt   3000

tctctctgaa agcagaaaaa ggcactgata taaagggaag agaaggaggc tcaccggagg   3060

gaagagaaca tagtgaagat tcccgccttt ggggaggtct ggaccaccca gggcctccac   3120

tgccaccttg gctggcaagg gagaaatgtg ttgtgttgtc ttagctttaa aacagtcaca   3180

gttcttgctc tatcatagat gaacaaatac tttcttgatc attctgtaag accaggaggt   3240

tggtaagagt gactaaccag cctaacttta atacacatgt ataaagatgt tcacagagaa   3300

agatgctctg tagagaattt gctaccgaag ttggctcaag aatttgtttt tagtgttatt   3360

taccaagatt aggacgtcag tggcttaaat tctttgaatt cttttcaagg actgcaagat   3420

tatttgataa agagtagcat gaatcttgtg ctctaatatt acacagtaag ttcaaagaaa   3480

ggatgtaagt caaagacttg ttacatagag ggaaaatgga ctgggataga ggacagactg   3540

atagtttctt tctttcatat cacatgtata gagaaataat tatatcagaa actcacaaac   3600

ctagacatgg aaaaacagat tactgtctat tgtcagcatc attttcatct gtaagtcact   3660

actggaatat atttttcttt taatttccag tgactttaga atacacacag tttttccgac   3720

ttttcaaaaa tttgattaaa tggttttata gtataatatt gggaccccat accgttagcc   3780

cttgtatgta taccaacact gccaaagtaa aacattaggt caggcatggt ggctcaggcc   3840

tgtaatccca gcattttggg aggctgaggc aagtggataa cttgaggtca tgagttcgaa   3900

accagcctgg ccaaaacagt gaaaccccgt ctctactaaa aatacaaaat tagccagatg   3960

tggtggcgca cacctgtaat cccagctact caggaagctg aggcaggaaa atcgcttgaa   4020

cctgggaggt ggaagttgca gtgagccgag atcgcaccac tgcactccag cctgggtgac   4080

aagagcgaaa ctccatctc                                                4099
```

<210> SEQ ID NO 52
<211> LENGTH: 2508
<212> TYPE: DNA
<213> ORGANISM: Homo sapiens

<400> SEQUENCE: 52

```
cgcgcccctc cctcctcgcg gacctggcgg tgccggcgcc cggagtggcc ctttaaaagg     60

cagcttattg tccggagggg gcgggcgggg ggcgccgacc gcggcctgag gcccggcccc    120

tcccctctcc ctccctctgt ccccgcgtcg ctcgctggct agctcgctgg ctcgctcgcc    180

cgtccggcgc acgctccgcc tccgtcagtt ggctccgctg tcgggtgcgc ggcgtggagc    240

ggcagccggt ctggacgcgc ggccggggct gggggctggg agcgcggcgc gcaagatctc    300

cccgcgcgag agcggcccct gccaccgggc gaggcctgcg ccgcgatggc agagatgggc    360

agtaaagggg tgacggcggg aaagatcgcc agcaacgtgc agaagaagct cacccgcgcg    420

caggagaagg ttctccagaa gctggggaag gcagatgaga ccaaggatga gcagtttgag    480

cagtgcgtcc agaatttcaa caagcagctg acggagggca cccggctgca gaaggatctc    540

cggacctacc tggcctccgt caaagccatg cacgaggctt ccaagaagct gaatgagtgt    600

ctgcaggagg tgtatgagcc cgattggccc ggcagggatg aggcaaacaa gatcgcagag    660

aacaacgacc tgctgtggat ggattaccac cagaagctgg tggaccaggc gctgctgacc    720

atggacacgt acctgggcca gttccccgac atcaagtcac gcattgccaa gcgggggcgc    780

aagctggtgg actacgacag tgcccggcac cactacgagt cccttcaaac tgccaaaaag    840

aaggatgaag ccaaaattgc caagcctgtc tcgctgcttg agaaagccgc cccccagtgg    900
```

-continued

```
tgccaaggca aactgcaggc tcatctcgta gctcaaacta acctgctccg aaatcaggcc    960
gaggaggagc tcatcaaagc ccagaaggtg tttgaggaga tgaatgtgga tctgcaggag   1020
gagctgccgt ccctgtggaa cagccgcgta ggtttctacg tcaacacgtt ccagagcatc   1080
gcgggcctgg aggaaaactt ccacaaggag atgagcaagc tcaaccagaa cctcaatgat   1140
gtgctggtcg gcctggagaa gcaacacggg agcaacacct tcacggtcaa ggcccagccc   1200
agtgacaacg cgcctgcaaa agggaacaag agcccttcgc ctccagatgg ctcccctgcc   1260
gccacccccg agatcagagt caaccacgag ccagagccgg ccggcggggc cacgcccggg   1320
gccaccctcc ccaagtcccc atctcagttt gaggccccgg ggcctttctc ggagcaggcc   1380
agtctgctgg acctggactt tgacccccctc ccgcccgtga cgagccctgt gaaggcaccc   1440
acgccctctg gtcagtcaat tccatgggac ctctgggagc ccacagagag tccagccggc   1500
agcctgcctt ccggggagcc cagcgctgcc gagggcacct ttgctgtgtc ctggcccagc   1560
cagacggccg agccggggcc tgcccaacca gcagaggcct cggaggtggc gggtgggacc   1620
caacctgcgg ctggagccca ggagccaggg gagacggcgg caagtgaagc agcctccagc   1680
tctcttcctg ctgtcgtggt ggagaccttc ccagcaactg tgaatggcac cgtggagggc   1740
ggcagtgggg ccgggcgctt ggacctgccc ccaggtttca tgttcaaggt acaggcccag   1800
cacgactaca cggccactga cacagacgag ctgcagctca aggctggtga tgtggtgctg   1860
gtgatcccct tccagaaccc tgaagagcag gatgaaggct ggctcatggg cgtgaaggag   1920
agcgactgga accagcacaa ggagctggag aagtgccgtg gcgtcttccc cgagaacttc   1980
actgagaggg tcccatgacg gcggggccca ggcagcctcc gggcgtgtga agaacacctc   2040
ctcccgaaaa atgtgtggtt cttttttttg ttttgtttc gtttttcatc ttttgaagag   2100
caaagggaaa tcaagaggag acccccaggc agaggggcgt tctcccaaag attaggtcgt   2160
tttccaaaga gccgcgtccc ggcaagtccg gcggaattca ccagtgttcc tgaagctgct   2220
gtgtcctcta gttgagtttc tggcgcccct gcctgtgccc gcatgtgtgc ctggccgcag   2280
ggcggggctg gggctgccg agccaccatg cttgcctgaa gcttcggccg cgccacccgg   2340
gcaagggtcc tcttttcctg gcagctgctg tgggtggggc ccagacacca gcctagcctg   2400
gctctgcccc gcagacggtc tgtgtgctgt ttgaaaataa atcttagtgt tcaaaacaaa   2460
atgaaacaaa aaaaaaatga taaaaactct caaaaaaaaa aaaaaaaa                 2508
```

<210> SEQ ID NO 53
<211> LENGTH: 2278
<212> TYPE: DNA
<213> ORGANISM: Homo sapiens

<400> SEQUENCE: 53

```
ggggagtgct ccattttccc cgacagcgaa tttcccctga gaaacgatac tagaccctgg     60
gtttgcccac cttgtaactc ttccttatct cctccttttc atccctaatt catcctccct    120
ctggcatgga attgacgccc gtgcagtaca tttgccaagt ggcaccttct ttcaatttat    180
gttttatttt gctatggtgg tgattcttta tttgctggtt gtcttttctc acacatcttt    240
ctctctgtct ctctctttcc tgctctttgt tttctgccc agaaaaacct gacttcgata    300
ccaaaaaaga tgaaactaca gaaactcaaa tttaaaaaaa actttaaaag aaacaaaaaa    360
atactcaacg attctttcag ctttattaac attttccatt gtttcttgcg acttgtgtct    420
cgttctttgt agtattgatg atgaacattt gataatgaat gttcttgtat attcagataa    480
```

-continued

```
agaaaaaaaa aaccaaaaaa gcggtctgaa tttaatagtg tttataataa aaattttaaa    540
aatgaccctc atagcacgca aaacaggatg gggaatttcc cctcttcttt ctgtgacaat    600
gcgcatcatt cctgcattag tttttaacac cagactacct acattcatca tttccctcat    660
ttttctttta ttttcttgca tttgtgaatt agttcaagaa tgctagaaaa gtgtcgagtt    720
gtgcacatcc atttcttgtt tcacaatgtt taaaagtgac agtaattcat tttgtaaact    780
aaaaaaaaaa aaaaaaaggt tggaatagtg agcataatag gtacaaccta acacattatt    840
atgtttatta actttgagac ccagaaataa attcttttct tttcttgatt cttgctctta    900
aaaatacaaa aaaaaaaatg ttttgttttg tgttattttt ggtttgttta ttggggggct    960
ttttttaatt gtcaggatta tgatcttgct gtttttcttc aatatgtata caaggtgatg   1020
tgaaaagatg acttgggcag aggagtaaga acaagtaggc ttgttcttct actttgcttc   1080
agaattcagt taatgccaaa agcgaagatc aagcccatgt tgatgtctcg ttgctcacct   1140
gcatttccag agagtgtgac actcatgcag tccctgagaa aaataaaatc agggacatac   1200
ttctcctttt agccttttaa aaattcaaaa acgtttagtc caagggaact ttttatgcta   1260
tcaggaaagg tttttgctgt ttttgattct gattatcaca gccaagtact ttgttttatt   1320
tctccctaat taataactac attccatgag gcctcttcca accaaagagg cctttttcttc  1380
caggagagtc ccgcaggaga tgctggtatg atgggcacca ttggttaagt aaactacatg   1440
caggaagaag tccttggggc cagtctgcca gctgagtcct ggttttggat gaagagttaa   1500
tgagatattg ggccaggctc aatgctgtag ttttaatgct aagaggttac gtttacttca   1560
cagagtacac ctcttagtaa cctctgactt aggcagctgc ttaaagcaaa ttgcaaaact   1620
ggcttgattt ggaatgtttt tattagagga aaaaagaaag ccatattatc tggaaaaaaa   1680
ttcattttaa ataccatcat tcaacaaatt atgttcagaa agtggtcaga acttaagcaa   1740
gaaaagtaaa gaaagaatgc agaattgtgg agcaatgctt taggaaatat ttctacctga   1800
acacttgtac tcttgaagtc acaacaaaat aatgatgagc ttttcacatc acctttatgg   1860
tttcaatccc tagctcaaag cttcctggaa tcttttattt tttgtaaact tttttttctt   1920
ttgttaaaat aaataaaaca ttcaatgttt ttctcctttt ctctcttatt acttctttcc   1980
tttggcattt tcaatttgaa atgctttcct ttggttgttg gttttattct ccccctaccc   2040
ctccccttttt cttattattc agaatataaa cctgcaaagc tctgctctgt tttggttttg  2100
aaagtttaag cttttctgct tctgtgagag cacaggcttc tgtccctttt gattccaact   2160
gaacttttgt gttctctaat gatactaaca cggtgtaggt tttacagtct cctaatttgt   2220
actggtaatg catattccaa ataaatagtt tcttttgttg caaaaaaaaa aaaaaaaa     2278
```

<210> SEQ ID NO 54
<211> LENGTH: 4322
<212> TYPE: DNA
<213> ORGANISM: Homo sapiens

<400> SEQUENCE: 54

```
cccccagagg cgccggagcc cggaatcccg ctcggagcca gccagccgtc ccgagctacc     60
agcaggtttc attgaaaaca gatcctgcaa aagttccagg tgcccacact ggaaacttgg    120
agatcctgct tcccagacca cagctgtggg gaacttgggg tggagcagag aagtttctgt    180
attcagctgc ccaggcagag gagaatgggg tctccacagc ctgaagaatg aagacacgac    240
agaataaaga ctcgatgtca atgaggagtg gacggaagaa agaggcccct gggccccggg    300
aagaactgag atcgaggggc cgggcctccc ctggaggggt cagcacgtcc agcagtgatg    360
```

-continued

```
gcaaagctga gaagtccagg cagacagcca agaaggcccg agtagaggaa gcctccaccc    420
caaaggtcaa caagcagggt cggagtgagg agatctcaga gagtgaaagt gaggagacca    480
atgcaccaaa aaagaccaaa actgaggaac tccctcggcc acagtctccc tccgatctgg    540
atagcttgga cgggcggagc cttaatgatg atggcagcag cgaccctagg gatatcgacc    600
aggacaaccg aagcacgtcc cccagtatct acagccctgg aagtgtggag aatgactctg    660
actcatcttc tggcctgtcc cagggcccag cccgccccta ccacccacct ccactctttc    720
ctccttcccc tcaaccgcca gacagcaccc ctcgacagcc agaggctagc tttgaacccc    780
atccttctgt gacacccact ggatatcatg ctcccatgga gccccccaca tctcgaatgt    840
tccaggctcc tcctggggcc cctccccctc acccacagct ctatcccggg ggcactggtg    900
gagttttgtc tggaccccca atgggtccca agggggggagg ggctgcctca tcagtggggg    960
gccctaatgg gggtaagcag cacccccccac ccactactcc catttcagta tcaagctctg   1020
gggctagtgg tgctccccca acaaagccgc ctaccactcc agtgggtggt gggaacctac   1080
cttctgctcc accaccagcc aacttccccc atgtgacacc gaacctgcct cccccacctg   1140
ccctgagacc cctcaacaat gcatcagcct ctccccctgg cctgggggcc caaccactac   1200
ctggtcatct gccctctccc cacgccatgg gacagggtat cggtggactt cctcctggcc   1260
cagagaaggg cccaactctg gctccttcac cccactctct gcctcctgct tcctcttctg   1320
ctccagcgcc ccccatgagg tttccttatt catcctctag tagtagctct gcagcagcct   1380
cctcttccag ttcttcctcc tcttcctctg cctccccctt cccagcttcc caggcattgc   1440
ccagctaccc ccactctttc cctcccccaa caagcctctc tgtctccaat cagcccccca   1500
agtatactca gccttctctc ccatcccagg ctgtgtggag ccagggtccc ccaccacctc   1560
ctccctatgg ccgcctctta gccaacagca atgcccatcc aggcccccttc cctccctcta   1620
ctggggccca gtccaccgcc cacccaccag tctcaacaca tcaccatcac caccagcaac   1680
agcaacagca gcagcagcag cagcagcagc agcagcatca cggaaactct gggccccctc   1740
ctcctggagc atttccccac ccactggagg gcggtagctc ccaccacgca cacccttacg   1800
ccatgtctcc ctccctgggg tctctgaggc cctacccacc agggccagca cacctgcccc   1860
cacctcacag ccaggtgtcc tacagccaag caggccccaa tggccctcca gtctcttcct   1920
cttccaactc ttcctcttcc acttctcaag ggtcctaccc atgttcacac ccctcccctt   1980
cccagggccc tcaaggggcg ccctaccctt tcccaccggt gcctacggtc accacctctt   2040
cggctaccct ttccacggtc attgccaccg tggcttcctc gccagcaggc tacaaaacgg   2100
cctccccacc tgggccccca ccgtacggaa agagagcccc gtccccgggg gcctacaaga   2160
cagccacccc acccggatac aaacccgggt cgcctccctc cttccgaacg gggaccccac   2220
cgggctatcg aggaacctcg ccacctgcag gcccagggac cttcaagccg ggctcgccca   2280
ccgtgggacc tgggcccctg ccacctgcgg ggccctcagg cctgccatcg ctgccaccac   2340
cacctgcggc ccctgcctca gggccgcccc tgagcgccac gcagatcaaa caggagccgg   2400
ctgaggagta tgagaccccc gagagcccgg tgcccccagc ccgcagcccc tcgccccctc   2460
ccaaggtggt agatgtaccc agccatgcca gtcagtctgc caggttcaac aaacacctgg   2520
atcgcggctt caactcgtgc gcgcgcagcg acctgtactt cgtgccactg gagggctcca   2580
agctggccaa gaagcgggcc gacctggtgg agaaggtgcg gcgcgaggcc gagcagcgcg   2640
cgcgcgaaga aaaggagcgc gagcgcgagc gggaacgcga gaaagagcgc gagcgcgaga   2700
```

-continued

```
aggagcgcga gcttgaacgc agcgtgaagt tggctcagga gggccgtgct ccggtggaat   2760

gcccatctct gggcccagtg ccccatcgcc ctccatttga accgggcagt gcggtggcta   2820

cagtgccccc ctacctgggt cctgacactc cagccttgcg cactctcagt gaatatgccc   2880

ggcctcatgt catgtctcct ggcaatcgca accatccatt ctacgtgccc ctgggggcag   2940

tggacccggg gctcctgggt tacaatgtcc cggccctgta cagcagtgat ccagctgccc   3000

gggagaggga acgggaagcc cgtgaacgag acctccgtga ccgcctcaag cctggctttg   3060

aggtgaagcc tagtgagctg gaacccctac atggggtccc tgggccgggc ttggatccct   3120

ttccccgaca tgggggcctg gctctgcagc ctggcccacc tggcctgcac cctttcccct   3180

ttcatccgag cctggggccc ctggagcgag aacgtctagc gctggcagct gggccagccc   3240

tgcggcctga catgtcctat gctgagcggc tggcagctga gaggcagcac gcagaaaggg   3300

tggcggccct gggcaatgac ccactggccc ggctgcagat gctcaatgtg actccccatc   3360

accaccagca ctcccacatc cactcgcacc tgcacctgca ccagcaagat gctatccatg   3420

cagcctctgc ctcggtgcac cctctcattg accccctggc ctcagggtct caccttaccc   3480

ggatccccta cccagctgga actctcccta acccccctgct tcctcaccct ctgcacgaga   3540

acgaagttct tcgtcaccag ctctttgctg ccccttaccg ggacctgccg gcctcccttt   3600

ctgccccgat gtcagcagct catcagctgc aggccatgca cgcacagtca gctgagctgc   3660

agcgcttggc gctggaacag cagcagtggc tgcatgccca tcacccgctg cacagtgtgc   3720

cgctgcctgc ccaggaggac tactacagtc acctgaagaa ggaaagcgac aagccactgt   3780

agaacctgcg atcaagagag caccatggct cctacattgg accttggagc acccccaccc   3840

tccccccacc gtgcccttgg cctgccaccc agagccaaga gggtgctgct cagttgcagg   3900

gcctccgcag ctggacagag agtgggggag ggagggacag acagaaggcc aaggcccgat   3960

gtggtgtgca gaggtgggga ggtggcgagg atggggacag aaagcgcaca gaatcttgga   4020

ccaggtctct cttccttgtc ccccctgctt ttctcctccc ccatgcccaa cccctgtggc   4080

cgccgcccct cccctgcccc gttggtgtga ttatttcatc tgttagatgt ggctgttttg   4140

cgtagcatcg tgtgccaccc ctgcccctcc ccgatccctg tgtgcgcgcc ccctctgcaa   4200

tgtatgcccc ttgccccttc cccacactaa taatttatat atataaatat ctatatgacg   4260

ctcttaaaaa aacatcccaa ccaaaaccaa ccaaacaaaa acatcctcac aactccccag   4320

ga                                                                  4322
```

```
<210> SEQ ID NO 55
<211> LENGTH: 808
<212> TYPE: DNA
<213> ORGANISM: Homo sapiens

<400> SEQUENCE: 55

tgctcccttg ggctctagag aggaggcccc tcttagccct cagcccctcc ttcctctcta     60

tcttaaagta atttgatcct caggaatttg ttccgccctc atctggcccg gccaaatccc    120

gatttgacaa atgccaggaa aaggaaactg ttgagaaacc gaaactactg ggaaaggga    180

gggctcactg agtaaccatc ccagtaaccc gaccgccgct ggtcttcgct ggacaccatg    240

agtcacactg tccaaacctt cttctctcct gtcaacagtg gccagccccc caactatgag    300

atgctcaagg aggagcacga ggtggctgtg ctgggggggc cccacaaccc tgctcccccg    360

acgtccaccg tgatccacat ccgcagcgag acctccgtgc ccgaccatgt cgtctggtcc    420

ctgttcaaca ccctcttcat gaacccctgc tgcctgggct tcatagcatt cgcctactcc    480
```

-continued

```
gtgaagtcta gggacaggaa gatggttggc gacgtgaccg gggcccaggc ctatgcctcc    540

accgccaagt gcctgaacat ctgggccctg attctgggca tcctcatgac cattctgctc    600

atcgtcatcc cagtgctgat cttccaggcc tatggataga tcaggaggca tcactgaggc    660

caggagctct gcccatgacc tgtatcccac gtactccaac ttccattcct cgccctgccc    720

ccggagccga gtcctgtatc agccctttat cctcacacgc ttttctacaa tggcattcaa    780

taaagtgcac gtgtttctgg tgctgctg                                        808
```

<210> SEQ ID NO 56
<211> LENGTH: 3454
<212> TYPE: DNA
<213> ORGANISM: Homo sapiens

<400> SEQUENCE: 56

```
ggaaatgact gctgtccatg caggcaacat aaacttcaag tgggatccta aaagtctaga     60

gatcaggact ctggcagttg agagactgtt ggagcctctt gttacacagg ttacaaccct    120

tgtaaacacc aatagtaaag ggccctctaa taagaagaga ggtcgttcta agaaggccca    180

tgttttggct gcatctgttg aacaagcaac tgagaatttc ttggagaagg gggataaaat    240

tgcaaaagag agccagtttc tcaaggagga gcttgtggtt gctgtagaag atgttcgaaa    300

acaaggtgat ttgatgaagg ctgctgctgg agagttcgca gatgatccct gctcttctgt    360

gaagcgaggc aacatggttc gggcagctcg agctttgctc tctgctgtta cccggttgct    420

cattttggct gacatggcag atgtctacaa attacttgtt cagctgaaag ttgtggaaga    480

tggtatattg aaactgagga atgctggcaa tgaacaagac ttagggaatc agtataaagc    540

cctaaaacct gaagtggata agctgaacat tatggcagca aaaagacaac aggaattgaa    600

agatgttggg catcgtgatc agatggctgc ggctagagga atcctgcaga gcaacgttcc    660

gatcctctat actgcatccc aggcatgcct acagcaccct gatgtcgcag cctataaggc    720

caacagggac ctgatataca agcagctgca gcaggcggtc acagggattt ccaatgcagc    780

ccaggccact gcctcagacg atgcctcaca gcaccagggt ggaggaggag gagaactggc    840

atatgcactc aataactttg acaaacaaat cattgtggac cccttgagct tcagcgagga    900

gcgctttagg ccttccctgg aggagcgtct ggaaagcatc attagtgggg ctgccttgat    960

ggccgactcg tcctgcacgc gtgatgaccg tcgtgagcga attgtggcag agtgtaatgc   1020

tgtccgccag gcctgcagga cctgcgtttc ggagtacatg ggcaatgctg gacgtaaaga   1080

aagaagtgat gcactcaatt ctgcaataga taaaatgacc aagaagacca gggacttgcg   1140

tagacagctt cgcaaagctg tcatggacca cgtttcagat tctttcctgg aaaccaatgt   1200

tccactttttg gtattgattg aagctgcaaa gaatggaaat gagaaagaag ttaaggaata   1260

tgcccaagtt ttccgtgaac atgccaacaa attgattgag gttgccaact tggcctgttc   1320

catctcaaat aatgaagaag gtgtaaagct tgttcgaatg tctgcaagcc agttagaagc   1380

cggttgtcct caggttatta atgctgcaac ctgggcttta gcaccaaaac cacagagtaa   1440

actggcccaa gagaacatgg atctttttaa agaacaatgg gaaaaacaag tccgtgttct   1500

cacagatgct gtcgatgaca ttacttccat tgatgacttc ttggctgtct cagagaatca   1560

cattttggaa gatgtgaaca aatgtgtcat tgctctccaa gagaaggatg tggatggcct   1620

ggaccgcaca gctggtgcaa ttcgaggccg ggcagcccgg gtcattcacg tagtcacctc   1680

agagatggac aactatgagc caggagtcta cacagagaag gttctggaag ccactaagct   1740
```

-continued

```
gctctccaac acagtcatgc cacgttttac tgagcaagta gaagcagccg tggaagccct   1800
cagctcggac cctgcccagc ccatggatga gaatgagttt atcgatgctt cccgcctggt   1860
atatgatggc atccgggaca tcaggaaagc agtgctgatg ataaggaccc ctgaggagtt   1920
ggatgactct gactttgaga cagaggattt tgatgtcaga agcgagacga gcgtccagac   1980
agaagacgat cagctgatag ctggccagag tgcccgggcg atcatggctc agcttcccca   2040
ggagcaaaaa gcgaagattc gggaacaggt ggccagcttc caggaagaaa agagcaagct   2100
ggatgctgaa gtgtccaaat gggacgacag tggcaatgac atcattgtgc tggccaagca   2160
gatgtgcatg attatgatgg agatgacaga ctttacccga ggtaaaggac cactcaaaaa   2220
tacatcggat gtcatcagtg ctgccaagaa aattgctgag gcaggatcca ggatggacaa   2280
gcttggccgg accattcgag accattgccc cgactcggct tgcaagcagg acctgctggc   2340
ctacctgcaa cgcatcgccc tctactgcca ccagctgaac atctgcagca aggtcaaggc   2400
cgaggtgcag aatctcggcg gggagcttgt tgtctctggg gtggacagcg ccatgtccct   2460
gatccaggca gccaagaact tgatgaatgc tgtggtgcag acagtgaagg catcctacgt   2520
cgcctctacc aaataccaaa agtcacaggg tatggcttcc ctcaaccttc ctgctgtgtc   2580
aatgaagatg aaggcaccag agaaaaagcc attggtgaag agagagaaac aggatgagac   2640
acagaccaag attaaacggg catctcagaa gaagcacgtg aacccagtgc aggccctcag   2700
cgagttcaaa gctatggaca gcatctaagt ctgcccaggc cggccgcccc cacccctctg   2760
gctcctgaat atcagtcact gttcgtcact caaatgaatt tgctaaatac aacactgata   2820
ctagattcca cagggaaatg ggcagactga accagtccag gtggtgaatt ttccaagaac   2880
atagtttaag ttgattaaaa atgcttttag aatgcaggag cctacttcta gctgtatttt   2940
ttgtatgctt aaataaaata aaattcataa ccaagagatc cacattagct tgttagtaat   3000
gctctgacca agccgagatg ccattctctt agtgatggcg gcgttaggtt tgagagaagg   3060
aattggctca acttcagttg agagggtgca gtccagacag cttgactgct tttaaatgac   3120
caaagatgac ctgtggtaag caacctggca tcttaggaag cagtccttga gaaggcatgt   3180
tccagaaagg tctctgagga caaactcact cagtaaaaca taatgtatca tgaagaaaac   3240
tgattctcta tgacatgaaa tgaaaatttt aatgcattgt tataattact aatgtacgct   3300
gctgcaggac attaataaag ttgctttttt aggctacagt gtctcgatgc cataatcaga   3360
acacactttt tttcctcttt ctcccagctt caaatgcaca attcatcatt gggctcactt   3420
ctaataactg cagtgtttcc gccttgcgtt gcag                               3454
```

<210> SEQ ID NO 57
<211> LENGTH: 5128
<212> TYPE: DNA
<213> ORGANISM: Homo sapiens

<400> SEQUENCE: 57

```
ccgagtgcct cgcagcccct cccgaggcgc agccgccaga ccagtggagc cggggcgcag     60
ggcgggggcg gaggcgccgg ggcgggggat gcggggccgc ggcgcagccc cccggccctg    120
agagcgagga cagcgccgcc cggcccgcag ccgtcgccgc ttctccacct cggcccgtgg    180
agccggggcg tccgggcgta gccctcgctc gcctgggtca gggggtgcgc gtcgggggag    240
gcagaagcca tggatcccgg gcagcagccg ccgcctcaac cggcccccca gggccaaggg    300
cagccgcctt cgcagccccc gcaggggcag ggcccgccgt ccggacccgg gcaaccggca    360
cccgcggcga cccaggcggc gccgcaggca ccccccgccg ggcatcagat cgtgcacgtc    420
```

-continued

```
cgcggggact cggagaccga cctggaggcg ctcttcaacg ccgtcatgaa ccccaagacg    480
gccaacgtgc cccagaccgt gcccatgagg ctccggaagc tgcccgactc cttcttcaag    540
ccgccggagc ccaaatccca ctcccgacag gccagtactg atgcaggcac tgcaggagcc    600
ctgactccac agcatgttcg agctcattcc tctccagctt ctctgcagtt gggagctgtt    660
tctcctggga cactgacccc cactggagta gtctctggcc cagcagctac acccacagct    720
cagcatcttc gacagtcttc ttttgagata cctgatgatg tacctctgcc agcaggttgg    780
gagatggcaa agacatcttc tggtcagaga tacttcttaa atcacatcga tcagacaaca    840
acatggcagg accccaggaa ggccatgctg tcccagatga acgtcacagc ccccaccagt    900
ccaccagtgc agcagaatat gatgaactcg gcttcagcca tgaaccagag aatcagtcag    960
agtgctccag tgaaacagcc accacccctg gctccccaga gcccacaggg aggcgtcatg   1020
ggtggcagca actccaacca gcagcaacag atgcgactgc agcaactgca gatggagaag   1080
gagaggctgc ggctgaaaca gcaagaactg cttcggcagg tgaggccaca ggagttagcc   1140
ctgcgtagcc agttaccaac actggagcag gatggtggga ctcaaaatcc agtgtcttct   1200
cccgggatgt ctcaggaatt gagaacaatg acgaccaata gctcagatcc tttccttaac   1260
agtggcacct atcactctcg agatgagagt acagacagtg gactaagcat gagcagctac   1320
agtgtccctc gaaccccaga tgacttcctg aacagtgtgg atgagatgga tacaggtgat   1380
actatcaacc aaagcaccct gccctcacag cagaaccgtt tcccagacta ccttgaagcc   1440
attcctggga caaatgtgga ccttggaaca ctggaaggag atggaatgaa catagaagga   1500
gaggagctga tgccaagtct gcaggaagct ttgagttctg acatccttaa tgacatggag   1560
tctgttttgg ctgccaccaa gctagataaa gaaagctttc ttacatggtt atagagccct   1620
caggcagact gaattctaaa tctgtgaagg atctaaggag acacatgcac cggaaatttc   1680
cataagccag ttgcagtttt caggctaata cagaaaaaga tgaacaaacg tccagcaaga   1740
tactttaatc ctctattttg ctcttccttg tccattgctg ctgttaatgt attgctgacc   1800
tctttcacag ttggctctaa agaatcaaaa gaaaaaaact ttttatttct tttgctatta   1860
aaactactgt tcattttggg ggctggggga agtgagcctg tttggatgat ggatgccatt   1920
ccttttgccc agttaaatgt tcaccaatca ttttaactaa atactcagac ttagaagtca   1980
gatgcttcat gtcacagcat ttagtttgtt caacagttgt ttcttcagct tcctttgtcc   2040
agtggaaaaa catgatttac tggtctgaca agccaaaaat gttatatctg atattaaata   2100
cttaatgctg atttgaagag atagctgaaa ccaaggctga agactgtttt actttcagta   2160
ttttctttc ctcctagtgc tatcattagt cacataatga ccttgatttt attttaggag   2220
cttataaggc atgagacaat ttccatataa atatattaat tattgccaca tactctaata   2280
tagattttgg tggataattt tgtgggtgtg cattttgttc tgttttgttg ggttttttgt   2340
tttttttgtt tttggcaggg tcggtggggg ggttggttgg ttggttggtt ttgtcggaac   2400
ctaggcaaat gaccatatta gtgaatctgt taatagttgt agcttgggat ggttattgta   2460
gttgttttgg taaaatcttc atttcctggt tttttttacc accttattta aatctcgatt   2520
atctgctctc tcttttatat acatacacac acccaaacat aacatttata atagtgtggt   2580
agtggaatgt atcctttttt aggtttccct gctttccagt taatttttaa aatggtagcg   2640
ctttgtatgc atttagaata catgactagt agtttatatt tcactggtag tttaaatctg   2700
gttggggcag tctgcagatg tttgaagtag tttagtgttc tagaaagagc tattactgtg   2760
```

-continued

```
gatagtgcct aggggagtgc tccacgccct ctgggcatac ggtagatatt atctgatgaa   2820
ttggaaagga gcaaaccaga aatggcttta ttttctccct tggactaatt tttaagtctc   2880
gattggaatt cagtgagtag gttcataatg tgcatgacag aaataagctt tatagtggtt   2940
taccttcatt tagctttgga agttttcttt gccttagttt tggaagtaaa ttctagtttg   3000
tagttctcat ttgtaatgaa cacattaacg actagattaa aatattgcct tcaagattgt   3060
tcttacttac aagacttgct cctacttcta tgctgaaaat tgaccctgga tagaatacta   3120
taaggttttg agttagctgg aaaagtgatc agattaataa atgtatattg gtagttgaat   3180
ttagcaaaga aatagagata atcatgatta tacctttatt tttacaggaa gagatgatgt   3240
aactagagta tgtgtctaca ggagtaataa tggtttccaa agagtatttt ttaaaggaac   3300
aaaacgagca tgaattaact cttcaatata agctatgaag taatagttgg ttgtgaatta   3360
aagtggcacc agctagcacc tctgtgtttt aagggtcttt caatgtttct agaataagcc   3420
cttattttca agggttcata acaggcataa aatctcttct cctggcaaaa gctgctatga   3480
aaagcctcag cttgggaaga tagatttttt tccccccaat tacaaaatct aagtattttg   3540
gcccttcaat ttggaggagg gcaaaagttg gaagtaagaa gttttatttt aagtactttc   3600
agtgctcaaa aaaatgcaat cactgtgttg tatataatag ttcataggtt gatcactcat   3660
aataattgac tctaaggctt ttattaagaa aacagcagaa agattaaatc ttgaattaag   3720
tctgggggga aatggccact gcagatggag ttttagagta gtaatgaaat tctacctaga   3780
atgcaaaatt gggtatatga attacatagc atgttgttgg gatttttttt aatgtgcaga   3840
agatcaaagc tacttggaag gagtgcctat aatttgccag tagccacaga ttaagattat   3900
atcttatata tcagcagatt agctttagct tagggggagg gtgggaaagt ttgggggggg   3960
ggttgtgaag atttaggggg accttgatag agaactttat aaacttcttt ctctttaata   4020
aagacttgtc ttacaccgtg ctgccattaa aggcagctgt tctagagttt cagtcaccta   4080
agtacaccca caaaacaata tgaatatgga gatcttcctt taccccctcaa ctttaatttg   4140
cccagttata cctcagtgtt gtagcagtac tgtgatacct ggcacagtgc tttgatctta   4200
cgatgccctc tgtactgacc tgaaggagac ctaagagtcc tttccctttt tgagtttgaa   4260
tcatagcctt gatgtggtct cttgttttat gtccttgttc ctaatgtaaa agtgcttaac   4320
tgcttcttgg ttgtattggg tagcattggg ataagatttt aactgggtat tcttgaattg   4380
cttttacaat aaaccaattt tataatcttt aaatttatca actttttaca tttgtgttat   4440
tttcagtcag ggcttcttag atctacttat ggttgatgga gcacattgat ttggagtttc   4500
agatcttcca aagcactatt tgttgtaata acttttctaa atgtagtgcc tttaaaggaa   4560
aaatgaacac agggaagtga ctttgctaca aataatgttg ctgtgttaag tattcatatt   4620
aaatacatgc cttctatatg gaacatggca gaaagactga aaaataacag taattaattg   4680
tgtaattcag aattcatacc aatcagtgtt gaaactcaaa cattgcaaaa gtgggtggca   4740
atattcagtg cttaacactt ttctagcgtt ggtacatctg agaaatgagt gctcaggtgg   4800
attttatcct cgcaagcatg ttgttataag aattgtgggt gtgcctatca taacaattgt   4860
tttctgtatc ttgaaaaagt attctccaca ttttaaatgt tttatattag agaattcttt   4920
aatgcacact tgtcaaatat atatatatag taccaatgtt accttttttat tttttgtttt   4980
agatgtaaga gcatgctcat atgttaggta cttacataaa ttgttacatt attttttctt   5040
atgtaatacc tttttgtttg tttatgtggt tcaaatatat tctttcctta aaaaaaaaaa   5100
aaaaaaaaaa aaaaaaaaaa aaaaaaaa                                      5128
```

<210> SEQ ID NO 58
<211> LENGTH: 1454
<212> TYPE: DNA
<213> ORGANISM: Homo sapiens

<400> SEQUENCE: 58

```
aattgcttcc ggggagttgc gagggagcga gggggaataa aggacccgcg aggaagggcc     60
cgcggatggc gcgtccctga gggtcgtggc gagttcgcgg agcgtgggaa ggagcggacc    120
ctgctctccc cgggctgcgg gccatggcca cggcggagcg gagagccctc ggcatcggct    180
tccagtggct ctctttggcc actctggtgc tcatctgcgc cgggcaaggg ggacgcaggg    240
aggatggggg tccagcctgc tacggcggat ttgacctgta cttcattttg gacaaatcag    300
gaagtgtgct gcaccactgg aatgaaatct attactttgt ggaacagttg gctcacaaat    360
tcatcagccc acagttgaga atgtccttta ttgttttctc cacccgagga acaaccttaa    420
tgaaactgac agaagacaga gaacaaatcc gtcaaggcct agaagaactc cagaaagttc    480
tgccaggagg agacacttac atgcatgaag gatttgaaag ggccagtgag cagatttatt    540
atgaaaacag acaagggtac aggacagcca gcgtcatcat tgctttgact gatggagaac    600
tccatgaaga tctctttttc tattcagaga gggaggctaa taggtctcga gatcttggtg    660
caattgttta ctgtgttggt gtgaaagatt tcaatgagac acagctggcc cggattgcgg    720
acagtaagga tcatgtgttt cccgtgaatg acggctttca ggctctgcaa ggcatcatcc    780
actcaatttt gaagaagtcc tgcatcgaaa ttctagcagc tgaaccatcc accatatgtg    840
caggagagtc atttcaagtt gtcgtgagag gaaacggctt ccgacatgcc cgcaacgtgg    900
acagggtcct ctgcagcttc aagatcaatg actcggtcac actcaatgag aagccctttt    960
ctgtggaaga cacttattta ctgtgtccag cgcctatctt aaaagaagtt ggcatgaaag   1020
ctgcactcca ggtcagcatg aacgatggcc tctcttttat ctccagttct gtcatcatca   1080
ccaccacaca ctgttctgac ggttccatcc tggccatcgc cctgctgatc ctgttcctgc   1140
tcctagccct ggctctcctc tggtggttct ggcccctctg ctgcactgtg attatcaagg   1200
aggtccctcc acccccctgcc gaggagagtg aggaaaataa aataaaataa caagaagaag   1260
aaagaaagaa atcccacaga aacagataac ctaacacagc ccgtgcaacg tattttatac   1320
aatgctctga aaatcatagt ctcaatctag acagtctttt cctctagttc cctgtattca   1380
aatcccagtg tctaacattc aataaatagc tatatgaaat caaaaaaaaa aaaaaaaaaa   1440
aaaaaaaaaa aaaa                                                     1454
```

<210> SEQ ID NO 59
<211> LENGTH: 2828
<212> TYPE: DNA
<213> ORGANISM: Homo sapiens

<400> SEQUENCE: 59

```
agcagccggc acggggacag ccggccgcac aacggatctg caggcgcgga gcaaaatgca     60
cccgccgcgc cgcgcggtcc tgcagccccg ccacggcccc gcggcccgca cccccccggg    120
gcgacagtga gcctctcccg ccaccaccgg gggccgagcg gagggctctc gggtgggaga    180
gcgggaccag atctcgacag ctgttcattt ccaggaagcc accgcagcca gagcgaaagg    240
ggaccttctg ccaccagcgg ggcatcagcc agcggcgcgc atggatttat gaagacactc    300
atgcaagaag tgggcaggac ttggacaaac ttttccaccg gctccgcgtc cgccgctccc    360
```

-continued

```
cgcgcctcgt ctcctttccc ctcctctccc ggcggccgcc gctgcccgcg atggtggccg    420
cgctgctggg cggcggcggc gaggcccgcg gggggacagt gccgggcgcc tggctgtgcc    480
tgatggcgct gctgcagctg ctgggctcgg cgccgcgggg atcggggctg gcgcacggcc    540
gccgcctcat ctgctggcag gcgctgctgc agtgccaggg ggagccggag tgcagctacg    600
cctacaacca gtacgccgag gcgtgcgcgc cggtgctggc gcagcacggc gggggcgacg    660
cgcccggggc cgccgccgcc gctttcccgg cctcggccgc ctctttctcg tcgcgctggc    720
gctgcccgag tcactgcatc tcggccctca ttcagctcaa ccacacgcgc cgcgggcccg    780
ccctggagga ctgtgactgc gcgcaggacg agaactgcaa gtccaccaag cgcgccattg    840
agccgtgcct gccccggacg agcggcggcg gcgcgggcgg ccccggcgcg ggcggggtca    900
tgggctgcac cgaggcccgg cggcgctgcg accgcgacag ccgctgcaac ctggcgctga    960
gccgctacct gacctactgc ggcaaagtct tcaacgggct gcgctgcacg gacgaatgcc   1020
gcaccgtcat tgaggacatg ctggctatgc ccaaggtggc gctgctcaac gactgcgtgt   1080
gcgacggcct cgagcggccc atctgcgagt cggtcaagga gaacatggcc cgcctgtgct   1140
tcggcgccga gctgggcaac ggccccggca gcagcggctc ggacgggggc ctggacgact   1200
actacgatga ggactacgat gacgagcagc gcaccggggg cgcgggtggt gagcagccgc   1260
tggacgacga cgacggcgtc ccgcacccac cgcgcccggg cagcggcgct gctgcatcgg   1320
gcggccgcgg ggacctgccc tatgggcctg ggcgcaggag cagcggcggc ggcggccgct   1380
tggcgccccg gggcgcctgg accccactcg cctccatctt gctgctgctg cttgggccgc   1440
tcttttagcc ctcgcgcccc ccgccgttgg ctgcgggaga gcccgcgtcc cactcccgtg   1500
ctcgcctcga ccccgcgccg ggcacctgtg gcttgggaca gatagaaggg atggttgggg   1560
atacttccca aaactttttc caagtcaact tggtgtagcc ggttccccgg ccacgactct   1620
gggcacttcc cctgaagctc ctctccggag cttgacttct tggacctcct cccccgcccc   1680
aattccaagc tccagaaact cccaactcgt ctgccgtcca gaaagctagc tgcagtgttc   1740
aggacgtccg ggaggaagca agcatgtggg ggacagaaca gtagtcctgg actcgaaagg   1800
gaaggtgctg accagtgggg ccttagcaat ttgaagggtt gggaaggagg aattatattt   1860
gcaaagggc tgtctattag catatttcct ttgagggggc aaaaaaaagt gccagtatcg   1920
acttttacag attgtggcca gtgaggatat tataatccta tgtaaacaga aaagtcccac   1980
ttaccgattc attctttcac tgtttgtatc tgcgcccaga attctcagtg acgtgggggt   2040
gagggtgggt ggcgattgcc ttagagggaa cccctaaatt ggttttggat aagtttgagc   2100
ccttgacctt aatttcattg ctaccactct gatctcttag cacatttctt aggattaagg   2160
gtccaaaaat gctgatctaa ggggttgcca tggtgttgaa caatgcaact ttttatttaa   2220
aaaagctctg cactgccatg tatgaaagtc tctttatgat gtttgttttt ttgtcatttt   2280
tgttctttac atcaagaaat tttatgttta aatatgcgga gaatgtatat tgcctctgct   2340
cctatcaggg ttgctaaacc ctggtacatc gtatataaaa tgtattaaaa ctggggtttg   2400
ttaccagttg ctgtactttg tatatagaat ttttataaat tgtatgcttc agaaataatt   2460
tatttttaaa aagaaattaa aagttttaaa ctcacatcca tattacacct ttccccccctg   2520
aaatgtatag aatccatttg tcatcaggaa tcaaaaccca cagtccattg tgaagtgtgc   2580
tatatttaga acagtcttaa aatgtacagt gtattttata gaattgaagt taacattctt   2640
attttcaaga gaatttatgg acgttgtaga aatgtacaaa tgcatttcca aactgcctta   2700
aacgttgtat ttttatagac atgttttttt aaaaatccta agtttttaaa taactatgga   2760
```

-continued tttgtgtatt ttttttggtt atttgtttta ttaaaacatg tacatcagta aagagtttta 2820
aacaatga 2828

<210> SEQ ID NO 60
<211> LENGTH: 7568
<212> TYPE: DNA
<213> ORGANISM: Homo sapiens

<400> SEQUENCE: 60
gcgcggaggc agggaaccgg agccttggag cgacccaacc cctcgtctcg ctgccctccc 60
gcgcctgcaa cggtgcgcgg agactccggc gaactcagac acccaacggc ggagaacaga 120
agcggcaggc ggcggacgtg gcccggaagc tgcgcgccga acgcagcgca cccgctgccg 180
agcagaggag ccgcgccttt ccccgaccct cggctccagc cccggcgcc tgccgcctcg 240 cagcccctct gcgtcctcgg ctcgggggcc ggcaccggcg atgccgagcg gacgctccag 300
tcctccgacc cgctgaagaa gcagcagccg ctcgcccgga gcctacgggg attgtgcgag 360
cggatcgtgc tcggtggagg ctcgggctgc ggggcgcggg gactccgggg ggcgggggga 420
gggaccgctc tgtcggtgcc cggcgccagc cgcggctttg aagggtctcc ctcccctgcc 480
cttagcagct ctgccacgga ctccgggagg ctgcgggcgg cgtcctgagg gctccccagc 540
agacccaatc ggacttgaga aggtgatcgc tctgctctcc caaccccctt ccctccccat 600
tccccccact taactttttg tctccgttca tccgcggctt cgtcccctcc ccggcagacc 660
cacccgcggc tgtgacaacc gcccggggca tgggcccccc aacacggctc ctagaggccc 720
cgcggcctcg caagatgtga gaggccctcc ccgggcagaa tcggagcttc aggagaggag 780
ctaatacccc gcccccgtc cctcacatca ggcggggtgg aggtgcgcgc tgagccccg 840 cggtgctgag cgtcccggag cgcccaatcc tgggctggaa cgagtagctg gccggaggcg 900
cgccgcggag agccggctgt catgccctat tgatccccct ctgcccccg ccaagtatgt 960 ttgggctgga ccaattcgag ccccaggtca acagcaggaa cgctggccag ggcgagagga 1020
actttaacga gaccggactg agcatgaaca cccactttaa ggccccggct ttccacactg 1080
gggggccccc tggccctgtg gatcctgcta tgagcgcgct ggggcaaccc ccgatcttgg 1140
gcatgaacat ggagccctac ggcttccacg cgcgcggcca ctcggagttg cacgcagggg 1200
ggctgcaagc gcagcctgtg cacggcttct ttggcggcca gcagcctcac cacggccacc 1260
cgggaagtca tcatccccac cagcatcacc cccactttgg gggcaacttc ggtggcccgg 1320
accccggggc ctcgtgcctg cacgggggtc gcctgctcgg ctacggcggc gcagccggag 1380
gcctgggcag ccagccgccc ttcgccgagg gctatgagca catggcggag agccaggggc 1440
ctgagagctt cggcccgcag cgaccgggga acctcccgga cttccacagt tcaggtgcct 1500
ccagccaccg cgtgccggcc ccatgcctgc cgctggacca gagccctaac cgagccgcct 1560
ccttccacgg cctgccgtcc tccagcggct ccgattccca cagtctggag ccacggaggg 1620
tgacgaacca aggagccgtc gactcgctgg aatacaatta ccgggcgagg cgccctcggg 1680
acattttgac atgttttcgc cctctgactc cgaagggcag ctgcctcatt atgcagcggg 1740
tcgccaggtt cctgggggc ggctttcccg gggcgccctc ggccatgccc agagctgcgg 1800
gcatggtggg cttgtccaaa atgcacgccc agccaccgca gcagcagccc cagcagcagc 1860
agcagcccca gcagcagcag cagcatggtg tgttctttga gaggttcagt ggggccagaa 1920
agatgcctgt gggtctggag ccctcagtgg gctccaggca cccgttaatg cagcctcccc 1980

-continued

```
agcaggcccc gccacccccct cagcagcagc ccccgcagca gccgccacag cagcagccgc   2040
cgccgccacc cgggcttcta gtccgacaaa attcgttgcc cgcctgcgct ccctcggccc   2100
cagcagggcg aggcgggcac gcccagcggc ggcctgcagg acggaggccc catgctgccc   2160
agccagcacg cgcaattcga gtatcccatc caccggctgg agaaccggag catgcaccct   2220
tattccgagc ctgttttcag catgcagcat cctcctccgc agcaggcgcc caaccagcgg   2280
ctgcagcatt tcgacgcgcc cccctacatg aacgtggcca agaggcgcgc ttcgactttc   2340
cgggcagcgc gggagtggac cgctgcgctt cgtggaacgg cagcatgcac aacggcgctc   2400
tggataatca cctctcccct tccgcctacc caggcctacc cggcgagttc acaccgcctg   2460
tgcccgacag cttcccttcg ggccgcccc tgcagcatcc ggccccggac caccagtccc   2520
tgcaacagca gcagcagcag cagcagcagc agcaacagca gcagcagcag cagcaacagc   2580
aacagcaaca gcagcagcag cagcagcgcc aaaacgcggc cctcatgatt aagcagatgg   2640
cgtcgcggaa tcagcagcag cggctgcgcc agcccaacct ggctcagcta ggccaccccg   2700
gggacgtggg ccagggcggc ctggtgcatg gcggcccggt gggcggcttg gcccagccga   2760
actttgagcg cgaaggcggc agcacgggcg ccgggcgtct gggcaccttc gagcagcagg   2820
cgccgcactt ggcgcaagag agcgcgtggt tctcaggtcc gcatccgccg cccggagacc   2880
tgctgccccg taggatgggc ggctcgggtc tgcccgctga ctgtggcccg cacgacccca   2940
gcctggcgcc ccctcctccg cctggtggct cgggggtgct gttccggggc cctctgcagg   3000
agccgatgag gatgcccgga gaggccacgt gccgcgctgc cttcaccggc ctgcagttcg   3060
ggggcagtct gggaggcctg ggtcagctgc agtcgcccgg ggcgggcgtg gggctcccca   3120
gcgctgcttc ggagcgccgg cccccgccgc cggactttgc tacgtctgcg ctcgggggcc   3180
agccgggctt tccgtttggt gcagccggcc ggcagtccac gccgcacagc ggtccaggcg   3240
tgaactcgcc ccccagcgcg ggagggggcg gtggcagctc tggtggcggc ggtggcgggg   3300
gtgcctaccc gccgcagcct gatttccagc ccagccagcg cacctcggcc agtaaattgg   3360
gcgcgctctc gctgggctcc ttcaacaagc ccagctccaa ggacaacctg ttcggccaga   3420
gctgcctggc tgcgctctcc accgcttgcc agaacatgat cgccagcctc ggggccccca   3480
acctcaacgt gaccttcaac aagaagaacc cgccagaggg caagaggaaa ctgagccaga   3540
acgagaccga cggcgcggca gtggccggca acccgggctc ggattacttc ccaggaggga   3600
ctgctcctgg gggccccagg acccggaggc cgtccgggac cagtagcagc ggctccaaag   3660
cctcggggcc gcccaaccct ccagcccagg gggacggcac cagcctctcc cccaactaca   3720
ccctggaatc cacgtcgggg aatgacggca agccggtctc cgggggcggc ggccggggac   3780
ggggtcgcag aaaaagggac agtggtcacg tgagccctgg caccttcttt gacaagtact   3840
cggcggctcc ggacagcggg ggcgcacctg ggtgagccc agggcagcag caagcgtcag    3900
gcgcagccgt cgggggaagc tccgcaggcg agacgcgcgg ggcaccgacg ccccacgaaa   3960
aggcgctcac gtcgccatcc tgggggaagg gggctgagtt gctcctgggg gatcagccgg   4020
acctcattgg gtccctggac ggcggggcca agtcggacag tagttcgcca aacgtgggtg   4080
agttcgcctc ggacgaggtg agcacgagct acgccaatga ggacgaggtg tcgtccagct   4140
ctgacaaccc ccaggcacta gttaaagcga gcaggagtcc cctggtgacc ggctcgccca   4200
aactccctcc ccgtggggta ggcgccgggg aacacggacc gaaggcgccc ccgcccgccc   4260
tcggcctggg catcatgtct aactctacct cgacccctga cagctacggc ggcggtgggg   4320
gcccgggcca tccgggcact ccgggcctgg agcaggtccg caccccgacg agcagcagcg   4380
```

-continued

```
gcgccccgcc acccgacgag atccaccccc tggagatcct tcaggcgcag atccagctac   4440
agaggcagca gttcagcatc tccgaggacc agcctctggg gctgaagggt ggcaagaagg   4500
gtgagtgcgc cgtcggggcc tcaggggcgc agaatggcga cagcgagctg ggcagctgct   4560
gctccgaggc ggtcaagagc gccatgagca ccattgacct ggactcgctg atggcagagc   4620
acagcgctgc ctggtacatg cccgctgaca aggccctggt ggacagcgcg gacgacgaca   4680
agacgttggc gccctgggag aaggccaaac cccagaaccc caacagcaaa gaagcccacg   4740
acctccctgc aaacaaggcc tcagcatccc agcctggcag ccacttgcag tgcctgtctg   4800
tccactgcac agacgacgtg ggtgacgcca aggctcgagc ctccgtgccc acctggcggt   4860
ccctgcattc tgacatctcc aacagatttg ggacattcgt ggctgcccta acttgaatga   4920
caagaaagat cccctcctct accaggccct tcctctcccc ctgtctgttt ccttccccct   4980
caaccttacc ccacccctct gttaatttga aagggccact attgctgagt ggatgagttt   5040
tttttttttc ctctaggttg gtacctgctt agtggcatat ggaccggaaa gggttaattt   5100
aaaggggggg aacctcaaaa gtttttttaa aaaagaaact tgtctgccac agtatgttac   5160
cagtgttaac ccttctgcag ttagcaaact tttgcttaag ccttttttcct ctagatactc   5220
cccatgtttc ggtaatcttg gcatacattt tttagatgac ctctttcctt gttttgtttt   5280
catgctgctg tatgtccaag tattgttatt tcataataag acaagagttg ctttcttttt   5340
tattcttttt ccttttctta ccccctcccc ttttattttc tttttgcttt gttcactgct   5400
tattaaaatg gaaatcctgg agaatagtag ttctggaata ttgccgggtg aaagtccaat   5460
tgtcatcaca atgttatata ttgacacccc agtgtcatca gtcaggcagg agccaaacaa   5520
tgaatgcccc tcttaggtat tccgcctggg attttgtttt gtctgttccc taagaaaata   5580
tattttcatt cctgcaaaca cagtgctcag ccttcagttc ccttccactt gagttctctc   5640
ttctcctgct ggaagccgcc cctctctgcg atggacgtga ggacgtgtcc agctctgctc   5700
tgtgggaagg agttggaatg ttcgacagca gtgttttctc tccttttctg ggcctcctcg   5760
caaatgccca ggccctgcat tttcacgctg tgctaagcag cctttggtct gcatgggggga   5820
tggtgtgctc ccagcctgca gtctttggag caaggctgct gcccgtgcct tgggtgctgg   5880
agttggagga ggctgttctc agccctttcc cttttctgaa agctgttcct ggccgggcat   5940
cccagggaag aaggagggga ctgcgtgtat ctcctccacc tctcccattc catccccagt   6000
ccagcctggg caaccccacc cctgggaggg atgaggcacc ctcttgctca gcctgctcag   6060
ccttctctga gcctttgcag ggatctgcag actcctgagg gctagaggac agagaaagag   6120
aatagaatga aatgactttg attcctgcgc cttttagttt tgaactctgg aattcctctg   6180
cccccctcccc aacatttttt tggaatctca ccctgttgca aaactagagc catgtcccaa   6240
gcatctcaca aaggaataac tgctctgagc agagatgagt ggtggttggc aggggcaggc   6300
aactttgggt gctgctgatg cctgcaaaag ccatttatgg cttgtggtgg ggggcacata   6360
gattccccgg tgggttagac aggaagtaac tgatatcact tcacccaaat atataaccgt   6420
gatggttatc tatttaattt cagtttttgt taacgagcgt gtcttactaa aacgctccac   6480
tttgagctcc cccaccccct ccaggtcctc agagtttgca gatctgggct ttctaaagca   6540
agtgacctga aggctctggg ctcaccatac aacacccacg ttgtttattt caaagaactt   6600
ttcagcgaag ggagaggagc tttcagaaaa acctcactct ttcccctccc ttctcccctc   6660
tttccttctg ccggtccttt tggctggggt ctgagtctgc ggttctcgcc tgggcagtct   6720
```

-continued

```
tgacgaggag caaaccccgc cttcagaggg cagacaaagc aggtggcatg aattgatcag   6780

cgagaaaggt gtgagccgag gcagttcctg cgttctgcta caaaaggaat ggaaagggaa   6840

gggaatttcc ccccaccatg ggctgtggga gagttgaccg tattctgggc aagactccat   6900

gacccctctg attctgcagt gtacagctgt ttgagagcct catcatttta cttttgaaac   6960

aggaatgatt tctccttaat tgcttaaggc cggggagcaa agtgtcttaa cttctgtctt   7020

tgactttccc agcgttgagt catcaacact ttgccaatta gctcatggtc ctggcaacct   7080

cagaaacccc tgaagtttta aaaactttct cgctccccac gaccccagaa tgaaacagct   7140

ttaaaaatag ccttaagcaa aaggatgtta tttcattaaa tttggtttaa tggaaagaat   7200

aaaagtaaat gaaaaacaca ccctacacac tagactccga acactggtaa tcagtactgc   7260

atagcaaact ctttgggaaa gaaaacgaaa atgttattgc acatgtaaaa tatgaaaact   7320

taactctgct gtgtgttagg caatcctgta atcttttttg actcttaaaa gaaattcatt   7380

tctgaaatgc ttggttggaa gactgtgaca atagctcatg aaattgagtg ttattttttt   7440

ctttcttttt taaaaaaata tgtaaagtgc agtcttctgt attcctgcat attgtatata   7500

cctgtatatg ttttcctgag cagttaaata acaataaata tgacgttaat ggtgaaaaaa   7560

aaaaaaaa                                                            7568
```

<210> SEQ ID NO 61
<211> LENGTH: 691
<212> TYPE: DNA
<213> ORGANISM: Homo sapiens

<400> SEQUENCE: 61

```
gacccctcac actcacctag ccaccatgga catcgccatc caccacccct ggatccgccg     60

ccccttcttt cctttccact cccccagccg cctctttgac cagttcttcg gagagcacct    120

gttggagtct gatcttttcc cgacgtctac ttccctgagt ccccttctacc ttcggccacc    180

ctccttcctg cgggcaccca gctggtttga cactggactc tcagagatgc gcctggagaa    240

ggacaggttc tctgtcaacc tggatgtgaa gcacttctcc ccagaggaac tcaaagttaa    300

ggtgttggga gatgtgattg aggtgcatgg aaaacatgaa gagcgccagg atgaacatgg    360

tttcatctcc agggagttcc acaggaaata ccggatccca gctgatgtag accctctcac    420

cattacttca tccctgtcat ctgatggggt cctcactgtg aatggaccaa ggaaacaggt    480

ctctggccct gagcgcacca ttcccatcac ccgtgaagag aagcctgctg tcaccgcagc    540

cccaagaaa tagatgccct ttcttgaatt gcattttta aaacaagaaa gtttccccac    600

cagtgaatga aagtcttgtg actagtgctg aagcttatta atgctaaggg caggcccaaa    660

ttatcaagct aataaaatat cattcagcaa c                                   691
```

<210> SEQ ID NO 62
<211> LENGTH: 874
<212> TYPE: DNA
<213> ORGANISM: Homo sapiens

<400> SEQUENCE: 62

```
gcggccgcgt cgaccgctgc gcctgttggg gctgcacctc ggaccagggc ttctgctgca     60

tctgcagcca tgtcgggccg ctcagtgcca catgcccacc cggccaccgc cgagtacgaa    120

tttgccaacc cgagccgcct gggtgagcag cgcttcggag aaggcctcct gccagaagag    180

atcctgaccc ccacactcta ccatggctac tatgtccggc ctcgggccgc cccagctggg    240

gagggcagca gggcaggggc ctccgagctt aggctcagtg agggcaagtt ccaggcattt    300
```

```
ctggatgtga gccactttac cccagacgag gtgactgtga ggactgtgga taacctgctg    360

gaggtgtctg cccggcaccc ccagcgcctg gaccgccacg gcttcgtgtc ccgagagttc    420

tgccgcacct atgtcctgcc tgctgatgtc gacccctggc gagtccgagc tgctctctcc    480

catgatggca tcttaaacct ggaagcacct cggggtggcc gacatttgga cacagaggtc    540

aatgaggtct acatctccct gctccctgcg cctcctgatc cagaggaaga ggaggaggca    600

gccatagttg agccctgatt gccacagacc cagcacccag caaatccctc tctacctccc    660

aaggtgatat gggcagctgc ccaccactcc agaggtagca gcatccttgg gggaagggaa    720

aggtgcatgg tccacaatgt atggtttggt cccatgggac atgtcatagc cttggtttag    780

ttttgggtgg agctgaataa acccaaattt cagggcaaaa aaaaaaaaaa aaaagaaaaa    840

aaaaaaaaaa aaaaaaaaaa gtcgacgcgg ccgc                                874
```

```
<210> SEQ ID NO 63
<211> LENGTH: 2569
<212> TYPE: DNA
<213> ORGANISM: Homo sapiens

<400> SEQUENCE: 63

tccctcgtct ctctcgggca acatggcggg cgtggaggag gtagcggcct ccgggagcca     60

cctgaatggc gacctggatc cagacgacag ggaagaagga gctgcctcta cggctgagga    120

agcagccaag aaaaaaagac gaaagaagaa gaagagcaaa gggccttctg cagcagggga    180

acaggaacct gataaagaat caggagcctc agtggatgaa gtagcaagac agttggaaag    240

atcagcattg gaagataaag aaagagatga agatgatgaa gatggagatg gcgatggaga    300

tggagcaact ggaaagaaga agaaaaagaa gaagaagaag agaggaccaa aagttcaaac    360

agaccctccc tcagttccaa tatgtgacct gtatcctaat ggtgtatttc ccaaaggaca    420

agaatgcgaa tacccaccca cacaagatgg gcgaacagct gcttggagaa ctacaagtga    480

agaaaagaaa gcattagatc aggcaagtga agagatttgg aatgattttc gagaagctgc    540

agaagcacat cgacaagtta gaaaatacgt aatgagctgg atcaagcctg ggatgacaat    600

gatagaaatc tgtgaaaagt tggaagactg ttcacgcaag ttaataaaag agaatggatt    660

aaatgcaggc ctggcatttc ctactggatg ttctctcaat aattgtgctg cccattatac    720

tcccaatgcc ggtgacacaa cagtattaca gtatgatgac atctgtaaaa tagactttgg    780

aacacatata agtggtagga ttattgactg tgcttttact gtcactttta atcccaaata    840

tgatacgtta ttaaaagctg taaaagatgc tactaacact ggaataaagt gtgctggaat    900

tgatgttcgt ctgtgtgatg ttggtgaggc catccaagaa gttatggagt cctatgaagt    960

tgaaatagat gggaagacat atcaagtgaa accaatccgt aatctaaatg gacattcaat   1020

tgggcaatat agaatacatg ctggaaaaac agtgccgatt gtgaaaggag gggaggcaac   1080

aagaatggag gaaggagaag tatatgcaat tgaaaccttt ggtagtacag gaaaaggtgt   1140

tgttcatgat gatatggaat gttcacatta catgaaaaat tttgatgttg gacatgtgcc   1200

aataaggctt ccaagaacaa aacacttgtt aaatgtcatc aatgaaaact ttggaaccct   1260

tgccttctgc cgcagatggc tggatcgctt gggagaaagt aaatacttga tggctctgaa   1320

gaatctgtgt gacttgggca ttgtagatcc atatccacca ttatgtgaca ttaaaggatc   1380

atatacagcg caatttgaac ataccatcct gttgcgtcca acatgtaaag aagttgtcag   1440

cagaggagat gactattaaa cttagtccaa agccacctca acacctttat tttctgagct   1500
```

-continued

```
ttgttggaaa acatgatacc agaattaatt tgccacatgt tgtctgtttt aacagtggac   1560

ccatgtaata cttttatcca tgtttaaaaa agaaggaatt tggacaaagg caaaccgtct   1620

aatgtaatta accaacgaaa aagctttccg gacttttaaa tgctaactgt tttcccctt    1680

cctgtctagg aaaatgctat aaagctcaaa ttagttagga atgacttata cgttttgttt   1740

tgaataccta agagatactt tttggatatt tatattgcca tattcttact tgaatgcttt   1800

gaatgactac atccagttct gcacctatac cctctggtgt tgctttttaa ccttcctgga   1860

atccatttc taaaaaataa agacacattc ttctcagcac cacacaacac ctattccaaa    1920

atcgaccaca tatttggaag taaagctctc ctcagcaaat gtaaaagaac agaaattata   1980

acaaactgtc tctcagacca cagtataacc aaactagaac tcaggattaa gaaactcact   2040

caaaaccaca caactacatg gaaactgaac aacctgctcc tgaatgacta ctggatacat   2100

aacaaaatga aggcagaaat aaagatgttc tttaaaacca atgagaacaa agacacaaca   2160

taccagaatc tctgggacac attcaaagca gtgtgtagag ggaaatttat agcactaaat   2220

gcccacaaga gaaagcagga aatatctaaa attgacaccc taacatcaca attaaaagaa   2280

ctagagaagc aagagcaaac acattgaaaa gctaagagaa ggcaagaaat aactaagatc   2340

agagcagaac tgaaggaaat agagacacaa aaaactcttc aaaaaatcaa tgaatccagg   2400

agctggtttt ttgaaacgat caacaaaatt gatagacact agcaagacta ataaagaaga   2460

aaggagagaa gaatcaaata gaagcaataa aaaatgataa aggggatatc accaccaatc   2520

ccacagaaat aaaccaccat cagagaatac tacaaacacc tctacgcaa               2569
```

<210> SEQ ID NO 64
<211> LENGTH: 3672
<212> TYPE: DNA
<213> ORGANISM: Homo sapiens

<400> SEQUENCE: 64

```
acatgtgcat atttcattcc ccaggcagac attttttaga aatcaataca tgccccaata     60

ttggaaagac ttgttcttcc acggtgacta cagtacatgc tgaagcgtgc cgtttcagcc    120

ctcatttaat tcaatttgta agtagcgcac gagcctctgt gggggaggat aggctgaaaa    180

aaaaaagtgg gctcgtattt atctacagga ctccatatag tcatatatag gcatataaat    240

ctatgctttt tctttgtttt tttctttctt cctttctttc aaaggtttgc attaactttt    300

caaagtagtt cctatagggg cattgaggag cttcctcatt ctgggaaaac tgagaaaacc    360

catattctcc taatacaacc cgtaatagca tttttgcctg cctcgaggca gagtttcccg    420

tgagcaataa actcagcttt tttgtggggc acagtactgg atttgacagt gattccccac    480

gtgtgttcat ctgcacccac cgagccaggc agaggccagc cctccgtggt gcacacagca    540

cgcgcctcag tccatcccat tttagtcttt aaaccctcag gaagtcacag tctccggaca    600

ccacaccaca ttgagcccaa caggtccacg atggatccac ctagtcccac cccagccttt    660

ttctttcatc tgaacagaat gtgcattttt ggaagcctcc ctcactctcc atgctggcag    720

agcaggaggg agactgaagt aagagatggc agagggagat ggtggcaaaa aggtttagat    780

gcaggagaac agtaagatgg atggttccgg ccagagtcga tgtggggagg aacagagggc    840

tgaagggaga gggggctgac tgttccattc tagctttggc acaaagcagc agaaaggggg    900

aaaagccaat agaaatttcc ttagcttccc caccatatgt attttcatgg atttgagagg    960

aaagagagga aaatggggga atgggttgca aaatagaaat gagcttaatc caggccgcag   1020

agccagggaa ggtgagtaac cttaggaggg tgctagactt tagaagccag ataggaagaa   1080
```

-continued

```
tcagtctaaa ctggccatgc tttggaaggg acaagactat gtgctccgct gcccaccttc   1140
agcctgcaat gagggactga ggcccacgag tctttccagc tcttcctcca ttctggccag   1200
tccctgcatc ctccctgggg tggaggatgg aaggaaagct gggacaagca gggaacgcat   1260
gattcaggga tgctgtcact cggcagccag attccgaaac tcccattctc caatgacttc   1320
ctcaaccaat gggtggcctt gtgactgttc tttaaggctg aagatatcca ggaaaggggg   1380
cttggacact ggccaaggag acccccttcgt gctgtggaca cagctctctt cactctttgc   1440
tcatggcatg acacagcgga gaccgcctcc aacaacgaat ttggggctac gaagaggaat   1500
agcgaaaaag caaatctgtt tcaactgatg ggaaccctat agctatagaa cttgggggct   1560
atctcctatg cccctggaca ggacagttgg ctggggacag gagaagtgct caatcttcat   1620
gagacaaagg ggcccgatca aggcagccac aaggccttga cctgccgagt cagcatgccc   1680
catctctctc gacagctgtc ccctaaaccc aactcacgtt tctgtatgtc ttaggccagt   1740
atcccaaacc tcttccacgt cactgttctt tccacccatt ctccctttgc atcttgagca   1800
gttatccaac taggatctgc caagtggata ctggggtgcc actcccctga gaaaagactg   1860
agccaggaac tacaagctcc ccccacattc ctcccagcct ggacctaatt cttgagaggg   1920
gctctctctt cacggactgt gtctggactt tgagcaggct tctgcccctt gcgttggctc   1980
tttgctgcca gccatcaggt gggggattag agcctggtgt aagtgcgcca gactcttccg   2040
gtttccaaag ttcgtgcctg cgaacccaaa cctgtgagtc tcttctgcat gcaggagttt   2100
ctcctgggca gctggtcact ccccagagaa gctgggcctt catggacaca tggaactaag   2160
cctcccaaat gggagttctg gctgagccca gggtggggag atcctgggaa gggaggcact   2220
ggaggaagac ggcacctctt cccccatggc agggtgtgag ggaggcaggt ttggaatggt   2280
gcgagtatgg caatctaagc aggggtctgg tctctttgac tccaggctcg ctttggccga   2340
ctgtctgctc acccagagac cttggactcc ggactatcca tggctccgaa tctaagtgct   2400
gcccactccc atgctcacac ccacagaagg tcttcccatc ccctttagat tcgtgcctca   2460
ctccaccagt gaggaagatg cctctgtctt tcccacgact gccaggagat agggaagccc   2520
agccaggact gaccctcctt cctccagcct gccctgaccc acctggcaaa gcagggcaca   2580
tggggaggaa gagactggaa cctttctttg acagccaggc ctagacagac aggcctgggg   2640
acactggccc atgaggggag gaaggcaggc gcacgaggtc cagggaggcc cttttctgat   2700
catgcccctt ctctcccacc ccatctcccc accaccacct ctgtggcctc catggtaccc   2760
ccacagggct ggcctcccct agagggtggg cctcaaccac ctcgtcccgc cacgcaccgg   2820
ttagtgagac agggctgcca cgcaaccgcc aagccccccct caaggtggga cagtaccccg   2880
gacccatcca ctcactcctg agaggctccg gcccagaatg ggaacctcag agaagagctc   2940
taaggagaag aaaccccata gcgtcagaga ggatatgtct ggcttccaag agaaaggagg   3000
ctccgttttg caaagtggag gagggacgag ggacaggggt ttcaccagcc agcaacctgg   3060
gccttgtact gtctgtgttt ttaaaaccac taaagtgcaa gaattacatt gcactgtttc   3120
tccacttttt attttctctt aggcttttgt ttctatttca aacatacttt cttggttttc   3180
taatggagta tatagtttag tcatttcaca gactctggcc tcctctcctg aaatcctttt   3240
ggatggggaa agggaaggtg gggagggtcc gaggggaagg ggaccccagc ttccctgtgc   3300
ccgctcaccc cactccacca gtccccggtc gccagccgga gtctcctctc taccgccact   3360
gtcacaccgt agcccacatg gatagcacag ttgtcagaca agattccttc agattccgag   3420
```

```
ttgctaccgg ttgttttcgt tgttgttgtt gttgttttc tttttctttt ttttttgaa   3480

gacagcaata accacagtac atattactgt agttctctat agttttacat acattcatac   3540

cataactctg ttctctcctc ttttttgttt tcaactttaa aaacaaaaat aaacgatgat   3600

aatctttact ggtgaaaagg atggaaaaat aaatcaacaa atgcaaccag tttgtgagaa   3660

aaaaaaaaaa aa                                                        3672
```

<210> SEQ ID NO 65
<211> LENGTH: 1826
<212> TYPE: DNA
<213> ORGANISM: Homo sapiens

<400> SEQUENCE: 65

```
agtctgcact ggagctgcct ggtgaccaga agtttggagt ccgctgacgt cgccgcccag     60

atggcctcca ggctgaccct gctgaccctc ctgctgctgc tgctggctgg ggatagagcc    120

tcctcaaatc caaatgctac cagctccagc tcccaggatc cagagagttt gcaagacaga    180

ggcgaaggga aggtcgcaac aacagttatc tccaagatgc tattcgttga acccatcctg    240

gaggtttcca gcttgccgac aaccaactca acaaccaatt cagccaccaa aataacagct    300

aataccactg atgaacccac cacacaaccc accacagagc ccaccaccca acccaccatc    360

caacccaccc aaccaactac ccagctccca acagattctc ctacccagcc cactactggg    420

tccttctgcc caggacctgt tactctctgc tctgacttgg agagtcattc aacagaggcc    480

gtgttggggg atgctttggt agatttctcc ctgaagctct accacgcctt ctcagcaatg    540

aagaaggtgg agaccaacat ggccttttcc ccattcagca tcgccagcct ccttacccag    600

gtcctgctcg gggctgggca gaacaccaaa acaaacctgg agagcatcct ctcttacccc    660

aaggacttca cctgtgtcca ccaggccctg aagggcttca cgaccaaagg tgtcacctca    720

gtctctcaga tcttccacag cccagacctg gccataaggg acacctttgt gaatgcctct    780

cggaccctgt acagcagcag ccccagagtc ctaagcaaca acagtgacgc caacttggag    840

ctcatcaaca cctgggtggc caagaacacc aacaacaaga tcagccggct gctagacagt    900

ctgccctccg atacccgcct tgtcctcctc aatgctatct acctgagtgc caagtggaag    960

acaacatttg atcccaagaa aaccagaatg gaaccctttc acttcaaaaa ctcagttata   1020

aaagtgccca tgatgaatag caagaagtac cctgtggccc atttcattga ccaaactttg   1080

aaagccaagg tggggcagct gcagctctcc cacaatctga gtttggtgat cctggtaccc   1140

cagaacctga aacatcgtct tgaagacatg gaacaggctc tcagcccttc tgttttcaag   1200

gccatcatgg agaaactgga gatgtccaag ttccagccca ctctcctaac actaccccgc   1260

atcaaagtga cgaccagcca ggatatgctc tcaatcatgg agaaattgga attcttcgat   1320

ttttcttatg accttaacct gtgtgggctg acagaggacc cagatcttca ggtttctgcg   1380

atgcagcacc agacagtgct ggaactgaca gagactgggg tggaggcggc tgcagcctcc   1440

gccatctctg tggcccgcac cctgctggtc tttgaagtgc agcagccctt cctcttcgtg   1500

ctctgggacc agcagcacaa gttccctgtc ttcatggggc gagtatatga ccccagggcc   1560

tgagacctgc aggatcaggt tagggcgagc gctacctctc cagcctcagc tctcagttgc   1620

agccctgctg ctgcctgcct ggacttgccc ctgccacctc ctgcctcagg tgtccgctat   1680

ccaccaaaag ggctcctgag ggtctgggca agggacctgc ttctattagc ccttctccat   1740

ggccctgcca tgctctccaa accacttttt gcagctttct ctagttcaag ttcaccagac   1800

tctataaata aaacctgaca gaccat                                        1826
```

-continued

<210> SEQ ID NO 66
<211> LENGTH: 5489
<212> TYPE: DNA
<213> ORGANISM: Homo sapiens

<400> SEQUENCE: 66

```
ggctgagttt tatgacgggc ccggtgctga agggcaggga acaacttgat ggtgctactt     60
tgaactgctt ttcttttctc ctttttgcac aaagagtctc atgtctgata tttagacatg    120
atgagctttg tgcaaaaggg gagctggcta cttctcgctc tgcttcatcc cactattatt    180
ttggcacaac aggaagctgt tgaaggagga tgttcccatc ttggtcagtc ctatgcggat    240
agagatgtct ggaagccaga accatgccaa atatgtgtct gtgactcagg atccgttctc    300
tgcgatgaca taatatgtga cgatcaagaa ttagactgcc ccaacccaga aattccattt    360
ggagaatgtt gtgcagtttg cccacagcct ccaactgctc ctactcgccc tcctaatggt    420
caaggacctc aaggccccaa gggagatcca ggccctcctg gtattcctgg gagaaatggt    480
gaccctggta ttccaggaca accagggtcc cctggttctc ctggcccccc tggaatctgt    540
gaatcatgcc ctactggtcc tcagaactat tctccccagt atgattcata tgatgtcaag    600
tctggagtag cagtaggagg actcgcaggc tatcctggac cagctggccc cccaggccct    660
cccggtcccc ctggtacatc tggtcatcct ggttcccctg gatctccagg ataccaagga    720
ccccctggtg aacctgggca agctggtcct tcaggccctc caggacctcc tggtgctata    780
ggtccatctg gtcctgctgg aaaagatgga gaatcaggta gacccggacg acctggagag    840
cgaggattgc ctggacctcc aggtatcaaa ggtccagctg ggatacctgg attccctggt    900
atgaaaggac acagaggctt cgatggacga aatggagaaa agggtgaaac aggtgctcct    960
ggattaaagg gtgaaaatgg tcttccaggc gaaaatggag ctcctggacc catgggtcca   1020
agaggggctc ctggtgagcg aggacggcca ggacttcctg gggctgcagg tgctcggggt   1080
aatgacggtg ctcgaggcag tgatggtcaa ccaggccctc ctggtcctcc tggaactgcc   1140
ggattccctg gatcccctgg tgctaagggt gaagttggac ctgcagggtc tcctggttca   1200
aatggtgccc ctggacaaag aggagaacct ggacctcagg gacacgctgg tgctcaaggt   1260
cctcctggcc ctcctgggat taatggtagt cctggtggta aaggcgaaat gggtcccgct   1320
ggcattcctg gagctcctgg actgatggga gcccggggtc ctccaggacc agccggtgct   1380
aatggtgctc ctggactgcg aggtggtgca ggtgagcctg gtaagaatgg tgccaaagga   1440
gagcccggac cacgtggtga acgcggtgag gctggtattc caggtgttcc aggagctaaa   1500
ggcgaagatg gcaaggatgg atcacctgga gaacctggtg caaatgggct tccaggagct   1560
gcaggagaaa ggggtgcccc tgggttccga ggacctgctg gaccaaatgg catcccagga   1620
gaaaagggtc ctgctggaga gcgtggtgct ccaggccctg cagggcccag aggagctgct   1680
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaagg acccccaggg   1980
cctactgggc ctggtggtga caaaggagac acaggacccc ctggtccaca aggattacaa   2040
ggcttgcctg gtacaggtgg tcctccagga gaaaatggaa aacctgggga accaggtcca   2100
```

-continued

```
aagggtgatg ccggtgcacc tggagctcca ggaggcaagg gtgatgctgg tgcccctggt   2160
gaacgtggac ctcctggatt ggcaggggcc ccaggactta gaggtggagc tggtcccccct  2220
ggtcccgaag gaggaaaggg tgctgctggt cctcctgggc cacctggtgc tgctggtact   2280
cctggtctgc aaggaatgcc tggagaaaga ggaggtcttg gaagtcctgg tccaaagggt   2340
gacaagggtg aaccaggcgg cccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
gaaactggcc ctccaggacc tgctggtttc cctggtgctc ctggacagaa tggtgaacct   2580
ggtggtaaag gagaaagagg ggctccgggt gagaaaggtg aaggaggccc tcctggagtt   2640
gcaggacccc ctggaggttc tggacctgct ggtcctcctg gtccccaagg tgtcaaaggt   2700
gaacgtggca gtcctggtgg acctggtgct gctggcttcc ctggtgctcg tggtcttcct   2760
ggtcctcctg gtagtaatgg taacccagga cccccaggtc ccagcggttc tccaggcaag   2820
gatgggcccc caggtcctgc gggtaacact ggtgctcctg gcagccctgg agtgtctgga   2880
ccaaaaggtg atgctggcca accaggagag aagggatcgc ctggtgccca gggcccacca   2940
ggagctccag gcccacttgg gattgctggg atcactggag cacggggtct tgcaggacca   3000
ccaggcatgc caggtcctag gggaagccct ggccctcagg gtgtcaaggg tgaaagtggg   3060
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240
gcccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc cagaggacct   3540
gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
gccgctgcca ttgctgggat tggaggtgaa aaagctggcg gttttgcccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tggggaaaca   4020
tgcataagtg ccaatccttt gaatgttcca cggaaacact ggtggacaga ttctagtgct   4080
gagaagaaac acgtttggtt tggagagtcc atggatggtg gttttcagtt tagctacggc   4140
aatcctgaac ttcctgaaga tgtccttgat gtgcagctgg cattccttcg acttctctcc   4200
agccgagctt cccagaacat cacatatcac tgcaaaaata gcattgcata catggatcag   4260
gccagtggaa atgtaaagaa ggccctgaag ctgatggggt caaatgaagg tgaattcaag   4320
gctgaaggaa atagcaaatt cacctacaca gttctggagg atggttgcac gaaacacact   4380
ggggaatgga gcaaaacagt ctttgaatat cgaacacgca aggctgtgag actacctatt   4440
gtagatattg caccctatga cattggtggt cctgatcaag aatttggtgt ggacgttggc   4500
```

-continued

```
cctgtttgct ttttataaac caaactctat ctgaaatccc aacaaaaaaa atttaactcc   4560

atatgtgttc ctcttgttct aatcttgtca accagtgcaa gtgaccgaca aaattccagt   4620

tatttatttc caaaatgttt ggaaacagta taatttgaca aagaaaaatg atacttctct   4680

tttttgctg ttccaccaaa tacaattcaa atgctttttg ttttattttt ttaccaattc   4740

caatttcaaa atgtctcaat ggtgctataa taaataaact tcaacactct ttatgataac   4800

aacactgtgt tatattcttt gaatcctagc ccatctgcag agcaatgact gtgctcacca   4860

gtaaaagata acctttcttt ctgaaatagt caaatacgaa attagaaaag ccctccctat   4920

tttaactacc tcaactggtc agaaacacag attgtattct atgagtccca gaagatgaaa   4980

aaaattttat acgttgataa aacttataaa tttcattgat taatctcctg gaagattggt   5040

ttaaaaagaa aagtgtaatg caagaattta aagaaatatt tttaaagcca caattatttt   5100

aatattggat atcaactgct tgtaaaggtg ctcctctttt ttcttgtcat tgctggtcaa   5160

gattactaat atttgggaag gctttaaaga cgcatgttat ggtgctaatg tactttcact   5220

tttaaactct agatcagaat tgttgacttg cattcagaac ataaatgcac aaaatctgta   5280

catgtctccc atcagaaaga ttcattggca tgccacaggg attctcctcc ttcatcctgt   5340

aaaggtcaac aataaaaacc aaattatggg gctgcttttg tcacactagc atagagaatg   5400

tgttgaaatt taactttgta agcttgtatg tggttgttga tcttttttt ccttacagac   5460

acccataata aaatatcata ttaaaattc                                   5489
```

```
<210> SEQ ID NO 67
<211> LENGTH: 5222
<212> TYPE: DNA
<213> ORGANISM: Homo sapiens

<400> SEQUENCE: 67

ttctgcccgc cgccgccgct gccgagcgcc gcctttgttc cctgcaggaa gggcgagcgc     60

gcgggccagc gctcagccag cgcctcacga cccttcgtcc tccgctaagc tccaacgctc    120

tgctcgacta gccgcgcgcc ttccggggct ccgcagaccc gcgagatggc accaaggagg    180

aacaacgggc agtgctggtg tctgctgatg ctgctctcgg tctccacgcc cctccctgct    240

gtcacccaga cccgcggtgc gacagagact gcttcccagg gtcacctgga cctcacgcag    300

ctcatcggtg tcccgctgcc ctcgtccgta tcctttgtca caggctatgg tggcttcccg    360

gcctacagtt tcgggcctgg tgccaatgtt ggccgcccag ccaggactct catcccatcc    420

accttcttca gggacttcgc catcagggtc gtggtgaagc ccagcagcac ccgtggtggc    480

gtgctcttcg ccatcactga cgccttccag aaggtcatct acctgggcct gcggctctca    540

ggtgtggagg acggccacca gcggatcatc ctctactaca cggagccagg ctcccatgtg    600

tcccaagaag ctgctgcctt ctcggtgcct gtgatgaccc acaggtggaa ccgcttcgcc    660

atgattgtcc agggtgagga agtgaccctc ctcgtgaact gtgaggagca cagccgcatc    720

cccttccagc ggtcctccca ggctttggct tttgagtcca gcgctggaat cttcatgggc    780

aatgcaggag ctacagggct cgagagattc actggctccc tccagcagct caccgtgcac    840

cccgacccca ggactcccga ggagctgtgt gaccctgaag agtcctcggc atctggagag    900

accagtgggc tgcaggaggc agacggagta gctgagatct tagaagccgt cacctacact    960

caagcctcgc ccaaagaagc aaaagttgaa cccataaaca cacctccaac tccatcctcc   1020

ccctttgaag acatggaact ttctggtgaa cctgtacccg aggggaccct ggaaaccacc   1080
```

-continued

```
aacatgagca tcatccagca cagcagcccc aaacaagggt ctggtgagat cctgaatgac   1140

acactggagg gggttcattc tgtggatggt gaccccatta ctgacagcgg ctcaggggct   1200

ggggccttcc ttgacattgc tgaagaaaag aatttagcag caacagcagc ggggctggcc   1260

gaggtgccca tcagcactgc tggagaagca gaggccagca gtgtgcccac cgggggacca   1320

accctctcta tgtccacgga gaacccagag gaaggggtca ctccaggtcc agataatgaa   1380

gagcgtttac gagcaacagc agcaggggag gccgaggcac tcgccagcat gcctggggaa   1440

gtggaggcca gtggtgtggc ccccggggag ctggacctct ccatgtccgc ccagagcctc   1500

ggggaagagg ccactgtggg tccaagcagt gaagacagtt taacaacagc tgcagctgca   1560

accgaagtgt ccctcagtac ttttgaggat gaggaagcca gtggggtccc cacagatggc   1620

ctggctcccc tcacagccac catggcccct gagcgggcag tcacttctgg tcctggtgat   1680

gaagaagact tggcagcagc cacaacagag gagcccctca tcacagctgg gggtgaagag   1740

tccggcagcc ctcccccctga tggccaccg ctgcccctgc ccacagtggc tcctgaaaga   1800

tggatcactc cagctcaaag agaacatgtg ggaatgaaag gacaggctgg gcccaaagga   1860

gaaaagggtg atgctgggga ggagcttcct ggccctcctg aaccttctgg gcctgttgga   1920

cccacggcag gagcagaagc agagggctct ggcctaggct ggggctcgga cgtcggctct   1980

ggctctggtg acctggtggg cagtgagcag ctgctgagag gtcctccagg acccccaggg   2040

ccacctggct tacctgggat tccaggaaaa ccaggaactg atgttttcat gggaccccct   2100

ggatctcctg gagaggatgg acctgctggt gaacctgggc ccccgggccc tgagggacag   2160

cctggagttg atggagccac cggccttccc gggatgaaag gggagaaggg agcaagaggg   2220

cctaatggct cagttggtga aaagggtgac cctggcaaca gaggcttacc tggacccccg   2280

gggaaaaagg gacaagctgg ccctcctggg gtcatgggac cccagggcc tcctggaccc   2340

cctgggcccc caggccctgg atgcacaatg ggacttggat tcgaggatac cgaaggctct   2400

ggaagcaccc agctattgaa tgaacccaaa ctctccagac caacggctgc aattggtctc   2460

aaaggagaga aaggagaccg gggacccaag ggagaaaggg ggatggatgg agccagtatt   2520

gtgggacccc ctgggccgag agggccacct gggcacatca aggtcttgtc taattccttg   2580

atcaatatca cccatggatt catgaatttc tcggacattc ctgagctggt ggggcctccg   2640

gggccggacg ggttgcctgg gctgccagga tttccaggtc ctagaggacc aaaaggtgac   2700

actggtttac ctggctttcc aggactaaaa ggagaacagg gcgagaaggg agagccgggt   2760

gccatcctga cagaggacat tcctctggaa aggctgatgg ggaaaaaggg tgaacctgga   2820

atgcatggag ccccaggacc aatggggccc aaaggaccac caggacataa aggagaattt   2880

ggccttcccg ggcgacctgg tcgcccagga ctgaatggcc tcaagggtac caaaggagat   2940

ccaggggtca ttatgcaggg cccacctggc ttacctggcc ctccaggccc ccctgggcca   3000

cctggagctg tgattaacat caaaggagcc attttcccaa tacccgtccg accacactgc   3060

aaaatgccag ttgatactgc tcatcctggg agtccagagc tcatcacttt tcacggtgtt   3120

aaaggagaga aaggatcctg ggtcttcct ggctcaaagg gagaaaaagg cgaccaggga   3180

gcccagggac caccaggtcc tccacttgat ctagcttacc tgagacactt tctgaacaac   3240

ttgaaggggg agaatggaga caaggggttc aaaggtgaaa aaggagaaaa aggagacatt   3300

aatggcagct tccttatgtc tgggcctcca ggcctgcccg gaaatccagg cccggctggc   3360

caaaaagggg agacagtcgt tgggccccaa ggacccccag gtgctcctgg tctgcctggg   3420

ccacctggct ttggaagacc tggtgatcct gggccaccgg ggcccccggg gccaccagga   3480
```

-continued

```
cctccagcta tcctgggagc agctgtggcc cttccaggtc cccctggccc tccaggacag   3540
ccagggcttc ccggatccag aaacctggtc acagcattca gcaacatgga tgacatgctg   3600
cagaaagcgc atttggttat agaaggaaca ttcatctacc tgagggacag cactgagttt   3660
ttcattcgtg ttagagatgg ctggaaaaaa ttacagctgg gagaactgat ccccattcct   3720
gccgacagcc ctccaccccc tgcgctttcc agcaacccac atcagcttct gcctccacca   3780
aaccctattt caagtgccaa ttatgagaag cctgctctgc atttggctgc tctgaacatg   3840
ccatttctgg gggacattcg agctgatttt cagtgcttca agcaggccag agctgcagga   3900
ctgttgtcca cctaccgagc attcttatct tcccatttgc aagatctgtc caccattgtg   3960
aggaaagcag agagatacag ccttcccata gtgaacctca agggccaagt actttttaat   4020
aattgggact caattttttc tggccacgga ggtcagttca atatgcatat tccaatatac   4080
tcctttgatg gtcgagacat aatgacagat ccttcttggc cccagaaagt catttggcat   4140
ggctccagcc cccatggcgt ccgccttgtg gataactact gtgaagcatg gcgaaccgcg   4200
gacacagcgg tcacgggact tgcctccccg ctgagcacgg ggaagattct ggaccagaaa   4260
gcatacagct gtgctaatcg gctaattgtc ctatgtatcg aaaacagttt catgacagac   4320
gctaggaagt aatggccttc tgatgattct taaagagttt tcaatttttt cttatgtgaa   4380
gagttgacac tgaaatctaa aatgtttaat tgttgtaaat attacagttt tttttttttt   4440
actacatatt ctttacaaca gcaaccaaag aaaacatacc tcaatacact caaaactgaa   4500
gacatagagg actcagatca aagacaaaat ctgatccata tattggtgct agattctgca   4560
ggaaacccca gcagtgtgaa cgcatcccaa cataggttaa gagcaagttg aaaacaaagg   4620
ccagattctg ccactgcatc cttcagacag ttatatcctc cttttaaacc attgttgttg   4680
agtgtaagat gtccttcatg ttttcttata aagtcagtgt ttagaaatgt tacccttttct  4740
aagttatata cagatcaaat gctttttttct ttcacgtaca tccatcattt gcaactgctg  4800
ttcgtacaca gaaacaggac tgctcaaatg atcctatttg tattttctga tgctatcaga   4860
ctctaatgtt tttttcccta aaatattatt gccatcatgc tttaggaatt tttatatttt   4920
tacacaatca tattttagta tggtgtctgt ttatgtaact ctgacttgct ggaaaagttg   4980
aaactccaaa taatctgaaa ctagaaaaga aatagcacat aattactacc ttccccttgg   5040
cggctctcct cccccaaccc ccaccccaca attttatgac ttccatttgg caattgttga   5100
attataactg cgactgaaac aaacaggttc atagagatga attttctgag aaacatatat   5160
ctacatgttg tataattgga ttttttttcc atgtaagtga acataaaaac atcttttccg   5220
gg                                                                  5222
```

<210> SEQ ID NO 68
<211> LENGTH: 4079
<212> TYPE: DNA
<213> ORGANISM: Homo sapiens

<400> SEQUENCE: 68

```
ggagcggcgg gcgggcggga gggctggcgg ggcgaacgtc tgggagacgt ctgaaagacc     60
aacgagactt tggagaccag agacgcgcct ggggggacct ggggcttggg gcgtgcgaga    120
tttcccttgc attcgctggg agctcgcgca gggatcgtcc catggccggg gctcggagcc    180
gcgacccttg gggggcctcc gggatttgct acctttttgg ctccctgctc gtcgaactgc    240
tcttctcacg ggctgtcgcc ttcaatctgg acgtgatggg tgccttgcgc aaggagggcg    300
```

-continued

```
agccaggcag cctcttcggc ttctctgtgg ccctgcaccg gcagttgcag ccccgacccc    360
agagctggct gctggtgggt gctccccagg ccctggctct tcctgggcag caggcgaatc    420
gcactggagg cctcttcgct tgcccgttga gcctggagga gactgactgc tacagagtgg    480
acatcgacca gggagctgat atgcaaaagg aaagcaagga gaaccagtgg ttgggagtca    540
gtgttcggag ccaggggcct gggggcaaga ttgttacctg tgcacaccga tatgaggcaa    600
ggcagcgagt ggaccagatc ctggagacgc gggatatgat tggtcgctgc tttgtgctca    660
gccaggacct ggccatccgg gatgagttgg atggtgggga atggaagttc tgtgagggac    720
gcccccaagg ccatgaacaa tttgggttct gccagcaggg cacagctgcc gccttctccc    780
ctgatagcca ctacctcctc tttggggccc caggaaccta taattggaag gggttgcttt    840
ttgtgaccaa cattgatagc tcagaccccg accagctggt gtataaaact ttggaccctg    900
ctgaccggct cccaggacca gccggagact tggccctcaa tagctactta ggcttctcta    960
ttgactcggg gaaaggtctg gtgcgtgcag aagagctgag ctttgtggct ggagcccccc   1020
gcgccaacca caagggtgct gtggttatcc tgcgcaagga cagcgccagt cgcctggtgc   1080
ccgaggttat gctgtctggg gagcgcctga cctccggctt tggctactca ctggctgtgg   1140
ctgacctcaa cagtgatggc tggccagacc tgatagtggg tgcccccctac ttctttgagc   1200
gccaagaaga gctgggggt gctgtgtatg tgtacttgaa ccagggggt cactgggctg   1260
ggatctcccc tctccggctc tgcggctccc ctgactccat gttcgggatc agcctggctg   1320
tcctggggga cctcaaccaa gatggctttc cagatattgc agtgggtgcc ccctttgatg   1380
gtgatgggaa agtcttcatc taccatggga gcagcctggg ggttgtcgcc aaaccttcac   1440
aggtgctgga gggcgaggct gtgggcatca agagcttcgg ctactccctg tcaggcagct   1500
tggatatgga tgggaaccaa taccctgacc tgctggtggg ctccctggct gacaccgcag   1560
tgctcttcag ggccagaccc atcctccatg tctcccatga ggtctctatt gctccacgaa   1620
gcatcgacct ggagcagccc aactgtgctg gcggccactc ggtctgtgtg gacctaaggg   1680
tctgtttcag ctacattgca gtccccagca gctatagccc tactgtggcc ctggactatg   1740
tgttagatgc ggacacagac cggaggctcc ggggccaggt tccccgtgtg acgttcctga   1800
gccgtaacct ggaagaaccc aagcaccagg cctcgggcac cgtgtggctg aagcaccagc   1860
atgaccgagt ctgtggagac gccatgttcc agctccagga aaatgtcaaa gacaagcttc   1920
gggccattgt agtgaccttg tcctacagtc tccagacccc tcggctccgg cgacaggctc   1980
ctggccaggg gctgcctcca gtggccccca tcctcaatgc ccaccagccc agcacccagc   2040
gggcagagat ccacttcctg aagcaaggct gtggtgaaga caagatctgc cagagcaatc   2100
tgcagctggt ccacgcccgc ttctgtaccc gggtcagcga cacggaattc caacctctgc   2160
ccatggatgt ggatggaaca acagccctgt ttgcactgag tgggcagcca gtcattggcc   2220
tggagctgat ggtcaccaac ctgccatcgg acccagccca gccccaggct gatggggatg   2280
atgcccatga agcccagctc ctggtcatgc ttcctgactc actgcactac tcaggggtcc   2340
gggccctgga ccctgcggag aagccactct gcctgtccaa tgagaatgcc tcccatgttg   2400
agtgtgagct ggggaacccc atgaagagag gtgcccaggt caccttctac ctcatcctta   2460
gcacctccgg gatcagcatt gagaccacgg aactggaggt agagctgctg ttggccacga   2520
tcagtgagca ggagctgcat ccagtctctg cacgagcccg tgtcttcatt gagctgccac   2580
tgtccattgc aggaatggcc attccccagc aactcttctt ctctggtgtg gtgaggggcg   2640
agagagccat gcagtctgag cgggatgtgg gcagcaaggt caagtatgag gtcacggttt   2700
```

-continued

```
ccaaccaagg ccagtcgctc agaaccctgg gctctgcctt cctcaacatc atgtggcctc   2760

atgagattgc caatgggaag tggttgctgt acccaatgca ggttgagctg gagggcgggc   2820

aggggcctgg gcagaaaggg ctttgctctc ccaggcccaa catcctccac ctggatgtgg   2880

acagtaggga taggaggcgg cgggagctgg agccacctga gcagcaggag cctggtgagc   2940

ggcaggagcc cagcatgtcc tggtggccag tgtcctctgc tgagaagaag aaaaacatca   3000

ccctggactg cgcccggggc acggccaact gtgtggtgtt cagctgccca ctctacagct   3060

ttgaccgcgc ggctgtgctg catgtctggg gccgtctctg gaacagcacc tttctggagg   3120

agtactcagc tgtgaagtcc ctggaagtga ttgtccgggc caacatcaca gtgaagtcct   3180

ccataaagaa cttgatgctc cgagatgcct ccacagtgat cccagtgatg gtatacttgg   3240

accccatggc tgtggtggca gaaggagtgc cctggtgggt catcctcctg gctgtactgg   3300

ctgggctgct ggtgctagca ctgctggtgc tgctcctgtg gaagatggga ttcttcaaac   3360

gggcgaagca ccccgaggcc accgtgcccc agtaccatgc ggtgaagatt cctcgggaag   3420

accgacagca gttcaaggag gagaagacgg gcaccatcct gaggaacaac tggggcagcc   3480

cccggcggga gggcccggat gcacacccca tcctggctgc tgacgggcat cccgagctgg   3540

gccccgatgg gcatccaggg ccaggcaccg cctaggttcc catgtcccag cctggcctgt   3600

ggctgccctc catcccttcc ccagagatgg ctccttggga tgaagagggt agagtgggct   3660

gctggtgtcg catcaagatt tggcaggatc ggcttcctca ggggcacaga cctctcccac   3720

ccacaagaac tcctcccacc caacttcccc ttagagtgct gtgagatgag agtgggtaaa   3780

tcagggacag ggccatgggg tagggtgaga agggcagggg tgtcctgatg caaaggtggg   3840

gagaagggat cctaatccct tcctctccca ttcaccctgt gtaacaggac cccaaggacc   3900

tgcctccccg gaagtgcctt aacctagagg gtcggggagg aggttgtgtc actgactcag   3960

gctgctcctt ctctagtttc ccctctcatc tgaccttagt ttgctgccat cagtctagtg   4020

gtttcgtggt ttcgtctatt tattaaaaaa tatttgagaa caaaaaaaaa aaaaaaaaa    4079
```

<210> SEQ ID NO 69
<211> LENGTH: 6276
<212> TYPE: DNA
<213> ORGANISM: Homo sapiens

<400> SEQUENCE: 69

```
gagtgtggct gcagtgcgcc gggacaccag ggctccgcgc tccgcactca agaggctccc     60

gcgtcccaac ccctcgcgcc cgcgcgttcg cggatccagg ccgaggaccg aaaggggccg    120

cccgagcccc cggggccggc gcccagagag cccagcaagg ccggccgccc tgccggtgtg    180

ccgccggcgg gtgcttctgg aagggccaat gcgttcgggc agcagccctg aagccgagcc    240

cgaggctaag tgggactgac cggggcccag agtggacgaa ccgccagcat ggggagagac    300

cagcgcgcgg tggccggccc tgccctacgg cggtggctgc tgctggggac agtgaccgtg    360

gggttcctcg cccagagcgt cttggcgggt gtgaagaagt ttgatgtgcc gtgtggagga    420

agagattgca gtgggggctg ccagtgctac cctgagaaag gtggacgtgg tcagcctggg    480

ccagtgggcc cccaggggta caatgggcca ccaggattac aaggattccc cgggctgcag    540

ggacgtaaag gagacaaggg tgaaagggga gcccccggag taacaggacc caagggcgac    600

gtgggagcaa gaggcgtttc tggattccct ggtgccgatg gaattcctgg acacccgggg    660

caaggtgggc ccaggggaag gccgggctac gatggctgca acggaaccca gggagactca    720
```

-continued

```
ggtccacagg ggccccccgg ctctgagggg ttcaccgggc ctcccgggcc ccaaggacca    780
aaagggcaga aaggtgagcc ttatgcactg cctaaagagg agcgcgacag atatcggggt    840
gaacctggag agcctggatt ggtcggtttc cagggacctc ccggccgccc tgggcatgtg    900
ggacagatgg gtccagttgg agctccaggg agaccaggac cacctggacc ccctggacca    960
aaaggacagc aaggcaacag aggacttggt ttctacggag ttaagggtga aaagggtgac   1020
gtagggcagc cgggacccaa cgggattcca tcagacaccc tccaccccat catcgcgccc   1080
acaggagtca ccttccaccc agatcagtac aagggtgaaa aaggcagtga gggggaacca   1140
ggaataagag gcatttcctt gaagggagaa gaaggaatca tgggctttcc tggacttagg   1200
ggttaccctg gcttgagtgg tgaaaaagga tcaccaggac agaagggaag ccgaggcctg   1260
gatggctatc aagggcctga tggaccccgg ggacctaagg gagaagccgg agacccaggg   1320
ccccctggac tacctgccta ctcccctcac ccttccctag caaaaggtgc cagaggtgac   1380
ccaggattcc caggggccca aggggagcca ggaagccagg gtgagccagg agacccgggc   1440
ctcccaggtc cccctggcct ctccattgga gatggagatc agaggagagg cctgccgggt   1500
gagatgggac ccaagggctt catcggagac ccccggcatcc ctgcgctcta cgggggccca   1560
cctggacctg atggaaagcg agggcctcca ggaccccccg ggctccctgg accacctgga   1620
cctgatggct tcctgtttgg gctgaaagga gcaaaaggaa gagcaggctt ccctgggctt   1680
cccggctccc ctggagcccc cggaccaaag ggtggaaaag gtgacgctgg ggaatgcaga   1740
tgtacagaag gcgacgaagc tatcaaaggt cttccaggac tgccaggacc caagggcttc   1800
gcaggcatca acggggagcc ggggaggaaa ggggacaaag gagaccccgg ccaacacggc   1860
ctccctgggt tcccagggct caagggagtg cctggcaaca ttggtgctcc cggacccaaa   1920
ggagcaaaag gagattccag aacaatcaca accaaaggtg agcggggaca gcccggcgtc   1980
ccaggtgtgc ccgggatgaa aggtgacgat ggcagcccag gccgcgatgg gctcgatgga   2040
ttccccggcc tcccaggccc tcccggtgat ggcatcaagg gccctccagg ggacccaggt   2100
tatccaggaa tacctggaac gaagggtact ccaggagaaa tgggcccccc aggactgggc   2160
cttcccggcc tcaaaggcca acgtggtttc cctggagacg ccggcttacc tggaccacca   2220
ggcttcctgg gccctcctgg ccccgcaggg accccaggac aaatagattg tgacacagat   2280
gtgaaaaggg ccgttggagg tgacagacag gaggccatcc agccaggttg cataggaggg   2340
cccaagggat tgccaggcct gccaggaccc ccaggcccca caggtgccaa aggcctccga   2400
ggaatcccag gcttcgcagg agctgatgga ggaccagggc ccaggggctt gccaggagac   2460
gcaggtcgtg aagggttccc aggaccccca gggttcatag gaccccgagg atccaaaggt   2520
gcagtgggcc tccctggccc agatggatcc ccaggtccca tcggcctgcc agggccagat   2580
gggcccccctg gggaaagggg cctccctgga gaagtcctgg gagctcagcc cgggccacgg   2640
ggagatgctg gtgtgcctgg acagcctggg cttaaaggcc ttcccggaga cagaggcccc   2700
cctggattca gaggaagcca agggatgcct gggatgccag ggctgaaggg ccagccaggc   2760
ctcccaggac cttccggcca gccaggcctg tatgggcctc caggactgca tggattccca   2820
ggagctcctg gccaagaggg gcccttgggg ctgccaggaa tcccaggccg tgaaggtctg   2880
cctggtgata gaggggaccc tggggacaca ggcgctcctg gccctgtggg catgaaaggt   2940
ctctctggtg acagaggaga tgctggcttc acaggggagc aaggccatcc aggaagccct   3000
ggatttaaag gaattgatgg aatgcctggg acccccgggc taaaaggaga tagaggctca   3060
cctgggatgg atggtttcca aggcatgcct ggactcaaag ggagacccgg gtttccaggg   3120
```

-continued

```
agcaaaggcg aggctggatt tttcggaata cccggtctga agggtctggc tggtgagcca   3180
ggttttaaag gcagccgagg ggaccctggg cccccaggac cacctcctgt catcctgcca   3240
ggaatgaaag acattaaagg agagaaagga gatgaagggc ctatggggct gaaaggatac   3300
ctgggcgcaa aaggtatcca aggaatgcca ggcatcccag ggctgtcagg aatccctggg   3360
ctgcctggga ggcccggcca catcaaagga gtcaagggag acatcggagt ccccggcatc   3420
cccggtttgc caggattccc tggggtggct ggcccccctg gaattacggg attcccagga   3480
ttcataggaa gccggggtga caaaggtgcc ccagggagag caggcctgta tggcgagatt   3540
ggcgcgactg gtgatttcgg tgacatcggg gacactataa atttaccagg aagaccaggc   3600
ctgaaggggg agcggggcac cactggaata ccaggtctga agggattctt tggagagaag   3660
ggaacagaag gtgacatcgg cttccctggg ataacaggcg tgactggagt ccaaggccct   3720
cctggactta aaggacaaac aggctttcca gggctgactg ggcctccagg gtcgcaggga   3780
gagctggggc ggattggact gcctggtggc aaaggagatg atggctggcc gggagctccg   3840
ggcttaccag gttttccggg actccgtggg atccgcggct tacacggctt gccaggcacc   3900
aagggctttc caggatcccc aggttctgac atccacggag acccaggctt cccaggccct   3960
cctggggaaa gaggtgaccc aggagaggcc aacacccttc caggccctgt gggagtccca   4020
ggacagaaag gagaccaagg agctccaggg gaacgaggcc cacctgggag cccaggactt   4080
caggggttcc caggcatcac acccccttcc aacatctctg ggcacctggg tgacaaaggg   4140
gcgccaggga tatttggcct gaaaggttat cggggcccac cagggccacc aggttctgct   4200
gctcttcctg gaagcaaagg tgacacaggg aacccaggag ctccaggaac cccagggacc   4260
aaaggatggg ccggggactc cgggccccag ggcaggcctg gtgtgtttgg tctcccagga   4320
gaaaaagggc ccaggggtga acaaggcttc atggggaaca ctggacccac cggggcggtg   4380
ggcgacagag gccccaaggg acccaaggga gacccaggat tccctggtgc ccccgggact   4440
gtgggagccc ccgggattgc aggaatcccc cagaagattg ccgtccaacc agggacagtg   4500
ggtccccagg ggaggcgagg ccccccctggg gcaccggggg agatggggcc ccagggcccc   4560
cccggagaac caggttttcg tggggctcca gggaaagctg ggccccaagg aagaggtggt   4620
gtgtctgctg ttcccggctt ccggggagat gaaggaccca taggccacca ggggccgatt   4680
ggccaagaag gtgcaccagg ccgtccaggg agcccgggcc tgccgggtat gccaggccgc   4740
agcgtcagca tcggctacct cctggtgaag cacagccaga cggaccagga gcccatgtgc   4800
ccggtgggca tgaacaaact ctggagtgga tacagcctgc tgtacttcga gggccaggag   4860
aaggcgcaca accaggacct ggggctggcg ggctcctgcc tggcgcggtt cagcaccatg   4920
cccttcctgt actgcaaccc tggtgatgtc tgctactatg ccagccggaa cgacaagtcc   4980
tactggctct ctaccactgc gccgctgccc atgatgcccg tggccgagga cgagatcaag   5040
ccctacatca gccgctgttc tgtgtgtgag gccccggcca tcgccatcgc ggtccacagt   5100
caggatgtct ccatcccaca ctgcccagct gggtggcgga gtttgtggat cggatattcc   5160
ttcctcatgc acacggcggc gggagacgaa ggcggtggcc aatcactggt gtcaccgggc   5220
agctgtctag aggacttccg cgccacacca ttcatcgaat gcaatggagg ccgcggcacc   5280
tgccactact acgccaacaa gtacagcttc tggctgacca ccattcccga gcagagcttc   5340
cagggctcgc cctccgccga cacgctcaag gccggcctca tccgcacaca catcagccgc   5400
tgccaggtgt gcatgaagaa cctgtgagcc ggcgcgtgcc aggaagggcc attttggtgc   5460
```

```
ttattcttaa cttattacct caggtgccaa cccaaaaatt ggctttattt ttttcttaaa   5520

aaaaaaaaag tctaccaaag gaatttgcat ccagcagcag cacttagacc tgccagccac   5580

tgtcaccgag cgggtgcaag cactcggggt ccctggaggg caagccctgc ccacagaaag   5640

ccaggagcag ccctggcccc catcagccct gctagacgca ccgcctgaag gcacagctaa   5700

ccacttcgca cacacccatg taaccactgc actttccaat gccacagaca actcacattg   5760

ttcaactccc ttctcggggt gggacagacg agacaacagc acacaggcag ccagccgtgg   5820

ccagaggctc gaggggctca ggggctcagg cacccgtccc cacacgaggg ccccgtgggt   5880

gggcctggcc ctgctttcta cgccaatgtt atgccagctc catgttctcc caaataccgt   5940

tgatgtgaat tattttaaag gcaaaaccgt gctctttatt ttagaaaaca ctgataatca   6000

cactgcggta ggtcattctt ttgccacatc cctatagacc actgggtttg gcaaaactca   6060

ggcagaagtg gagacccttc tagacatcac tgtcagcctt gctacttgaa ggtacacccc   6120

atagggtcgg aggtgctgtc cccactgccc cacgttgtcc ctgagattta acccctccac   6180

tgctgggggt gagctgtact cttctgactg ccccctcctg tgtaacgact acaaaataaa   6240

acttggttct gaatattttt aaaaaaaaaa aaaaaa                             6276
```

<210> SEQ ID NO 70
<211> LENGTH: 1018
<212> TYPE: DNA
<213> ORGANISM: Homo sapiens

<400> SEQUENCE: 70

```
ggcacgaggc tcaagattca cagcatctca gacgcagcct aggttcccat ggacttgtca     60

taagacaaaa gaggacagct gtgctgaggg ggcagggtct gcagcctcct ggctgtgcca    120

ggaccacacc taccaaggcc gcaccaggat gtcggacacc gaggagcagg aatatgagga    180

ggagcagccg gaagaggagg ctgcggagga ggaggaggaa gaagaggaac gccccaaacc    240

aagccgcccc gtggtgcctc ctttgatccc gccaaagatc ccagaagggg agcgcgttga    300

cttcgatgac atccaccgca agcgcatgga gaaagacctg ctggagctgc agacactcat    360

cgatgtacat ttcgagcagc ggaagaagga ggaagaggag ctggttgcct tgaaggagcg    420

cattgagcgg cgccggtcag agagagccga gcaacagcgc ttcagaactg agaaggaacg    480

cgaacgtcag gctaagctgg cggaggagaa gatgaggaag gaagaggaag aggccaagaa    540

gcgggcagag gatgatgcca agaaaaagaa ggtgctgtcc aacatggggg cccattttgg    600

cggctacctg gtcaaggcag aacagaagcg tggtaagcgg cagacggggc gggagatgaa    660

ggtgcgcatc ctctccgagc gtaagaagcc tctggacatt gactacatgg gggaggaaca    720

gctccgggag aaagcccagg agctgtcgga ctggatccac cagctggagt ctgagaagtt    780

cgacctgatg gcgaagctga aacagcagaa atatgagatc aacgtgctgt acaaccgcat    840

cagccacgcc cagaagttcc ggaagggggc agggaagggc cgcgttggag gccgctggaa    900

gtgaggatgc cgccccggac agtggcacct gggaagcctg ggagtgtttg tcccatcggt    960

agcttgaaat aaacgctccc ctcagacact caaaaaaaaa aaaaaaaaaa aaaaaaaa     1018
```

<210> SEQ ID NO 71
<211> LENGTH: 2895
<212> TYPE: DNA
<213> ORGANISM: Homo sapiens

<400> SEQUENCE: 71

```
ccgaggagcg ctcgggctgt ctgcggaccc tgccgcgtgc aggggtcgcg gccggctgga     60
```

-continued

```
gctgggagtg aggcggcgga ggagccaggt gaggaggagc caggaaggca gttggtggga    120
agtccagctt gggtccctga gagctgtgag aaggagatgc ggctgctgct ggccctgttg    180
ggggtcctgc tgagtgtgcc tgggcctcca gtcttgtccc tggaggcctc tgaggaagtg    240
gagcttgagc cctgcctggc tcccagcctg gagcagcaag agcaggagct gacagtagcc    300
cttgggcagc ctgtgcggct gtgctgtggg cgggctgagc gtggtggcca ctggtacaag    360
gagggcagtc gcctggcacc tgctggccgt gtacggggct ggaggggccg cctagagatt    420
gccagcttcc tacctgagga tgctggccgc tacctctgcc tggcacgagg ctccatgatc    480
gtcctgcaga atctcacctt gattacaggt gactccttga cctccagcaa cgatgatgag    540
gaccccaagt cccataggga cctctcgaat aggcacagtt acccccagca agcaccctac    600
tggacacacc cccagcgcat ggagaagaaa ctgcatgcag tacctgcggg gaacaccgtc    660
aagttccgct gtccagctgc aggcaacccc acgcccacca tccgctggct taaggatgga    720
caggcctttc atggggagaa ccgcattgga ggcattcggc tgcgccatca gcactggagt    780
ctcgtgatgg agagcgtggt gccctcggac cgcggcacat acacctgcct ggtagagaac    840
gctgtgggca gcatccgcta taactacctg ctagatgtgc tggagcggtc cccgcaccgg    900
cccatcctgc aggccgggct cccggccaac accacagccg tggtgggcag cgacgtggag    960
ctgctgtgca aggtgtacag cgatgcccag ccccacatcc agtggctgaa gcacatcgtc   1020
atcaacggca gcagcttcgg agccgacggt ttcccctatg tgcaagtcct aaagactgca   1080
gacatcaata gctcagaggt ggaggtcctg tacctgcgga acgtgtcagc cgaggacgca   1140
ggcgagtaca cctgcctcgc aggcaattcc atcggcctct cctaccagtc tgcctggctc   1200
acggtgctgc caggtactgg gcgcatcccc cacctcacat gtgacagcct gactccagca   1260
ggcagaacca agtctcccac tttgcagttc tccctggagt caggctcttc cggcaagtca   1320
agctcatccc tggtacgagg cgtgcgtctc tcctccagcg gccccgcctt gctcgccggc   1380
ctcgtgagtc tagatctacc tctcgaccca ctatgggagt tcccccggga caggctggtg   1440
cttgggaagc ccctaggcga gggctgcttt ggccaggtag tacgtgcaga ggcctttggc   1500
atggaccctg cccggcctga ccaagccagc actgtggccg tcaagatgct caaagacaac   1560
gcctctgaca aggacctggc cgacctggtc tcggagatgg aggtgatgaa gctgatcggc   1620
cgacacaaga acatcatcaa cctgcttggt gtctgcaccc aggaagggcc cctgtacgtg   1680
atcgtggagt gcgccgccaa gggaaacctg cgggagttcc tgcgggcccg gcgcccccca   1740
ggccccgacc tcagccccga cggtcctcgg agcagtgagg ggccgctctc cttcccagtc   1800
ctggtctcct gcgcctacca ggtggcccga ggcatgcagt atctggagtc ccggaagtgt   1860
atccaccggg acctggctgc ccgcaatgtg ctggtgactg aggacaatgt gatgaagatt   1920
gctgactttg ggctggcccg cggcgtccac cacattgact actataagaa aaccagcaac   1980
ggccgcctgc ctgtgaagtg gatggcgccc gaggccttgt ttgaccgggt gtacacacac   2040
cagagtgacg tgtggtcttt tgggatcctg ctatgggaga tcttcaccct cgggggctcc   2100
ccgtatcctg gcatcccggt ggaggagctg ttctcgctgc tgcgggaggg acatcggatg   2160
gaccgacccc cacactgccc cccagagctg tacgggctga tgcgtgagtg ctggcacgca   2220
gcgccctccc agaggcctac cttcaagcag ctggtggagg cgctggacaa ggtcctgctg   2280
gccgtctctg aggagtacct cgacctccgc ctgaccttcg gaccctattc cccctctggt   2340
ggggacgcca gcagcacctg ctcctccagc gattctgtct tcagccacga ccccctgcca   2400
```

```
ttgggatcca gctccttccc cttcgggtct ggggtgcaga catgagcaag gctcaaggct   2460

gtgcaggcac ataggctggt ggccttgggc cttggggctc agccacagcc tgacacagtg   2520

ctcgaccttg atagcatggg gcccctggcc cagagttgct gtgccgtgtc caagggccgt   2580

gcccttgccc ttggagctgc cgtgcctgtg tcctgatggc ccaaatgtca gggttctgct   2640

cggcttcttg gaccatggcg cttagtcccc atcccgggtt tggctgagcc tggctggaga   2700

gctgctatgc taaacctcct gcctcccaat accagcagga ggttctgggc ctctgaaccc   2760

cctttcccca cacctccccc tgctgctgct gccccagcgt cttgacggga gcattggccc   2820

ctgagcccag agaagctgga agcctgccga aaacaggagc aaatggcgtt ttataaatta   2880

tttttttgaa ataaa                                                    2895
```

<210> SEQ ID NO 72
<211> LENGTH: 1356
<212> TYPE: DNA
<213> ORGANISM: Homo sapiens

<400> SEQUENCE: 72

```
ttctcccgca accttccctt cgctccctcc cgtccccccc agctcctagc ctccgactcc     60

ctcccccccct cacgcccgcc ctctcgcctt cgccgaacca aagtggatta attacacgct   120

ttctgtttct ctccgtgctg ttctctcccg ctgtgcgcct gcccgcctct cgctgtcctc   180

tctcccctc gccctctctt cggccccccc ctttcacgtt cactctgtct ctcccactat    240

ctctgccccc ctctatcctt gatacaacag ctgacctcat ttcccgatac cttttccccc   300

ccgaaaagta caacatctgg cccgccccag cccgaagaca gcccgtcctc cctggacaat   360

cagacgaatt ctcccccccc ccccaaaaaa aaaagccatc cccccgctct gccccgtcgc   420

acattcggcc cccgcgactc ggccagagcg gcgctggcag aggagtgtcc ggcaggaggg   480

ccaacgcccg ctgttcggtt tgcgacacgc agcagggagg tgggcggcag cgtcgccggc   540

ttccagacac caatgggaat cccaatgggg aagtcgatgc tggtgcttct caccttcttg   600

gccttcgcct cgtgctgcat tgctgcttac cgccccagtg agaccctgtg cggcggggag   660

ctggtggaca ccctccagtt cgtctgtggg gaccgcggct tctacttcag caggcccgca   720

agccgtgtga gccgtcgcag ccgtggcatc gttgaggagt gctgtttccg cagctgtgac   780

ctggccctcc tggagacgta ctgtgctacc cccgccaagt ccgagaggga cgtgtcgacc   840

cctccgaccg tgcttccgga caacttcccc agataccccg tgggcaagtt cttccaatat   900

gacacctgga agcagtccac ccagcgcctg cgcaggggcc tgcctgccct cctgcgtgcc   960

cgccggggtc acgtgctcgc caaggagctc gaggcgttca gggaggccaa acgtcaccgt  1020

cccctgattg ctctacccac ccaagacccc gcccacgggg gcgccccccc agagatggcc  1080

agcaatcgga agtgagcaaa actgccgcaa gtctgcagcc cggcgccacc atcctgcagc  1140

ctcctcctga ccacggacgt ttccatcagg ttccatcccg aaaatctctc ggttccacgt  1200

cccccctgggg cttctcctga cccagtcccc gtgccccgcc tccccgaaac aggctactct  1260

cctcggcccc ctccatcggg ctgaggaagc acagcagcat cttcaaacat gtacaaaatc  1320

gattggcttt aaacaccctt cacataccct cccccc                             1356
```

<210> SEQ ID NO 73
<211> LENGTH: 2281
<212> TYPE: DNA
<213> ORGANISM: Homo sapiens

<400> SEQUENCE: 73

-continued

```
aaacaataag catatctaag caactacgat atctgtatgg atcaggccaa agtcccgcta     60
agattctcca atgttttcat ggtctgagcc cccctcctgt tcccatctcc actgcccctc    120
ggccctgtct gtgccctgcc tctcagagga gggggctcag atggtgcggc ctgagtgtgc    180
ggccggcggc atttgggata cacccgtagg gtgggcgggg tgtgtcccag gcctaattcc    240
atctttccac catgacagag atgcccttgt gaggctggcc tccttggcgc ctgtccccac    300
ggcccccgca gcgtgagcca cgatgctccc catacccac ccattcccga tacaccttac     360
ttactgtgtg ttggcccagc cagagtgagg aaggagtttg gccacattgg agatggcggt    420
agctgagcag acatgccccc acgagtagcc tgactccctg gtgtgctcct ggaaggaaga    480
tcttggggac ccccccaccg gagcacacct agggatcatc tttgcccgtc tcctggggac    540
cccccaagaa atgtggagtc ctcgggggcc gtgcactgat gcggggagtg tgggaagtct    600
ggcggttgga ggggtgggtg gggggcagtg ggggctgggc ggggggagtc ctggggtagg    660
aagtggtccc gggagatttt ggatggaaaa gtcaggagga ttgacagcag acttgcagaa    720
ttacatagag aaattaggaa cccccaaatt tcatgtcaat tgatctattc cccctctttg    780
tttcttgggg catttttcct ttttttttt tttgtttttt ttttacccct ccttagcttt    840
atgcgctcag aaaccaaatt aaaccccccc cccatgtaac aggggggcag tgacaaaagc    900
aagaacgcac gaagccagcc tggagaccac cacgtcctgc cccccgccat ttatcgccct    960
gattggattt tgtttttcat ctgtccctgt tgcttgggtt gagttgaggg tggagcctcc   1020
tggggggcac tggccactga gcccccttgg agaagtcaga ggggagtgga gaaggccact   1080
gtccggcctg gcttctgggg acagtggctg gtccccagaa gtcctgaggg cggagggggg   1140
ggttgggcag ggtctcctca ggtgtcagga gggtgctcgg aggccacagg agggggctcc   1200
tggctggcct gaggctggcc ggaggggaag gggctagcag gtgtgtaaac agagggttcc   1260
atcaggctgg ggcagggtgg ccgccttccg cacacttgag gaaccctccc ctctccctcg   1320
gtgacatctt gcccgcccct cagcaccctg ccttgtctcc aggaggtccg aagctctgtg   1380
ggacctcttg ggggcaaggt ggggtgaggc cggggagtag ggaggtcagg cgggtctgag   1440
cccacagagc aggagagctg ccaggtctgc ccatcgacca ggttgcttgg gccccggagc   1500
ccacgggtct ggtgatgcca tagcagccac caccgcggcg cctagggctg cggcagggac   1560
tcggcctctg ggaggtttac ctcgccccca cttgtgcccc cagctcagcc cccctgcacg   1620
cagcccgact agcagtctag aggcctgagg cttctgggtc ctggtgacgg ggctggcatg   1680
accccggggg tcgtccatgc cagtccgcct cagtcgcaga gggtccctcg gcaagcgccc   1740
tgtgagtggg ccattcggaa cattggacag aagcccaaag agccaaattg tcacaattgt   1800
ggaacccaca ttggcctgag atccaaaacg cttcgaggca ccccaaatta cctgcccatt   1860
cgtcaggaca cccacccacc cagtgttata ttctgcctcg ccggagtggg tgttcccggg   1920
ggcacttgcc gaccagcccc ttgcgtcccc aggtttgcag ctctcccctg ggccactaac   1980
catcctggcc cgggctgcct gtctgacctc cgtgcctagt cgtggctctc catcttgtct   2040
cctccccgtg tccccaatgt cttcagtggg gggccccctc ttgggtcccc tcctctgcca   2100
tcacctgaag acccccacgc caaacactga atgtcacctg tgcctgccgc ctcggtccac   2160
cttgcggccc gtgtttgact caactcagct cctttaacgc taatatttcc ggcaaaatcc   2220
catgcttggg ttttgtcttt aaccttgtaa cgcttgcaat cccaataaag cattaaaagt   2280
c                                                                   2281
```

<210> SEQ ID NO 74
<211> LENGTH: 1124
<212> TYPE: DNA
<213> ORGANISM: Homo sapiens

<400> SEQUENCE: 74

```
cgggaaacct gcactgactt ttttctcctt ttggagggag agcagagacc atgtctgaca     60

tagaagaggt ggtggaagag tacgaggagg aggagcagga agaagcagct gttgaagagc    120

aggaggaggc agcggaagag gatgctgaag cagaggctga gaccgaggag accagggcag    180

aagaagatga agaagaagag gaagcaaagg aggctgaaga tggcccaatg gaggagtcca    240

aaccaaagcc caggtcgttc atgcccaact tggtgcctcc caagatcccc gatggagaga    300

gagtggactt tgatgacatc caccggaagc gcatggagaa ggacctgaat gagttgcagg    360

cgctgattga ggctcacttt gagaacagga agaaagagga ggaggagctc gtttctctca    420

aagacaggat cgagagacgt cggcagagc gggccgagca gcagcgcatc cggaatgagc    480

gggagaagga gcggcagaac cgcctggctg aagagagggc tcgacgagag gaggaggaga    540

acaggaggaa ggctgaggat gaggcccgga agaagaaggc tttgtccaac atgatgcatt    600

ttgggggtta catccagaag caggcccaga cagagcggaa aagtgggaag aggcagactg    660

agcgggaaaa gaagaagaag attctggctg agaggaggaa ggtgctggcc attgaccacc    720

tgaatgaaga tcagctgagg gagaaggcca aggagctgtg gcagagcatc tataacttgg    780

aggcagagaa gttcgacctg caggagaagt tcaagcagca gaaatatgag atcaatgttc    840

tccgaaacag gatcaacgat aaccagaaag tctccaagac ccgcgggaag gctaaagtca    900

ccgggcgctg gaaatagagc ctggcctcct tcaccaaaga tctgctcctc gctcgcacct    960

gcctccggcc tgcactcccc cagttcccgg gccctcctgg gcaccccagg cagctcctgt   1020

ttggaaatgg ggagctggcc taggtgggag ccaccactcc tgcctgcccc cacacccact   1080

ccacaccagt aataaaaagc caccacacac tgaaaaaaaa aaaa                     1124
```

<210> SEQ ID NO 75
<211> LENGTH: 855
<212> TYPE: DNA
<213> ORGANISM: Homo sapiens

<400> SEQUENCE: 75

```
atctcatctc ccagacgcca cgtctctcgg tttcttctta gatcactcct ctgccaaaga     60

tcccaacaag acaacatggc tcccaagaag cctgagccta agaaggaggc agccaagcca    120

gctccagctc cagctccagc ccctgcacca gcccctgccc cagctcctga ggctcccaag    180

gaacctgcct ttgaccccaa gagtgtaaag atagacttca ctgccgacca gattgaagag    240

ttcaaagagg ccttttcatt gtttgaccgg accccgactg gagagatgaa gatcacctac    300

ggccagtgcg gggatgtact gcgggccctg ggccagaacc ctaccaatgc cgaggtgctg    360

cgtgtgctgg gcaagcccaa gcctgaagag atgaatgtca agatgctgga ctttgagacg    420

ttcttgccca tcctgcagca catttcccgc aacaaggagc agggcaccta tgaggacttc    480

gtggagggcc tgcgtgtctt tgacaaggag agcaatggca cggtcatggg tgctgagctt    540

cggcacgtcc ttgccaccct gggagagaag atgactgagg ctgaagtgga gcagctgtta    600

gctgggcaag aggatgccaa tggctgcatc aattatgaag cctttgtcaa gcacatcatg    660

tcagggtgaa gcagagtctt ccaggtgcct ggcccttggc tttagccata ccagggtgag    720

ttaaagagag gccccggctg ggtgagctga gatggagtcc tcgacttatc accacaccac    780
```

-continued

```
tgccccaagg accttacagg ccctccctgt taataaacag ctctaacacg gccaggctgg    840

gctctgggat tctga                                                      855
```

<210> SEQ ID NO 76
<211> LENGTH: 1404
<212> TYPE: DNA
<213> ORGANISM: Homo sapiens

<400> SEQUENCE: 76

```
gccgggcagc catggctgag acactcttct ggactcctct cctcgtggtt ctcctggcag     60
ggctggggga caccgaggcc cagcagacca cgctacaccc acttgtgggc cgtgtctttg    120
tgcacacctt ggaccatgag acgtttctga gccttcctga gcatgtcgct gtcccacccg    180
ctgtccacat cacctaccac gcccacctcc agggacaccc agacctgccc cggtggctcc    240
gctacaccca gcgcagcccc caccaccctg gcttcctcta cggctctgcc accccagaag    300
atcgtgggct ccaggtcatt gaggtcacag cctacaatcg ggacagcttt gataccactc    360
ggcagaggct ggtgctggag attggggacc cagaaggccc cctgctgcca taccaagccg    420
agttcctggt gcgcagccac gatgcggagg aggtgctgcc ctcaacacct gccagccgct    480
tcctctcagc cttgggggga ctctgggagc ccggagagct tcagctgctc aacgtcacct    540
ctgccttgga ccgtgggggc cgtgtccccc ttcccattga gggccgaaaa gaaggggtat    600
acattaaggt gggttctgcc tcaccttttt ctacttgcct gaagatggtg gcatcccccg    660
atagccacgc ccgctgtgcc cagggccagc ctccacttct gtcttgctac gacaccttgg    720
caccccactt ccgcgttgac tggtgcaatg tgaccctggt ggataagtca gtgccggagc    780
ctgcagatga ggtgcccacc ccaggtgatg ggatcctgga gcatgacccg ttcttctgcc    840
cacccactga ggccccagac cgtgacttct tggtggatgc tctggtcacc ctcctggtgc    900
ccctgctggt ggccctgctt ctcaccttgc tgctggccta tgtcatgtgc tgccggcggg    960
agggaaggct gaagagagac ctggctacct ccgacatcca gatggtccac cactgcacca   1020
tccacgggaa cacagaggag ctgcggcaga tggcggccag ccgcgaggtg ccccggccac   1080
tctccaccct gcccatgttc aatgtgcaca caggtgagcg gctgcctccc cgcgtggaca   1140
gcgcccaggt gcccctcatt ctggaccagc actgacagcc cagccagtgg ttccaggtcc   1200
agccctgact tcatcctccc ttctctgtcc acaccacgag tggcacatcc cacctgctga   1260
ttccagctcc tggccctcct ggaacccagg ctctaaacaa gcagggagag ggggtggggt   1320
ggggtgagag tgtgtggagt aaggacattc agaataaata tctgctgctc tgctcaccaa   1380
ttgctgctgg cagcctctcc cgtc                                           1404
```

<210> SEQ ID NO 77
<211> LENGTH: 1610
<212> TYPE: DNA
<213> ORGANISM: Homo sapiens

<400> SEQUENCE: 77

```
gcatcagaaa ccagcacacc agagcaccag ggcggggggc ttctccgcag caagtttcca     60
aacaagccct cagtgaacat cattgaagcg tgactgcctg tctgcaggga gaaggattcc    120
atttttcttc tcagctggtc cccaggccca cgggcacagg gagagggaca actgcagcag    180
tggggaggag gcacagctag ctgcacagtt ctctcttctc cttgtcctag tcagatgaag    240
gaggctgcac tacaaaccca aattctgcaa aaaaaataaa aataagccac aaaactaaaa    300
```

-continued

```
ggcctggccc cattctggaa aaggcaaagc tgcatgagac acagccttct gcctcctcgc    360
ctctcctgga ctggcttcct ctttgagaaa atgcacaaag ccctgggaga tgacaagcac    420
aaggactgac tcaagctgtg tctttcagac caaggaacat cagagaagct gtggggctgc    480
ctgccaggca ggatcatggc tgccatcaag ccttttctgg atccagccat caaggacatg    540
tttgtggtgt gatgcacact tttgcaagcg tgtaagatgt tacctggttt gtctcttttg    600
gaaaacaaaa atcagaaggc tgcattctag agggcagaga aattccccg aagactgagc    660
tggttgcctg catcctctat cttctttgac ccttatgact gaaagatcat cagtttggaa    720
ggtactggtc caatttattt aggaagtatc tcttggagtt tcagaaatgc tagcttggac    780
aactgaaaag tcacatcaca gctggcattc tgggggctac caaaacaccc cttctggagt    840
agaagctgct ggaaggcagg cctgagccat tcaccacgga caggaagagc agctctggct    900
atcaccactg gcctctgggg tcttcatatc ttgccatctc atccagggtt ccatgaaagt    960
tacccagggt cctcatgtcc ttccttagag cctgagtggt gtgaggtgac aggtctctct   1020
ctccactgcc cctttctggt ttaaaaaaat ggtgcttgat gagggaaggt agactcttcc   1080
ctaggactga cgagttacgg ctgccagatg cctgcatggg aagaggtgga catctgcatc   1140
ttccattggt ggtcaaggat gggtgtggga gaaccacacc tagtgcaagc ctggtactca   1200
gtaaatattt gttgaaatga atgataagag cattggtccc caagccagag agccagaagc   1260
catcacccaa tgaccgcccc ttccttccgg tctacaagag ctctcaaggc tgggtctgcc   1320
accactctgc tttgcccaag tgtgacagca ctggggagga gagacaggat aaagggcaga   1380
tgtcagcaat actaagggct tcctcatggg agggcatgag gctccactca ttgtcttgtg   1440
acttccatcc ctgctgaatg gggctgcaag gccaaggctc cttaggggag aggtccttac   1500
ctctgatcca cttagagcaa taaccacttt ttaaatgtaa aataaaaaga caaatgaaaa   1560
ggcaaaaaaa aaaaaaaaaa aaaaaaaaaa aaaaaaaaaa aaaaaaaaaa              1610
```

<210> SEQ ID NO 78
<211> LENGTH: 1356
<212> TYPE: DNA
<213> ORGANISM: Homo sapiens

<400> SEQUENCE: 78

```
ttctcccgca accttccctt cgctccctcc cgtccccccc agctcctagc ctccgactcc     60
ctcccccct cacgcccgcc ctctcgcctt cgccgaacca aagtggatta attacacgct    120
ttctgtttct ctccgtgctg ttctctcccg ctgtgcgcct gcccgcctct cgctgtcctc    180
tctcccctc gccctctctt cggccccccc ctttcacgtt cactctgtct ctcccactat    240
ctctgccccc ctctatcctt gatacaacag ctgacctcat ttcccgatac cttttccccc    300
ccgaaaagta caacatctgg cccgccccag cccgaagaca gcccgtcctc cctggacaat    360
cagacgaatt ctcccccccc ccccaaaaaa aaaagccatc cccccgctct gccccgtcgc    420
acattcggcc cccgcgactc ggccagagcg gcgctggcag aggagtgtcc ggcaggaggg    480
ccaacgcccg ctgttcggtt tgcgacacgc agcagggagg tgggcggcag cgtcgccggc    540
ttccagacac caatgggaat cccaatgggg aagtcgatgc tggtgcttct caccttcttg    600
gccttcgcct cgtgctgcat tgctgcttac cgccccagtg agaccctgtg cggcggggag    660
ctggtggaca ccctccagtt cgtctgtggg gaccgcggct tctacttcag caggcccgca    720
agccgtgtga gccgtcgcag ccgtggcatc gttgaggagt gctgtttccg cagctgtgac    780
ctggccctcc tggagacgta ctgtgctacc cccgccaagt ccgagaggga cgtgtcgacc    840
```

```
cctccgaccg tgcttccgga caacttcccc agataccccg tgggcaagtt cttccaatat     900

gacacctgga agcagtccac ccagcgcctg cgcaggggcc tgcctgccct cctgcgtgcc     960

cgccggggtc acgtgctcgc caaggagctc gaggcgttca gggaggccaa acgtcaccgt    1020

cccctgattg ctctacccac ccaagacccc gcccacgggg gcgccccccc agagatggcc    1080

agcaatcgga agtgagcaaa actgccgcaa gtctgcagcc cggcgccacc atcctgcagc    1140

ctcctcctga ccacggacgt ttccatcagg ttccatcccg aaaatctctc ggttccacgt    1200

cccccctgggg cttctcctga cccagtcccc gtgccccgcc tccccgaaac aggctactct    1260

cctcggcccc ctccatcggg ctgaggaagc acagcagcat cttcaaacat gtacaaaatc    1320

gattggcttt aaacaccctt cacataccct cccccc                              1356
```

<210> SEQ ID NO 79
<211> LENGTH: 2330
<212> TYPE: DNA
<213> ORGANISM: Homo sapiens

<400> SEQUENCE: 79

```
gaattcggca cgagcgacgc ggcccagagg ccaggaacat tccgcgcgtg gaccagccgg      60

gccagggcga tgctgcgggt gcggtgtctg cgcggcggga gccgcggcgc cgaggcggtg     120

cactacatcg gatctcggct tggacgaacc ttgacaggat gggtgcagcg aactttccag     180

agcacccagg cagctacggc ttcctcccgg aactcctgtg cagctgacga caaagccact     240

gagcctctgc ccaaggactg ccctgtctct tcttacaacg aatgggaccc cttagaggaa     300

gtgatagtgg gcagagcaga aaacgcctgt gttccaccgt tcaccatcga ggtgaaggcc     360

aacacatatg aaaagtactg gccattttac cagaagcaag gagggcatta ttttcccaaa     420

gatcatttga aaaaggctgt tgctgaaatt gaagaaatgt gcaatatttt aaaaacggaa     480

ggagtgacag taaggaggcc tgaccccatt gactggtcat tgaagtataa aactcctgat     540

tttgagtcta cgggtttata cagtgcaatg cctcgagaca tcctgatagt tgtgggcaat     600

gagattatcg aggctcccat ggcatggcgt tcacgcttct ttgagtaccg agcgtacagg     660

tcaattatca aagactactt ccaccgtggc gccaagtgga caacagctcc taagcccaca     720

atggctgatg agctttataa ccaggattat cccatccact ctgtagaaga cagacacaaa     780

ttggctgctc agggaaaatt tgtgacaact gagtttgagc catgctttga tgctgctgac     840

ttcattcgag ctggaagaga tatttttgca cagagaagcc aggttacaaa ctacctaggc     900

attgaatgga tgcgtaggca tcttgctcca gactacagag tgcatatcat ctcctttaaa     960

gatcccaatc ccatgcatat tgatgctacc ttcaacatca ttggacctgg tattgtgctt    1020

tccaaccctg accgaccatg tcaccagatt gatcttttca agaaagcagg atggactatc    1080

attactcctc caacaccaat catcccagac gatcatccac tctggatgtc atccaaatgg    1140

ctttccatga atgtcttaat gctagatgaa aaacgtgtta tggtggatgc caatgaagtt    1200

ccaattcaaa agatgtttga aaagctgggt atcactacca ttaaagttaa cattcgtaat    1260

gccaattccc tgggaggagg cttccattgc tggacctgcg atgtccggcg ccgaggcacc    1320

ctacagtcct acttggactg aacaggcctg atggagcttg tggctggcct cagatacacc    1380

taagaagctt aggggcaagg ttcattctcc tgctttaaaa agtgcatgaa ctgtagtgct    1440

ttaaacaatc atctccttaa caggggtcgt aagcctggtt tgcttctatt acttttcttt    1500

gacataaaga aaataacttc tgctaggtat tactctctac tcctaaagtt atttactatt    1560
```

-continued

```
tggcttcaag tataaaattt tggtgaatgt gtaccaagaa aaaattagtc acctgagtaa   1620
cttggccact aataattaac catctacctc tgtttttaat tttctttcca aaaggcagct   1680
tgaaatgttg gtcctaatct taattttttt tcctcttcta tagacttgag aatgtttttc   1740
tctaaatgag agaaagactt agaatgtaca cagatccaaa atagaatcag attatctctt   1800
tttttctaaa ggagagaaag acttagaaca tacacagatc ctaagtagaa ccaggtaatt   1860
gtctcttttt ctaataagga atttgggtaa tttttaattt tttgtttttt aaaaaaataac   1920
ctagactatg caaaacatca aagtgaattt tccatgaatg tttttaatat tctcatctca   1980
acattgtgat atatgctact aaaaaccttt tcatatacat cttacctcat ttcaagtgaa   2040
ttattttaat ctttttctct ctttccaaaa atttacagga atgtttagtg taattggatt   2100
tcgctatcag ttcccatcct taagttttga tattcaatat ctgatagata cactgcatct   2160
ttggtcatct aagatttgtt tacaaatgtg caaattattt agagcataga ctttataagc   2220
attaaaaaaa actaatggag gtaaaaccta aatgcgatgt gaaataattt tagtgttgat   2280
actgtatgtg tatttttatt ctaataaact tttgtgttcc agattgaaaa              2330
```

<210> SEQ ID NO 80
<211> LENGTH: 2436
<212> TYPE: DNA
<213> ORGANISM: Homo sapiens

<400> SEQUENCE: 80

```
ggctcccaca gtgggtggcg gaaaacaact ttcagagctt tgtaaatgcc agttgtgccc     60
atcctcagct gctaaaagga agaagcattt ttgctgttag cccagatggc tttgtgtgtg    120
atgattttcc caaaccccag atcacggttc agccagaaac acagtcggca ataaaaggtt    180
ccaatttgag tttcatctgc tcagctgcca gcagcagtga ttccccaatg acttttgctt    240
ggaaaaaaga caatgaacta ctgcatgatg ctgaaatgga aaattatgca cacctccggg    300
cccaaggtgg cgaggtgatg gagtatacca ccatccttcg gctgcgcgag gtggaatttg    360
ccagtgaggg gaaatatcag tgtgtcatct ccaatcactt tggttcatcc tactctgtca    420
aagccaagct tacagtaaat atgcttccct cattcaccaa gacccccatg gatctcacca    480
tccgagctgg ggccatggca cgcttggagt gtgctgctgt ggggcaccca gcccccccaga    540
tagcctggca gaaggatggg ggcacagact tcccagctgc acgggagaga cgcatgcatg    600
tgatgcccga ggatgacgtg ttctttatcg tggatgtgaa gatagaggac attggggtat    660
acagctgcac agctcagaac agtgcaggaa gtatttcagc aaatgcaact ctgactgtcc    720
tagaaacacc atcatttttg cggccactgt tggaccgaac tgtaaccaag ggagaaacag    780
ccgtcctaca gtgcattgct ggaggaagcc ctccccctaa actgaactgg accaaagatg    840
atagcccatt ggtggtaacc gagaggcact tttttgcagc aggcaatcag cttctgatta    900
ttgtggactc agatgtcagt gatgctggga aatacacatg tgagatgtct aacacccttg    960
gcactgagag aggaaacgtg cgcctcagtg tgatccccac tccaacctgc gactcccctc   1020
agatgacagc cccatcgtta gacgatgacg gatgggccac tgtgggtgtc gtgatcatag   1080
ccgtggtttg ctgtgtggtg ggcacgtcac tcgtgtgggt ggtcatcata taccacacaa   1140
ggcggaggaa tgaagattgc agcattacca acacagatga gaccaacttg ccagcagata   1200
ttcctagtta tttgtcatct cagggaacgt tagctgacag gcaggatggg tacgtgtctt   1260
cagaaagtgg aagccaccac cagtttgtca catcttcagg tgctggattt ttcttaccac   1320
aacatgacag tagtgggacc tgccatattg acaatagcag tgaagctgat gtggaagctg   1380
```

-continued ccacagatct gttcctttgt ccgtttttgg gatccacagg ccctatgtat ttgaagggaa 1440
atgtgtatgg ctcagatcct tttgaaacat atcatacagg ttgcagtcct gacccaagaa 1500
cagttttaat ggaccactat gagcccagtt acataaagaa aaaggagtgc tacccatgtt 1560
ctcatccttc agaagaatcc tgcgaacgga gcttcagtaa tatatcgtgg ccttcacatg 1620
tgaggaagct acttaacact agttactctc acaatgaagg acctggaatg aaaaatctgt 1680
gtctaaacaa gtcctcttta gattttagtg caaatccaga gccagcgtcg gttgcctcga 1740
gtaattcttt catgggtacc tttggaaaag ctctcaggag acctcaccta gatgcctatt 1800
caagctttgg acagccatca gattgtcagc caagagcctt ttatttgaaa gctcattctt 1860
ccccagactt ggactctggg tcagaggaag atgggaaaga aaggacagat tttcaggaag 1920
aaaatcacat ttgtaccttt aaacagactt tagaaaacta caggactcca aattttcagt 1980
cttatgactt ggacacatag actgaatgag accaaaggaa aagcttaaca tactacctca 2040
agtgaacttt tatttaaaag agagagaatc ttatgttttt taaatggagt tatgaatttt 2100
aaaaggataa aaatgcttta tttatacaga tgaaccaaaa ttacaaaaag ttatgaaaat 2160
ttttatactg ggaatgatgc tcatataaga atacctttt aaactatttt ttaactttgt 2220
tttatgcaaa aaagtatctt acgtaaatta atgatataaa tcatgattat tttatgtatt 2280
tttataatgc cagatttctt tttatggaaa atgagttact aaagcatttt aaataatacc 2340
tgccttgtac cattttttaa atagaagtta cttcattata ttttgcacat tatatttaat 2400
aaaatgtgtc aatttgaaaa aaaaaaaaaa aaaaaa 2436

<210> SEQ ID NO 81
<211> LENGTH: 2121
<212> TYPE: DNA
<213> ORGANISM: Homo sapiens

<400> SEQUENCE: 81
ctgctcgcgg ccgccaccgc cgggccccgg ccgtccctgg ctcccctcct gcctcgagaa 60
gggcagggct tctcagaggc ttggcgggaa aaaagaacgg agggagggat cgcgctgagt 120
ataaaagccg gttttcgggg ctttatctaa ctcgctgtag taattccagc gagaggcaga 180
gggagcgagc gggcggccgg ctagggtgga agagccgggc gagcagagct gcgctgcggg 240
cgtcctggga agggagatcc ggagcgaata gggggcttcg cctctggccc agccctcccg 300
cttgatcccc caggccagcg gtccgcaacc cttgccgcat ccacgaaact ttgcccatag 360
cagcgggcgg gcactttgca ctggaactta caacacccga gcaaggacgc gactctcccg 420
acgcggggag gctattctgc ccatttgggg acacttcccc gccgctgcca ggacccgctt 480
ctctgaaagg ctctccttgc agctgcttag acgctggatt tttttcgggt agtggaaaac 540
cagcagcctc ccgcgacgat gcccctcaac gttagcttca ccaacaggaa ctatgacctc 600
gactacgact cggtgcagcc gtatttctac tgcgacgagg aggagaactt ctaccagcag 660
cagcagcaga gcgagctgca gcccccggcg cccagcgagg atatctggaa gaaattcgag 720
ctgctgccca ccccgcccct gtcccctagc cgccgctccg ggctctgctc gccctcctac 780
gttgcggtca caccettctc ccttcgggga gacaacgacg gcggtggcgg gagcttctcc 840
acggccgacc agctggagat ggtgaccgag ctgctgggag gagacatggt gaaccagagt 900
ttcatctgcg acccggacga cgagaccttc atcaaaaaca tcatcatcca ggactgtatg 960
tggagcggct tctcggccgc cgccaagctc gtctcagaga agctggcctc ctaccaggct 1020

-continued

```
gcgcgcaaag acagcggcag cccgaacccc gcccgcggcc acagcgtctg ctccacctcc   1080

agcttgtacc tgcaggatct gagcgccgcc gcctcagagt gcatcgaccc ctcggtggtc   1140

ttcccctacc ctctcaacga cagcagctcg cccaagtcct gcgcctcgca agactccagc   1200

gccttctctc cgtcctcgga ttctctgctc tcctcgacgg agtcctcccc gcagggcagc   1260

cccgagcccc tggtgctcca tgaggagaca ccgcccacca ccagcagcga ctctgaggag   1320

gaacaagaag atgaggaaga aatcgatgtt gtttctgtgg aaaagaggca ggctcctggc   1380

aaaaggtcag agtctggatc accttctgct ggaggccaca gcaaacctcc tcacagccca   1440

ctggtcctca agaggtgcca cgtctccaca catcagcaca actacgcagc gcctccctcc   1500

actcggaagg actatcctgc tgccaagagg gtcaagttgg acagtgtcag agtcctgaga   1560

cagatcagca acaaccgaaa atgcaccagc cccaggtcct cggacaccga ggagaatgtc   1620

aagaggcgaa cacacaacgt cttggagcgc cagaggagga acgagctaaa acggagcttt   1680

tttgccctgc gtgaccagat cccggagttg gaaaacaatg aaaaggcccc caaggtagtt   1740

atccttaaaa aagccacagc atacatcctg tccgtccaag cagaggagca aaagctcatt   1800

tctgaagagg acttgttgcg gaaacgacga gaacagttga aacacaaact tgaacagcta   1860

cggaactctt gtgcgtaagg aaaagtaagg aaaacgattc cttctaacag aaatgtcctg   1920

agcaatcacc tatgaacttg tttcaaatgc atgatcaaat gcaacctcac aaccttggct   1980

gagtcttgag actgaaagat ttagccataa tgtaaactgc ctcaaattgg actttgggca   2040

taaaagaact tttttatgct taccatcttt ttttttctt taacagattt gtatttaaga   2100

attgttttta aaaaatttta a                                              2121
```

<210> SEQ ID NO 82
<211> LENGTH: 2121
<212> TYPE: DNA
<213> ORGANISM: Homo sapiens

<400> SEQUENCE: 82

```
ctgctcgcgg ccgccaccgc cgggccccgg ccgtccctgg ctcccctcct gcctcgagaa     60

gggcagggct tctcagaggc ttggcgggaa aaaagaacgg agggagggat cgcgctgagt    120

ataaaagccg gttttcgggg ctttatctaa ctcgctgtag taattccagc gagaggcaga    180

gggagcgagc gggcggccgg ctagggtgga agagccgggc gagcagagct gcgctgcggg    240

cgtcctggga agggagatcc ggagcgaata gggggcttcg cctctggccc agccctcccg    300

cttgatcccc caggccagcg gtccgcaacc cttgccgcat ccacgaaact ttgcccatag    360

cagcgggcgg gcactttgca ctggaactta caacacccga gcaaggacgc gactctcccg    420

acgcggggag gctattctgc ccatttgggg acacttcccc gccgctgcca ggacccgctt    480

ctctgaaagg ctctccttgc agctgcttag acgctggatt tttttcgggt agtggaaaac    540

cagcagcctc ccgcgacgat gcccctcaac gttagcttca ccaacaggaa ctatgacctc    600

gactacgact cggtgcagcc gtatttctac tgcgacgagg aggagaactt ctaccagcag    660

cagcagcaga gcgagctgca gcccccggcg cccagcgagg atatctggaa gaaattcgag    720

ctgctgccca ccccgcccct gtcccctagc cgccgctccg ggctctgctc gccctcctac    780

gttgcggtca cacccttctc ccttcgggga gacaacgacg gcggtggcgg gagcttctcc    840

acggccgacc agctggagat ggtgaccgag ctgctgggag gagacatggt gaaccagagt    900

ttcatctgcg acccggacga cgagaccttc atcaaaaaca tcatcatcca ggactgtatg    960

tggagcggct tctcggccgc cgccaagctc gtctcagaga agctggcctc ctaccaggct   1020
```

```
gcgcgcaaag acagcggcag cccgaacccc gcccgcggcc acagcgtctg ctccacctcc   1080

agcttgtacc tgcaggatct gagcgccgcc gcctcagagt gcatcgaccc ctcggtggtc   1140

ttcccctacc ctctcaacga cagcagctcg cccaagtcct gcgcctcgca agactccagc   1200

gccttctctc cgtcctcgga ttctctgctc tcctcgacgg agtcctcccc gcagggcagc   1260

cccgagcccc tggtgctcca tgaggagaca ccgcccacca ccagcagcga ctctgaggag   1320

gaacaagaag atgaggaaga aatcgatgtt gtttctgtgg aaaagaggca ggctcctggc   1380

aaaaggtcag agtctggatc accttctgct ggaggccaca gcaaacctcc tcacagccca   1440

ctggtcctca agaggtgcca cgtctccaca catcagcaca actacgcagc gcctccctcc   1500

actcggaagg actatcctgc tgccaagagg gtcaagttgg acagtgtcag agtcctgaga   1560

cagatcagca acaaccgaaa atgcaccagc cccaggtcct cggacaccga ggagaatgtc   1620

aagaggcgaa cacacaacgt cttggagcgc cagaggagga acgagctaaa acggagcttt   1680

tttgccctgc gtgaccagat cccggagttg gaaaacaatg aaaaggcccc caaggtagtt   1740

atccttaaaa aagccacagc atacatcctg tccgtccaag cagaggagca aaagctcatt   1800

tctgaagagg acttgttgcg gaaacgacga gaacagttga aacacaaact tgaacagcta   1860

cggaactctt gtgcgtaagg aaaagtaagg aaaacgattc cttctaacag aaatgtcctg   1920

agcaatcacc tatgaacttg tttcaaatgc atgatcaaat gcaacctcac aaccttggct   1980

gagtcttgag actgaaagat ttagccataa tgtaaactgc ctcaaattgg actttgggca   2040

taaaagaact tttttatgct taccatcttt ttttttctt taacagattt gtatttaaga   2100

attgttttta aaaaatttta a                                              2121
```

<210> SEQ ID NO 83
<211> LENGTH: 3597
<212> TYPE: DNA
<213> ORGANISM: Homo sapiens

<400> SEQUENCE: 83

```
ggcgaatgga gcaggggcgc gcagataatt aaagatttac acacagctgg aagaaatcat     60

agagaagccg ggcgtggtgg ctcatgccta taatcccagc acttttggag gctgaggcgg    120

gcagatcact tgagatcagg agttcgagac cagcctggtg ccttggcatc tcccaatggg    180

gtggctttgc tctgggctcc tgttccctgt gagctgcctg gtcctgctgc aggtggcaag    240

ctctgggaac atgaaggtct tgcaggagcc cacctgcgtc tccgactaca tgagcatctc    300

tacttgcgag tggaagatga atggtcccac caattgcagc accgagctcc gcctgttgta    360

ccagctggtt tttctgctct ccgaagccca cacgtgtatc cctgagaaca acggaggcgc    420

ggggtgcgtg tgccacctgc tcatggatga cgtggtcagt gcggataact atacactgga    480

cctgtgggct gggcagcagc tgctgtggaa gggctccttc aagcccagcg agcatgtgaa    540

acccagggcc ccaggaaacc tgacagttca caccaatgtc tccgacactc tgctgctgac    600

ctggagcaac ccgtatcccc ctgacaatta cctgtataat catctcacct atgcagtcaa    660

catttggagt gaaaacgacc cggcagattt cagaatctat aacgtgacct acctagaacc    720

ctccctccgc atcgcagcca gcaccctgaa gtctgggatt tcctacaggg cacgggtgag    780

ggcctgggct cagtgctata acaccacctg gagtgagtgg agccccagca ccaagtggca    840

caactcctac agggagccct tcgagcagca cctcctgctg ggcgtcagcg tttcctgcat    900

tgtcatcctg gccgtctgcc tgttgtgcta tgtcagcatc accaagatta agaaagaatg    960
```

-continued

```
gtgggatcag attcccaacc cagcccgcag ccgcctcgtg gctataataa tccaggatgc   1020
tcaggggtca cagtgggaga agcggtcccg aggccaggaa ccagccaagt gcccacactg   1080
gaagaattgt cttaccaagc tcttgccctg ttttctggag cacaacatga aaagggatga   1140
agatcctcac aaggctgcca aagagatgcc tttccagggc tctggaaaat cagcatggtg   1200
cccagtggag atcagcaaga cagtcctctg gccagagagc atcagcgtgg tgcgatgtgt   1260
ggagttgttt gaggccccgg tggagtgtga ggaggaggag gaggtagagg aagaaaaagg   1320
gagcttctgt gcatcgcctg agagcagcag ggatgacttc caggagggaa gggagggcat   1380
tgtggcccgg ctaacagaga gcctgttcct ggacctgctc ggagaggaga atgggggctt   1440
ttgccagcag gacatggggg agtcatgcct tcttccacct tcgggaagta cgagtgctca   1500
catgccctgg gatgagttcc caagtgcagg gcccaaggag gcacctccct ggggcaagga   1560
gcagcctctc cacctggagc caagtcctcc tgccagcccg acccagagtc cagacaacct   1620
gacttgcaca gagacgcccc tcgtcatcgc aggcaaccct gcttaccgca gcttcagcaa   1680
ctccctgagc cagtcaccgt gtcccagaga gctgggtcca gacccactgc tggccagaca   1740
cctggaggaa gtagaacccg agatgccctg tgtcccccag ctctctgagc caaccactgt   1800
gccccaacct gagccagaaa cctgggagca gatcctccgc cgaaatgtcc tccagcatgg   1860
ggcagctgca gcccccgtct cggcccccac cagtggctat caggagtttg tacatgcggt   1920
ggagcagggt ggcacccagg ccagtgcggt ggtgggcttg ggtcccccag gagaggctgg   1980
ttacaaggcc ttctcaagcc tgcttgccag cagtgctgtg tccccagaga aatgtgggtt   2040
tggggctagc agtggggaag aggggtataa gcctttccaa gacctcattc ctggctgccc   2100
tggggaccct gccccagtcc ctgtcccctt gttcaccttt ggactggaca gggagccacc   2160
tcgcagtccg cagagctcac atctcccaag cagctcccca gagcacctgg gtctggagcc   2220
gggggaaaag gtagaggaca tgccaaagcc cccacttccc caggagcagg ccacagaccc   2280
ccttgtggac agcctgggca gtggcattgt ctactcagcc cttacctgcc acctgtgcgg   2340
ccacctgaaa cagtgtcatg gccaggagga tggtggccag acccctgtca tggccagtcc   2400
ttgctgtggc tgctgctgtg gagacaggtc ctcgcccccct acaacccccc tgagggcccc   2460
agacccctct ccaggtgggg ttccactgga ggccagtctg tgtccggcct ccctggcacc   2520
ctcgggcatc tcagagaaga gtaaatcctc atcatccttc catcctgccc ctggcaatgc   2580
tcagagctca agccagaccc ccaaaatcgt gaactttgtc tccgtgggac ccacatacat   2640
gagggtctct taggtgcatg tcctcttgtt gctgagtctg cagatgagga ctagggctta   2700
tccatgcctg ggaaatgcca cctcctggaa ggcagccagg ctggcagatt tccaaaagac   2760
ttgaagaacc atggtatgaa ggtgattggc cccactgacg ttggcctaac actgggctgc   2820
agagactgga ccccgcccag cattgggctg ggctcgccac atcccatgag agtagagggc   2880
actgggtcgc cgtgccccac ggcaggcccc tgcaggaaaa ctgaggccct tgggcacctc   2940
gacttgtgaa cgagttgttg gctgctccct ccacagcttc tgcagcagac tgtccctgtt   3000
gtaactgccc aaggcatgtt ttgcccacca gatcatggcc cacgtggagg cccacctgcc   3060
tctgtctcac tgaactagaa gccgagccta gaaactaaca cagccatcaa gggaatgact   3120
tgggcggcct tgggaaatcg atgagaaatt gaacttcagg gagggtggtc attgcctaga   3180
ggtgctcatt catttaacag agcttcctta ggttgatgct ggaggcagaa tcccggctgt   3240
caaggggtgt tcagttaagg ggagcaacag aggacatgaa aaattgctat gactaaagca   3300
gggacaattt gctgccaaac acccatgccc agctgtatgg ctgggggctc ctcgtatgca   3360
```

-continued

```
tggaaccccc agaataaata tgctcagcca ccctgtgggc cgggcaatcc agacagcagg   3420
cataaggcac cagttaccct gcatgttggc ccagacctca ggtgctaggg aaggcgggaa   3480
ccttgggttg agtaatgctc gtctgtgtgt tttagtttca tcacctgtta tctgtgtttg   3540
ctgaggagag tggaacagaa ggggtggagt tttgtataaa taaagtttct ttgtctc      3597
```

<210> SEQ ID NO 84
<211> LENGTH: 2709
<212> TYPE: DNA
<213> ORGANISM: Homo sapiens

<400> SEQUENCE: 84

```
gggaatagca gaataggagc aagccagcac tagtcagcta actaagtgac tcaaccaagg     60
cctttttcc ttgttatctt tgcagatact tcattttctt agcgtttctg gagattacaa    120
catcctgcgg ttccgtttct gggaacttta ctgatttatc tccccctca cacaaataag     180
cattgattcc tgcatttctg aagatctcaa gatctggact actgttgaaa aaatttccag    240
tgaggctcac ttatgtctgt aaagatggga aaaaaataca agaacattgt tctactaaaa    300
ggattagagg tcatcaatga ttatcatttt agaatggtta agtccttact gagcaacgat    360
ttaaaactta atttaaaaat gagagaagag tatgacaaaa ttcagattgc tgacttgatg    420
gaagaaaagt tccgaggtga tgctggtttg ggcaaactaa taaaaatttt cgaagatata    480
ccaacgcttg aagacctggc tgaaactctt aaaaaagaaa agttaaaagt aaaaggacca    540
gccctatcaa gaaagaggaa gaaggaagtg catgctactt cacctgcacc ctccacaagc    600
agcactgtca aaactgaagg agcagaggca actcctggag ctcagaaaag aaaaaaatca    660
accaaagaaa aggctggacc caaagggagt aaggtgtccg aggaacagac tcagcctccc    720
tctcctgcag gagccggcat gtccacagcc atgggccgtt ccccatctcc caagacctca    780
ttgtcagctc cacccaacag ttcttcaact gagaacccga aaacagtggc caaatgtcag    840
gtaactccca gaagaaatgt tctccaaaaa cgcccagtga tagtgaaggt actgagtaca    900
acaaagccat ttgaatatga gaccccagaa atggagaaaa aaataatgtt tcatgctaca    960
gtggctacac agacacagtt cttccatgtg aaggttttaa acaccagctt gaaggagaaa   1020
ttcaatggaa agaaaatcat catcatatca gattatttgg aatatgatag tctcctagag   1080
gtcaatgaag aatctactgt atctgaagct ggtcctaacc aaacgtttga ggttccaaat   1140
aaaatcatca acagagcaaa ggaaactctg aagattgata ttcttcacaa acaagcttca   1200
ggaaatattg tatatggggt atttatgcta cataagaaaa cagtaaatca gaagaccaca   1260
atctacgaaa ttcaggatga tagaggaaaa atggatgtag tggggacagg acaatgtcac   1320
aatatcccct gtgaagaagg agataagctc cagcttttct gctttcgact tagaaaaaag   1380
aaccagatgt caaaactgat ttcagaaatg catagtttta tccagataaa gaaaaaaaca   1440
aacccgagaa acaatgaccc caagagcatg aagctacccc aggaacagcg tcagcttcca   1500
tatccttcag aggccagcac aaccttccct gagagccatc ttcggactcc tcagatgcca   1560
ccaacaactc catccagcag tttcttcacc aagaaaagtg aagacacaat ctccaaaatg   1620
aatgacttca tgaggatgca gatactgaag gaagggagtc attttccagg accgttcatg   1680
accagcatag gcccagctga gagccatccc cacactcctc agatgcctcc atcaacacca   1740
agcagcagtt tcttaaccac gttgaaacca agactgaaga ctgaacctga agaagtttcc   1800
atagaagaca gtgcccagag tgacctcaaa gaagtgatgg tgctgaacgc aacagaatca   1860
```

```
tttgtatatg agcccaaaga gcagaagaaa atgtttcatg ccacagtggc aactgagaat   1920

gaagtcttcc gagtgaaggt ttttaatatt gacctaaagg agaagttcac cccaaagaag   1980

atcattgcca tagcaaatta tgtttgccgc aatgggttcc tggaggtata tcctttcaca   2040

cttgtggctg atgtgaatgc tgaccgaaac atggagatcc caaaaggatt gattagaagt   2100

gccagcgtaa ctcctaaaat caatcagctt tgctcacaaa ctaaaggaag ttttgtgaat   2160

ggggtgtttg aggtacataa gaaaaatgta aggggtgaat tcacttatta tgaaatacaa   2220

gataatacag ggaagatgga agtggtggtg catggacgac tgaacacaat caactgtgag   2280

gaaggagata aactgaaact caccagcttt gaattggcac cgaaaagtgg gaataccggg   2340

gagttgagat ctgtaattca tagtcacatc aaggtcatca agaccaggaa aaacaagaaa   2400

gacatactca atcctgattc aagtatggaa acttcaccag actttttctt ctaaaatctg   2460

gatgtcattg acgataatgt ttatggagat aaggtctaag tccctaaaaa aatgtacata   2520

tacctggttg aaatacaaca ctatacatac acaccaccat atatactagc tgttaatcct   2580

atggaatggg ggtattggga gtgctttttt aatttttcat agtttttttt taataaaatg   2640

gcatattttg catctacaac ttctataata agaaaaaata aataaacatt atcttttttg   2700

tgaaaaaaa                                                           2709
```

<210> SEQ ID NO 85
<211> LENGTH: 777
<212> TYPE: DNA
<213> ORGANISM: Homo sapiens

<400> SEQUENCE: 85

```
ttcttcaaac cctcctcttc cctgtgttct cctacagaga ttgctgattt ctccttaagc     60

aagagattca ctgccgctaa gcatggctca gaccaactcg ttcttcatgc tgatctcctc    120

cctgatgttc ctgtctctga gccaaggcca agaggcccag acagagttgc cccaggcccg    180

gatcagctgc ccagaaggca ccaatgccta tcgctcctac tgctactact ttaatgaaga    240

ccgtgagacc tgggttgatg cagatctcta ttgccagaac atgaattcgg gcaacctggt    300

gtctgtgctc acccaggccg agggtgcctt tgtggcctca ctgattaagg agagtggcac    360

tgatgacttc aatgtctgga ttggcctcca tgaccccaaa aagaaccgcc gctggcactg    420

gagcagtggg tccctggtct cctacaagtc ctggggcatt ggagccccaa gcagtgttaa    480

tcctggctac tgtgtgagcc tgacctcaag cacaggattc cagaaatgga aggatgtgcc    540

ttgtgaagac aagttctcct ttgtatgcaa gttcaaaaac tagaggcagc tggaaaatac    600

atgtctagaa ctgatccagc aattacaacg gagtcaaaaa ttaaaccgga ccatctctcc    660

aactcaactc aacctggaca ctctcttctc tgctgagttt gccttgttaa tcttcaatag    720

ttttacctac cccagtcttt ggaaccctaa ataataaaaa taaacatgtt ttccact       777
```

<210> SEQ ID NO 86
<211> LENGTH: 2043
<212> TYPE: DNA
<213> ORGANISM: Homo sapiens

<400> SEQUENCE: 86

```
gtgcttaggc actgcagttg agtggctcac aaggagctaa aatttcacta atgcgtattc     60

agtgggtggt tctggtttgc ctgatttttg cctctgggca tggctgtttc agcctgagag    120

gctgttccaa gaatgttgct ttactaggag ctcatgccgc ctggtggtaa atatgaagta    180

cagcagtgca acagaccagt tttactccaa ggaaaccctg tagagatgac agcaatggtt    240
```

```
ggtgatttct gcctcaatta tgaaagtgat ctggtgttac agggccagag aagactaggg    300

gagttcgggt tttctagacc aaacagacac tcagtcctgg gcctggaggt ctctgcagtg    360

aggtgctgcc acagacagag ccaccttaac tcctcaggac aaccagtggc ttccgacaca    420

cactatgcac tggagggcaa gcagctctca gcttgggagc aactgaggat ggtgaacagc    480

ctgggcaagg agtgctctga ggctaagacc ctgaacagca ggaaccgaag tgcagctccc    540

cacttcaggt aatgtgattc taccctttgc ctgagaaaca tatccatcct aattgccatg    600

tgctcagctg gaccactaga gggagccatc ctgtaacggg tgaggtcaac ctaacaaatg    660

gtatcagtcg agtattgatc ggaggccaac gcaagaagtt accagtagcc tatttcagat    720

ttattaaaaa acacataggt aacgagtcag agctttggct aggaatgatt tggaaaagaa    780

ctgaaggcat aattccacag gacattcaca gttgtgtgct agagacagag aggagcagga    840

aagtgtttta gaagcatttg cggtggacaa tggaaggccc ggcttcatcg tattcctgtt    900

tgctgatcca catctgctgg aaggtggaca gagaggccag gatggagcca ccgatccaga    960

cagagtattt gcgctccgga ggggcaatga tctgtcagtc aagatgaaaa agaatggtca   1020

ttaatgtcat cattagtgca gtcgttagtg cggtaggaca gagcctggat gttctaccat   1080

ggcctagttt cttgttcagc agggacacag gcttgtctgt tagatgccaa ttgtgtccta   1140

attgtgtcat gttcttggca ggaccgccag agggagccat ggatttagaa attcttcagt   1200

ggtttcatgg atgccagcag actccatccc tggaaaagag acacaggcca tggtccttaa   1260

gtggagagta aaacccaggc tagacatgga agaccagact tgaacatctg gatgatcttg   1320

cagtggactg aggctgggaa gacataataa tctaggaacc acctgtctga gagacaaaag   1380

ggtcttgtta tgctctatgt cttcctgcct gccttctaat gaggaaggcc tgctgcagca   1440

tcctgaggtg tgggctacaa cagaaatgct tttggtcttg ggcaaccgt cacttgtctc    1500

catgttctgg aggctggctt gatatggaag aagacaatga ctccccttcc caggaaaagg   1560

gcgtttgttg cctaccgatg aaggatggct ggaacagggt ctctgggcag cggaaacgtt   1620

catttccgat ggtgatcact tgcccatcag gcaactcgta actcttctca agggaggatg   1680

aggatgcggc agtggccatc tcattttcaa agtccagagc tacataacac agtttctcct   1740

tgatgtcccg gacaatctca cgctcagctg tcaaccagat acaaacattg tggcaaacat   1800

tagggtctgc acaggtggca aagattcacc tgccctactg cagtctctcc ctcaagacat   1860

gtgccatcaa aaaatgtgtc agttcaatat tctgcaatcc aaaatccaca atgataatga   1920

cgtagtaggg ccaccaggga accacctctg ttcctaggac agtgtctcat gcatagtagg   1980

ccctcagcat gcattgtctg ggaaatgcat aacaagaata aaatgagcta gctagagaaa   2040

ggc                                                                 2043
```

```
<210> SEQ ID NO 87
<211> LENGTH: 1501
<212> TYPE: DNA
<213> ORGANISM: Homo sapiens

<400> SEQUENCE: 87

agcgagtcct tcttttcctg actgcagctc ttttcatttt gccatccttc tccagctcca     60

tgatggttct gcaggtttct gcggcccccc ggacagtggc tctgacggcg ttactgatgg    120

tgctgctcac atctgtggtc cagggcaggg ccactccaga gaattacgtg taccagggac    180

ggcaggaatg ctacgcgttt aatgggacac agcgcttcct ggagagatac atctacaacc    240
```

```
gggaggagta cgcgcgcttc gacagcgacg tgggggagtt ccgggcggtg acggagctgg    300

ggcggcctgc tgcggagtac tggaacagcc agaaggacat cctggaggag aagcgggcag    360

tgccggacag ggtatgcaga cacaactacg agctggacga ggccgtgacc ctgcagcgcc    420

gagtccagcc taaggtgaac gtttccccct ccaagaaggg gcccctgcag caccacaacc    480

tgcttgtctg ccacgtgaca gatttctacc caggcagcat tcaagtccga tggttcctga    540

atggacagga ggaaacagct ggggtcgtgt ccaccaacct gatccgtaat ggagactgga    600

ccttccagat cctggtgatg ctggaaatga ccccccagca gggagacgtc tacatctgcc    660

aagtggagca caccagcctg gacagtcctg tcaccgtgga gtggaaggca cagtctgatt    720

ctgcccagag taagacattg acgggagctg gggcttcgt gctggggctc atcatctgtg     780

gagtgggcat cttcatgcac aggaggagca agaaagttca acgaggatct gcataaacag    840

ggttcctgac ctcaccgaaa agactaatgt gccttagaac aagcatttgc tgtgttttgt    900

taacacctgg ttccaggaca gaccctcagc ttcccaagag gatactgctg ccaagaagtt    960

gctctgaagt cagtttctat cgttctgctc tttgattcaa agcactgttt ctctcactgg   1020

gcctccaacc atgttccctt cttcttagca ccacaaataa tcaaaaccca acataagtgt   1080

ttgctttcct ttaaaaatat gcatcaaatc gtctctcatt acttttctct gagggtttta   1140

gtaaacagta ggagttaata aagaagttca ttttggttta cacgtaggaa agaagagaag   1200

catcaaagtg gagatatgtt aactattgta taatgtggcc tgttatacat gacactcttc   1260

tgaattgact gtatttcagt gagctgcccc caaatcaagt ttagtgccct catccattta   1320

tgtctcagac cgctattctt aactattcaa tggtgagcag actgcaaatc tgcctgatag   1380

gacccatatt cccacagcac taattcaaca tatatcttac tgagagcatg ttttatcatt   1440

accattaaga agttaaatga acatcagaat ttaaaatcat aaatataatc taatacactt   1500

t                                                                   1501
```

<210> SEQ ID NO 88
<211> LENGTH: 1096
<212> TYPE: DNA
<213> ORGANISM: Homo sapiens

<400> SEQUENCE: 88

```
atgatcctaa acaaagctct gctgctgggg gccctcgctc tgaccaccgt gatgagcccc     60

tgtggaggtg aagacattgt ggctgaccac gttgcctctt gtggtgtaaa cttgtaccag    120

ttttacggtc cctctggcca gtacacccat gaatttgatg gagatgagca gttctacgtg    180

gacctggaga ggaaggagac tgcctggcgg tggcctgagt tcagcaaatt tggaggtttt    240

gacccgcagg gtgcactgag aaacatggct gtggcaaaac acaacttgaa catcatgatt    300

aaacgctaca actctaccgc tgctaccaat gaggttcctg aggtcacagt gttttccaag    360

tctcccgtga cactgggtca gcccaacacc ctcatttgtc ttgtggacaa catctttcct    420

cctgtggtca acatcacatg gctgagcaat gggcagtcag tcacagaagg tgtttctgag    480

accagcttcc tctccaagag tgatcattcc ttcttcaaga tcagttacct caccttcctc    540

ccttctgctg atgagattta tgactgcaag gtggagcact ggggcctgga ccagcctctt    600

ctgaaacact gggagcctga gattccagcc cctatgtcag agctcacaga gactgtggtc    660

tgtgccctgg ggttgtctgt gggcctcatg ggcattgtgg tgggcactgt cttcatcatc    720

caaggcctgc gttcagttgg tgcttccaga caccaagggc cattgtgaat cccatcctgg    780

aagggaaggt gcatcgccat ctacaggagc agaagaatgg acttgctaaa tgacctagca    840
```

```
ctattctctg gcccgattta tcatatccct tttctcctcc aaatatttct cctctcacct    900

tttctctggg acttaagctg ctatatcccc tcagagctca caaatgcctt tacattcttt    960

ccctgacctc ctgatttttt ttttcttttc tcaaatgtta cctacaatac atgcctgggg   1020

taagccaccc ggctacctaa ttcctcagta acctccatct aaaatctcca aggaagcaat   1080

aaattccttt tatgag                                                   1096
```

<210> SEQ ID NO 89
<211> LENGTH: 1100
<212> TYPE: DNA
<213> ORGANISM: Homo sapiens

<400> SEQUENCE: 89

```
ctaaagctgg gttggtagct cctacctact gtgtggcaag aaggtatggg tcatgaacag     60

aaccaaggag ctgcgctgct acagatgtta ccacttctgt ggctgctacc ccactcctgg    120

gccgtccctg aagctcctac tccaatgtgg ccagatgacc tgcaaaacca cacattcctg    180

cacacagtgt actgccagga tgggagtccc agtgtgggac tctctgaggc ctacgacgag    240

gaccagcttt tcttcttcga cttttcccag aacactcggg tgcctcgcct gcccgaattt    300

gctgactggg ctcaggaaca gggagatgct cctgccattt tatttgacaa agagttctgc    360

gagtggatga tccagcaaat agggccaaaa cttgatggga aaatcccggt gtccagaggg    420

tttcctatcg ctgaagtgtt cacgctgaag cccctggagt ttggcaagcc caacactttg    480

gtctgttttg tcagtaatct cttcccaccc atgctgacag tgaactggca gcatcattcc    540

gtccctgtgg aaggatttgg gcctactttt gtctcagctg tcgatggact cagcttccag    600

gccttttctt acttaaactt cacaccagaa ccttctgaca ttttctcctg cattgtgact    660

cacgaaattg accgctacac agcaattgcc tattgggtac cccggaacgc actgccctca    720

gatctgctgg agaatgtgct gtgtggcgtg gcctttggcc tgggtgtgct gggcatcatc    780

gtgggcattg ttctcatcat ctacttccgg aagccttgct caggtgactg attcttccag    840

accagagttt gatgccagca gcttcggcca tccaaacaga ggatgctcag atttctcaca    900

tcctgcccag gatctcctct tagggtagaa gaagtctctg ggacatccct ggggtgtgtg    960

tgtagatttc ccacctgggg actctgctgt ccctgggctt gcatcccagg gatcccagag   1020

tggcctgcct atcacaacca catcccttcc ccccacaagg caataaatct catttcttta   1080

aaaaaaaaaa aaaaaaaaaa                                               1100
```

<210> SEQ ID NO 90
<211> LENGTH: 3526
<212> TYPE: DNA
<213> ORGANISM: Homo sapiens

<400> SEQUENCE: 90

```
ccacgcgtcc ggacaggctt aagcatggcc aagaagcttg agagaagaaa aatttcagaa     60

aaattgtctc aatttgacta gaatatcaat gaaccaggaa aactgaagca ccttccctaa    120

agaaaacttg ggtatacaat tactccacag acagagctga gggtttttta cccaaatcag    180

tcactggatt ttgctgcctg atacgtgaat cttcttggaa tttttctcat gtggatctaa    240

ggggaatgct ttattatggc tgctgttgtc caacagaacg acctagtatt tgaatttgct    300

agtaacgtca tggaggatga acgacagctt ggtgatccag ctatttttcc tgccgtaatt    360

gtggaacatg ttcctggtgc tgatattctc aatagttatg ccggtctagc ctgtgtggaa    420
```

-continued

```
gagcccaatg acatgattac tgagagttca ctggatgttg ctgaagaaga aatcatagac    480
gatgatgatg atgacatcac ccttacagtt gaagcttctt gtcatgacgg ggatgaaaca    540
attgaaacta ttgaggctgc tgaggcactc ctcaatatgg attcccctgg ccctatgctg    600
gatgaaaaac gaataaataa taatatattt agttcacctg aagatgacat ggttgttgcc    660
ccagtcaccc atgtgtccgt cacattagat gggattcctg aagtgatgga aacacagcag    720
gtgcaagaaa aatatgcaga ctcaccggga gcctcatcac cagaacagcc taagaggaaa    780
aaaggaagaa aaactaaacc accacgacca gattccccag ccactacgcc aaatatatct    840
gtgaagaaga aaaacaaaga tggaaaggga aacacaattt atctttggga gtttttactg    900
gcactgctcc aggacaaggc tacttgtcct aaatacatca agtggaccca gcgagagaaa    960
ggcattttta aattggtgga ttctaaagca gtgtccaggt tgtgggggaa gcacaaaaac   1020
aaacctgata tgaattatga gaccatggga agagcactca ggtactatta ccaaaggggt   1080
attctggcaa aagtggaagg tcagcgcttg gtgtatcagt ttaaagaaat gccaaaagat   1140
cttatatata taaatgatga ggatccaagt tccagcatag agtcttcaga tccatcacta   1200
tcttcatcag ccacttcaaa taggaatcaa accagccggt cgagagtatc ttcaagtcca   1260
ggggtaaaag gaggagccac tacagttcta aaaccaggga attctaaagc tgcaaaaccc   1320
aaagatcctg tggaagttgc acaaccatca gaagttttga ggacagtgca gcccacgcag   1380
tctccatatc ctacccagct cttccggact gttcatgtag tacagccagt acaggctgtc   1440
ccagagggag aagcagctag aaccagtacc atgcaggatg aaacattaaa ttcttccgtt   1500
cagagtatta ggactataca ggctccaacc caagttccag tggttgtgtc tcctaggaat   1560
cagcagttgc atacagtaac actccaaaca gtgccactca caacagttat agccagcaca   1620
gatccatcag caggtactgg atctcagaag tttattttac aagccattcc atcatcacag   1680
cccatgacag tactgaaaga aaatgtcatg ctgcagtcac aaaaggcggg ctctcctcct   1740
tcaattgtct tgggccctgc ccaggttcag caggtcctta ctagcaatgt tcagaccatt   1800
tgcaatggaa ccgtcagtgt ggcttcctct ccatccttca gtgctactgc acctgtggtg   1860
accttttctc ctcgcagttc acagctggtt gctcacccac ctggcactgt aatcacttca   1920
gttatcaaaa ctcaagaaac aaaaactctt acacaggaag tagagaaaaa ggaatctgaa   1980
gatcatttga aagagaacac tgagaaaacg gagcagcagc cacagcctta tgtgatggta   2040
gtgtccagtt ccaatggatt tacttctcag gtagctatga aacaaaacga actgctggaa   2100
cccaactctt tttagttaat ataccaaagc ttatgaataa ttgtttgtta attgaacatt   2160
ttcaattata tgcagactga ctgattctaa gataaattct aaggaggttt ctaattttgt   2220
aattgttaaa aatagagtta attttgactt tgttagatga gggaggaaaa ctcaactgtt   2280
tctctttgtt atctaaatgt ttcagaattc aatcgtgaag gaacaggcat tttacactat   2340
gaagacattc ttttgagatt tttatttcag ttgctatatc ataagcattt ttaaagtttc   2400
ttttctaatt ttacattgta ttagattttc tgattctttt gtaaatacag aacttaaata   2460
gaaggcaaca ggaaatttat ataggaacta ttttcattcc acttgtgtaa gttaagtctt   2520
gactctttca aatgcaaaaa acctatttta tgctttgtta aaattatggt gtcacttaga   2580
ttgactttag ttgactgcac tatataatat agaactatga atatgtagaa taacatgaaa   2640
aattggaggt gctggtggta tggctgaccc tgtttcagaa gcaggatagt ataaaagcat   2700
cagcctaaga atggcactcc cactaactag ctatgtaatc ttgacctctt tgggctttag   2760
ttcctctcat aaaaggaaga gatgtattgg attagactag attatcacca ctttctcttc   2820
```

```
tagttctaat ttttttaatt ctaataccta tattttcaag ttatgtcaat taaatcatta   2880

tcaggttatt tcctaatgta agaatagcta aaatgttgca gagaaataag tgacccaaca   2940

aaatttattc atctgttatg ggtaagatct gccataaatt cttcctaaat aatttgttta   3000

ctaactcttt aggccactgt gctttgcggt ccattagtaa acttgtgttg ctaagtgcta   3060

aacagaatac tgctattttg agagagtcaa gactctttct taagggccaa gaaagcaact   3120

tgagccttgg gctaatctgg ctgagtagtc agttataaaa gcataattgc tttatatttt   3180

ggatcatttt ttactggggg cggacttggg gggggttgca tacaaagata acatatatat   3240

ccaactttct gaaatgaaat gtttttagat tactttttca actgtaaata atgtacattt   3300

aatgtcacaa gaaaaaaatg tcttctgcaa attttctagt ataacagaaa tttttgtaga   3360

tgaaaaaaat cattatgttt agaggtctaa tgctatgttt tcatattaca gagtgaattt   3420

gtatttaaac aaaaatttaa attttggaat cctctaaaca tttttgtatc tttaattggt   3480

ttattattaa ataaatcata taaaaattct caaaaaaaaa aaaaaa                  3526
```

```
<210> SEQ ID NO 91
<211> LENGTH: 1968
<212> TYPE: DNA
<213> ORGANISM: Homo sapiens

<400> SEQUENCE: 91

aattccgccg ggcgcttaga acagaggctt gcacaggtgg agatgtggaa gtctgtagtg     60

ggccatgatg tgtctgtttc cgtggagacc cagggtgatg attgggacac agatcctgac    120

tttgtgaatg acatctctga aaaggagcaa cgatggggag ccaagaccat cgaggggtct    180

ggacgcacag aacacatcaa catccaccag ctgaggaaca aagtatcaga ggagcatgat    240

gttctcagga agaaagagat ggagtcaggg cccaaagcat cccatggcta tggaggtcgg    300

tttggagtag aaagagaccg aatggacaag agtgcagtgg gccatgagta tgttgccgag    360

gtggagaagc actcttctca gacggatgct gccaaaggct ttgggggcaa gtacggagtt    420

gagagggaca gggcagacaa gtcagcagtc ggctttgatt ataaaggaga agtggagaag    480

catacatctc agaaagatta ctctcgtggc tttggtggcc ggtacggggt ggagaaggat    540

aaatgggaca aagcagctct gggatatgac tacaagggag agacggagaa acacgagtcc    600

cagagagatt atgccaaggg ctttggtggc cagtatggaa tccagaagga ccgagtggat    660

aagagcgctg tcggcttcaa tgaaatggag gccccgacca cagcttataa gaagacgacg    720

cccatagaag ccgcttctag tggtgcccgt gggctgaagg cgaaatttga gtccatggct    780

gaggagaaga ggaagcgaga ggaagaggag aaggcacagc aggtggccag gaggcaacag    840

gagcgaaagg ctgtgacaaa gaggagccct gaggctccac agccagtgat agctatggaa    900

gagccagcag taccggcccc actgcccaag aaaatctcct cagaggcctg gcctccagtt    960

gggactcctc catcatcaga gtctgagcct gtgagaacca gcagggaaca cccagtgccc   1020

ttgctgccca ttaggcagac tctcccggag gacaatgagg agcccccagc tctgcccccct  1080

aggactctgg aaggcctcca ggtggaggaa gagccagtgt acgaagcaga gcctgagcct   1140

gagcccgagc ctgagcccga gcctgagaat gactatgagg acgttgagga gatggacagg   1200

catgagcagg aggatgaacc agagggggac tatgaggagg tgctcgagcc tgaagattct   1260

tctttttctt ctgctctggc tggatcatca ggctgcccgg ctggggctgg ggctggggct   1320

gtggctctgg ggatctcagc tgtggctcta tatgattacc aaggagaggg aagtgatgag   1380
```

```
ctttcctttg atccggacga cgtaatcact gacattgaga tggtggacga gggctggtgg   1440

cggggacgtt gccatggcca ctttggactc ttccctgcaa attatgtcaa gcttctggag   1500

tgactagagc tcactgtcta ctgcaactgt gatttcccat gtccaaagtg gctctgctcc   1560

accccctccc tattcctgat gcaaatgtct aaccagatga gtttctggac agacttccct   1620

ctcctgcttc attaagggct tggggcagag acagcatggg gaaggaggtc cccttcccca   1680

agagtcctct ctatcctgga tgagctcatg aacatttctc ttgtgttcct gactccttcc   1740

caatgaacac ctctctgcca ccccaagctc tgctctcctc ctctgtgagc tctgggcttc   1800

ccagtttgtt tacccgggaa agtacgtcta gattgtgtgg tttgcctcat tgtgctattt   1860

gcccactttc cttccctgaa gaaatatctg tgaaccttct ttctgttcag tcctaaaatt   1920

cgaaataaag tgagactatg gttcacctgt aaaaaaaaaa aaggaatt               1968
```

```
<210> SEQ ID NO 92
<211> LENGTH: 2088
<212> TYPE: DNA
<213> ORGANISM: Homo sapiens

<400> SEQUENCE: 92

gaattcggca cgagcgcgcg gcgaatctca acgctgcgcc gtctgcgggc gcttccgggc     60

caccagtttc tctgctttcc accctggcgc cccccagccc tggctcccca gctgcgctgc    120

cccgggcgtc cacgccctgc gggcttagcg ggttcagtgg gctcaatctg cgcagcgcca    180

cctccatgtt gaccaagcct ctacaggggc ctcccgcgcc ccccgggacc cccacgccgc    240

cgccaggagg caaggatcgg gaagcgttcg aggccgagta tcgactcggc cccctcctgg    300

gtaagggggg ctttggcacc gtcttcgcag gacaccgcct cacagatcga ctccaggtgg    360

ccatcaaagt gattccccgg aatcgtgtgc tgggctggtc cccccttgtca gactcagtca    420

catgcccact cgaagtcgca ctgctatgga aagtgggtgc aggtggtggg caccctggcg    480

tgatccgcct gcttgactgg tttgagacac aggaaggctt catgctggtc ctcgagcggc    540

ctttgcccgc ccaggatctc tttgactata tcacagagaa gggcccactg ggtgaaggcc    600

caagccgctg cttctttggc caagtagtgg cagccatcca gcactgccat tcccgtggag    660

ttgtccatcg tgacatcaag gatgagaaca tcctgataga cctacgccgt ggctgtgcca    720

aactcattga ttttggttct ggtgccctgc ttcatgatga accctacact gactttgatg    780

ggacaagggt gtacagcccc ccagagtgga tctctcgaca ccagtaccat gcactcccgg    840

ccactgtctg gtcactgggc atcctcctct atgacatggt gtgtggggac attccctttg    900

agagggacca ggagattctg gaagctgagc tccacttccc agcccatgtc tccccagact    960

gctgtgccct aatccgccgg tgcctggccc ccaaaccttc ttcccgaccc tcactggaag   1020

agatcctgct ggacccctgg atgcaaacac cagccgagga tgttacccct caacccctcc   1080

aaaggaggcc ctgccccttt ggcctggtcc ttgctaccct aagcctggcc tggcctggcc   1140

tggcccccaa tggtcagaag agccatccca tggccatgtc acagggatag atggacattt   1200

gttgacttgg ttttacaggt cattaccagt cattaaagtc cagtattact aaggtaaggg   1260

attgaggatc aggggttaga agacataaac caagtttgcc cagttccctt cccaatccta   1320

caaaggagcc ttcctcccag aacctgtggt ccctgatttt ggagggggaa cttcttgctt   1380

ctcattttgc taaggaagtt tattttggtg aagttgttcc cattttgagc cccgggactc   1440

ttattttgat gatgtgtcac cccacattgg cacctcctac taccaccaca caaacttagt   1500

tcatatgctt ttacttgggc aagggtgctt tccttccaat accccagtag cttttatttt   1560
```

```
agtaaaggga ccctttcccc tagcctaggg tcccatattg ggtcaagctg cttacctgcc   1620

tcagcccagg atttttattt ttgggggagg taatgccctg ttgttacccc aaggcttctt   1680

tttttttttt tttttttttg ggtgagggga ccctactttg ttatcccaag tgctcttatt   1740

ctggtgagaa gaaccttaat tccataattt gggaaggaat ggaagatgga caccaccgga   1800

caccaccaga caataggatg ggatggatgg tttttttgggg gatgggctag gggaaataag   1860

gcttgctgtt tgttttcctg ggcgctcccc tccaattttg cagatttttg caacctcctc   1920

ctgagccggg attgtccaat tactaaaatg taaataatca cgtattgtgg ggaggggagt   1980

tccaagtgtg ccctcctttt ttttcctgcc tggattattt aaaaagccat gtgtggaaac   2040

ccactattta ataaaagtaa tagaatcaga aaaaaaaaaa aaaaaaaa               2088
```

<210> SEQ ID NO 93
<211> LENGTH: 415
<212> TYPE: DNA
<213> ORGANISM: Homo sapiens

<400> SEQUENCE: 93

```
ccgctgcgtg ttttcctctt gatcgggaac tcctgcttct ccttgcctcg aaatggaccc     60

caactgctcc tgctcgcctg ttggctcctg tgcctgtgcc ggctcctgca aatgcaaaga    120

gtgcaaatgc acctcctgca agaagagctg ctgctcctgc tgccctgtgg gctgtgcmaa    180

gtgtgcccag ggctgcatct gcaaagggac gtcagacaag tgcagctgct gtgcctgatg    240

ccaggacagc tgtgctctca gatgtaaata gagcaaccta tataaacctg gatttttttt    300

tttttttttt tgtacaaccc tgacccgttt gctacatctt tttttctatg aaatatgtga    360

atggcaataa attcatctag actaaaaaaa aaaaaaaaaa aaaaaaaaaa aaaaa         415
```

<210> SEQ ID NO 94
<211> LENGTH: 5725
<212> TYPE: DNA
<213> ORGANISM: Homo sapiens

<400> SEQUENCE: 94

```
cctggaggag ggctctggaa gtcacgtcag gttggctctt caggttcatt tccatagttc     60

cctgcggcct ctgccttggg gagttatgtt ttgttaccga gatccgcgct accagattgc    120

accggggctg atttgggggc tgggaatttg ccattctgct gtacagacac tgattttttt    180

ttcttctttt taaaaagcaa ggtttgtttt cattttggat tttaggtgat gggcaagtca    240

gaaagtcaga tggatataac tgatatcaac actccaaagc caaagaagaa acagcgatgg    300

actcgactgg agatcagcct ctcggtcctt gtcctgctcc tcaccatcat agctgtgaga    360

atgatcgcac tctatgcaac ctacgatgat ggtatttgca agtcatcaga ctgcataaaa    420

tcagctgctc gactgatcca aaacatggat gccaccactg agccttgtag agactttttc    480

aaatatgctt gcggaggctg gttgaaacgt aatgtcattc ccgagaccag ctcccgttac    540

ggcaactttg acattttaag agatgaacta gaagtcgttt tgaaagatgt ccttcaagaa    600

cccaaaactg aagatatagt agcagtgcag aaagcaaaag cattgtacag gtcttgtata    660

aatgaatctg ctattgatag cagaggtgga gaacctctac tcaaactgtt accagacata    720

tatgggtggc cagtagcaac agaaaactgg gagcaaaaat atggtgcttc ttggacagct    780

gaaaaagcta ttgcacaact gaattctaaa tatgggaaaa aagtccttat taatttgttt    840

gttggcactg atgataagaa ttctgtgaat catgtaattc atattgacca acctcgactt    900
```

-continued

```
ggcctccctt ctagagatta ctatgaatgc actggaatct ataaagaggc ttgtacagca    960
tatgtggatt ttatgatttc tgtggccaga ttgattcgtc aggaagaaag attgcccatc   1020
gatgaaaacc agcttgcttt ggaaatgaat aaagttatgg aattggaaaa agaaattgcc   1080
aatgctacgg ctaaacctga agatcgaaat gatccaatgc ttctgtataa caagatgaga   1140
ttggcccaga tccaaaataa cttttcacta gagatcaatg ggaagccatt cagctggttg   1200
aatttcacaa atgaaatcat gtcaactgtg aatattagta ttacaaatga ggaagatgtg   1260
gttgtttatg ctccagaata tttaaccaaa cttaagccca ttcttaccaa atattctgcc   1320
agagatcttc aaaatttaat gtcctggaga ttcataatgg atcttgtaag cagcctcagc   1380
cgaacctaca aggagtccag aaatgctttc cgcaaggccc tttatggtac aacctcagaa   1440
acagcaactt ggagacgttg tgcaaactat gtcaatggga atatggaaaa tgctgtgggg   1500
aggctttatg tggaagcagc atttgctgga gagagtaaac atgtggtcga ggatttgatt   1560
gcacagatcc gagaagtttt tattcagact ttagatgacc tcacttggat ggatgccgag   1620
acaaaaaaga gagctgaaga aaaggcctta gcaattaaag aaaggatcgg ctatcctgat   1680
gacattgttt caaatgataa caaactgaat aatgagtacc tcgagttgaa ctacaaagaa   1740
gatgaatact tcgagaacat aattcaaaat ttgaaattca gccaaagtaa acaactgaag   1800
aagctccgag aaaaggtgga caaagatgag tggataagtg gagcagctgt agtcaatgca   1860
ttttactctt caggaagaaa tcagatagtc ttcccagccg gcattctgca gcccccccttc   1920
tttagtgccc agcagtccaa ctcattgaac tatgggggca tcggcatggt cataggacac   1980
gaaatcaccc atggcttcga tgacaatggc agaaacttta acaaagatgg agacctcgtt   2040
gactggtgga ctcaacagtc tgcaagtaac tttaaggagc aatcccagtg catggtgtat   2100
cagtatggaa acttttcctg ggacctggca ggtggacagc accttaatgg aattaataca   2160
ctgggagaaa acattgctga taatggaggt cttggtcaag catacagagc ctatcagaat   2220
tatattaaaa agaatggcga agaaaaatta cttcctggac ttgacctaaa tcacaaacaa   2280
ctatttttct tgaactttgc acaggtgtgg tgtggaacct ataggccaga gtatgcggtt   2340
aactccatta aaacagatgt gcacagtcca ggcaatttca ggattattgg gactttgcag   2400
aactctgcag agttttcaga agcctttcac tgccgcaaga attcatacat gaatccagaa   2460
aagaagtgcc gggtttggtg atcttcaaaa gaagcattgc agcccttggc tagacttgcc   2520
aacaccacag aaatggggaa ttctctaatc gaaagaaaat gggccctagg ggtcactgta   2580
ctgacttgag ggtgattaac agagagggca ccatcacaat acagataaca ttaggttgtc   2640
ctagaaaggg tgtggaggga ggaagggggt ctaaggtcta tcaagtcaat catttctcac   2700
tgtgtacata atgcttaatt tctaaagata atattactgt ttatttctgt ttctcatatg   2760
gtctaccagt ttgctgatgt ccctagaaaa caatgcaaaa cctttgaggt agaccaggat   2820
ttctaatcaa aagggaaaag aagatgttga agaatagagt taggcaccag aagaagagta   2880
ggtgacacta tagtttaaaa cacattgcct aactactagt ttttactttt atttgcaaca   2940
tttacagtcc ttcaaaatcc ttccaaagaa ttcttataca cattggggcc ttggagctta   3000
catagtttta aactcatttt tgccatacat cagttattca ttctgtgatc atttatttta   3060
agcactctta aagcaaaaaa tgaatgtcta aaattgtttt ttgttgtacc tgctttgact   3120
gatgctgaga ttcttcaggc ttcctgcaat tttctaagca atttcttgct ctatctctca   3180
aaacttggta tttttcagag atttatataa atgtaaaaat aataattttt atatttaatt   3240
attaactaca tttatgagta actattatta taggtaatca atgaatattg aagtttcagc   3300
```

-continued

```
ttaaaataaa cagttgtgaa ccaagatcta taaagcgata tacagatgaa aatttgagac   3360
tatttaaact tataaatcat attgatgaaa agatttaagc acaaacttta gggtaaaaat   3420
tgcgattgga cagttgtcta gagatatata tacttgtggt tttcaaattg gactttcaaa   3480
attaaatctg tccctgagag tgtctctgat aaaagggcaa atctgcacct atgtagctct   3540
gcatctcctg tcttttcagg tttgtcatca gatggaaata ttttgataat aaattgaaat   3600
tgtgaactca ttgctcccta agactgtgac aactgtctaa ctttagaagt gcatttctga   3660
atagaaatgg gaggcctctg atggaccttc tagaattata agtcacaaag agttctggaa   3720
aagaactgtt tactgcttga taggaattca tcttttgagg cttctgttcc tctcttttcc   3780
tgttgtattg actattttcg ttcattactt gattaagatt ttacaaaaga ggagcacttc   3840
caaaattctt atttttccta acaaaagatg aaagcaggga atttctatct aaatgatgag   3900
tattagttcc ctgtctcttg aaaaatgccc atttgccttt aaaaaaaaaa gttacagaaa   3960
tactataaca tatgtacata aattgcataa agcataagta tacagttcaa taaacttaac   4020
tttaactgaa caatggccct gtagccagca cctgtaagaa acagagcagt accagcgctc   4080
taaaagcacc tccttgtcac tttattactc ccagaacaac aactatcctg acttctaata   4140
tcattcacta gctttgcctg gttttgtctt ttatgcagat agaatcaatc agtatgtatt   4200
cttttgtgcc tggcttcttt ctctcagcct tacatttgtg agattcctct gtattgtgct   4260
gattgtggat cttttcattc tcattgcaga ataatgttct attgtgggac ttattacaat   4320
ttgttcatcc tattgttgat gggcacttga gaactttcca ttttggcgct attacaaata   4380
gtgcaactat gaatgtactg catgttacca tcttacttga gcctttaatg gacttatttc   4440
ttcaaatcct tccaaaaatt attataagca ttgaaattat agtttcaagc caactgtgga   4500
taccctttacc ctttcctcct ttatcacaac caccgttaca agtatactta tatttcccta   4560
aaatacattt aaaacttacc taagtgacat ttgtagttgg agtaatagga gcttccagct   4620
ctaataaaac agctgtctct aacttatttt atttccatca tgtcagagca ggtgaagagc   4680
cagaagtgaa gagtgactag tacaaattat aaaaagccac tagactcttc actgttagct   4740
ttttaaaaca ttaggctccc atccctatgg aggaacaact ctccagtgcc tggatcccct   4800
ctgtctacaa atataagatt ttctgggcct aaaggataga tcaaagtcaa aaatagcaat   4860
gcctccctat ccctcacaca tccagacatc atgaatttta catggtactc ttgttgagtt   4920
ctatagagcc ttctgatgtc tctaaagcac taccgattct ttggagttgt cacatcagat   4980
aagacatatc tctaattcca tccataaatc cagttctact atggctgagt tctggtcaaa   5040
gaaagaaagt ttagaagctg agacacaaag ggttgggagc tgatgaaact cacaaatgat   5100
ggtaggaaga agctctcgac aatacccgtt ggcaaggagt ctgcctccat gctgcagtgt   5160
tcgagtggat tgtaggtgca agatggaaag gattgtaggt gcaagctgtc cagagaaaag   5220
agtccttgtt ccagccctat tctgccactc ctgacagggt gaccttgggt atttgcaata   5280
ttcctttggg cctctgcttc tctcacctaa aaaaagagaa ttagattata ttggtggttc   5340
tcagcaagag aaggagtatg tgtccaatgc tgccttccca tgaatctgtc tcccagttat   5400
gaatcagtgg gcaggataaa ctgaaaactc ccatttaagt gtctgaatcg agtgagacaa   5460
aattttagtc caaataacaa gtaccaaagt tttatcaagt ttgggtctgt gctgctgtta   5520
ctgttaacca tttaagtggg gcaaaacctt gctaattttc tcaaaagcat ttatcattct   5580
tgttgccaca gctggagctc tcaaactaaa agacatttgt tattttggaa agaagaaaga   5640
```

-continued

```
ctctattctc aaagtttcct aatcagaaat ttttatcagt ttccagtctc aaaaatacaa   5700

aataaaaaca aacgttttta atact                                         5725
```

```
<210> SEQ ID NO 95
<211> LENGTH: 3259
<212> TYPE: DNA
<213> ORGANISM: Homo sapiens

<400> SEQUENCE: 95

gacgcgcgcc gggagccggc ggccgggcca gccggcgccg gggcccagtg cgccgcgctc     60

gcagccggta gcgcgccagc cgtaggcgtc gctcggcagc cgcggggccc taggcgtgcc    120

ggggaggggg cgagggcggc caggcgcctg ccgccccgga ggcaggatga gcatcgagat    180

cccggcggga ctgacggagc tgctgcaggg cttcacggtg gaggtgctga ggcaccagcc    240

cgcggacctg ctggagttcg cgctgcagca cttcacccgc ctgcagcagg agaacgagcg    300

caaaggcacc gcgcgcttcg gccatgaggg caggacctgg ggggacctgg gcgccgctgc    360

cgggggcggc acccccagca agggggtcaa cttcgccgag gagcccatgc agtccgactc    420

cgaggacggg gaggaggagg aggcggcgcc cgcggacgca ggggcgttca atgctccagt    480

aataaaccga ttcacaaggc gtgcctcagt atgtgcagaa gcttataatc ctgatgaaga    540

agaagatgat gcagagtcca ggattataca tccaaaaact gatgatcaaa gaaataggtt    600

gcaagaggct tgcaaagaca tcctgctgtt taagaatctg gatccggagc agatgtctca    660

agtattagat gccatgtttg aaaaattggt caaagatggg gagcatgtaa ttgatcaagg    720

tgacgatggt gacaactttt atgtaattga tagaggcaca tttgatattt atgtgaaatg    780

tgatggtgtt ggaagatgtg ttggtaacta tgataatcgt gggagtttcg gcgaactggc    840

cttaatgtac aatacaccca gagcagctac aatcactgct acctctcctg gtgctctgtg    900

ggtttggac agggtaacct tcaggagaat aattgtgaaa aacaatgcca aaaagagaaa    960

aatgtatgaa agctttattg agtcactgcc attccttaaa tctttggagt tttctgaacg   1020

cctgaaagta gtagatgtga taggcaccaa agtatacaac gatggagaac aaatcattgc   1080

tcagggagat tcggctgatt cttttttcat tgtagaatct ggagaagtga aaattactat   1140

gaaaagaaag ggtaaatcag aagtggaaga gaatggtgca gtagaaatgc ctcgatgctc   1200

gcggggacag tactttggag agcttgccct ggtaactaac aaacctcgag cagcttctgc   1260

ccacgccatt gggactgtca aatgtttagc aatggatgtg caagcatttg aaaggcttct   1320

gggaccttgc atggaaatta tgaaaaggaa catcgctacc tatgaagaac agttagttgc   1380

cctgtttgga acgaacatgg atattgttga acccactgca tgaagcaaaa gtatggagca   1440

agacctgtag tgacaaaatt acacagtagt ggttagtcca ctgagaatgt gtttgtgtag   1500

atgccaagca ttttctgtga tttcaggttt tttccttttt ttacatttac aacgtatcaa   1560

taaacagtag tgatttaata gtcaataggc tttaacatca ctttctaaag agtagttcat   1620

aaaaaaatca acatactgat aaaatgactt tgtactccac aaaattatga ctgaaaggtt   1680

tattaaaatg attgtaatat atagaaagta tctgtgttta agaagataat taaaggatgt   1740

tatcataggc tatatgtgtt ttacttattc agactgataa tcatattagt gactatcccc   1800

atgtaagagg gcacttggca attaaacatg ctacacagca tggcatcact tttttttata   1860

actcattaaa cacagtaaaa ttttaatcat ttttgtttta aagttttcta gcttgataag   1920

ttatgtgctg ccttggccta ttggtgaaat ggtataaaat atcatatgca gttttaaaac   1980

tttttatatt tttgcaataa agtacatttt gactttgttg gcataatgtc agtaacatac   2040
```

```
atattccagt ggttttatgg acaggcaatt tagtcattat gataataagg aaaacagtgt   2100

tttagatgag agatcattaa tgcatttttc cctcatcaag catatatctg cttttttta    2160

ttttgcaatt ctctgtattc tatgtcttta aaaatttgat cttgacattt aatgtcacaa   2220

agttttgttt ttttaaaaag tgatttaaac ttaagatccg acattttttg tattctttaa   2280

gattttacac ctaaaaaatc tctcctatcc caaaaataat gtgggatcct tatcagcatg   2340

cccacagttt atttctttgt tcttcactag gcctgcataa tacagtccta tgtagacatc   2400

tgttcccttg ggtttccgtt ctttcttagg atggttgcca acccacaatc tcattgatca   2460

gcagccaata tgggtttgtt tggttttttt aattcttaaa aacatcctct agaggaatag   2520

aaacaaattt ttatgagcat aaccctatat aaagacaaaa tgaatttctg accttaccat   2580

atataccatt aggccttgcc attgctttaa tgtagactca tagttgaaat tagtgcagaa   2640

agaactcaga tgtactagat tttcattgtt cattgatatg ctcagtatgc tgccacataa   2700

gatgaattta attatattca accaaagcaa tatactctta catgatttct aggccccatg   2760

acccagtgtc tagagacatt aattctaacc agttgtttgc ttttaaatga gtgatttcat   2820

tttgggaaac aggtttcaaa tgaatatata tacatgggta aaattactct gtgctagtgt   2880

agtcttacta gagaatgttt atggtcccac ttgtatatga aaatgtggtt agaatgttaa   2940

ttggataatg tatatataag aagttaaagt atgtaaagta taacttcagc cacattttta   3000

gaacactgtt taacattttt gcaaaacctt cttgtaggaa aagagagctc tctacatgaa   3060

gatgacttgt tttatatttc agattttatt ttaaaagcca tgtctgttaa acaagaaaaa   3120

acacaaaaga actccagatt cctggttcat cattctgtat tcttactcac tttttcaagt   3180

tatctatttt gttgcataaa ctaattgtta actattcatg gaacagcaaa cgcctgttta   3240

ataaagaact ttgaccaag                                                3259
```

<210> SEQ ID NO 96
<211> LENGTH: 2376
<212> TYPE: DNA
<213> ORGANISM: Homo sapiens

<400> SEQUENCE: 96

```
cgagggcagc gccggtcggg agcgcagcgc ggcgcagctc ggcgcgcacg gcgggagcgg     60

cgcgcgagtg gtcgggcctg gcggctggac gggcgcccct cgctgccccg cgcgctcccc    120

gccgcccccc atgagcgcag ccccgcgcgg cccgggtccg taggcggcgg ggcgcccccc    180

atgctgctgc agcccgcgcc gtgcgccccg agcgcgggct tcccgcggcc cctggccgcc    240

cccggcgcca tgcacggctc gcagaaggac accacgttca ccaagatctt cgtgggcggc    300

ctgccgtacc acactaccga cgcctcgctc aggaagtact tcgagggctt cggcgacatc    360

gaggaggccg tggtcatcac cgaccgccag acgggcaagt cccgcggcta cggcttcgtg    420

accatggccg accgggcggc agctgagagg gcttgcaaag acccgaaccc catcatcgac    480

ggccgcaagg ccaacgtgaa cctggcatat ctgggcgcca agccgcggag cctccagacg    540

ggctttgcca ttggggtgca gcagctgcac cccaccttga tccagcggac ttacgggctg    600

accccgcact acatctaccc accagccatc gtgcagccca gcgtggtgat cccagccgcc    660

cctgtcccgt cgctgtcctc gccctacatt gagtacacgc cggccagccc ggcctacgcc    720

cagtacccac cggccaccta tgaccagtac ccatacgccg cctcgcctgc cacggctgcc    780

agcttcgtgg gctacagcta ccctgccgcc gtgccccagg ccctctcagc cgcagcaccc    840
```

-continued

```
gcgggcacca ctttcgtgca gtaccaggcg ccgcagctgc agcctgacag gatgcagtga     900

ggggcgttcc tgccccgagg actgtggcat tgtcaccttc acagcagaca gagctgccag     960

gccatgatgg gctggcgaca gcccggctga gctttagtga ggtgccacca gcacccgtgc    1020

ctccgaagac cgctcgggca ttccgcctgc gccctgggac agcggagaga tggcttctct    1080

ttaatctagg tcccattgtg tcttgaggga ggactttaag aatgactgag aactatttaa    1140

agacgcaatc ccaggttcct tgcacaccat ggcagcctct tcttgcacct tctcctgcct    1200

ctccacactc caggttccct caggcttgtg tccccactgc tgcatcgtgg cggggtgtca    1260

cagaccctct gcagcccctg gctgccctgg actgtgcaga gatgcctgac tccagggaaa    1320

cctgaaagca agaagttaat ggactgttta ttgtaacttg atcctcccga gctgtgagcg    1380

cagtctgagg tgtgaggaca cggcctcctg ttggagtccc atttctccca tcagggcacg    1440

tgggcggctt cctcaagccc ggaggagctc ccaggcgcac aggggccgcc ggtaacaggg    1500

gccgccggcc aaaggcccct ttccagtcat agcactgaag ttgcaacttt tttcttgtaa    1560

ttgttttgct actaagataa tttcagaagt tcagtctatt ttttcagcgg atactgccgc    1620

caccaagaat ccaaaaccta tttttgactt ggagagactt gcttttgttg gttccgcccg    1680

tggagacgac gacagtgttt ctgtataata aagtgtctgc cggctcgcgg gccaggatcc    1740

tctcggtggg atgggcacca cagacaggag gcccctcagg cccgtgcggg ccactgtctg    1800

ctgccgcctg ccggggtggc agagtgagtt gtctcaggac cccgtcactg cgacgttgac    1860

actctctcct tccttccttc cccaactccc caaacactgt ggaagggaag aaggaagtga    1920

tccacagcat tcaggccact tggggtctag accatggtgg tgccagcctg gggggggcag    1980

tggccctcag ctctgcccgc tggagcggtt gagtgcagaa gggtgcgcct cttccctcta    2040

cccccgcacc acctgctgtg tgccagcctg agacggttcc tgcctgtctt gggggttggt    2100

ggagggtgga ggcagttctg ccagccgtgg cagggctgct atggggcatc cagggctgtg    2160

ggggtctgga ggaggggaca tgaggtgaga ggtatcctgg ccgagggcgg ggggcagcgg    2220

ggggtctccc tccggaccta cctcagggag ctgagcgtgc aggcgctcca gggcaggcct    2280

gggacagagt caaggctcag agaataaagg tagctaatct catcataata tttttattag    2340

aatgttctga tgataaaaat aaaacttgtt ttcttt                              2376


<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97

gttgtaaaac gacggccagt g                                                21


<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98

cacacaggaa acagctatg                                                   19


<210> SEQ ID NO 99
<211> LENGTH: 21
```

-continued

```
<212> TYPE: DNA
<213> ORGANISM: Artificial Sequence
<220> FEATURE:
<223> OTHER INFORMATION: Primer

<400> SEQUENCE: 99

tttttttttt ttttttttt v                                              21
```

METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

STATEMENT OF RIGHTS TO INVENTION MADE UNDER FEDERALLY SPONSORED RESEARCH AND DEVELOPMENT

The work performed during the development of this application utilized support from the National Institutes of Health. The United States government has certain rights in the invention.

FIELD OF THE INVENTION

The invention relates generally to the use of supervised pattern recognition methods to classify and diagnose disease. More specifically, the invention relates to the use of supervised pattern recognition methods, such as artificial neural networks for the classification, diagnosis, prognosis and prediction of disease using high dimensional data, such as gene expression profiling data.

BACKGROUND OF THE INVENTION

Disease is generally diagnosed based on a myriad of factors, both objective and subjective, including but not limited to symptoms, laboratory test values, demographic factors and environmental factors. Diagnosis relies on a clinician such as a physician or a veterinarian being able to identify and evaluate the relevant factors. Often this task can be difficult, and becomes exceedingly more so as the number of factors to be considered increases.

An example of a disease whose diagnosis is difficult is tumors. Tumors are currently diagnosed on the basis of clinical presentation, routine histology, immunohistochemistry and electron microscopy. However the histological appearance may not reveal the genetic aberrations or underlying biologic processes that contribute to the malignancy. Monitoring global gene expression levels using DNA microarrays would provide an additional tool for elucidating tumor biology as well as the potential for molecular diagnostic classification of cancers. Several studies have demonstrated that gene expression profiling using DNA microarrays is able to classify tumors with a high accuracy, and discover new cancer classes.

A specific type of tumors which could benefit is the small, round blue cell tumors (SRBCTs) of childhood as a model. SRBCTs include, neuroblastoma (NB), rhabdomyosarcoma (RMS), non-Hodgkin lymphoma (NHL) and the Ewing family of tumors (EWS), are so named because of their similar appearance on routine histology. However, accurate diagnosis of SRBCTs is essential because the treatment options, responses to therapy, and prognoses vary widely depending on the diagnosis. As their name implies, these cancers are difficult to distinguish by light microscopy, and currently no single test can precisely distinguish these cancers.

In clinical practice, several techniques are used for diagnosis, including immunohistochemistry, cytogenetics, interphase fluorescence in situ hybridization and reverse transcription (RT)-PCR. Immunohistochemistry allows the detection of protein expression, but it can only examine one protein at a time. Molecular techniques such as RT-PCR are used increasingly for diagnostic confirmation following the discovery of tumor-specific translocations such as EWS-FLI1; t(11;22)(q24;q12) in EWS, and the PAX3-FKHR; t(2;13)(q35;q14) in alveolar rhabdomyosarcoma (ARMS). However, molecular markers do not always provide a definitive diagnosis, as on occasion there is failure to detect the classical translocations, due to either technical difficulties or the presence of variant translocations.

An example of a diagnostic method replete with such problems is the diagnostic method for Ewing sarcoma. Ewing sarcoma is diagnosed by immunohistochemical evidence of MIC2 expression and lack of expression of the leukocyte common antigen CD45 (excluding lymphoma), muscle-specific actin or myogenin (excluding RMS). However, reliance on detection of MIC2 alone can lead to incorrect diagnosis as MIC2 expression occurs occasionally in other tumor types including RMS and NHL.

One objective factor that can, in certain circumstances, be entirely predictive of a diseased state is the genetic makeup of the individual. Genetic makeup of an individual can also be considered in terms of the level of expression of the genes of that individual through gene expression data.

DNA microarray technology is a recently developed high throughput technology for monitoring gene expression at the transcription level. Its use is akin to performing tens of thousands of northern blots simultaneously, and has the potential for parallel integration of the expression levels of an entire genome. A DNA microarray consists of DNA probes immobilized on a solid support such as a glass microscope slide. The DNA probes can be double stranded cDNA or short (25 mers) or long (50-70 mers) oligonucleotides of known sequences. An ideal DNA microarray should be able to interrogate all of the genes expressed in an organism.

In DNA microarrays using cDNA, the probes are PCR amplified from plasmid cDNA clones that have been purified and robotically printed onto coated glass slides. DNA microarrays using oligonucleotide have an advantage over cDNA microarrays because physical clones are not necessary. The oligonucleotides can either be previously synthesized and printed on glass slides, or can be synthesized directly on the surface of silicon or glass slides. Several print-ready oligonucleotide (60-70 men) sets are commercially available for human, mouse and other organisms (cgen/com.operon/com).

Another technique for fabricating oligonucleotides microarrays chemically synthesizes the oligonucleotides (25 mers) on a silicon surface using photolithography techniques. (Affymetrix Inc., Santa Clara, Calif.). Originally such arrays were designed to detect single-nucleotide mutations, but now have applications for gene expression profiling studies. Yet another technique delivers single nucleic acids, which ultimately form longer oligonucleotides (60 mers), by ink-jet onto glass surfaces.

One method of utilizing gene expression data from microarrays is given by Tusher et al., PNAS 98(9) p. 5116-21, April, 2001. The method of Tusher et al. is a statistical method titled Significance Analysis of Microarrays ("SAM"). The general approach in SAM is based on commonly used statistical tests, t-tests specifically, to find genes that discriminate between two classes in a gene-by-gene fashion. SAM uses replication of experiments to assign a significance to the discriminating genes in terms of a false discover rate. SAM therefore offers a method of choosing particular genes from a set of gene expression data, but does not offer a diagnosis based on those genes.

DNA microarrays would be an invaluable tool for disease diagnosis. Gene-expression profiling using DNA microarrays permits a simultaneous analysis of multiple markers, and can be used for example to categorize cancers into subgroups. The only limitation associated with the use of DNA microarrays is the vast amount of data generated thereby. A method that would allow for the easy and automated use of DNA microarray data in disease diagnosis is therefore desirable. Despite the many statistical techniques to analyze gene-expression data, none so far has been rigorously tested for their ability to accurately distinguish diseases belonging to several diagnostic categories. Such methods have also not been used to extract the genes or features that are the most important for the classification performance. Such genes would also generally be those that are of use to biologists and physicians as offering avenues to research in investigating cures.

Therefore, there remains a need for a method of using gene expression data to diagnose, predict, or prognosticate about a disease condition.

However, these other methods have not been used to extract the genes or features that are most important for the classification performance and which also will be of interest to cancer biologists.

SUMMARY OF THE INVENTION

In accordance with the invention, there is provided a method of diagnosing, predicting, and/or prognosticating about a disease including obtaining experimental data, wherein the experimental data includes high dimensional data, filtering noise from the data, reducing the dimensionality of the data by using one or more methods of analysis, training a supervised pattern recognition and/or classification method, ranking individual data from the overall data based on the relevance of the individual data to the diagnosis, prediction, prognosis or classification, choosing multiple individual data members, wherein the choice is based on the relative ranking of the individual data, and using the chosen data to determine if an unknown set of experimental data indicates a particular diseased condition, prognosis, prediction, or classification.

The invention offers a method of diagnostic classification of cancers from their gene-expression signatures and also identifies the genes that contributed to this classification. One embodiment of the method diagnoses SRBCTs of childhood, which occasionally present diagnostic difficulties.

The invention also offers a method of diagnosing, predicting, and/or prognosticating about SRBCTs including obtaining gene expression data, filtering noise from the gene expression data, reducing the dimensionality of the data by using principal component analysis (PCA), training an ANN, ranking the individual genes from the gene expression data, choosing multiple genes from the gene expression data, wherein the choice is based on the relative ranking of the individual genes and using the chosen genes to determine if an unknown set of gene expression data indicates a particular diseased condition, prognosis, and/or a prediction.

Methods of the invention can be utilized in a number of different applications. For example, diagnostic chips can be fabricated based on the identification of the diagnostic genes. Such chips would be very useful in clinical settings, as it would allow clinicians to diagnose cancers from a relatively small set of genes instead of purchasing entire gene sets.

Methods of the invention can also be used to define which patients with the same types of cancers are likely to respond to treatment. This would allow a physician to intensify treatment for those with a more negative prognosis based on their gene expression profiles as detected utilizing a method of the invention.

Methods of the invention can also be used for identifying pharmaceutical targets. Pharmaceutical companies can utilize methods of the invention to determine which genes to target in efforts to target specific diseases.

Methods of the invention can also be utilized as a research tool for analyzing all types of gene expression data including cDNA and oligonucleotide microarray data.

Methods of the invention can also be utilized to identify and rank, by importance, the genes that contribute to a diagnosis. A minimal set of genes that can correctly classify and identify diagnostic categories can also be determined using methods of the invention.

Methods of the invention identify the most significant genes, by calculating the sensitivity of the classification to a change in the expression level of each gene. A list of genes, ranked by their significance to the classification, is produced thereby. In an embodiment of the invention utilized for classifying SRBCTs the most important 96 genes reduced the misclassifications to zero. This allows for cost effective fabrication of SRBCT subarrays for diagnostic use. When a method of the invention used the 96 genes on 25 unknown samples, all 20 samples of SRBCTs and 5 non-SRBCTs were correctly classified.

One embodiment of the invention calibrates ANN models on the expression profiles of 63 SRBCTs of 4 diagnostic categories. Preferred embodiments of the invention utilize linear (that is no hidden layers) ANN models because of the high performance achieved. Methods of the invention may utilize other linear methods as well, and methods of the invention can easily accommodate nonlinear features of expression data if required. Hidden layers will be utilized for non linear data. Preferably, both tumor samples and cell line samples are used in order to compensate for heterogeneity within unknown samples (which contain both malignant and stromal cells) based on possible artifacts due to growth of cell lines in tissue culture.

Data from such samples is complementary, because tumor tissue, though complex, provides a gene-expression pattern representative of tumor growth in vivo, while cell lines contain a uniform malignant population without stromal contamination. Despite using only neuroblastoma (NB) cell lines for calibrating the ANN models, all four NB tumors among the test samples were correctly diagnosed with high confidence. This not only demonstrates the high similarity of NB cell lines to the tumors of origin, but also validates the use of cell lines for ANN calibration. One embodiment of a method of the invention accurately classified all 63 training SRBCTs and showed no evidence of over-training, thereby demonstrating the robustness of this method.

BRIEF DESCRIPTION OF THE FIGURES

FIG. 7 represents two projections of the MDS plot of the training samples.

FIG. 8 represents a hierarchical clustering of the samples and genes, where each row represents one of the 96 cDNA clones, and each column represents a separate sample.

DETAILED DESCRIPTION OF THE PREFERRED EMBODIMENTS

The invention is a method of classifying, diagnosing, prognosticating about, and predicting disease conditions or other biological states using supervised pattern recognition methods to analyze high dimensional data.

Figure 1:
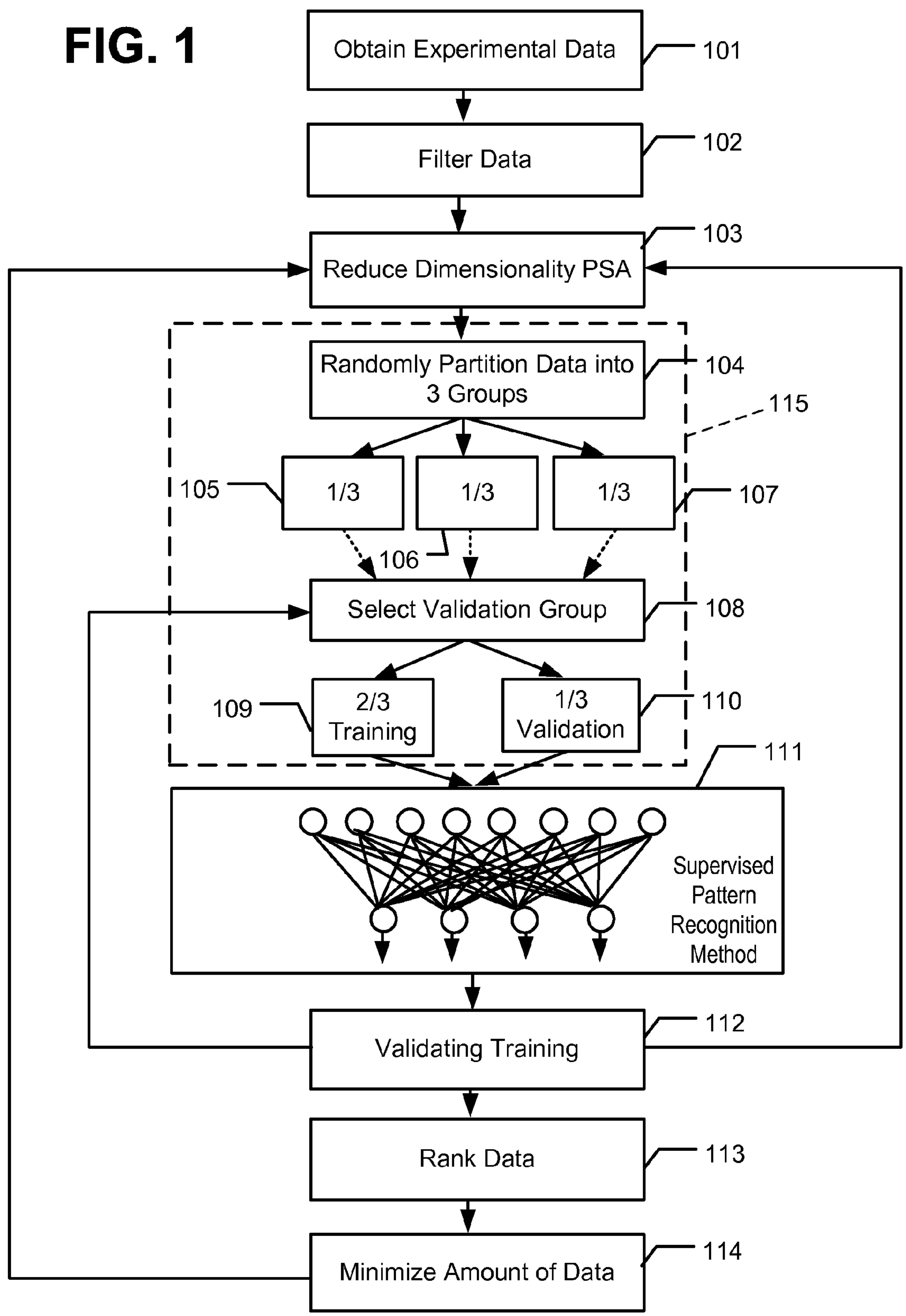
FIG. 1 illustrates a process flow for a method to classify and diagnose diseases using artificial neural networks according to one embodiment of the invention.

One embodiment of the invention is illustrated in FIG. 1. This process flow describes an embodiment of the method that includes obtaining experimental data 101, filtering the data 102, reducing the dimensionality of the data 103, setting up a validation method 115, training a supervised pattern recognition method 111, validating the outcome of the supervised pattern recognition method 112, and once the supervised pattern recognition method is validated, ranking the data based on the outcome of the supervised pattern recognition method 113. Further detail and more specific embodiments of methods of the invention are described below.

Any diagnostic categories can be diagnosed using the technology described here. It includes distinguishing patients with multiple sclerosis, rheumatoid arthritis, and other inflammatory or autoimmune diseases. It may also diagnose other systemic diseases based on gene expression profiles of white cells, including infections with particular organisms, cancer, or myocardial infarctions.

Obtaining Experimental Data

The first step in methods of the invention is to obtain experimental data. Experimental data utilized in methods of the invention is high dimensional data. High dimensional data is data that has at least hundreds of individual pieces of information associated with one sample. An example of high dimensional data useful in methods of the invention is gene expression data. Gene expression data is high dimensional data because each sample or person has a large number of gene expression levels. Generally speaking, gene expression data generally has thousands of gene expression levels for each sample. Other examples of high dimensional data useful in the invention include but are not limited to protein arrays and protein chips, cell array based expression analysis, analysis of patterns of single nucleotide polymorphisms in disease conditions, and comparative genomic hybridization on methaphase, BAC genomic, cDNA and oligonucleotide arrays.

Preferably, the gene expression data is obtained through use of DNA microarray technology. DNA microarrays are preferred as a source of data because they generally offer a more complete picture of the interactions of a large number of genes with a limited number, or even one experiment. An example of a general description of how gene expression data can be obtained by using cDNA microarray technology is given below.

DNA microarrays, although a relatively new technology, have already been saddled with a number of different names, biochip, DNA chip, gene chip, genome chip, cDNA microarray, and gene array. The use of any of these terms herein refers generally to DNA microarrays. The underlying principle of DNA microarrays is base pairing or hybridization i.e., A-T and G-C for DNA, and A-U and G-C for RNA.

DNA microarrays provide a medium for matching known and unknown DNA samples based on the base pairings given above. DNA microarrays can either be fabricated by high-speed robotics or can be fabricated in a laboratory setting. They are generally patterned on glass, but can also be fabricated on nylon substrates. Microarrays generally have sample spot sizes of less than 200 μm diameter, and generally contain thousands of DNA spots on one microarray.

One method of fabricating cDNA microarrays begins by first producing gene-specific DNA by polymerase chain reaction (PCR) amplification of purified template plasmid DNAs from cloned expressed sequence tags (ESTs). The PCR product is then purified, resuspended and printed onto a substrate. cDNA microarrays are also commercially available from a number of sources, including but not limited to Affymetric, Inc. (Santa Clara, Calif.), Agilent Technologies (Palo Alto, Calif.), and Research Genetics (Huntsville, Ala.).

One general procedure for a cDNA microarray experiment begins by preparing DNA samples and arraying them (either with an arraying robot, or by hand), to form a DNA microarray. Next, the RNA samples are extracted from the cells of interest, purified, reverse transcribed into cDNA and differentially fluorescently labeled to create probes. Then, the fluorescently labeled cDNA probes are hybridized to the cDNA microarray. If a probe contains a cDNA whose sequence is complementary to the DNA on a given spot, the cDNA probe will hybridize to that spot. After the cDNA probes are hybridized to the array, and any loose probe has been washed away, the microarray is imaged to determine how much of each probe is hybridized to each spot. This indicates how much of each gene from the microarray is expressed in the two samples.

The experimental high dimensional data, preferably obtained from gene expression experiments, preferably performed using cDNA microarrays, is then further analyzed by a method of the invention.

Filtering the Data

The next step in a method of the invention is filtering the data 102 to remove individual pieces of data that are deemed undesirable. This filtering step functions to eliminate weak and/or problematic data from further use in the method. Accomplishment of the step of filtering depends greatly on the type of high dimensional data utilized. Any method known to those of ordinary skill in the art can be used to eliminate data determined to be undesirable.

One basis for carrying out this filtering, if a DNA microarray is being utilized for obtaining the high dimensional data, is the intensity of the fluorescence from the individual microarray spots. This basis of omitting data is based on failure or error in the imaging of the specific spots. A preferred method of performing initial data filtering on cDNA microarray data to remove those spots where imaging was a problem is to utilize the intensity of the various spots and utilize only those spots that have an intensity over a certain threshold value. Other methods of filtering DNA microarray data include but are not limited to eliminating spots in which the number of pixels represented is less than a threshold defined by the user, eliminating spots in which the standard deviation of the signal on the spots is too large, as defined by the user, eliminating spots in which the background intensity of a single spot is too high, or any combination thereof. In addition quality values based on intensity, can be assigned to each spot, standard deviation of intensity, background and/or size of each spot, then a spot could be eliminated if its quality value falls below a threshold as defined by the user.

Reducing the Dimensionality of the Data

The next step in methods of the invention is reducing the dimensionality of the data 103. The number of samples needed to calibrate a classifier with good predictive ability, depends critically on the number of features used in the design of the classifier. In the case of high-dimensional data, such as microarray data, where the number of samples is much smaller than the number of individual pieces of data there exists a large risk of over-fitting. There are two different solutions to this problem. First, the calibration process can be carefully monitored using a cross-validation scheme to avoid over-fitting (see below). Second, the dimension of the data can be reduced, either by using a dimensional reduction algorithm or by selecting a smaller set of data for input to the supervised pattern recognition method. Dimensionality reduction allows the number of parameters representing each sample to be reduced. This allows for the design of a classifier that has less risk of over-fitting, thereby increasing its predictive ability. Examples of methods of reducing the dimensionality of the data include but are not limited to principal component analysis (PCA), weighted gene analysis, t-test, rank based Wilcoxon or Mann-Whitney tests, signal-to-noise statistic, Fisher's discriminant analysis, or ANOVA tests.

In a preferred embodiment of the invention, PCA is used to reduce the dimensionality of the data.

In the case of PCA on gene expression data, reduction of the dimensionality is achieved by rotating gene expression space, such that the variance of the expression is dominated by as few linear combinations of genes as possible Even though the formal dimension of the problem is given by the number of individual data points, the effective dimension is just one less than the number of samples. Hence the eigenvalue problem underlying PCA can be solved without diagonalizing 2308×2308 matrices by using singular value decomposition. Thus each sample is represented by 88 numbers, which are the results of projections of the data using the PCA eigenvectors.

A potential risk when using PCA on relatively few samples is that components might be singled out due to strong noise in the data. It could be argued that the outputs (labels) should be included in the dimensional reduction, using e.g. the Partial Least Squares (PLS) algorithm, in order to promote components with strong relevance for the output. However, based on explorations with similar data sets, this is not optimal; bias is introduced and implicitly "over-trains" from the outset by including the outputs in the procedure.

Setting Up a Validation Method for the Supervised Pattern Recognition Method

Once the data has been filtered 102 and its dimensionality reduced 103, a validation method is set up for monitoring and validating the training of the supervised pattern recognition method 115. Any method commonly used by those of skill in the art for validating the training of a supervised pattern recognition method can be used.

In one embodiment, the first step in setting up a validation method is to randomly divide the data into three groups of data, 105, 106, and 107. Then, one of those groups is chosen as a validation group 108. The first two of the groups 105 and 106 are combined into a training group 109, which is used to train the supervised pattern recognition method 111 and the third group 107 is used to validate the performance of the supervised pattern recognition method 111, once trained, and is called a validation group 110.

In this specific preferred embodiment, the 3-fold cross validation procedure (steps 104 through 110) is performed on all of the samples. A data group having 63 samples is given as an example. The 63 known (labeled) samples are randomly shuffled 104 and split into 3 equally sized groups (105, 106, and 107). The supervised pattern recognition method 111 is then calibrated as discussed below using the training group 109. The third group, a validation group 110, is reserved for testing predictions. Comparisons with the known answers refer to the results from the validation group 110 (i.e. when using a model, the samples used for training the model are never used in predictions). This procedure is repeated 3 times, each time with a different group used for validation. The random shuffling 104 is done about 100 to 10000 times. For each shuffling, one supervised pattern recognition method 111 model is generated. Thus, in total each sample belongs to a validation group 110, 1250 times and 3750 supervised pattern recognition methods 111 have been calibrated.

Training the Supervised Pattern Recognition Method

The supervised pattern recognition method 111 is then trained. The specific method of training the supervised pattern recognition method 111 is dependent on the specific form that the supervised pattern recognition method 111 takes. The choice of the supervised pattern recognition method 111 and the training thereof is well within one of skill in the art, having read this specification.

One example of a supervised pattern recognition method is an artificial neural network (ANN). ANNs are computer-based algorithms that are modeled on the structure and behavior of neurons in the human brain and can be trained to recognize and categorize complex patterns. Pattern recognition is achieved by adjusting parameters of the ANN by a process of error minimization through learning from experience. They can be calibrated using any type of input data, such as gene-expression levels generated by cDNA microarrays, and the output can be grouped into any given number of categories. ANNs have been recently applied to clinical problems such as diagnosing myocardial infarcts and arrhythmias from electrocardiograms and interpreting radiographs and magnetic resonance images. However, ANNs have not been used to decipher gene-expression signatures of SRBCTs or for diagnostic classification.

In embodiments where an artificial neural network (ANN) is employed as the supervised pattern recognition method 111, calibration is preferably performed using JETNET (C. Peterson, T. Roegnvaldsson and L. Loennblad, "JETNET 3.0—A versatile artificial neural network package," *Computer Physics Communications* 81, 185-220 (1994)). Preferably, the software is used with a learning rate $\eta$=0.7, momentum coefficient p=0.3 and the learning rate is decreased with a factor 0.99 after each iteration. Initial weight values are chosen randomly from [−r, r], where $r=0.1/\max_i F_i$ and the "fanin" $F_i$ is the number of nodes connecting to node i. The calibration is performed using a training set and it is monitored both for the training set and a validation set, which is not subject to calibration (see below). The weight values are updated after every 10 samples and the calibration is terminated after 100 passes (epochs) through the entire training set. In one embodiment of a method of the invention, the resulting parameters for the completed training of a supervised pattern recognition method 111 defines a "model".

In preferred embodiments, due to the limited amount of calibration data and the fact that four output nodes are needed (Ewing's sarcoma (EWS), Burkitt's lymphoma (BL), neuroblastoma (NB) and rhabdomyo sarcoma (RMS)), linear perceptrons (LP) with 10 input nodes representing the PCA components described above are utilized. In other words, the supervised pattern recognition method 111 generally contains 44 parameters including four threshold units. Since 10 components could be used without risking "over-training" the optimization of the number of components to a smaller number is generally not necessary.

The possibility of using all the PCA components as inputs followed by a subsequent pruning of weights to avoid "over-fitting" is also one alternative. This resulted in the dominant 4-8 PCA components (depending on the composition of the training set 107) being the surviving inputs. Generally, the less dominant PCA components contain variance not related to separating the four cancers, but rather to, for example, experimental conditions (noise) or variance related to sub-groupings within a cancer type.

Verifying the Outcome of the Supervised Pattern Recognition Method

Once the supervised pattern recognition method 111 is trained, the next step is to determine whether the validation of the supervised pattern recognition method 111 is successful 112. This step determines whether the supervised pattern recognition method 111 adequately predicted the results for the validation data set 110 using any number of performance measurements and error measurements.

Any method known to those of ordinary skill in the art can be utilized to evaluate the performance of the training of the supervised pattern recognition method 111. Generally speaking, the performance is evaluated by comparison with some predetermined level of correct predictions that the user has determined is acceptable.

If the performance of the supervised pattern recognition method 111 is sufficiently poor, and a measure of error is greater than an allowable threshold, the processing may return to module 103 where the dimensionality of the data is reduced in a different manner and the entire training and validation process is repeated.

Ranking the Data

Once module 112 determines that the network 111 has been adequately trained, the processing proceeds to rank the output of the supervised pattern recognition method 113.

The outcome of the supervised pattern recognition method 111 can be looked at either independently or in a compiled form. Each supervised pattern recognition method 111 gives a number between 0 (not this disease type) and 1 (this disease type) as an output for each disease type. If the predictions are viewed independently, the maximal output is forced to 1 while the other outputs are forced to 0. Then it is determined how many of the predictions are correct. If the predictions are viewed in a compiled form, all of the predicted outputs are considered in their numerical form, after which all of the numbers are averaged and the resulting average is forced to 0 or 1.

In one embodiment of the method, the predictions, as compiled, are used to classify samples. For validation samples the compilation is based on 1250 models, while for additional unknown samples all 3750 models are used in the compilation.

In one embodiment, each sample is classified as belonging to the disease type corresponding to the largest average in the compilation. In addition, it is desirable to be able to reject the second largest vote as well as test samples that do not belong to any of the disease types. In order to reject those samples that do not belong, a distance $d_c$ from a sample to the ideal vote for each disease type is defined as:

$$d_c = \frac{1}{2}\sum_{i=1}^{4}(o_i - \delta_{i,c})^2 \quad (1)$$

where c is a disease type, $o_i$ is the average from the compilation for disease type i, and $\delta_{i,c}$ is unity if i corresponds to disease type c and zero otherwise. The distance is normalized such that the distance between two ideal samples belonging to different disease categories is unity. Based on the validation group, an empirical probability distribution of its distances is generated for each disease type.

The empirical probability distributions are preferably built using each supervised pattern recognition method 111 independently (not the average from the compilation). Thus, the number of entries in each distribution is given by 1250 multiplied by the number of samples belonging to the disease type. For a given test sample, the possible classifications based on these probability distributions can be rejected. This means that for each disease category a cutoff distance from an ideal sample is defined, within which, based on the validation samples, a sample of this category is expected to be. The distance given by the 95th percentile of the probability distribution is preferably chosen as a cutoff, which means that if a sample is outside of this cutoff distance it cannot be confidently diagnosed. It should be noted that the classification as well as the extraction of important genes (see below) converges using less than 100 supervised pattern recognition method 111 models. 3750 supervised pattern recognition method 111 models are preferred is because sufficient statistics exist for these empirical probability distributions.

For each disease category the sensitivity and specificity of the diagnosis may be calculated (see Table 1 below). Table 1 gives sensitivity, specificity and ROC curve areas for both validation and test samples. Both the sensitivity and the specificity are very high for all categories. It should be noted, that they generally depend on the kind of samples that are used as test samples.

TABLE 1

| Category | Sensitivity | Specificity | ROC curve area |
|---|---|---|---|
| EWS | 93% | 100% | 1.0 |
| BL | 100% | 100% | 1.0 |
| NB | 100% | 100% | 1.0 |
| RMS | 96% | 100% | 1.0 |

For example, in the case of SRBCT classification, using normal muscle samples as tests makes it harder to separate out RMS samples. If only samples from the four categories were used as blind distance cutoffs, it could easily have been designed such that both the sensitivity and the specificity would have been 100% for all diseases. However, it is preferred that the method is tested using a variety of blind tests. If it is desirable to improve rejection of for example normal muscle samples, one could incorporate them as a fifth category in the training process. However, using more samples of all four categories in the training is initially probably the best way to improve the diagnostic separation.

The Receiver Operator Characteristic (ROC) curve area is identical to another more intuitive and easily computed measure of discrimination: the probability that in a randomly chosen pair of samples, one belonging to and one not belonging to the disease category, the one belonging to the category is the one with the closest distance to the ideal for that particular category. Since the ROC curve areas are unity for all disease categories (see Table 1), it is possible to define cutoff distances such that both the sensitivity and the specificity are 100% for all diseases. However, based on the training and validation groups it is difficult to motivate such cutoff distances.

The next step in a method in accordance with the invention is to actually rank the data. This step can in principle be done in two ways; (1) model-independent and (2) model-dependent analysis respectively. Due to the relative small number of samples, the model-dependent analysis is preferred when using ANN models.

The sensitivity (S) of the outputs (O) with respect to any of the 2308 input variables ($x_k$) is defined as:

$$S_k = \frac{1}{N_s}\frac{1}{N_o}\sum_{s=1}^{N_s}\sum_{i=1}^{N_o}\left|\frac{\delta o_i}{\delta x_k}\right| \quad (2)$$

where $N_s$ is the number of samples (63 or 88) and $N_o$ is the number of outputs (4). The procedure for computing $S_k$ involves a committee of 3750 models. In addition we have defined a sensitivity for each output i ($S_i$), which is analogous to Eq. (2) but without the sum over outputs. Furthermore, a sensitivity can be defined for each sample (or subsets of samples) individually, by only using that sample(s) in the sum over samples in Eq. (2). For all these sensitivities the sign of the sensitivity has also been defined. The sign signals whether the largest contribution to the sensitivity stems from positive or negative terms. A positive sign implies that increasing the expression rate of the gene increases the possibility that the sample belongs to this cancer type, while a negative sign means that decreasing the expression rate of the gene increases the same possibility. In other words, the sign does not tell whether a gene is up- or down-regulated but if it is more or less expressed in this cancer type as compared to the others. This means the genes are ranked not only according to their importance for the total classification, but also according to their importance for the different disease categories separately. The genes are preferably given a total rank as well as a separate rank for each disease category. Based on these ranks each gene is classified according to which disease category it is highly expressed in.

In one embodiment, once ranked, a relevant set of data can be selected module 114 by minimizing the amount of data to be used to classify and identify a particular disease. In one embodiment, a predetermined amount of data having the highest ranking are selected. Of course, other selection methods may be employed without deviating from the spirit and scope of the present invention as recited in the attached claims.

Implementation of Methods of the Invention

Figure 2:
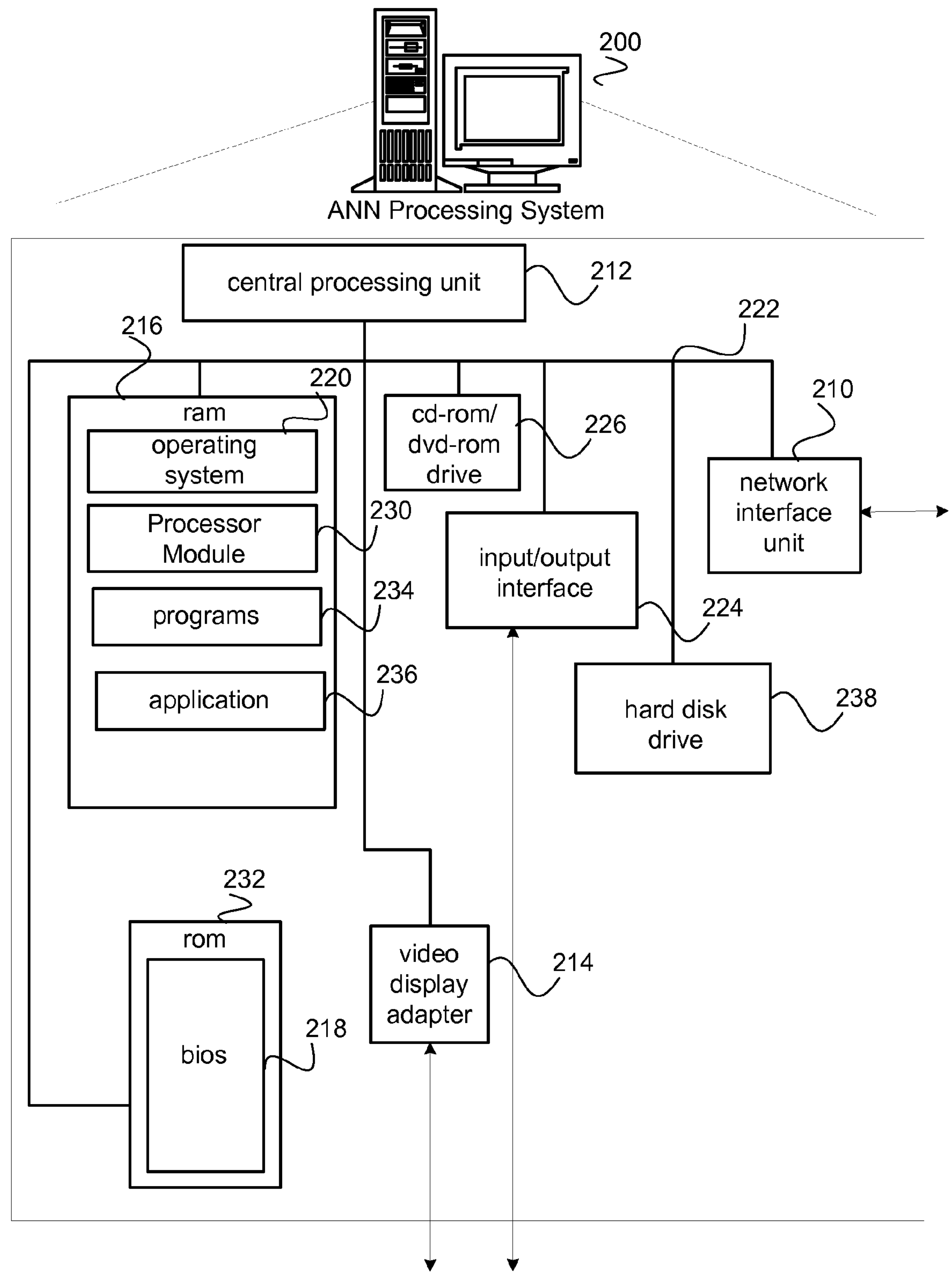
FIG. 2 illustrates a general purpose computing system utilized as part of an artificial neural network according to another embodiment of the invention.

In embodiments of the method in which the supervised pattern recognition method 111 is an artificial neural network, a general purpose computing system as depicted in FIG. 2 can be utilized. An exemplary ANN processing system 200 provides an artificial neural network that also receives experimental data to train the artificial neural network, to verify the output of an artificial neural network, and to identify relevant genes using the neural network.

Those of ordinary skill in the art will appreciate that the ANN processing system 200 may include many more components than those shown in FIG. 2. However, the components shown are sufficient to disclose an illustrative embodiment for practicing the present invention. As shown in FIG. 2, the ANN processing system 200 is connected to a WAN/LAN, or other communications network, via network interface unit 210. Those of ordinary skill in the art will appreciate that network interface unit 210 includes the necessary circuitry for connecting the ANN processing system 200 to a WAN/LAN, and is constructed for use with various communication protocols including the TCP/IP protocol. Typically, network interface unit 210 is a card contained within the ANN processing system 200.

The ANN processing system 200 also includes processing unit 212, video display adapter 214, and a mass memory, all connected via bus 222. The mass memory generally includes RAM 216, ROM 232, and one or more permanent mass storage devices, such as hard disk drive 228, a tape drive, CD-ROM/DVD-ROM drive 226, and/or a floppy disk drive. The mass memory stores operating system 220 for controlling the operation of ANN processing system 200. It will be appreciated that this component may comprise a general purpose server operating system as is known to those of ordinary skill in the art, such as UNIX, LINUX, MAC OS?, or Microsoft WINDOWS NT?. Basic input/output system ("BIOS") 218 is also provided for controlling the low-level operation of ANN processing system 200.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing an ANN processing and network development. More specifically, the mass memory stores applications including ANN processing module 230, programs 234, and other applications 236. ANN processing module 230 includes computer executable instructions which, when executed by ANN processing system 200, performs the logic described above.

The ANN processing system 200 also comprises input/output interface 224 for communicating with external devices, such as a mouse, keyboard, scanner, or other input devices not shown in FIG. 2. Likewise, ANN processing system 200 may further comprise additional mass storage facilities such as CD-ROM/DVD-ROM drive 226 and hard disk drive 228. Hard disk drive 228 is utilized by ANN processing system 200 to store, among other things, application programs, databases, and program data used by ANN processing module 230. For example, customer databases, product databases, image databases, and relational databases may be stored. The operation and implementation of these databases is well known to those skilled in the art.

Figure 3:
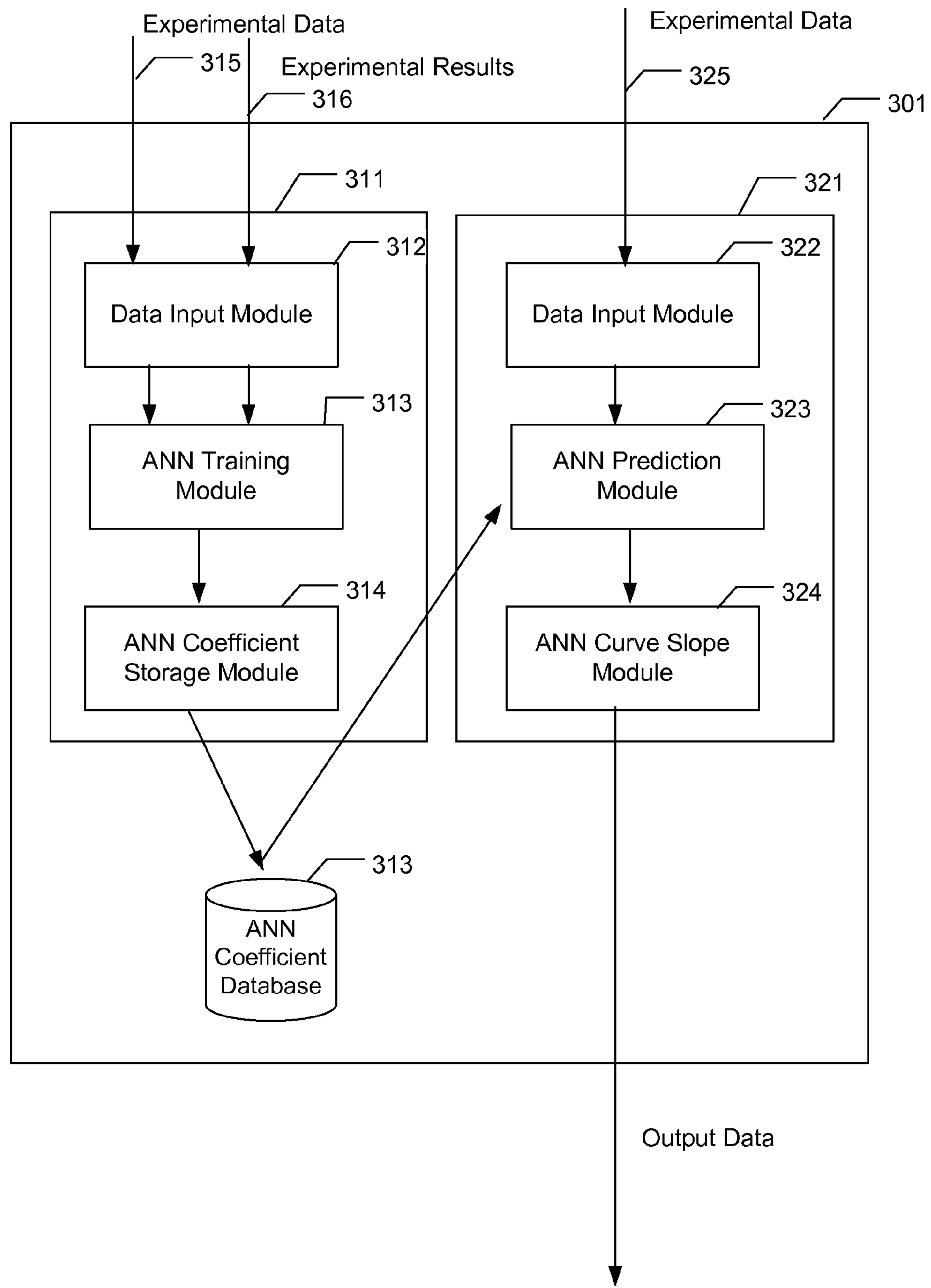
FIG. 3 illustrates a set of processing modules making up an embodiment of an artificial neural network according to the invention.

A set of processing modules making up an embodiment of an artificial neural network according to the invention is illustrated in FIG. 3. The artificial neural network disclosed herein corresponds to a generic neural network of no particular topology for the network of nodes contained therein. The neural network typically utilizes a form of competitive learning for the operation of the nodes within the network. Within competitive learning networks, a large number of data vectors are distributed in a highly dimensional space. These data vectors represent known values for experimental data that typically reflect a probability distribution of the input experimental data. From this probability distribution representation, predictions for unknown values for similar input data may be determined.

In all of these competitive learning networks, the networks are typically presented a set of input data that possesses a corresponding set of results data. From these data values, the network of nodes "learns" a relationship between the input data and its corresponding results data. In this process, the probability distribution relationship is estimated using the multi-dimensional network of nodes. This relationship is represented within a set of artificial neural network coefficients for a particular topology of nodes.

One skilled in the art will recognize that competitive learning networks include a nearly infinite number of network topologies that may be used to represent a particular probability distribution relationship without deviating from the spirit and scope of the present invention as recited within the attached claims. In addition, artificial neural networks may utilize various well-known algorithm architectures, including hard-competitive learning (i.e. "winner-take-all" learning), soft competitive learning without a fixed network dimensionality, and soft competitive learning with a fixed network dimensionality, to specify an artificial neural network according to the invention as recited within the attached claims. Each of these algorithm architectures represents the same probability distribution relationship; however each of the various algorithm architectures better optimize corresponding processing parameters, which are often mutually exclusive with each other. These parameters include error minimization or the minimization of an expected quantization error, entropy maximization for the reference vectors used within a network, and topology-preserving or feature mapping architectures that attempt to map high-dimensional inputs signals onto lower-dimensional structures in a manner that attempts to preserve similar relationships found within the original data within the post-mapping data. As such, any of these types of algorithm architectures may be used to construct an artificial neural network without deviating from the spirit and scope of the present invention as recited within the attached claims.

Now referring to FIG. 3, an artificial neural network processing system 301 comprises a learning module 311, a prediction module 321, and a database of network node coefficients 313. The learning module 311 is used with a set of experimental data 315 that possesses a corresponding set of experimental results 316 to generate a set of network node coefficients that represent a probability distribution relationship for the experimental data 315-experimental result 316 data set for a particular neural network topology and algorithm architecture. The learning module 311 includes a data learning input module 312 that receives the experimental data 315-experimental result 316 data set generated using the process described above. The learning module 311 also includes an ANN training module 313 that processes the experimental data 315-experimental result 316 data set to generate the coefficients used to specify the probability distribution relationship and an ANN coefficient storage module 314 for storing the coefficients that have been previous generated within the database 313 for later use.

The data processing within the learning module 311 may proceed in a batch processing fashion in which all of the vectors within the experimental data 315-experimental result 316 data set are processed at a single time. In such a process, the experimental data 315-experimental result 316 data set is received by the input module 312, processed by the training module 313, and the generated coefficients are placed within the database 313 by the storage module 314. Alternatively, the experimental data 315-experimental result 316 data set may be processed as a sequence of smaller data sets in which the experimental data 315-experimental result 316 data set data values are generated at different times. In such a process, the training module 313 uses the previously stored coefficients retrieved by the storage module along with a new small data set provided by the input module 312 to generate an updated set of coefficients. These updated coefficients may be once again stored within the database 313 for use at a later time.

Once an artificial neural network 301 has been trained, the prediction module 321 may be used to predict, or classify, a particular test data value 325. The prediction module 321 includes a data prediction input module 322, an ANN prediction module 323, and an ANN curve slope module 324. The data prediction input module 322 receives the input test data generated as described above for use in the prediction module. The ANN prediction module 323 receives and utilizes the network coefficient values for the neural network from the ANN coefficient database 313 to predict the possible result for the probability distribution relationship specified within the neural network. This output value is used by the ANN curve slope module 324 to determine all possible values for a given gene, in the manner discussed above, to determine a curve slope value. This slope value is then output for later use in ranking and classifying the individual genes used to determine the presence, or lack there of, for a disease.

The embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the invention describe the use of an artificial neural network to identify relevant genes associated with diseases and use the identified genes to classify and identify diseases, one skilled in the are will recognize that the use of the processing system discussed above are merely example embodiments of the invention. As long as experimental data is used to self-train a processing system using competitive learning processing, the present invention to would be useable in other data processing systems. It is to be understood that other embodiments may be utilized and operational changes may be made without departing from the scope of the present invention as recited in the attached claims.

WORKING EXAMPLES

The following examples provide a nonlimiting illustration of various embodiments of the invention.

Example 1

Preparation of Microarrays

Preparation of glass cDNA microarrays, probe labeling, hybridization and image acquisition were performed according to the protocol given below, which is a standard NHGRI protocol (nhgri/nih/gov).

Gene-specific DNA was produced by PCR amplification of purified template plasmid DNAs from cloned ESTs. The PCR product was purified by ethanol precipitation, thoroughly resuspended in 3×SSC, and printed onto a poly-L-lysine coated slide.

The materials, reagents, and solutions used include: 96 well alkaline lysis miniprep kit (Edge BioSystems, Gaithersburg, Md.); LB Broth (Biofluids, Rockville, Md.); Superbroth (Biofluids, Rockyille, Md.); dATP, dCTP, dGTP, dTTP, 100 mM each #27-2035-02, store frozen, −20° C. (Pharmacia, Peapack, N.J.); PCR primer AEK M13F (5'-GTTGTAAAACGACGGCCAGTG-3') (SEQ ID NO. 97) and AEK M13R (5'-CACACAGGAAACAGCTATG-3') (SEQ ID NO. 98) at 1 mM concentration, store frozen, −20° C.; 10×PCR Buffer, # N808-0189, and Ampli-Taq DNA polymerase, # N808-4015 store frozen, −20° C. (Perkin Elmer, Norwalk, Conn.); Carbenicillin (Gibco-BRL, Rockville, Md.); Ethanol (200 Proof USP Ethyl Alcohol); 1M Tris-HCl (pH 8); 0.5M NaEDTA (pH 8); T Low E; Buffer; 20×SSC; Glycerol (enzyme grade); Sodium Acetate (tri-hydrate); Boric Acid; Sodium Hydroxide (1M); Glacial Acetic Acid; Succinic anhydride, #23969-0 and 1-methyl-2-pyrrolidinone, #32863-4 (Aldrich Chemical Co., St. Louis, Mo.); Diethyl Pyrocarbonate (DEPC) treated $H_2O$; Master set of clone-purified, sequence verified human ESTs (e.g. gf211 release, Research Genetics, Huntsville, Ala.); 96 pin inoculating block (#VP 4088, V&P Scientific, Inc, San Diego, Calif.); Airpore Tape Sheets, (#19571, QIAGEN Inc., Valencia, Calif.); Sterile 96-well plate seals, (e.g. #SEAL-THN-STR (Elkay Products, Inc., Shrewsbury, Mass.); 96-well U-Bottom Microtiter Plates, #3799 and 96-well V-Bottom Microtiter Plates, #3894 (Corning Inc., Corning, N.Y.); Thin wall PCR plate and Cylcieseal PCR plate sealer (e.g. #1038-50-0 and #1044-39-4, Robbins Scientific Corp. Sunnyvale, Calif.); household one-gallon sealable storage bags (e.g. Glad Lock); heat sealable storage bags and heat sealer; 0.2 mm Sterile Filtration unit; Diamond scribe for writing on slides; Pyrex baking dish (~24×34×5 cm); UV transparent plastic wrap (e.g. Glad Cling Wrap); 30 slide rack (stainless steel) #113 and 30 slide glass tank, #122 (Shandon Lipshaw, Pittsburgh, Pa.); 1 L glass tank; 1 L glass beaker; 1 L graduated; cylinder; Stir bar; Slide Box (plastic with no paper or cork liners), (e.g. #60-6306-02, PGC Scientific, Gaithersburg, Md.); PCR heat cycler (e.g. DNA Engine Tetrad, MJ Research, Waltham, Mass.); Centrifuge with a horizontal ("swinging bucket") rotor with a depth capacity of 6.2 cm for spinning microtiter plates and filtration plates (e.g. Sorvall Super T 21, Sorvall Inc., Newtown, Conn.); 37° C. Shaker incubator with holders for deep-well plates; 37° C. Waterbath; 65° C. Incubator; Vortex mixer; Immunowash microtiter plate washer, #1575 (BioRad, Hercules, Calif.); pH Meter; Platform Shaker; UV Stratalinker 2400, (Stratagene La Jolla, Calif.); Stirrer/Hotplate; Robotic slide printer; −80° C. Freezer; −20° C. Freezer; 45% (w/v) Sterile Glycerol; 450 grams enzyme grade glycerol per liter 9 Autoclave and store at room temperature); T low E Buffer; 1M Tris-HCl (pH 8.0) 10 mL; 0.5 M EDTA (pH 8.0) 0.2 mL; DEPC treated $H_2O$ 990 mL (Autoclave and store at room temperature); Carbenicillin stock solution (1 gram of carbenicillin in 10 mls of sterile water, Sterile filter with a 0.2 micron filter, Store frozen at −20° C.); LB with 100 μg/ml carbenicillin (Add 1 ml of carbenicillin stock solution to 1 liter of LB, Make fresh); 3M Sodium Acetate pH=6.0 (408.24 grams sodium acetate (tri-hydrate) per liter, 3M acetic acid (172.4 ml per liter), Titrate the pH of the 3M sodium acetate solution to pH 6.0 with the 3M acetic acid solution, Filter sterilize using a 0.2 micron filter, Store at room temperature); Ethanol/acetate mix Ethanol (100%) 950 ml, Sodium acetate pH=6.0, 50 ml); 1000 ml 3×SSC; DEPC $H_2O$ 42.5 ml; 20×SSC 7.5 ml; 50 ml 70% Ethanol; Ethanol (100%) 350 ml; DEPC $H_2O$ 150 ml; 500 ml.

The first step was to grow the EST clones. The cDNA clones were obtained from Research Genetics (Huntsville, Ala.) and were their standard microarray set, which consisted of 3789 sequence-verified known genes and 2778 sequence-verified ESTs.

The sealed master plates were incubated over night at 37° C. Most suppliers provide low density bacterial cultures. Replicating directly from these dilute stocks frequently results in non-growth in the secondary culture. If making the template from a plate that had previously been cultured to high density before freezing, this initial growth step should not be used, as it will reduce the viability of the cultures.

A set of standard 96 well round (U) bottom plates were then prepared by labeling all plates and placing 100 μl of LB broth containing 100 ?g/ml carbenicillin in each well. These plates were used as working copies. To preserve the master set of plates, it was useful to make replicate copies of the master plate to serve as working copies when the master plate was first replicated. The EST clones were then checked to insure that they were in a vector conferring ampicillin resistance, as is common with human IMAGE clones.

The master plates were spun briefly (about two minutes) at 1000 rpm in a horizontal microtiter plate rotor to remove condensation and droplets from the seals before opening. Bacterial culture fluid on the sealers can easily be transferred from one well to others, cross-contaminating the stocks.

Then a container was partially filled with 100% alcohol. The 96 pin-replicating tool was dipped in the alcohol, removed and then the pins were flamed.

The inoculation block was allowed to cool briefly, then the replicating tool was dipped in the master plate and then into the daughter plate. This was repeated as necessary for each plate inoculated. It is useful to color the plate corner near the A-1 well of all master and daughter plates with a marker pen before beginning the replication process in order to reduce mistakes in the relative orientation of the plates. The suggested plates have a notch at this corner as well.

The inoculated LB plates, with the lids on, were placed into a one gallon sealable bag containing a moistened paper towel and grow overnight at 37° C. Many 37° C. incubators tend to dry out microtiter plate cultures. Placing the plates in a highly humidified bag avoids this problem.

Next, deep well plates were filled with 1 ml of Superbroth (100 μg/ml carbenicillin) per well. These plates served as the source of culture for template preparation. Using the replicating tool, the deep well plates were then inoculated directly from the freshly grown LB plates. Next, the openings of the deep well plates were covered with Qiagen Airpore Tape Sheets and the plastic lids were placed over the sheet. The plates were then placed in a 37° C. shaker incubator at 200 RPM for twenty-four hours. 50 μl of 45% (w/v) sterile glycerol was added to each well of any working plates that are to be frozen (−80° C.) and subsequently used as culture sources.

After the EXT clones were grown, the plasmid templates have to be isolated. First, the lysis buffer (Edge Biosystems Kit) was warmed to 37° C. to dissolve the SDS. Then the RNAse solution was added to the resuspension buffer (Edge Biosystems Kit), 1 ml/100 ml, and stored at 4° C. The receiving plates were prepared from the Edge Biosystems Kit by adding 350 μl of ethyl alcohol to each well of the receiving plates. The filter plate was then placed on top and secured with tape. The bacterial cultures in the deep well plates were centrifuged at 1500×g for seven minutes in a centrifuge equipped with a horizontal rotor for 96-well plates. They were then briefly inverted and excess media was tapped out on a clean paper towel. The pellets will loosen and may be lost when pouring off excess media if this step is delayed.

The pellet was then resuspended in 100 µl of Resuspension Buffer, and Vortexed until the entire pellet was re-suspended. This step is critical. Poor resuspension of the cells results in clumps of cells that do not lyse in subsequent steps. This reduces the yield and decreases the purity of the product. 100 µl of Lysis Buffer was then added and the solution was mixed gently by rocking the plates from side to side, to avoid shearing the bacterial chromosomal DNA. 100 µl of Precipitation buffer was added to each well and briefly mixed. Then, 100 µl of Neutralization buffer was added to each well and Vortexed.

The contents of the deep wells were then transferred to the waiting filter plates/receiving plate stacks using the wide bore pipette tips provided in the kits. The stacked plates were then centrifuged at 1500×g for twelve minutes in a centrifuge equipped with a horizontal rotor for 96-well plates. The stacked plates were then removed from the centrifuge. The filter plates were removed and discarded. The alcohol and filtrate were decanted from the receiver plate and the excess alcohol was touched off on clean paper towels. 500 µl of 70% ethanol was added to each well and immediately decanted and excess alcohol was touched off with a clean paper towel. Then, the plates were placed in a clean drawer without their lids, covered with a clean paper towel and allowed to dry overnight.

The next day, the DNA was resuspended in 200 µl of T Low E Buffer. The top was sealed with plate sealer and rehydrated at 4° C. for at least two days before using. They were stored at −20° C. in the interim.

After the plasmid templates have been isolated, the EST inserts were amplified. For each 96 well plate to be amplified, a PCR reaction mixture was prepared containing the following ingredients: 1000 µl of 10×PCR Buffer, 20 ?L of dATP (100 mM), 20 ?L of dGTP (100 mM), 20 ?L of dCTP (100 mM), 20 ?L of dTTP (100 mM), 5 ?L of AEK M13F primer (1 mM), 5 µL of AEK M13R primer (1 mM), 100 µL of AmpliTaq polymerase (5 U/µl), and 8800 mL of $H_2O$. The 96-well PCR plates were then labeled and 100 µl of the PCR reaction mixture from above was aliquoted to each well. The plates were then gently tapped to insure that no air bubbles were trapped at the bottom of the wells. 1 µl of purified EST plasmid template from above was then added to each well. The donor and recipient plates were then marked at the corner, near the A1 well to facilitate correct orientation during transfer of the template. It was important to make sure that the pipette tips were all submerged in the PCR reaction mix when delivering the template. Missing the liquid was easier when multi-channel pipettes were used.

The following thermal cycle series was then performed: 1 initial cycle of heating to 96° C. and holding for 30 sec, 25 cycles of denaturing at 94° C. for 30 sec, reannealing at 55° C. for 30 sec, and extending at 72° C. for 150 sec, one final cycle of holding at 72° C. for 5 minutes, then cooling to ambient temperature. After the above cycle, the plates were held at 4° C. while quality controls were performed.

The quality control was done by agarose gel electrophoresis of the ESTs. If this was the first time the template for these ESTs was being amplified, 2 µl of each PCR product was analyzed on a 2% agarose gel. If amplified products from this template had been previously tested, then one row of wells from each plate amplified was analyzed. Gel imaging allowed a rough quantitation of product while giving an excellent characterization of the product. Band size, as well as the number of bands observed in the PCR products, contributed to an understanding of the final results of the hybridization. The use of gel well formats suitable for loading from 96 well plates and programmable pipetters made this form of analysis feasible on a large scale.

The materials, reagents and solutions for the quality control check included: Electrophoresis apparatus with capacity for four 50 well combs, (e.g. #D3, Owl Scientific, Woburn, Mass.); 50× Tris-Acetate Electrophoresis BufferM; Agarose; Dye Solution (Xylene Cyanol/Bromophenol Blue) (e.g. #351-081-030, Quality Biological Inc., Gaithersburg Md.); Glycerol (enzyme grade); Ethidium Bromide solution (10 mg/ml); 100 base-pair ladder size standard; Programmable, 12-channel pipetter (e.g. #2019, Matrix Technologies, Lowell, Mass.); Disposable microtiter mixing trays (e.g. Falcon #353911, Becton Dickinson, Franklin Lake, N.J.); Electrophoresis power supply; 1×TAE Buffer; 50×TAE Buffer 40 ml; Ethidium Bromide (10 mg/ml) 0.1 ml and Water 960 ml; 1000 ml; Loading Buffer; Glycerol (enzyme grade) 4.0 ml, DEPC Water 0.9 ml, and Dye Solution*0.1 ml for a total of 5.0 ml (*This solution is 0.25% (w/v) Xylene Cyanol and 0.25% (w/v) Bromophenol Blue); 100 bp Size Standards; DNA ladder (1 mg/ml) 50 µL, 1 M Tris-HCl (pH 8.0) 5 µl, 0.5 M EDTA (pH 8.0) 5 µl, and Loading Buffer 440 µl for a total of 500 µl The electrophoresis was carried out with a 2% agarose gel (1×TAE) with four combs (50 tooth) that was submerged in an electrophoresis apparatus with sufficient 1×TAE buffer to just cover the surface of the gel. A reservoir of Loading Buffer was prepared, using 12 wells of a microtiter plate. Then a pipetter was programmed to sequentially carry out the following steps: fill with 2 µl, fill with 1 µL, fill with 2 µl, mix a volume of 5 µl five times, expel 5 µl. Twelve (12) disposable tips were then placed on the pipetter. 2 µl of PCR product from wells A1-A12 of the PCR plate were loaded, followed by 1 µl of air, then 2 µl of Loading Buffer from the reservoir. The tips were then placed in clean wells of a disposable mixing tray and the pipette was allowed to mix the sample and loading dye. The pipette tip was then placed in a 50 well row so that the tip containing the PCR product from well A1 is in the second well of the row, and the other tips are in every other succeeding well.

The process was repeated (changing tips each time), to load PCR plate row B starting in the 3rd well, interleaved with the A row, the C row starting at well 26, and the D row at well 27, interleaved with the C row. Then 5 µl of 100 bp Size Standards were placed in wells 1 and 50. This process was repeated, to load samples from rows E, F, G, and H in the second, 50 well row of gel wells, to load samples from two 96 well PCR plates per gel, or single row samples from 16 PCR plates. To reduce diffusion and mixing, a voltage was applied to the gel for a minute between loading each well strip. This caused the DNA to enter the gel, and reduced band spreading and sample loss.

A voltage was then applied to the gel and it was run until the bromophenol blue (faster band) had nearly migrated to the next set of wells. For a gel that is 14 cm in the running dimension, and 3 cm between each row of wells, 200 volts were applied for 15 minutes. Digital photos of the gel were taken and the images stored for future reference. The gels should show bands of fairly uniform brightness distributed in size between 600 to 2000 base-pairs. Further computer analysis of such images can be carried out with image analysis packages to provide a list of the number and size of bands. Ideally this information can be made available during analysis of the data from hybridizations involving these PCR products.

After the quality control checks are run on the plates, the next step involves purifying the PCR products. 96 well V-bottom plates were filled with 200 µl per well of ethanol/acetate mix. The ethanol acetate solution used for precipitation is less acidic (pH 6) than is typically used. In this instance, more acidic solutions produce precipitates which are harder to resuspend without improving yield.

100 μl per well of PCR product was transferred into V-bottom plates and mixed by pipetting a volume of 75 μl per well four times. The plates were then placed in a −80° C. freezer for one hour or stored overnight at −20° C. The plates were stored at −20° C. if they were to be left for more than one hour, because aggressive precipitation produces precipitates which are hard to resuspend. The plates were then thawed to reduce brittleness and melt any ice, which may have formed in the wells.

The plates were loaded into a centrifuge with a horizontal microtiter plate rotor and spun at 2600×g for 40 minutes at 4° C. Next, the supernatant from each well was aspirated using the Immunowash plate washer. Settings for the depth of aspiration by the plate washer needed to be adjusted to suit the microtiter plates used. It is advisable to leave approximately 10-20 ml in the bottom of the well to avoid disturbing the pellet.

200 μl of 70% ethanol was delivered to each well in the plate using the Immunowash plate washer, and the plates were centrifuged at 2600×g for 40 minutes. The supernatant was aspirated from each well using the Immunowash plate washer, and the plates were dried overnight in a closed drawer. They should not be dried in a speed-vac because desiccated PCR products are hard to resuspend.

After the PCR products were purified, they were then resuspended by adding 40 μl of 3×SSC per well. The plates were then sealed with a foil sealer, taking care to achieve a tight seal over each well. The plates were then placed in heat sealable bags with paper towels moistened with 3×SSC and the bag was sealed with a heat sealer. The high external humidity within the sealed bag helped to keep the volumes in the individual wells from varying. The bags were then placed in a 65° C. incubator for 2 hours. The heat in the incubator was then turned off, and the plates were allowed to cool gradually in the incubator to avoid condensation on the sealers. The plates were stored at −20° C.

The yield of the PCR suspension was then checked by fluorometric determination of DNA concentration. 1 μl of resuspended PCR product from one row of wells from each plate on a 2% agarose gel was analyzed as previously described. Adequate precipitation and resuspension produced very intense bands, with no material failing to leave the loading well, and no smear of material from the band towards the loading well.

While it would be ideal to be able to exactingly quantify each EST PCR product and spot each DNA species at equivalent concentrations, it is impractical for most labs to do so when thousands of ESTs must be prepared. Fortunately, it is possible to use a strategy where excess DNA is spotted, so that the exact quantities used do not produce much variation in the observed results. When using this strategy, it is necessary to track the average productivity of the PCR reactions. Fluorometry provides a simple way to obtain an approximate concentration of the double-stranded PCR product in the PCR reaction mix.

Next, the double stranded DNA was quantified. The materials, reagents, and solutions necessary include: reference double-stranded DNA (0.5 mg/ml) (e.g. #15612-013 Gibco/BRL, Bethesda, Md.), 96 well plates for fluorescent detection (e.g. #7105, Dynex, Chantilly, Va.), Fluorometer (e.g. #LS50B, Perkin Elmer, Norwalk, Conn.), FluoReporter Blue dsDNA Quantitation Kit (#F-2962, Molecular Probes, Eugene, Oreg.), TE, 12 channel multi-pipetters, Computer equipped with Microsoft Excel software, Ds-DNA Standards: 50 μg/ml, 100 μg/ml, 250 μg/ml, 500 μg/ml, μl TE 90, 80, 50, 0 μl ds-DNA (0.5 mg/ml) 10, 20, 50, 100, (It is good practice to check both the integrity (agarose gel) and the concentration (absorbance) of the standard before use); Fluor Buffer (Hoechst 33258 solution (contains the dye at an unspecified concentration in a 1:4 mixture of DMSO:$H_2O$) (from kit) 25 μl, TNE Buffer (TNE Buffer is 10 mM Tris-HCl (pH 7.4), 2 M NaCl, 1 mM EDTA) (from kit) 10 ml.

The double stranded DNA was quantified as follows. 96 well plates were labeled for fluorescence assay. 200 μl of Fluor Buffer was added to each well. 1 μl of PCR product from each well in a row of a PCR plate was added to a row of the fluorometry plate. Samples were added to rows A through G of the fluorometry plate. In the final row of the fluorometry plate 1 μl of each of the series of ds-DNA standards 0 μg/ml (TE only), 50, 100, 250 and 500 μg/ml ds-DNA were added. This series was repeated twice in the final row.

The fluorometer was set for excitation at 346 nm and emission at 460 nm, and adjusted as necessary to read the plate. If the fluorometer used did not support automated analysis, the data table was exported to Excel. The response for the standards was tested to see that it was linear and reproducible from the range of 0 to 500 μg/ml of ds-DNA.

Next, the concentration of ds-DNA in the PCR reactions was calculated using the following equation, after subtracting the average 0 μg/ml value from all other sample and control values:

$$[ds\text{-DNA}(\mu g/ml)]=((\text{PCR sample value})/(\text{average } 100\ \mu g/ml \text{ value}))*100$$

Constantly tracking the yields of the PCRs makes it possible to rapidly detect many ways in which PCR can fail or perform poorly. This assay can also be applied after precipitation and resuspension of the PCR products to monitor overall recovery of product. 1 μl of amplified products from one row of wells from each amplified plate by fluorometry was analyzed.

Slides were then coated with poly-L-lysine to have a surface that is both hydrophobic and positively charged. The hydrophobic character of the surface minimizes spreading of the printed spots, and the charge appears to help position the DNA on the surface in a way that makes cross-linking more efficient.

Materials, reagents, and solutions for coating the slides includes: Gold Seal Microscope Slides (#3011, Becton Dickinson, Franklin Lake, N.J.), Ethanol (100%), Poly-L-lysine (#P8920, Sigma, St. Louis, Mo.), 50 Slide Stainless Steel Rack, #900401, and 50 Slide Glass Tank, #900401, (Wheaton Science Products, Millville, N.J.), Sodium Hydroxide, Stir Plate, Stir Bar, Platform Shaker, 30 Slide Rack, #196, plastic, and 30 slide Box, #195, plastic, (Shandon Lipshaw, Pittsburgh, Pa.), Sodium Chloride, Potassium Chloride, Sodium Phosphate Dibasic Heptahydrate, Potassium Phosphate Monobasic, Autoclave, 0.2 mm Filter: Nalgene, Centrifuge: Sorvall Super 20, Slide Box (plastic with no paper or cork liners), (e.g. #60-6306-02, PGC Scientific, Gaithersburg, Md.), 1 L Glass Beaker; 1 L Graduated Cylinder, 1M Sodium Borate (pH 8.0) (Dissolve 61.83 g of Boric acid in 900 ml of DEPC $H_2O$. Adjust the pH to 8.0 with 1N NaOH. Bring volume up to one liter. Sterilize with a 0.2 micron filter and store at room temperature), Cleaning Solution ($H_2O$ 400 ml, Ethanol 600 ml, NaOH 100 g—Dissolve NaOH in $H_2O$. Add ethanol and stir until the solution clears. If the solution does not clear, add $H_2O$ until it does), and Poly-L-lysine Solution (poly-L-lysine (0.1% w/v) 35 ml PBS 35 ml $H_2O$ 280 ml 350 ml)

First, the slides are placed into 50 slide racks and the racks are placed in glass tanks with 500 ml of cleaning solution. Gold Seal Slides are highly recommended, as they have been found to have consistently low levels of autofluorescence. It was important to wear powder free gloves when handling the slides to avoid contamination.

The tanks are placed on platform shakers for two hours at 60 rpm. After being shook, the cleaning solution was poured out, and the slides were then washed in $H_2O$ for three minutes. This wash was repeated four times. The slides were then transferred to 30 slide plastic racks and placed into small plastic boxes for coating. The slides were then submerged in 200 ml poly-L-lysine solution per box. The slide boxes were then placed on platform shaker for one hour at 60 rpm. The slides were rinsed three times with $H_2O$, and submerged in $H_2O$ for one minute, and then centrifuged for two minutes at 400×g and the slide boxes used for coating were dried.

The slides were then placed back into the slide box used for coating and allowed to stand overnight before transferring to a new slide box for storage. This allowed the coating to dry before it was handled. The slides were allowed to age for two weeks on the bench, in a new slide box, before they were printing on. The coating dried slowly, becoming more hydrophobic with time.

Slide boxes used for long term storage should be plastic and free of cork lining. The glue used to affix the cork will leach out over time and give slides stored in these types of boxes a greasy film that has a high degree of autofluorescence. All glassware and racks used for slide cleaning and coating should be cleaned with highly purified $H_2O$ only, and detergent should not be used.

Once the slides were coated, they were printed. The variety of printers and pens for transferring PCR products from titer plates to slides precludes highly detailed descriptions of the process. The following steps provide a general description of the processing.

The print pens were pre-cleaned according to the manufacturer's specification. The printer slide deck was then loaded with poly-L-lysine coated slides from above. The plates containing the purified EST PCR products were thawed and centrifuged briefly, (about two minutes) at 1000 rpm in a horizontal microtiter plate rotor to remove condensation and droplets from the seals before being opening. 5 to 10 μl of the purified EST PCR products were transferred to a plate that served as the source of solution for the printer. Printing with quill-type pens usually requires that the volume of fluid in the print source was sufficiently low, so that when the pen was lowered to the bottom of the well, it was submerged in the solution to a depth of less than a millimeter. This keeps the pen from carrying a large amount of fluid on the outside of the pen shaft and producing variable, large spots on the first few slides printed.

A repetitive test print was run on the first slide. In this operation, the pens were loaded with the DNA solution, and then the pens serially deposited this solution on the first slide in the spotting pattern specified for the print. This test was run to check the size and shape of the specified spotting pattern, as well as its placement on the slide. It also served to verify that the pens were loading and spotting, and that a single loading produced as many spots as were required to deliver material to every slide in the printer. If one or more of the pens was not performing at the desired level, it was re-cleaned or substituted with another pen and tested again. If all pens were performing, the full print was carried out.

At the end of the print, the slides were removed from the printer, labeled with the print identifier and the slide number by writing on the edge of the slide with a diamond scribe and placed in a dust free slide box to age for one week. It was useful to etch a line, which outlined the printed area of the slide, onto the first slide. This served as a guide to locate the area after the slides have been processed, and the salt spots were then washed off.

The slides were placed, printed side face up, in a casserole dish and covered with cling wrap. The slides were then exposed to a 450 mJ dose of ultraviolet irradiation in the Stratalinker. Slides should have been and were aged at ambient temperature in a closed slide box for one week prior to blocking. The slides were then transferred to a 30 slide stainless steel rack and the rack was placed into a small glass tank. 6.0 g succinic anhydride was dissolved in 325 ml 1-methyl-2-pyrrolidinone in a glass beaker by stirring with a stir bar. Nitrile gloves were worn and the work was carried out in a chemical fume hood while handling 1-methyl-2-pyrrolidinone (a teratogen).

25 ml 1M sodium borate buffer (pH 8.0) was added to the beaker. The solution was allowed to mix for a few seconds, then rapidly poured into a glass tank with slides. Succinic anhydride hydrolyzed quite rapidly once the aqueous buffer solution was added. To obtain quantitative passivation of the poly-L-lysine coating, it was critical that the reactive solution be brought in contact with the slides as quickly as possible. The glass tank was placed on a platform shaker in a fume hood for 20 minutes. Small particulates resulting from precipitation of reaction products may be visible in the fluid.

While the slides were incubating on the shaker a boiling $H_2O$ bath was prepared to denature the DNA on the slides. After the slides were incubated for 20 minutes, they were transferred into the boiling $H_2O$ bath. The heating element was immediately turned off after the slides were submerged in the bath. The slides were allowed to stand in the $H_2O$ bath for 2 minutes. The slides were then transferred into a glass tank filled with 100% ethanol and incubated for 4 minutes. The slides were removed and centrifuged at 400 rpm for 3 minutes in a horizontal microtiter plate rotor to dry the slides. The slides were then transferred to a clean, dust free slide box and allowed to stand overnight before being used for collection of gene expression data.

Example 2

Cell Culture and Tumor Samples

The source and other information for the cell lines and tumor samples used herein are described in TABLE 2 below for both the training set and the test samples.

TABLE 2

Supplement Table: Known Molecular Characteristics of Samples.

| Sample Label | Histological Diagnosis | Molecular Markers | Source Label | Source |
|---|---|---|---|---|
| EWS-C1 | EWS-C | EWS-FLI1, 10-6 | A4573 | NCI |
| EWS-C2 | EWS-C | EWS-FLI1, type I | TC71 | NCI |

TABLE 2-continued

Supplement Table: Known Molecular Characteristics of Samples.

| Sample Label | Histo-logical Diagnosis | Molecular Markers | Source Label | Source |
|---|---|---|---|---|
| EWS-C3 | EWS-C | EWS-FLI1, type I | TC106 | NCI |
| EWS-C4 | EWS-C | EWS-FLI1, type I | 5838 | NCI |
| EWS-C6 | EWS-C | EWS-FLI1, type I | A673 | NCI |
| EWS-C7 | EWS-C | EWS-FLI1, type I | ES-CL1 | MSKCC |
| EWS-C8 | EWS-C | EWS-FLI1, type I | TC32 | NCI |
| EWS-C9 | EWS-C | EWS-FLI1, type II | SK-ES-1 | ATCC |
| EWS-C10 | EWS-C | EWS-FLI1, type II | SK-N-MC | ATCC |
| EWS-C11 | EWS-C | EWS-FLI1, type II | RDES | ATCC |
| EWS-T1 | EWS-T | EWS-FLI1, type I | ES20 | MSKCC |
| EWS-T2 | EWS-T | EWS-FLI1, type II | ES13 | MSKCC |
| EWS-T3 | EWS-T | EWS-FLI1, type I | ES16 | MSKCC |
| EWS-T4 | EWS-T | EWS-FLI1, type I | ES17 | MSKCC |
| EWS-T6 | EWS-T | EWS-FLI1, 7-8 | ES22 | MSKCC |
| EWS-T7 | EWS-T | EWS-ERG, 7-9 | ES25 | MSKCC |
| EWS-T9 | EWS-T | EWS-FLI1, type I | 9602P006 | CHTN |
| EWS-T11 | EWS-T | EWS-FLI1, type I | 9703P152 | CHTN |
| EWS-T12 | EWS-T | EWS-FLI1, type I | 9704P218 | CHTN |
| EWS-T13 | EWS-T | EWS-FLI1, type I | ES23 | MSKCC |
| EWS-T14 | EWS-T | EWE-FLI1, type I | 9605P074 | CHTN |
| EWS-T15 | EWS-T | EWE-FLI1, type I | 9609P027 | CHTN |
| EWS-T19 | EWS-T | EWS-FLI1, type I | SARC75 | CHTN |
| RMS-C2 | ERMS-C | — | RD | ATCC |
| RMS-C3 | ARMS-C | ND | RH4 | NCI |
| RMS-C4 | ARMS-C | PAX3-FKHR | RH3 | NCI |
| RMS-C5 | ARMS-C | PAX3-FKHR | RH5 | NCI |
| RMS-C6 | ARMS-C | PAX3-FKHR | RH28 | NCI |
| RMS-C7 | ARMS-C | ND | RH30 | NCI |
| RMS-C8 | ERMS-C | — | CTR | ATCC |
| RMS-C9 | ARMS-C | PAX3-FKHR | RH4 | NCI |
| RMS-C10 | ARMS-C | PAX3-FKHR | RMS13 | NCI |
| RMS-C11 | ERMS-C | — | TE671 | ATCC |
| RMS.T1 | ARMS-T | PAX3-FKHR | RMS3 | MSKCC |
| RMS.T2 | ARMS-T | PAX3-FKHR | RMS6 | MSKCC |
| RMS.T3 | ERMS-T | — | RMS2 | MSKCC |
| RMS.T4 | ERMS-T | no PAX-FKHR | RMS5 | MSKCC |
| RMS.T5 | ARMS-T | PAX3-FKHR | RMS10 | MSKCC |
| RMS.T6 | RMS-T | ND | RT1 | CHTN |
| RMS.T7 | ERMS-T | — | RT4 | CHTN |
| RMS.T8 | RMS-T | ND | RT5 | CHTN |
| RMS.T10 | RMS-T | ND | RT2 | CHTN |
| RMS.T11 | ERMS-T | — | RHAB2 | CHTN |
| NB-C1 | NB-C | MYCN amp | KCNR | NCI |
| NB-C2 | NB-C | — | GICAN | NCI |
| NB-C3 | NB-C | — | SK-N-AS | ATCC |
| NB-C4 | NB-C | MYCN amp | LAN5 | NCI |
| NB-C5 | NB-C | MYCN amp | SK-N-BE2 | ATCC |
| NB-C6 | NB-C | MYCN amp | SK-N-DZ | ATCC |
| NB-C7 | NB-C | — | GICAN | NCI |
| NB-C8 | NB-C | — | NGP | NCI |
| NB-C9 | NB-C | — | SH-SY5Y | ATCC |
| NB-C10 | NB-C | MYCN amp | SK-N-FI | ATCC |
| NB-C11 | NB-C | Single copy MYCN | SK-N-SH | ATCC |
| NB-C12 | NB-C, | MYCN amp | CHP-134B | NCI |
| BL-C1 | BL-C | — | RAMOS (RAI) | ATCC |
| BL-C2 | BL-C | — | ST486 | ATCC |
| BL-C3 | BL-C | — | CA46 | ATCC |
| BL-C4 | BL-C | — | ST486 | ATCC |
| BL-C5 | BL-C | — | RAJI | ATCC |
| BL-C6 | BL-C | — | MC116 | ATCC |
| BL-C7 | BL-C | — | DAUDI | ATCC |
| BL-C8 | BL-C | — | SULTAN | ATCC |
| Test 1 | NB-C | MYCN amp | IMR32 | ATCC |
| Test 2 | EWS-C | ND | CHOP1 | NCI |
| Test 3 | Osteo-sarcoma-C | — | OsA-CI | ATCC |
| Test 4 | ARMS-T | — | ARMD1 | CHTN |
| Test 5 | Sarcoma | — | A204 | ATCC |
| Test 6 | EWS-T | EWS-FLI1, type I | 9608P053 | CHTN |
| Test 7 | BL-C | — | EB1 | ATCC |
| Test 8 | NB-C | — | SMSSAN | NCI |
| Test 9 | Sk. Muscle | — | SkM1 | CHTN |
| Test 10 | ERMS-T | — | ERDM1 | CHTN |
| Test 11 | Prostate Ca.-C | — | PC3 | ATCC |
| Test 12 | EWS-T | — | SARC67 | CHTN |
| Test 13 | Sk. Muscle | — | SkM2 | CHTN |
| Test 14 | NB-T | Single copy MYCN | NB3 | DZNSG |
| Teat 15 | BL-C | — | EB2 | ATCC |
| Test 16 | NB-T | Single copy MYCN | NB1 | DZNSG |
| Test 17 | ARMS-T | — | ARMD2 | CHTN |
| Test 18 | BL-C | — | GA10 | ATCC |
| Test 19 | EWS-T | ND | ET3 | CHTN |
| Test 20 | EWS-T | EWS-FLI1, type I | 9903P1339 | CHTN |
| Test 21 | EWS-T | EWS-FLI1, type II | ES23 | MSKCC |
| Test 22 | ERMS-T | — | ERMD2 | CHTN |
| Test 23 | NB-T | Single copy MYCN | NB2 | DZNSG |
| Test 24 | ERMS-T | no PAX-FKHR | RMS4 | MSKCC |
| Test 25 | NB-T | Single copy MYCN | NB4 | DZNSG |

Supplement Table: Known molecular characteristics of samples. Table labels and abbreviations are described in Table 1 in the manuscript. EWS and ARMS samples with noted translocations were verified by RT-PCR. ND; not determined. Amp.: amplification.

All the original histological diagnoses were made at tertiary hospitals, which have reference diagnostic laboratories with extensive experience in the diagnosis of pediatric cancers. Approximately 20% of all samples in each category were randomly selected, blinded and set aside for testing. To augment this test set, we added 4 neuroblastoma tumors and 5 non-SRBCT samples (also blinded to the authors performing the analysis). The EWSs had a spectrum of the expected translocations, and the RMSs were a mixture of both ARMS containing the PAX3-FKHR translocation and embryonal rhabdomyosarcoma (ERMS). The NBs contained both MYCN amplified and single copy samples. The NHLs were cell lines derived from BL. TABLE 2 gives details of these samples as well.

This protocol details the methods used to extract RNA from cells, purify the RNA by a combination of phase extraction and chromatography, and prepare a labeled cDNA copy of the message fraction of the purified RNA. The protocol also describes the process of making fluorescent cDNA representations of the message pools within the isolated total RNA pools. This is accomplished by using the pure total RNA as a substrate for reverse transcription in the presence of nucleotides derivatized with either a Cy3 or a Cy5 fluorescent tag.

The materials, reagents, and solutions needed include: Trizol Reagent (#15596-018, Life Technologies, Rockville, Md.); RNeasy Maxi Kit (#75162, Qiagen, Valencia, Calif.); Chloroform; Ethanol (200 Proof USP Ethyl Alcohol); DPBS (Dulbecco's phosphate buffered saline); 3M sodium acetate (pH 5.2); dATP, dCTP, dGTP, dTTP, 100 mM each, store frozen, −20° C. (#27-2035-02, Pharmacia, Peapack, N.J.); pd(T)12-18 resuspend at 1 mg/ml, and store frozen −20° C. (#27-7858, Amersham Pharmacia Biotech); Anchored oligo primer (anchored; 5'-TTT TTT TTT TTT TTT TTT TTV N-3') (SEQ ID NO. 99); resuspend at 2 mg/ml, store frozen −20° C. (e.g. #3597-006, Genosys); CyTM3-dUTP, 1 mM, and CyTM5-dUTP, 1 mM, store −20° C., light sensitive; RNasinâ Rnase inhibitor, store −20° C. (#N211A, Promega); SUPERSCRIPT™ II Rnase H' Reverse Transcriptase Kit, store −20° C., (#18064-014, Life Technologies, Rockville, Md.); C0t-1 DNA, 1 mg/ml, store frozen −20° C. (#15279-011, Life Technologies, Rockville, Md.); 0.5M EDTA(pH 8.0); 1 N NaOH; 1M TRIS-HCL; (pH7.5); TE pH 7.4; DEPC water 50× Tris Acetate Buffer; 15 ml round bottom; polypropylene centrifuge tubes; 50 ml conical polypropylene centrifuge tubes; 1.5 ml; Eppendorf tubes; 0.2 ml thin wall PCR tube; MicroCon 100 (Amicon Cat No. 42412); High speed centrifuge for 15 ml tubes; Clinical centrifuge with horizontal rotor for 50 ml conical tubes; Tissue homogenizer (e.g. Polytron PT 1200 with Polytron-Aggregate-Dispergier-und-Mischtechnik 147a Ch6014 #027-30-520-0, Brinkmann Instruments Inc., Westbury, N.Y.); RPE Buffer (Add 4 volumes of ethanol per volume of RPE concentrate supplied in Quiagen Kit0; RW1 Buffer (Supplied in Qiagen Kit) 75% EtOH(Ethanol (100%) 375 ml, and DEPC H2O 125 ml for a total of 500 ml); 10× low T dNTP Mix (25 μL dGTP (100 mM), 25 μl dATP (100 mM), 25 μl dCTP (100 mM), 10 μl dTTP (100 mM), and 415 μL DEPC $H_2O$ for a total of 500 μl); 5× First Strand Buffer (Provided with Superscript II); TAE Buffer (50×Tris Acetate Electrophoresis Buffer 20 ml, and DEPC H2O 980 mL for a total of 1000 ml).

If the cells that were used were harvested from tissue culture, the cell pellet was washed twice in DPBS. If the cells that were used were from tissue culture, 1 ml of Trizol was added per $2\times10^7$ cells and mixed by shaking. If tissue was being used, 100 mg of frozen tissue was added directly to 4 ml of Trizol, and dissociate by homogenization with a rotating blade tissue homogenizer.

Whatever the source, 2⁄10 volume of chloroform was added to the cells and shook for 15 seconds, and then allowed to stand for 3 minutes, followed by centrifugation at 12,000×g for 15 minutes at 4° C. The supernatant was taken off and added to a polypropylene tube, while recording the volume of the supernatant.

Then 0.53 volumes of ethanol were slowly added to the supernatant while vortexing, this produced a final ethanol concentration of 35%. The ethanol was added drop by drop and allowed to mix completely with the supernatant before more ethanol is added. If a high local concentration of ethanol is produced, the RNA in that vicinity will precipitate.

The supernatant from an extraction of $2\times10^7$ to $1\times10^8$ cells was added to an RNeasy maxi column, which is seated in a 50 ml centrifuge tube. The tube was then centrifuged at 2880×g in a clinical centrifuge with a horizontal rotor at room temperature for 5 minutes. The flow-through was then poured back onto the top of the column and centrifuged again. This step is necessary because a significant amount of RNA is not captured by the column matrix in the first pass of the RNA containing solution through the column.

The flow-through was discarded and 15 ml of RW1 buffer was added to the column, followed by centrifugation at 2880×g for 5 minutes. The flow-through was discarded again and then 10 ml of RPE buffer was added, followed again by centrifugation at 2880×g for 5 minutes. Once again, the flow through was discarded and another 10 ml of RPE buffer was added, and the column was centrifuged at 2880×g for 10 minutes.

Next, the column was placed in a fresh 50 ml tube and add 1 ml of DEPC treated water from the kit was added to the column, and the column was allowed to stand for 1 minute. The column was then centrifuged at 2880×g for 5 minutes, and another 1 ml of water was added to the column. The column was allowed to stand for 1 minute, followed by centrifugation at 2880×g for 10 minutes.

Then, 400 μl portions of the column eluate was aliquotted to 1.5 ml Eppendorf tubes, to which 1⁄10 volume of 3M sodium acetate (pH 5.2) was added, along with 1 ml of ethanol. The tubes were then allowed to stand for 15 minutes, after which they were centrifuged at 12000×g at 4 C for 15 minutes. The pellet was then washed two times in 75% EtOH and stored at −80° C.

The RNA was resuspended at approximately 1 mg/ml in DEPC $H_2O$. It was then concentrated to greater than 7 mg/ml by centrifugation on a MicroCon 100 filter unit, centrifuged at 500×g, checking as necessary to determine the rate of concentration. This step removes many residual, small to medium sized, molecules that inhibit the reverse transcription reaction in the presence of fluorescently derivatized nucleotides. The concentration of RNA in the concentrated sample was then determined by spectrophotometry, and the sample was stored at −80° C.

If an anchored oligo dT primer was used, the primer was annealed to the RNA in the following 17 μl reaction (a 0.2 ml thin wall PCR tube was used so that incubations could be carried out in a PCR cycler):

| Component | addition for Cy5 labeling | addition for Cy3 labeling |
|---|---|---|
| Total RNA (>7 mg/ml) | 150-200 μg | 50-80 μg |
| Anchored primer (2 μg/μl) | 1 μl | 1 μl |
| DEPC H2O | to 17 μl | to 17 μl |

If an oligo dT(12-18) primer was used, the primer was annealed to the RNA in the following 17 μl reaction:

| Component | addition for Cy5 labeling | addition for Cy3 labeling |
|---|---|---|
| Total RNA (>7 mg/ml) | 150-200 μg | 50-80 μg |
| dT(12-18) primer (1 μg/μl) | 1 μl | 1 μl |
| DEPC H2O | to 17 μl | to 17 μl |

The incorporation rate for Cy5-dUTP is less than that of Cy3-dUTP, so more RNA is labeled to achieve more equivalent signal from each species.

It was then heated to 65° C. for 10 minutes and cooled on ice for 2 minutes. Then, 23 μl (8 μl of 5× first strand buffer, 4 μl of 10× low T dNTPs mix, 4 μl of Cy5 or Cy3 dUTP (1 mM), 4 μl of 0.1 M DTT, 1 μl of Rnasin (30 u/?l), and 2 ?l of Superscript II (200 u/?l)) of reaction mixture containing either Cy5-dUTP or Cy3-dUTP nucleotides was added, mixed well by pipetting and a brief centrifuge spin was used to concentrate it in the bottom of the tube. Superscript polymerase is very sensitive to denaturation at air/liquid interfaces, so we were careful to suppress foaming in all handling of this reaction.

It was then incubated at 42° C. for 30 min., after which 2 μl Superscript II was added, making sure the enzyme was well mixed in the reaction volume and incubated at 42O C for 30-60 min. Then, 5 μl of 0.5M EDTA was added, making sure the reaction was stopped with EDTA before adding NaOH (the next step), since nucleic acids precipitate in alkaline magnesium solutions.

Then, 10 μl 1N NaOH was added and it was incubated at 65? C for 60 minutes to hydrolyze residual RNA, after which it was cooled to room temperature. The purity of the sodium hydroxide solution used in this step is crucial. Slight contamination or long storage in a glass vessel can produce a solution that will degrade the Cy5 dye molecule, turning the solution yellow. Some researchers achieve better results by reducing the time of hydrolysis to 30 minutes.

It was then neutralized by adding 25 μl of 1M Tris-HCl (pH 7.5). Then, the labeled cDNA was desalted by adding the neutralized reaction, 400 μl of TE pH 7.5 and 20 μg of human C0t-1 DNA to a MicroCon 100 cartridge. It was then pipetted to mix, and spun for 10 minutes at 500×g. 200 μl TE pH 7.5 was added, and the solution was then concentrated to about 20-30 μl (approximately 8-10 min at 500×g). Alternatively, a smaller pore MicroCon 30 was used to speed the concentration step. In this case, the first wash was centrifuged for approximately 4.5 minutes at 16,000×g and the second (200 μl wash) for about 2.5 minutes at 16,000×g.

It was then recovered by inverting the concentrator over a clean collection tube and spinning for 3 min at 500×g. In some cases, the cy5 labeled cDNA formed a gelatinous blue precipitate that was recovered in the concentrated volume. The presence of this material signaled the presence of contaminants. The more extreme the contamination, the greater the fraction of cDNA which will be captured in this gel. Even if heat solubilized, this material tends to produce uniform, nonspecific binding to the DNA targets. When concentrating by centrifugal filtration, the times required to achieve the desired final volume were variable. Overly long spins can remove nearly all the water from the solution being filtered. When fluor-tagged nucleic acids are concentrated onto the filter in this fashion, they are very hard to remove, so it is necessary to approach the desired volume by conservative approximations of the required spin times. If control of volumes proves difficult, the final concentration can be achieved by evaporating liquid in the speed-vac. Vacuum evaporation, if not to dryness, does not degrade the performance of the labeled cDNA.

Next, a 2-3 μl aliquot of the Cy5 labeled cDNA was taken for analysis, leaving 18-28 μl for hybridization. This probe was run on a 2% agarose gel (6 cm wide×8.5 cm long, 2 mm wide teeth) in Tris Acetate Electrophoresis Buffer (TAE). For maximal sensitivity when running samples on a gel for fluor analysis, a loading buffer with minimal dye was used and no ethidium bromide was added to the gel or running buffer.

The gel was then scanned on a Molecular Dynamics Storm fluorescence scanner (setting: red fluorescence, 200 micron resolution, 1000 volts on PMT). Successful labeling produces a dense smear of probe from 400 bp to >1000 bp, with little pile-up of low molecular weight transcripts. Weak labeling and significant levels of low molecular weight material indicates a poor labeling. A fraction of the observed low molecular weight material is unincorporated fluor nucleotide.

Next, the fluorescent cDNA had to be hybridized to the microarray. The volume of hybridization solution required was first determined. The rule of thumb is to use 0.033 μl for each mm 2 of slide surface area covered by the cover slip used to cover the array. An array covered by a 24 mm by 50 mm cover slip required 40 μl of hybridization solution. The volume of the hybridization solution is critical. When too little solution is used, it is difficult to seat the cover slip without introducing air bubbles over some portion of the arrayed ESTs, and the cover slip will not sit at a uniform distance from the slide. If the cover slip is bowed toward the slide in the center, there will be less labeled cDNA in that area and hybridization will be non-uniform. When too much volume is applied, the cover slip will move easily during handling, leading to misplacement relative to the arrayed ESTs, and non-hybridization in some areas of the array.

For a 40 μl hybridization, the Cy3 and Cy5 labeled cDNAs were pooled into a single 0.2 ml thin wall PCR tube and the volume was adjusted to 30 μl by either adding DEPC $H_2O$, or removing water in a SpeedVac. If a vacuum device was used to remove water, high heat or heat lamps were not used to accelerate evaporation because the fluorescent dyes could be degraded.

For a 40 μl hybridization the following components were combined:

| | High Sample Blocking | High Array Blocking |
|---|---|---|
| Cy5 + Cy3 probe | 30 μl | 28 μl |
| Poly d(A) (8 mg/ml) | 1 μl | 2 μl |
| Yeast tRNA (4 mg/ml) | 1 μl | 2 μl |
| Human C0t-1 DNA (10 mg/ml) | 1 μl | 0 μl |
| 20x SSC | 6 μl | 6 μl |
| 50x Denhardt's blocking solution | 1 μl (optional) | 2 μl |
| Total volume | 40 ul | 40 ul |

Arrays and samples can vary somewhat, making it necessary to vary the composition of the hybridization cocktail. In cases where there is residual hybridization to control repeat DNA samples on the array, more C0t-1 DNA was used, as in the High Sample Blocking formulation. When there is diffuse background or a general haze on all of the array elements, more of the non-specific blocker components was used, as in the High Array Blocking formulation.

The components were mixed well by pipetting, heated at 98° C. for 2 minutes in a PCR cycler, cooled quickly to 25° C. and 0.6 ul of 10% SDS was added. It was then centrifuged for 5 min at 14,000×g. The fluor labeled cDNAs have a tendency to form small, very fluorescent, aggregates which result in bright, punctate background on the array slide. Hard centrifugation will pellet these aggregates, allowing you to avoid introducing them to the array.

The labeled cDNA was applied to a 24 mm×50 mm glass cover slip and then touched with the inverted microarray. Applying the hybridization mix to the array and cover slipping it is an operation which requires some dexterity to get the positioning of the cover slip and the exclusion of air bubbles just right. It was helpful to practice this operation with buffer and plain slides before attempting actual samples. The hybridization solution was added to the cover slip first, since some aggregates of fluor remain in the solution and will bind to the first surface they touch.

The slide was then placed in a microarray hybridization chamber, 5 μl of 3×SSC was added to the reservoir, if the chamber provided one, or at the scribed end of the slide and the chamber was sealed. The chamber was submerged in a 65° C. water bath and the slide was allowed to hybridize for 16-20 hours. There are a wide variety of commercial hybridization chambers. It was worthwhile to prepare a mock hybridization with a blank slide, load it in the chamber and incubate it to test for leaks, or drying of the hybridization fluid, either of which cause severe fluorescent noise on the array.

Next, the unbound fluorescent cDNA was washed off. The hybridization chamber was removed from the water bath, cooled and carefully dried off. The chamber was unsealed and the slide was removed. As there may be negative pressure in the chamber after cooling, it is necessary to remove water from around the seals so that it was not pulled into the chamber and onto the slide when the seals are loosened.

The slide was placed, with the cover slip still affixed, into a Coplin jar filled with 0.5×SSC/0.01% SDS wash buffer. The cover slip was allowed to fall from the slide and then removed from the jar with a forceps. The slide was allowed to wash for 2-5 minutes. The slide was transferred to a fresh Coplin jar filled with 0.06×SSC, and allowed to wash for 2-5 minutes. The sequence of washes may need to be adjusted to allow for more aggressive noise removal, depending on the source of the sample RNA. Useful variations are to add a first wash which is 0.5×SSC/0.1% SDS or to repeat the normal first wash twice.

The slide was then transferred to a slide rack and centrifuged at low rpm (700-1000) for 3 minutes in a clinical centrifuge equipped with a horizontal rotor for microtiter plates. If the slide is simply air dried, it frequently acquires a fluorescent haze. Centrifuging off the liquids results in a lower fluorescent background. As the rate of drying can be quite rapid, it is suggested that the slide be placed in the centrifuge immediately upon removal from the Coplin jar.

Image analysis was performed using DeArray software (Chen, Y., Dougherty, E. R. and Bittner, M. L. Ratio-based decisions and the quantitative analysis of cDNA microarray images, *Biomedical Optics* 2, 364-374 (1997).

Example 3

Data Analysis

To calibrate ANN models to recognize cancers in each of the four SRBCT categories, gene-expression data from cDNA microarrays as obtained via Examples 1 and 2 above were used. The 63 training samples included both tumor biopsy material (13 EWS and 10 RMS) and cell lines (10 EWS, 10 RMS, 12 NB and 8 Burkitt lymphomas (BL; a subset of NHL). For two samples, ST486 (BL-C2 and C4) and GICAN (NB-C2 and C7), we performed two independent microarray experiments to test the reproducibility of the experiments and these were subsequently treated as separate samples.

Genes were filtered based on the intensity of the fluorescence gathered from the cDNA microarray. This type of filtering was designed to remove spots for which image analysis failed. Genes were filtered by requiring that a gene have a red intensity greater than 20 across all experiments. The number of genes that passed this filter was 2308. Each slide was normalized across all experiments. Therefore the expression level was based on a relative (or normalized) red intensity (RRI) for each gene, RRI=mean intensity of that spot/mean intensity of filtered genes. The natural logarithm (ln) of RRI was used as a measure of the expression levels.

Principal component analysis (PCA) further reduced the dimensionality. To allow for a supervised regression model with no over-training (when we have low number of parameters as compared to the number of samples), the dimensionality of the samples was reduced by PCA using centralized In (RRI) values as input. Thus each sample was represented by 88 numbers, which are the results of projection of the gene expressions using PCA eigenvectors. We used the 10 dominant PCA components for subsequent analysis. These 10 dominant components contained 63% of the variance in the data matrix. The remaining PCA components contained variance unrelated to separating the four cancers.

Figure 5:
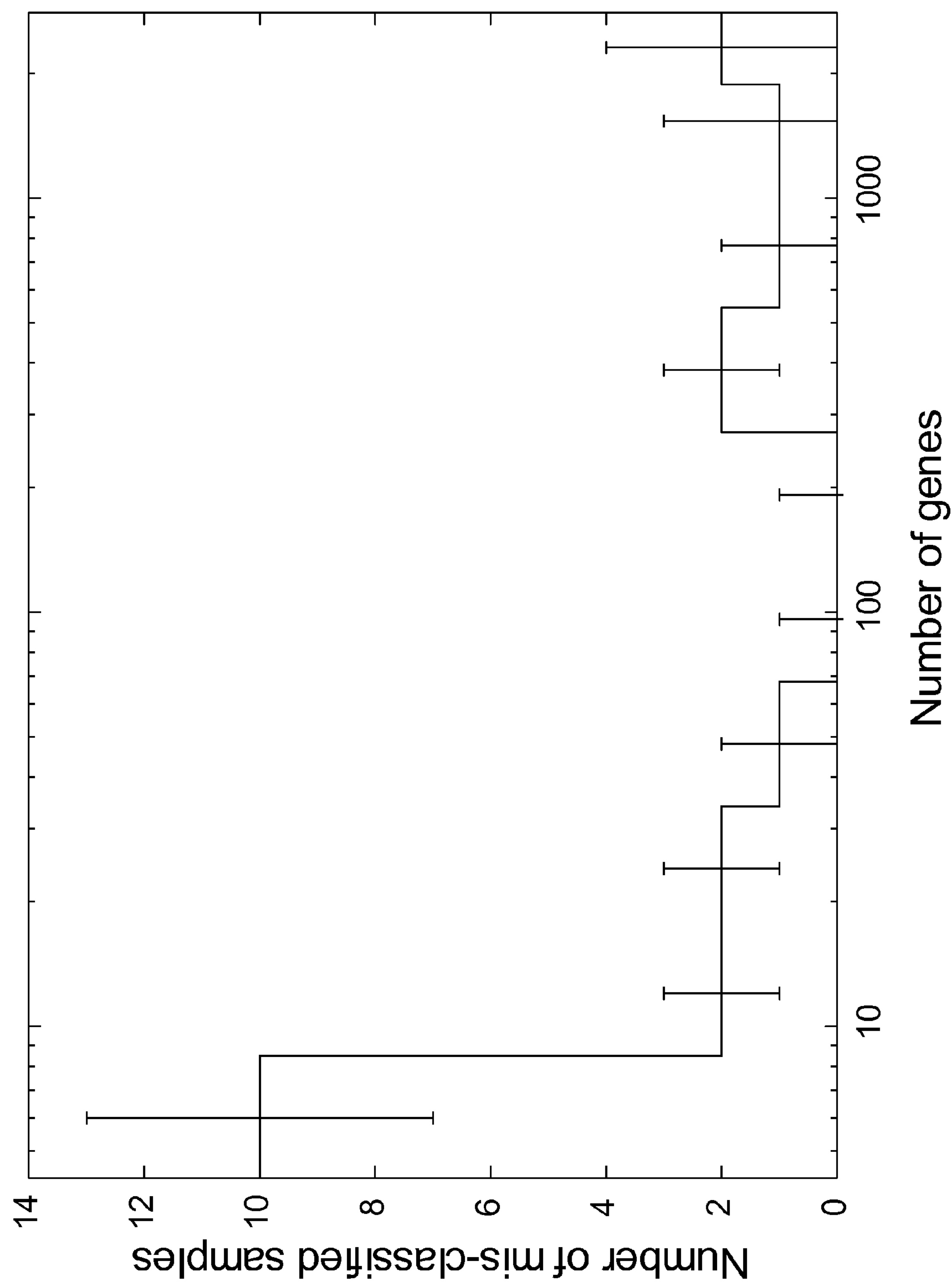
FIG. 5 represents a plot of the average number of misclassified samples for all 3750 models plotted against an increasing number of used genes.

We classified the training samples in the 4 categories using a 3-fold cross validation procedure: the 63 training (labeled) samples were randomly shuffled and split into 3 equally sized groups. Each linear ANN model was then calibrated with the 10 PCA input variables (normalized to centralized z-scores) using 2 of the groups, with the third group reserved for testing predictions (validation). This procedure was repeated 3 times, each time with a different group used for validation. The random shuffling was redone 1250 times and for each shuffling we analyzed 3 ANN models. Thus, in total, each sample belonged to a validation set 1250 times, and 3750 ANN models were calibrated. The three-fold cross-validation procedure produced at total of 3750 ANN models, and the training and validation was successful, see FIG. 5.

Figure 4:
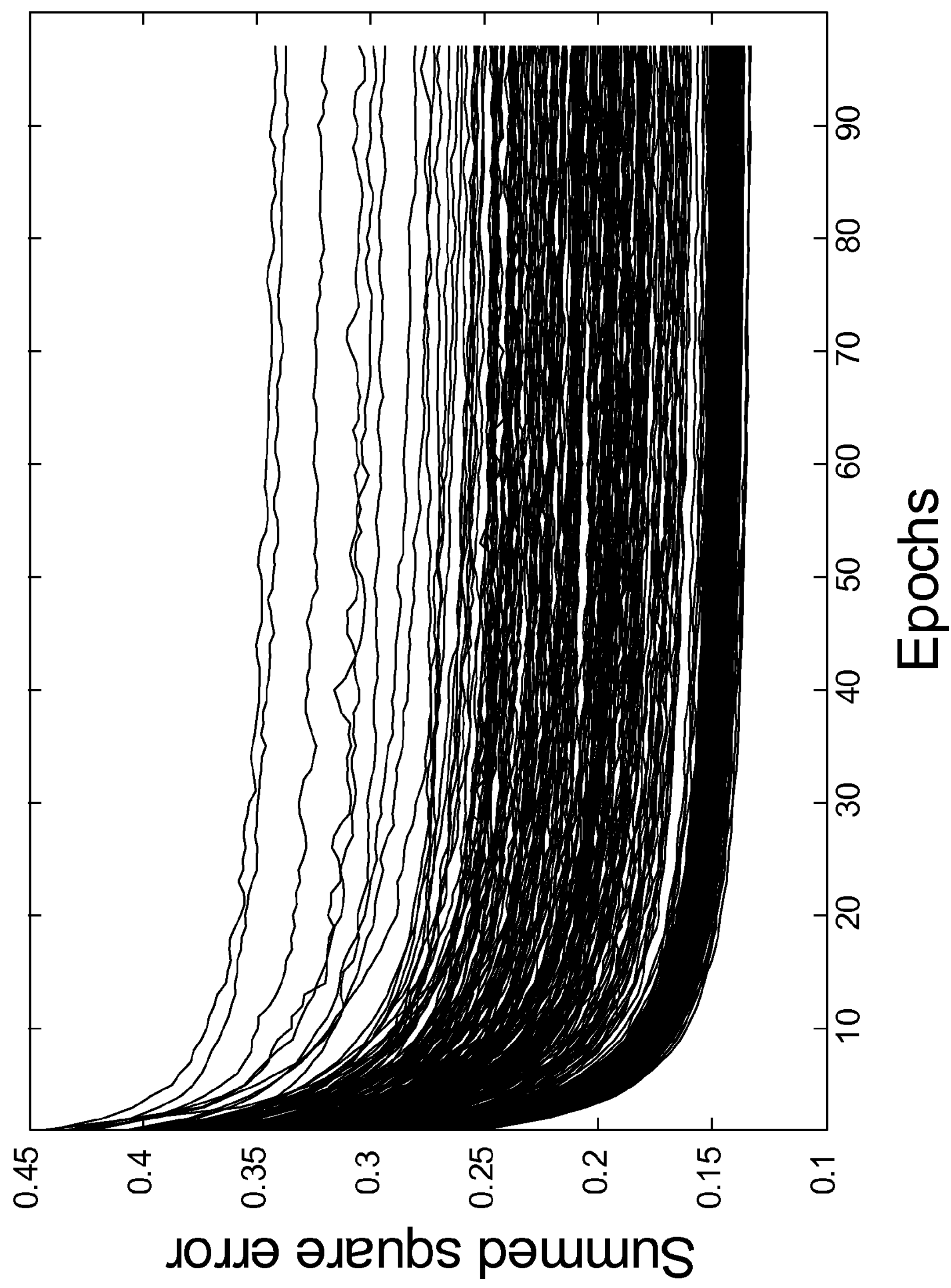
FIG. 4 represents a plot of the average classification error per sample (using a summed square error function) plotted during the training iterations (epochs) for both the training and validation samples.

In addition, there was no sign of 'over-training' of the models, as would be shown by a rise in the summed square error for the validation set with increasing training iterations or 'epochs', see FIG. 4.

For each diagnostic category (EWS, RMS, NB or BL), each ANN model gave an output between 0 (not this category) and 1 (this category). The 1250 outputs for each validation sample were used as a committee as follows. We calculated the average of all the predicted outputs (a committee vote) and then a sample was classified as a particular cancer if it received the highest committee vote for that cancer. In clinical settings, it is important to be able to reject a diagnostic classification including samples not belonging to any of the four diagnoses. Therefore, to be able to reject classification we did as follows. A squared Euclidean distance was computed for each cancer type, between the committee vote for a sample and the 'ideal' output for that cancer type; normalized such that it is unity between cancer types as described above. Using the 1250 ANN models for each validation sample we constructed for each cancer type an empirical probability distribution for the distances. Using these distributions, samples are only diagnosed as a specific cancer if they lie within the 95th percentile. All 3750 models were used to classify the additional 25 test samples.

Using these ANN models, all of the 63 training samples were correctly assigned/classified to their respective categories, having received the highest committee vote (average output) for that category.

Diagnostic results for the 63 training samples can be seen in TABLE 3 below.

TABLE 3

| Sample Label | Source Label | Training sample characteristics: Histological Diagnosis | ANN Committee Vote: EWS | ANN Committee Vote: RMS | ANN Committee Vote: NB | ANN Committee Vote: BL | Source |
|---|---|---|---|---|---|---|---|
| EWS-C1 | A4573 | EWS-C | 0.91 | 0.02 | 0.27 | 0.04 | NCI |
| EWS-C2 | TC71 | EWS-C | 0.85 | 0.03 | 0.16 | 0.08 | NCI |
| EWS-C3 | TC106 | EWS-C | 0.89 | 0.04 | 0.10 | 0.08 | NCI |
| EWS-C4 | 5838 | EWS-C | 0.87 | 0.09 | 0.08 | 0.04 | NCI |
| EWS-C6 | A673 | EWS-C | 0.93 | 0.11 | 0.03 | 0.05 | NCI |
| EWS-C7 | ES-CL1 | EWS-C | 0.94 | 0.06 | 0.08 | 0.04 | MSKCC |
| EWS-C8 | TC32 | EWS-C | 0.98 | 0.05 | 0.04 | 0.04 | NCI |
| EWS-C9 | SK-ES-1 | EWS-C | 0.94 | 0.10 | 0.03 | 0.05 | ATCC |
| EWS-C10 | SK-N-MC | EWS-C | 0.81 | 0.22 | 0.03 | 0.06 | ATCC |
| EWS-C11 | RDES | EWS-C | 0.93 | 0.05 | 0.03 | 0.07 | ATCC |
| EWS-T1 | ES20 | EWS-T | 0.99 | 0.04 | 0.03 | 0.06 | MSKCC |
| EWS-T2 | ES13 | EWS-T | 0.95 | 0.08 | 0.06 | 0.04 | MSKCC |
| EWS-T3 | ES16 | EWS-T | 0.97 | 0.10 | 0.05 | 0.03 | MSKCC |
| EWS-T4 | ES17 | EWS-T | 0.93 | 0.14 | 0.11 | 0.02 | MSKCC |
| EWS-T6 | ES22 | EWS-T | 0.97 | 0.12 | 0.04 | 0.04 | MSKCC |
| EWS-T7 | ES25 | EWS-T | 0.99 | 0.04 | 0.03 | 0.04 | MSKCC |
| EWS-T9 | 9602P006 | EWS-T | 0.95 | 0.13 | 0.03 | 0.03 | CHTN |
| EWS-T11 | 9703P152 | EWS-T | 0.99 | 0.03 | 0.06 | 0.03 | CHTN |
| EWS-T12 | 9704P218 | EWS-T | 1.00 | 0.02 | 0.03 | 0.03 | CHTN |
| EWS-T13 | ES23 | EWS-T | 0.67 | 0.28 | 0.16 | 0.04 | MSKCC |
| EWS-T14 | 9505P074 | EWS-T | 0.99 | 0.02 | 0.04 | 0.05 | CHTN |
| EWS-T15 | 9609P027 | EWS-T | 0.99 | 0.03 | 0.06 | 0.03 | CHTN |
| EWS-T19 | SARC75 | EWS-T | 0.93 | 0.06 | 0.09 | 0.04 | CHTN |
| RMS-C2 | RD | ERMS-C | 0.06 | 0.81 | 0.11 | 0.03 | ATCC |
| RMS-C3 | RH4 | ARMS-C | 0.04 | 0.84 | 0.05 | 0.03 | NCI |
| RMS-C4 | RH3 | ARMS-C | 0.00 | 0.88 | 0.11 | 0.05 | NCI |
| RMS-C5 | RH5 | ARMS-C | 0.01 | 0.91 | 0.09 | 0.04 | NCI |
| RMS-C6 | RH28 | ARMS-C | 0.00 | 0.87 | 0.07 | 0.07 | NCI |
| RMS-C7 | RH30 | ARMS-C | 0.01 | 0.88 | 0.09 | 0.03 | NCI |
| RMS-C8 | CTR | ERMS-C | 0.03 | 0.86 | 0.07 | 0.03 | ATCC |
| RMS-C9 | RH4 | ARMS-C | 0.05 | 0.85 | 0.03 | 0.05 | NCI |
| RMS-C10 | RMS13 | ARMS-C | 0.01 | 0.90 | 0.14 | 0.03 | NCI |
| RMS-C11 | TE671 | ERMS-C | 0.07 | 0.27 | 0.08 | 0.03 | ATCC |
| RMS-T1 | RMS3 | ARMS-T | 0.02 | 0.93 | 0.03 | 0.06 | MSKCC |
| RMS-T2 | RMS6 | ARMS-T | 0.06 | 0.85 | 0.03 | 0.04 | MSKCC |
| RMS-T3 | RMS2 | ERMS-T | 0.08 | 0.80 | 0.07 | 0.02 | MSKCC |
| RMS-T4 | RMS5 | ERMS-T | 0.07 | 0.93 | 0.03 | 0.03 | MSKCC |
| RMS-T5 | RMS10 | ARMS-T | 0.05 | 0.84 | 0.08 | 0.03 | MSKCC |
| RMS-T6 | RT1 | RMS-T | 0.04 | 0.93 | 0.05 | 0.03 | CHTN |
| RMS-T7 | RT4 | ERMS-T | 0.10 | 0.75 | 0.05 | 0.05 | CHTN |
| RMS-T8 | RT5 | RMS-T | 0.05 | 0.90 | 0.05 | 0.02 | CHTN |
| RMS-T10 | RT2 | RMS-T | 0.02 | 0.92 | 0.06 | 0.03 | CHTN |
| RMS-T11 | RHAB2 | ERMS-T | 0.03 | 0.76 | 0.06 | 0.03 | CHTN |
| NB-C1 | KCNR | NB-C | 0.00 | 0.08 | 0.83 | 0.03 | NCI |
| NB-C2 | GICAN | NB-C | 0.03 | 0.10 | 0.70 | 0.08 | NCI |
| NB-C3 | SK-N-AS | NB-C | 0.01 | 0.25 | 0.64 | 0.04 | ATCC |
| NB-C4 | LAN5 | NB-C | 0.02 | 0.03 | 0.85 | 0.06 | NCI |
| NB-C5 | SK-N-BE2 | NB-C | 0.02 | 0.02 | 0.92 | 0.06 | ATCC |
| NB-C6 | SK-N-DZ | NB-C | 0.02 | 0.02 | 0.89 | 0.09 | ATCC |
| NB-C7 | GICAN | NB-C | 0.07 | 0.05 | 0.80 | 0.08 | NCI |
| NB-C8 | NGP | NB-C | 0.00 | 0.06 | 0.96 | 0.04 | NCI |
| NB-C9 | SH-SY5Y | NB-C | 0.05 | 0.04 | 0.85 | 0.04 | ATCC |
| NB-C10 | SK-N-FI | NB-C | 0.00 | 0.12 | 0.91 | 0.03 | ATCC |
| NB-C11 | SK-N-SH | NB-C | 0.05 | 0.01 | 0.95 | 0.05 | ATCC |
| NB-C12 | CHP-1348 | NB-C | 0.02 | 0.24 | 0.41 | 0.06 | NCI |
| BL-C1 | RAMOS(RA1) | BL-C | 0.03 | 0.05 | 0.08 | 0.90 | ATCC |
| BL-C2 | ST486 | BL-C | 0.04 | 0.12 | 0.04 | 0.82 | ATCC |
| BL-C3 | CA46 | BL-C | 0.07 | 0.09 | 0.02 | 0.89 | ATCC |
| BL-C4 | ST486 | BL-C | 0.04 | 0.06 | 0.08 | 0.80 | ATCC |
| BL-C5 | RAJI | BL-C | 0.10 | 0.04 | 0.04 | 0.87 | ATCC |
| BL-C6 | MC116 | BL-C | 0.10 | 0.02 | 0.09 | 0.87 | ATCC |
| BL-C7 | DAUDI | BL-C | 0.09 | 0.04 | 0.02 | 0.93 | ATCC |
| BL-C8 | SULTAN | BL-C | 0.20 | 0.03 | 0.03 | 0.89 | ATCC |

Source label refers to the original name of the sample as labeled by the source. Histological diagnosis is defined as cancer type suffixed with -T for a tumor sample and -C for a cell line. Highlighted in gray is the ANN classification of the samples. NCI: National Cancer Institute, National Institutes of Health, ATCC: American Type Culture Collection, MSKCC: Memorial Sloan-Kettering Cancer Center, CHTN: Cooperative Human Tissue Network.

Example 4

Optimization of Genes Utilized for Classification

The contribution of each gene to the classification by the ANN models was determined by measuring the sensitivity of the classification to a change in the expression level of each gene, using the 3750 previously calibrated models.

The sensitivity to the different genes was determined by the absolute value of the partial derivative of the output with respect to the gene expressions, averaged over samples and ANN models. A large sensitivity implied that changing the expression influences the output significantly.

Figure 6:
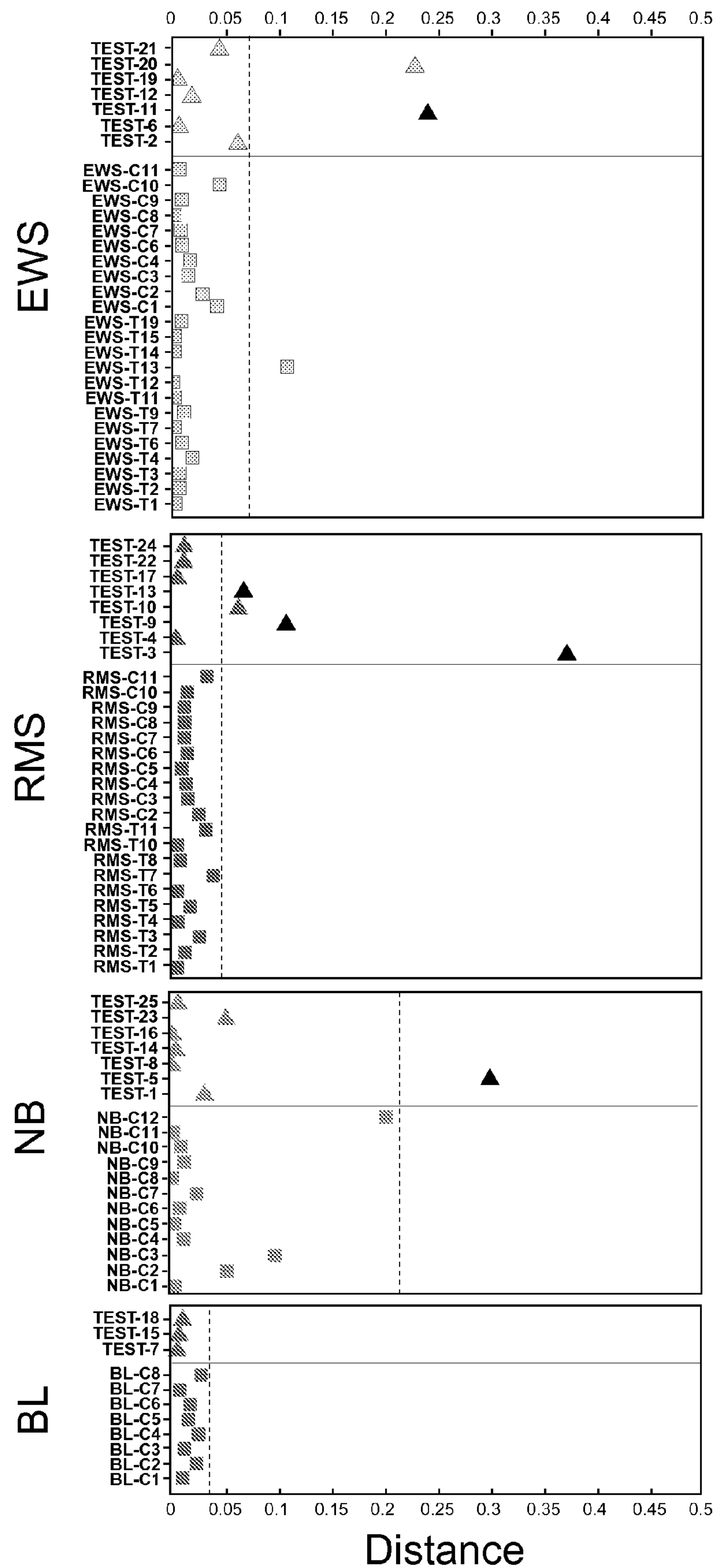
FIG. 6 represents a plot of the distance from the samples committee vote to the ideal vote for that diagnostic category.

In this way the genes were ranked according to their significant for the classification. We then determined the classification error rate using increasing numbers of these ranked genes. The classification error rate minimized to 0% at 96 genes, see FIG. 5. The 10 dominant PCA components for these 96 genes contained 79% of the variance in the data matrix. Using only these 96 genes, we recalibrated the ANN models and again correctly classified all 63 samples, see FIG. 6. Moreover, multidimensional scaling (MDS) analysis using these 96 genes clearly separated the four cancer types, see FIG. 7. The top 96 discriminators represented 93 unique genes, see FIG. 8, as IGF2 was represented by three independent clones and MYC by two.

Of the 96 genes, 13 were anonymous expressed sequence tags (ESTs); 16 genes were specifically expressed in EWS, 20 in RMS, 15 in NB and 10 in BL. Twelve genes were good discriminators on the basis of lack of expression in BL and variable expression in the other three types. One gene (EST; Clone ID 295985) discriminated EWS from other cancer types by its lack of expression in this cancer. The remainder of the genes was expressed in two of the four cancer types. To our knowledge, of the 61 genes that were specifically expressed in cancer type, 41 have not been previously reported as associated with these diseases.

Example 5

Diagnostic Classification and Hierarchical Clustering

The diagnostic classification capabilities of these ANN models were then tested on a set of 25 blinded test samples. Samples were classified to a diagnostic category if they received the highest vote for that category. As this classifier had only four possible outputs, all samples were classified to one of the four categories. We therefore established a diagnostic classification method based on a statistical cutoff to enable us to reject a diagnosis of a sample classified to a given category. If a sample falls outside the 95th percentile of the probability distribution of distances between samples and their ideal output (for example for EWS it is EWS=1, RMS=NB=BL=0), its diagnosis is rejected.

TABLE 4

| Sample | ANN committee vote | | | | ANN | ANN | Histological | Source | |
|---|---|---|---|---|---|---|---|---|---|
| label | EWS | RMS | NB | BL | classification | diagnosis | diagnosis | label | Source |
| Test 1 | 0.01 | 0.07 | 0.76 | 0.06 | NB | NB | NB-C | IMR32 | ATCC |
| Test 2 | 0.67 | 0.06 | 0.08 | 0.09 | EWS | EWS | EWS-C | CHOP1 | NCI |
| Test 3 | 0.11 | 0.17 | 0.16 | 0.11 | RMS | — | Osteosarcoma-C | OsA-CI | ATCC |
| Test 4 | 0.00 | 0.95 | 0.06 | 0.03 | RMS | RMS | ARMS-T | ARMD1 | CHTN |
| Test 5 | 0.11 | 0.11 | 0.25 | 0.10 | NB | — | Sarcoma-C | A204 | ATCC |
| Test 6 | 0.98 | 0.04 | 0.10 | 0.03 | EWS | EWS | EWS-T | 9608P053 | CHTN |
| Test 7 | 0.05 | 0.02 | 0.05 | 0.93 | BL | BL | BL-C | EB1 | ATCC |
| Test 8 | 0.00 | 0.05 | 0.94 | 0.04 | NB | NB | NB-C | SMSSAN | NCI |
| Test 9 | 0.22 | 0.60 | 0.03 | 0.06 | RMS | — | Sk. Muscle | SkM1 | CHTN |
| Test 10 | 0.10 | 0.68 | 0.11 | 0.04 | RMS | — | ERMS-T | ERDM1 | CHTN |
| Test 11 | 0.39 | 0.04 | 0.28 | 0.15 | EWS | — | Prostate Ca.-C | PC3 | ATCC |
| Test 12 | 0.89 | 0.05 | 0.14 | 0.03 | EWS | EWS | EWS-T | SARC67 | CHTN |
| Test 13 | 0.20 | 0.7 | 0.03 | 0.05 | RMS | — | Sk. Muscle | SkM2 | CHTN |
| Test 14 | 0.03 | 0.02 | 0.90 | 0.07 | NB | NB | NB-T | NB3 | DZNSG |
| Test 15 | 0.06 | 0.03 | 0.05 | 0.91 | BL | BL | BL-C | EB2 | ATCC |
| Test 16 | 0.03 | 0.02 | 0.93 | 0.05 | NB | NB | NB-T | NB1 | DZNSC |
| Test 17 | 0.01 | 0.90 | 0.05 | 0.03 | RMS | RMS | ARMS-T | ARMD2 | CHTN |
| Test 18 | 0.06 | 0.04 | 0.04 | 0.88 | BL | BL | BL-C | GA10 | ATCC |
| Test 19 | 0.99 | 0.02 | 0.04 | 0.05 | EWS | EWS | EWS-T | ET3 | CHTN |
| Test 20 | 0.40 | 0.30 | 0.10 | 0.06 | EWS | — | EWS-T | 9903P1339 | CHTN |
| Test 21 | 0.81 | 0.19 | 0.12 | 0.04 | EWS | EWS | EWS-T | ES23 | MSKCC |
| Test 22 | 0.01 | 0.88 | 0.09 | 0.04 | RMS | RMS | ERMS-T | ERMD2 | CHTN |
| Test 23 | 0.07 | 0.08 | 0.70 | 0.06 | NB | NB | NB-T | NB2 | DZNSG |
| Test 24 | 0.05 | 0.87 | 0.06 | 0.03 | RMS | RMS | ERMS-T | RMS4 | MSKCC |
| Test 25 | 0.05 | 0.02 | 0.89 | 0.06 | NB | NB | NB-T | NB4 | DZNSG |

Source label refers to the original name of the sample as designated by the source. Histological diagnosis is defined as cancer type suffixed with -T for a tumor sample and -C for a cell line. Normal skeletal muscle (Sk. Muscle) is also included in the test set. The ANN classification as determined by the committee vote is bolded, NCI: National Cancer Institute, National Institutes of Health, ATCC: American Type Culture Collection, MSKCC: Memorial Sloan-Kettering CancerCenter, CHTN: Cooperative Human Tissue Network, DZNSC: German Cancer Research Center, Heidelberg.

The test samples contained both tumors (5 EWS, 5 RMS and 4 NB) and cell lines (1 EWS, 2 NB and 3 BL). The ability of these models to reject a diagnosis on 5 non-SRBCTs was also tested (consisting of 2 normal muscle tissues (Tests 9 and 13) and 3 cell lines including an undifferentiated sarcoma (Test 5), osteosarcoma (Test 3) and a prostate carcinoma (Test 11)). Using the 3750 ANN models calibrated with the 96 genes, we correctly classified 100% of the 20 SRBCT tests (FIG. 6 and TABLE 4) as well as all 63 training samples, see TABLE 2. Three of these samples, Test 10, Test 20 and EWS-T13 were correctly assigned to their categories (RMS, EWS and EWS respectively), having received the highest vote for their respective categories. However, their distance from a perfect vote was greater than the expected 95th percentile distance (FIG. 6); therefore, we could not confidently diagnose them by this criterion. All of the five non-SRBCT samples were excluded from any of the four diagnostic categories, since they fell outside the 95th percentiles. Using these criteria for all 88 samples, the sensitivity of the ANN models for diagnostic classification was 93% for EWS, 96% for RMS and 100% for both NB and BL. The specificity was 100% for all four diagnostic categories.

Figure 9:
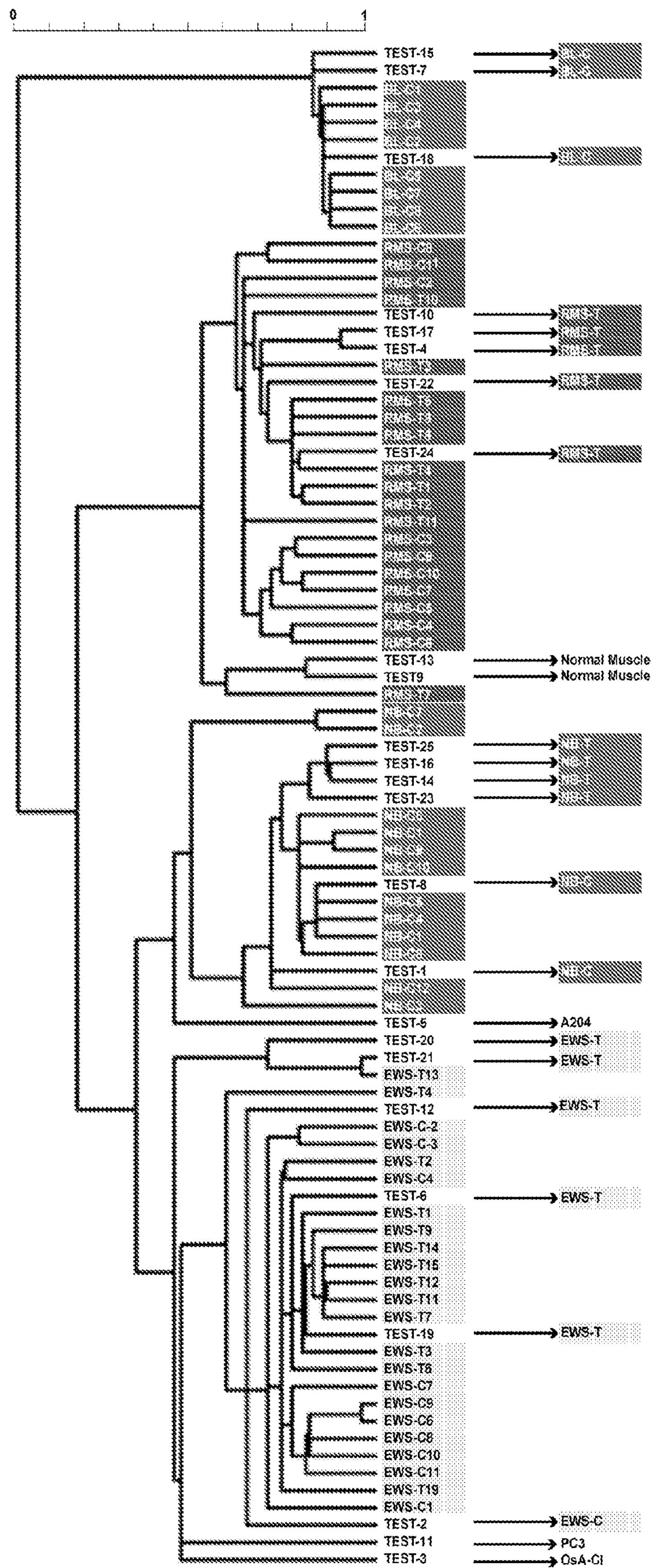
FIG. 9 represents a hierarchical clustering dendrogram of the samples in FIG. 8.

Also, hierarchical clustering using the 96 genes, identified from the ANN models, correctly clustered all 20 of the test samples (FIG. 9). Moreover, the two pairs of samples that were derived from two cell lines, BL-C2 and C4 (ST486) and NB-C2 and C7 (GICAN), were adjacent to one another in the same cluster.

Example 6

Expression of FGFR4 on SRBCT Tissue Array

To confirm the effectiveness of the ANN models to identify genes that show preferential high expression in specific cancer types at the protein level, we performed immunohistochemistry on SRBCT tissue arrays for the expression of fibroblast growth factor receptor 4 (FGFR4). This tyrosine kinase receptor is expressed during myogenesis but not in adult muscle, and is of interest because of its potential role in tumor growth and in prevention of terminal differentiation in muscle. Moderate to strong cytoplasmic immunostaining for FGFR4 was seen in all 26 RMSs tested (17 alveolar, 9 embryonal). We also observed generally weaker staining in EWS and NHL in agreement with the microarray results, except for one of anaplastic large cell lymphoma that was strongly positive (data not shown).

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and a computer data product containing a computer program for classifying and diagnosing disease using artificial neural networks.

The above specification, examples and data provide a complete description of the manufacture and use of the composition of the invention. Since many embodiments of the invention can be made without departing from the spirit and scope of the invention, the invention resides in the claims hereinafter appended.

The claimed invention is:

1. A method of diagnosing, predicting, or prognosticating about a disease comprising the steps of:

(a) obtaining experimental data from a biological sample from an organism having the disease by isolating nucleic acids or proteins from the biological sample and detecting the nucleic acids or protein from the sample, wherein said experimental data from the biological sample is obtained from methods using analysis selected from the group consisting of: Protein arrays, protein chips, cell array based expression analysis, analysis of patterns of single nucleotide polymorphisms in disease conditions, comparative genomic hybridization on metaphase BAC genomic DNA, cDNA, or oligonucleotide arrays and gene expression data;

(b) filtering said data;

(c) reducing the dimensionality of said data through the use of one or more methods;

(d) training a supervised pattern recognition method using the filtered and decreased dimensionality data, wherein said supervised pattern recognition method comprises an artificial neural network, wherein the artificial neural network when trained provides a probability distribution relationship between experimental data used as training data and a corresponding expected result for any of the disease, the predilection for the disease, or the prognosis for the disease;

(e) ranking individual experimental data points from said experimental data to provide a total rank and a rank for the disease, wherein said ranking is dependent on a model formed from the training data of said supervised pattern recognition method;

(f) choosing multiple data points from said experimental data, wherein said choice is based on said relative ranking of said individual data points for the disease;

(g) using said multiple data points to classify a second biological sample having an unknown result by determining if a set of experimental data from the second sample indicates any of the disease, the predilection for the disease, or the prognosis about the disease; and (h) displaying the indication to a user.

2. The method of claim 1, wherein said experimental data is gene expression data.

3. The method of claim 2, wherein said gene expression data is obtained by using a cDNA or an oligonucleotide microarray.

4. The method of 3, wherein said step of filtering said gene expression data is based on the intensity of the spots on said microarray.

5. The method of claim 1, wherein said multiple data points chosen from said data comprises at least 96 individual data points.

6. The method of claim 1, wherein said disease is chosen from the group consisting of multiple sclerosis, rheumatoid arthritis, and cancer.

7. The method of claim 6, wherein said disease is cancer.

8. The method of claim 7, wherein said cancer is a small round blue cell tumor.

9. The method of claim 8, wherein said cancer is neuroblastoma, rhabdomyosarcoma, non-Hodgkin lymphoma, or a Ewing family of tumors.

10. A method of diagnosing, predicting, or prognosticating about a disease comprising the steps of:

(a) obtaining experimental data from a biological sample from an organism having the disease by isolating nucleic acids or proteins from the biological sample and detecting the nucleic acids or protein from the sample, wherein said experimental data comprises gene expression data;

(b) filtering said gene expression data;

(c) reducing the dimensionality of said data through use of principal component analysis;

(d) training a supervised artificial neural network using the filtered and reduced dimensionality data so as to provide a probability distribution relationship between experimental data used as training data and a corresponding expected result for any of the at least one disease, the predilection for the disease, or the prognosis for the disease;

(e) ranking individual genes from said gene expression data to provide a total rank and a rank for each gene for the disease, wherein said ranking is dependent on a model formed from the training data of said artificial neural network;

(f) choosing multiple genes from said gene expression data, wherein said choice is based on the relative ranking of said individual genes;

(g) using said multiple genes to classify a second biological sample having an unknown result by determining if a set of experimental data from the second sample indicates any of the disease, the predilection for the disease, or the prognosis about the disease; and (h) displaying the indication to a user.

11. The method of claim 10, wherein said gene expression data is obtained through use of a cDNA or an oligonucleotide micro array.

12. The method of claim 11, wherein said step of filtering said gene expression data is based on the intensity of the spots on said micro array.

13. The method of claim 12, wherein said disease is cancer.

14. The method of claim 13, wherein said cancer is a small round blue cell tumor.

15. The method of claim 14, wherein said cancer is neuroblastoma, rhabdomyosarcoma, non-Hodgkin lymphoma, or a Ewing family of tumors.

16. The method of claim 10, wherein said disease is chosen from the group consisting of multiple sclerosis, rheumatoid arthritis, and cancer.

17. A computer-based method of determining a set of multiple data points for use in diagnosing, predicting, or prognosticating about a disease, the computer-based method comprising:

(a) receiving experimental data from a biological sample from an organism having the disease by isolating nucleic acids or proteins from the biological sample and detecting the nucleic acids or protein from the sample, wherein said experimental data comprises gene expression data;

(b) filtering the experimental data;

(c) reducing the dimensionality of the experimental data using one or more methods;

(d) dividing the experimental data into a training data set and a validation data set;

(e) training a supervised artificial neural network using the training data set to generate a trained artificial neural network that provides a probability distribution relationship between the training data set and a corresponding expected result for any of the disease, the predilection for the disease, or the prognosis for the disease;

(f) validating the performance of the trained neural network using the validation data set;

(g) generating a ranking data value corresponding to a relative ranking for individual data points data to provide a total rank and a rank for the disease using a model generated from the training data;

(h) choosing the set of multiple data points from the data using the ranking data values; and (i) displaying the chosen set of multiple data points to a user.

18. A computer-based method of determining a set of multiple data points for use in diagnosing, predicting, or prognosticating about a disease, the computer-based method comprising:

(a) receiving experimental data from a biological sample from an organism having the disease by isolating nucleic acids from the biological sample and detecting the nucleic acids from the sample, wherein said experimental data comprises gene expression data obtained through use of a cDNA or an oligonucleotide microarray;

(b) filtering the experimental data;

(c) reducing the dimensionality of the experimental data using one or more methods;

(d) dividing the experimental data into a training data set and a validation data set;

(e) training a supervised artificial neural network using the training data set to generate a trained artificial neural network that provides a probability distribution relationship between the training data set and a corresponding expected result for any of the disease, the predilection for the disease, or the prognosis for the disease;

(f) validating the performance of the trained neural network using the validation data set;

(g) generating a ranking data value corresponding to a relative ranking for individual data points data to provide a total rank and a rank for the disease using a model generated from the training data;

(h) choosing the set of multiple data points from the data using the ranking data values; and (i) displaying the chosen set of multiple data points to a user.

19. The method of claim 18, wherein said step of filtering said gene expression data is based on the intensity of the spots on said micro array.

20. The method of claim 19, wherein said disease is cancer.

21. The method of claim 20, wherein said cancer is a small round blue cell tumor.

22. The method of claim 20, wherein said cancer is neuroblastoma, rhabdomyosarcoma, non-Hodgkin lymphoma, or a Ewing family of tumors.

23. The method of claim 18, wherein said step of reducing the dimensionality of said data is accomplished by principal component analysis.

24. The method of claim 18, wherein said disease is chosen from the group consisting of multiple sclerosis, rheumatoid arthritis, and cancer.

25. A method of diagnosing, predicting, or prognosticating about a disease comprising the steps of:

(a) employing a disease model obtained by filtering gene expression data obtained from a biological sample from an organism having the disease by isolating nucleic acids or proteins from the biological sample and detecting the nucleic acids or protein from the sample, reducing dimensionality of the data, training a supervised artificial neural network so as to provide a probability distribution relationship between experimental data used as training data and a corresponding expected result for any of the disease, the predilection for the disease, or the prognosis for the disease, ranking individual gene data to provide a total rank and a rank for each disease from a model formed using said gene expression data, wherein said ranking is dependent on the outcome of said artificial neural network, and choosing multiple genes from said gene expression data, wherein said choice is based on the relative ranking of said individual genes for each disease;

(b) using said multiple genes to classify a second biological sample having an unknown result by determining if a set of experimental data from the second sample indicates the disease, the predilection for a disease, or the prognosis about a disease; and (c) displaying the indication to a user.

26. The method of claim 25, wherein said disease is chosen from the group consisting of multiple sclerosis, rheumatoid arthritis, and cancer.

27. A computer system including a model of a disease, the system comprising:

a filter module configured to filter experimental data comprising gene expression data and to reduce dimensionality of the experimental data;

a training module configured to train a supervised artificial neural network so as to provide a probability distribution relationship between experimental data used as training data and a corresponding expected result for any of the disease, the predilection for the disease, or the prognosis for the disease;

a ranking module configured to generate a ranking of individual genes from the gene expression data to provide a total rank and a rank for each gene and each disease, the ranking being dependent on an outcome of the artificial neural network;

a chooser module configured to choose multiple genes from the gene expression data based on the ranking of the individual genes; and an application module configured to use the multiple genes to classify a sample having an unknown result by determining if a set of experimental data from the sample indicates the disease, the predilection for the disease, or the prognosis about the disease; and a display module configured to display the classification of the sample.

28. The method of claim 27, wherein said gene expression data is obtained through use of a cDNA or an oligonucleotide microarray.

29. The method of claim 28, wherein said filter module is configured to filter said gene expression data based on an intensity of spots on said microarray.

30. The method of claim 27, wherein said filter module is configured to reduce the dimensionality of said data using principal component analysis.

31. The method of claim 27, wherein said disease is chosen from the group consisting of multiple sclerosis, rheumatoid arthritis, and cancer.

32. A computer system including a model of a disease, the system comprising:

a filter module configured to filter experimental data comprising gene expression data, to reduce dimensionality of the experimental data using principle component analysis and to divide the experimental data into a training set and a validation set;

a training module configured to train an artificial neural network using the training set to generate a trained artificial neural network so as to provide a probability distribution relationship between the training set and a corresponding expected result for any of the disease, the predilection for the disease, or the prognosis for the disease;

a validator module configured to validate a performance of the trained artificial neural network using the validation set;

a ranking module configured to generate a ranking data value corresponding to a relative ranking for individual data points data to provide a total rank and a rank for each disease using data from the trained artificial neural network; and a selection module configured to choose a set of multiple data points from the data using the ranking data values for each disease; and a display module configured to display the set of multiple data points.

33. The method of claim 32, wherein said gene expression data is obtained through use of a cDNA or an oligonucleotide micro array.

34. The method of claim 33, wherein said filter module is configured to filter said gene expression data based on an intensity of spots on said microarray.

35. The method of claim 32, wherein said disease is chosen from the group consisting of multiple sclerosis, rheumatoid arthritis, and cancer.

* * * * *

UNITED STATES PATENT AND TRADEMARK OFFICE

CERTIFICATE OF CORRECTION

PATENT NO. : 7,774,143 B2
APPLICATION NO. : 10/133937
DATED : August 10, 2010
INVENTOR(S) : Khan et al.

It is certified that error appears in the above-identified patent and that said Letters Patent is hereby corrected as shown below:

Col. 2, line 40: “(60-70 men) sets are” should read --(60-70 mers) sets are--

Col. 15, line 9: “(Biofluids, Rockyville, Md.); dATP,” should read --(Biofluids, Rockville, Md.); dATP,--

Signed and Sealed this
Fourteenth Day of February, 2012

David J. Kappos
*Director of the United States Patent and Trademark Office*